United States Patent
Berger et al.

(10) Patent No.: US 8,637,552 B2
(45) Date of Patent: *Jan. 28, 2014

(54) ANTHRANILAMIDE ARTHROPODICIDE TREATMENT

(75) Inventors: Richard Alan Berger, Claymont, DE (US); Isaac Billy Annan, Newark, DE (US); George Philip Lahm, Wilmington, DE (US); John Lindsey Flexner, Landenberg, PA (US); Thomas Paul Selby, Hockessin, DE (US); Thomas Martin Stevenson, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/571,677

(22) Filed: Aug. 10, 2012

(65) Prior Publication Data

US 2013/0031677 A1  Jan. 31, 2013

Related U.S. Application Data

(60) Continuation of application No. 12/711,285, filed on Feb. 24, 2010, now abandoned, which is a division of application No. 10/485,125, filed as application No. PCT/US02/30302 on Sep. 10, 2002, now Pat. No. 7,696,232.

(60) Provisional application No. 60/323,941, filed on Sep. 21, 2001.

(51) Int. Cl.
*A01N 43/40* (2006.01)

(52) U.S. Cl.
USPC ......... 514/341; 514/229.2; 514/354; 514/365

(58) Field of Classification Search
None
See application file for complete search history.

(56) References Cited

U.S. PATENT DOCUMENTS

| | | | |
|---|---|---|---|
| 4,321,371 A | 3/1982 | Parg et al. | |
| 5,602,126 A | 2/1997 | Barnette et al. | |
| 5,728,693 A | 3/1998 | Stevenson | |
| 5,998,424 A | 12/1999 | Galemmo, Jr. et al. | |
| 6,020,357 A | 2/2000 | Pinto et al. | |
| 6,403,620 B1 | 6/2002 | Galemmo, Jr. et al. | |
| 6,548,512 B1 | 4/2003 | Pinto et al. | |
| 6,602,895 B2 | 8/2003 | Galemmo, Jr. et al. | |
| 6,747,047 B2 | 6/2004 | Lahm et al. | |
| 6,965,032 B2 | 11/2005 | Freudenberger | |
| 6,995,178 B2 | 2/2006 | Lahm et al. | |
| 7,038,057 B2 | 5/2006 | Annis et al. | |
| 7,087,598 B2 | 8/2006 | Clark | |
| 7,157,475 B2 | 1/2007 | Clark | |
| 7,179,824 B2 | 2/2007 | Zimmerman | |
| 7,189,677 B2 * | 3/2007 | Harada et al. | 504/100 |
| 7,199,138 B2 * | 4/2007 | Finkelstein et al. | 514/341 |
| 7,232,836 B2 | 6/2007 | Lahm et al. | |
| 7,241,767 B2 | 7/2007 | Clark et al. | |
| 7,247,647 B2 | 7/2007 | Hughes et al. | |
| 7,288,554 B2 | 10/2007 | Finkelstein et al. | |
| 7,335,780 B2 | 2/2008 | Annis | |
| 7,339,057 B2 | 3/2008 | Taylor | |
| 7,666,882 B2 | 2/2010 | Lahm | |
| 7,696,232 B2 | 4/2010 | Berger et al. | |
| 7,696,233 B2 | 4/2010 | Lahm et al. | |
| 7,875,634 B2 | 1/2011 | Hughes et al. | |
| 8,022,067 B2 | 9/2011 | Annan et al. | |
| 8,268,750 B2 | 9/2012 | Funke et al. | |
| 8,268,751 B2 | 9/2012 | Funke et al. | |
| 8,299,036 B2 | 10/2012 | Funke et al. | |
| 2001/0004460 A1 | 6/2001 | Klittich et al. | |

(Continued)

FOREIGN PATENT DOCUMENTS

| | | |
|---|---|---|
| DE | 4428380 A | 8/1994 |
| DE | 19840322 A1 | 9/1998 |

(Continued)

OTHER PUBLICATIONS

XP002177117 Suto, Mark J. et al.; Tetrahedron Letters, vol. 36 No. 40, 1995, pp. 7213-7216, Elsevier Science Publishers, Amsterdam, NL.

(Continued)

*Primary Examiner* — Bethany Barham

(57) ABSTRACT

This invention pertains to methods for protecting a propagule or a plant grown therefrom from invertebrate pests comprising contacting the propagule or the locus of the propagule with a biologically effective amount of a compound of Formula I, its N-oxide or an agriculturally suitable salt thereof

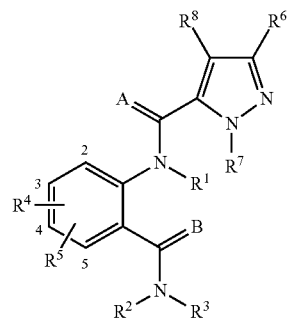

wherein A and B and $R^1$ through $R^8$ are as defined in the disclosure. This invention also relates to propagules treated with a compound of Formula I and compositions comprising a Formula I compound for coating propagules.

14 Claims, No Drawings

(56) References Cited

U.S. PATENT DOCUMENTS

| | | |
|---|---|---|
| 2003/0229050 A1 | 12/2003 | Lahm et al. |
| 2004/0102324 A1 | 5/2004 | Annis et al. |
| 2004/0110777 A1 | 6/2004 | Annis et al. |
| 2004/0138450 A1 | 7/2004 | Clark |
| 2004/0142984 A1 | 7/2004 | Lahm et al. |
| 2004/0171649 A1 | 9/2004 | Annis et al. |
| 2004/0186141 A1 | 9/2004 | Zimmerman |
| 2004/0192731 A1 | 9/2004 | Finkelstein et al. |
| 2004/0198984 A1 | 10/2004 | Lahm et al. |
| 2004/0198987 A1 | 10/2004 | Freudenberger et al. |
| 2004/0259913 A1 | 12/2004 | Clark |
| 2005/0075372 A1 | 4/2005 | Lahm et al. |
| 2005/0124600 A1 | 6/2005 | Clark et al. |
| 2005/0147633 A1 | 7/2005 | Stevenson |
| 2005/0215785 A1 | 9/2005 | Taylor |
| 2005/0215798 A1 | 9/2005 | Annis |
| 2007/0142327 A1 | 6/2007 | Funke et al. |
| 2007/0270416 A1 | 11/2007 | Funke et al. |
| 2008/0027046 A1 | 1/2008 | Annan et al. |
| 2008/0103044 A1 | 5/2008 | Tang et al. |
| 2008/0305093 A1 | 12/2008 | Gutsche et al. |
| 2009/0104145 A1 | 4/2009 | Annan et al. |
| 2009/0133318 A1 | 5/2009 | Lahm |
| 2010/0055084 A1 | 3/2010 | Gutsche et al. |
| 2010/0137374 A1 | 6/2010 | Annan et al. |
| 2010/0168042 A1 | 7/2010 | Funke et al. |
| 2010/0204281 A1 | 8/2010 | Taylor |
| 2010/0249070 A1 | 9/2010 | Funke et al. |
| 2011/0059846 A1 | 3/2011 | Gutsche et al. |
| 2011/0184183 A1 | 7/2011 | Oberholzer |
| 2011/0293533 A1 | 12/2011 | Annan et al. |
| 2012/0083491 A1 | 4/2012 | Funke et al. |
| 2012/0156262 A1 | 6/2012 | Gutsche et al. |
| 2012/0157305 A1 | 6/2012 | Tam |
| 2012/0171183 A1 | 7/2012 | Lahm et al. |
| 2013/0028879 A1 | 1/2013 | Lahm et al. |
| 2013/0123247 A1 | 5/2013 | Lahm et al. |
| 2013/0190259 A1 | 7/2013 | Lahm et al. |
| 2013/0190313 A1 | 7/2013 | Lahm et al. |
| 2013/0190362 A1 | 7/2013 | Lahm et al. |

FOREIGN PATENT DOCUMENTS

| | | |
|---|---|---|
| EP | 0289879 A | 11/1988 |
| EP | 0919542 A2 | 6/1999 |
| EP | 1193254 A1 | 1/2001 |
| EP | 0991625 B1 | 6/2005 |
| EP | 0946508 B1 | 9/2009 |
| NL | 9202078 A | 11/1992 |
| WO | WO96/38419 | 12/1996 |
| WO | WO98/28269 | 7/1998 |
| WO | WO98/57937 | 12/1998 |
| WO | WO99/29169 | 6/1999 |
| WO | WO01/02354 A1 | 1/2001 |
| WO | WO01/32628 A1 | 5/2001 |
| WO | WO01/70671 A2 | 9/2001 |
| WO | WO02/48115 A2 | 6/2002 |
| WO | WO02/070483 A1 | 9/2002 |
| WO | WO03/016284 A1 | 2/2003 |
| WO | WO03/106427 | 12/2003 |
| WO | 2005/048711 A1 | 6/2005 |
| WO | 2005/048712 A1 | 6/2005 |
| WO | 2005/048713 A1 | 6/2005 |
| WO | 2005/053393 A1 | 6/2005 |
| WO | 2005/053405 A1 | 6/2005 |
| WO | 2005/053406 A1 | 6/2005 |
| WO | 2005/079575 A1 | 9/2005 |
| WO | 2005/107468 A1 | 11/2005 |
| WO | WO2009/002810 | 12/2008 |
| WO | WO2009/002856 | 12/2008 |

OTHER PUBLICATIONS

Klaubert et al., J. Med. Chem., vol. 24, No. 6, pp. 748-752, 1981.

* cited by examiner

ANTHRANILAMIDE ARTHROPODICIDE TREATMENT

REFERENCE TO RELATED APPLICATIONS

This is a continuation of application Ser. No. 12/711,285, filed Feb. 24, 2010, now abandoned which is a divisional of application Ser. No. 10/485,125, filed on Jan. 26, 2004, now U.S. Pat. No. 7,696,232, which is a national filing under 35 U.S.C. 371 of International Application No. PCT/US02/30302, filed 10 Sep. 2002, which claims priority benefit of Provisional Application 60/323,941, filed 21 Sep. 2001.

FIELD OF THE INVENTION

This invention relates to the control of phytophagous invertebrate pests such as arthropod pests by contacting plant propagules or the locus of the propagules with certain anthranilamides and to propagule-coating compositions comprising the anthranilamides.

BACKGROUND OF THE INVENTION

The control of invertebrate pests such as arthropods is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals and nursery crops is also important.

Plants are subject to injury by invertebrate pests at all stages of growth, beginning with seeds or other propagules such as bulbs, tubers, rhizomes, corns, and stem and leaf cuttings and ending with mature plants. Besides the cost of materials, the effort and time required for application of invertebrate pest control substances make repetition of treatments undesirable. Ideally a single treatment of a plant at the propagule stage would protect the plant from invertebrate pests during its entire life.

A variety of techniques for treating propagules with plant protection substances are known. These include soaking propagules in arthropodicide-comprising solutions, coating propagules with films, pelleting materials and the like comprising arthropodicidal compositions, and applying arthropodicidal compounds to the growing medium surrounding the propagules. While some compounds can effectively protect propagules from certain phytophagous invertebrate pests, new compounds are needed that are more effective or have a broader spectrum of activity, are less costly, less toxic, environmentally safer or have different modes of action.

Particularly needed are invertebrate pest control treatments that can protect the plant not only at its propagule stage but also later in its development. Achieving this objective requires compounds that are active against invertebrate pests and can effectively translocate from the locus of the propagule up through the growing stems, leaves sad other aboveground plant parts. Furthermore the compounds need to have high activity against invertebrate pests to compensate for the dilution occasioned by the expanding plant mass. Also, the compounds cannot rapidly degrade and lose their biological potency in the environment of the plant's vascular tissues. The combination of these properties is rare. Treatments of propagules effective for protecting from phytophagous invertebrate pests not only the propagule but also the plant at later growth stages have now been discovered.

SUMMARY OF THE INVENTION

This invention, involves compounds of Formula I, their N-oxides and their agriculturally suitable salts

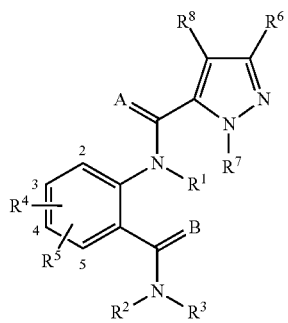

wherein
A and B are independently O or S;
$R^1$ is H, $C_1$-$C_6$ alkyl, $C_2$-$C_6$ alkoxycarbonyl or $C_2$-$C_6$ alylcarbonyl;
$R^2$ is H or $C_1$-$C_6$ alkyl;
$R^3$ is H; $C_1$-$C_6$ alkyl, $C_2$-$C_6$ alkenyl, $C_2$-$C_6$ alkynyl, or $C_3$-$C_6$ cycloalkyl each optionally substituted with one or more substituents selected from the group consisting of halogen, CN, $NO_2$, hydroxy, $C_1$-$C_4$ alkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxy carbonyl, $C_2$-$C_6$ alkycarbonyl, $C_3$-$C_6$ trialkylsilyl, phenyl, phenoxy, 5-membered heteroarmatic rings, and 6-membered heteroaromatic rings; each phenyl, phenoxy, 5-membered heteroaromatic ring, and 6-membered heteroaromatic ring optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_8$ (alkyl)(cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl and $C_3$-$C_6$ trialkylsilyl; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl or $C_2$-$C_6$ alylcarbonyl;
$R^4$ is H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, CN, halogen, $C_1$-$C_4$ alkoxy, $C_1$-$C_4$ haloalkoxy or $NO_2$;
$R^5$ is H, $C_1$-$C_6$ alkyl, $C_1$-$C_6$ haloalkyl, $C_1$-$C_4$ alkoxyalkyl, $C_1$-$C_4$ hydroxyalkyl, $C(O)R^{10}$, $CO_2R^{10}$, $C(O)NR^{10}R^{11}$, halogen, $C_1$-$C_4$ alkoxy, $C_1$-$C_4$ haloalkoxy, $NR^{10}R^{11}$, $N(R^{11})C(O)R^{10}$, $N(R^{11})CO_2R^{10}$ or $S(O)_nR^{12}$;
$R^6$ is H, $C_1$-$C_6$ alkyl, $C_1$-$C_6$ haloalkyl, halogen, CN, $C_1$-$C_4$ alkoxy or $C_1$-$C_4$ haloalkoxy;
$R^7$ is $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl or $C_3$-$C_6$ halocycloalkyl; or
$R^7$ is a phenyl ring, a benzyl ring, a 5- or 6-membered heteroaromatic ring, a naphthyl ring system or an aromatic 8-, 9- or 10-membered fused heterobicyclic ring system, each ring or ring system optionally substituted with one to three substituents independently selected from $R^9$;
$R^8$ is H, $C_1$-$C_6$ alkyl, $C_1$-$C_6$ haloalkyl, halogen, $C_1$-$C_4$ alkoxy or $C_1$-$C_4$ haloalkoxy;
each $R^9$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_5$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_8$ (alkyl)(cycloalkyl) amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^{10}$ is H, $C_1$-$C_4$ alkyl or $C_1$-$C_4$ haloalkyl;

$R^{11}$ is H or $C_1$-$C_4$ alkyl;

$R^{12}$ is $C_1$-$C_4$ alkyl or $C_1$-$C_4$ haloalkyl; and n is 0, 1 or 2.

This invention provides a method for protecting a propagule or a plant grown therefrom from an invertebrate pest. The method comprises contacting the propagate or the locus of the propagate with a biologically effective amount of a compound of Formula I, m N-oxide thereof or an agriculturally suitable salt thereof.

This invention also provides a propagate comprising a biologically effective amount of a compound of Formula I, its N-oxide or as agriculturally suitable salt thereof.

This invention further provides a propagate contacted with a biologically effective amount of a compound of Formula I, its N-oxide or an agriculturally suitable salt thereof.

This invention still further provides an invertebrate pest, control composition for coating a propagule comprising a biologically effective amount of a compound of Formula I, its N-oxide or an agriculturally suitable salt thereof and a film former or adhesive agent.

DETAILED DESCRIPTION OF THE INVENTION

As referred to in the present disclosure and claims, the term "propagule" means a seed or a regenerable plant, part. The term "regenerate plant part" means a part of a plant other than a seed from which a whole plant may be grows or regenerated when the plant part is placed in horticultural or agricultural growing media such as moistened soil, peat moss, sand, vermicalite, perlite, rock wool, fiberglass, coconut husk fiber, tree fern fiber and the like, or even a completely liquid medium such as water. Regenerable plant parts commonly include rhizomes, tubers, bulbs and corms of such geophytic plant species as potato, sweet potato, yam, onion, dahlia, tulip, narcissus, etc. Regenerable plant parts include plant parts that are divided (e.g., cut) to preserve their ability to grow into a new plant. Therefore regenerable plant parts include viable divisions of rhizomes, tubers, bulbs and corms which retain meristematic tissue, such, as an eye. Regenerable plant parts can also include other plant parts such as cut or separated stems and leaves from which some species of plants can be grown using horticultural or agricultural growing media. As referred to in the present disclosure and claims, unless otherwise indicated, the term "seed" includes both unsprouted seeds and sprouted seeds in which the testa (seed coat) still surrounds part of the emerging shoot and root.

In the above recitations, the term "alkyl", used either alone or in compound words such as "alkythio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as 1-propenyl, 2-propenyl, and the different butenyl, pentenyl and hexenyl isomers, "Alkenyl" also includes polyenes such as 1,2-propadienyl and 2,4-hexadienyl, "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Cycloalkyl" includes, for example, cyclopropyl, cyolobutyl, cyclopentyl and cyclohexyl.

The term "heterocyclic ring" or "heterocyclic ring system" denotes rings or ring systems in which at least one ring atom is not carbon and comprises 1 to 4 heteroatoms independently selected from the group consisting of nitrogen, oxygen and sulfur, provided that each heterocyclic ring comprises no more than 4 nitrogens, no more than 2 oxygens and no more than 2 sulfurs. The heterocyclic ring can be attached through any available carbon or nitrogen by replacement of hydrogen on said carbon or nitrogen. The term "aromatic ring system" denotes fully unsaturated carbocycles and heterocycles in which at least one ring of the polycyclic ring system is aromatic (where aromatic indicates that the Hückel rule is satisfied for the ring system). The term "heteroaromatic ring" denotes fully aromatic rings in which at least one ring atom is not carbon and comprises 1 to 4 heteroatoms independently selected from the group consisting of nitrogen, oxygen and sulfur, provided that each heterocyclic ring comprises no more than 4 nitrogens, no more than 2 oxygens and no more than 2 sulfurs (where aromatic indicates that the Hückel rule is satisfied). The heterocyclic ring can be attached through any available carbon or nitrogen by replacement of hydrogen, on said carbon or nitrogen. The term "aromatic heterocyclic ring system" includes fully aromatic heterocycles and heterocycles in which at least one ring of a polycyclio ring system is aromatic (where aromatic indicates that the Hückel rule is satisfied). The term "fused, heterobicyclic ring system" includes a ring system comprised of two fused rings in which at least one ring atom is not carbon and can be aromatic or non aromatic, as defined above.

The term "halogen" either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_3$, $CF_3CH_2$ and $CF_3CCl_2$. The terms "haloalkenyl", "haloalkynyl", "haloalkoxyl" and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CClCH_2O$, $HCF_2CH_2CH_2O$ and $CF_3CH_2O$.

The total number of carbon atoms in a substituent group is indicated by the "$C_i$-$C_j$" prefix where i and j are numbers from 1 to 8. For example, $C_3$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3CCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula I comprises a heterocyclic ring, all substituents are attached to this ring through any available carbon or nitrogen by replacement of a hydrogen on said carbon or nitrogen.

When a group has a substituent which can be hydrogen, for example $R^3$, then, when this substituent is taken as hydrogen, it is recognized that this is equivalent to said group being unsubstituted.

Compounds of Formula I can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of the invention may be present as a mixture of stereoisomers, individual stereoisomers, or as as optically active form.

The salts of compounds of Formula I include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Methods, propagules and compositions of the invention preferred for reason of cost, ease of chemical synthesis or application, and/or biological efficacy involve the following preferred compounds:

Preferred 1. A compound of Formula I wherein
A and B are both O;
$R^7$ is a phenyl ring or a 5- or 6-membered heteroaromatic ring selected from the group consisting of

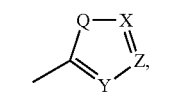
J-1

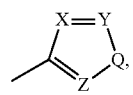
J-2

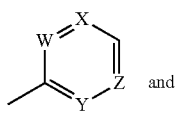
J-3
and

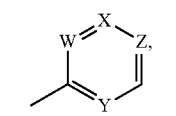
J-4 each ring optionally substituted with one to three substituents independently selected from $R^9$;
Q is O, S, NH or $NR^9$; and
W, X, Y and Z are independently N, CH or $CR^9$, provided that in J-3 and J-4 at least one of W, X, Y or Z is N.
Preferred 2. A compound of Preferred 1 wherein
$R^1$, $R^2$ and $R^8$ are all H;
$R^3$ is $C_1$-$C_4$ alkyl optionally substituted with halogen, CN, $OCH_3$ or $S(O)_pCH_3$;
$R^4$ group is attached at position 2;
$R^4$ is $CH_3$, $CF_3$, $OCF_3$, $OCHF_2$, CN or halogen;
$R^5$ is H, $CH_3$ or halogen;
$R^6$ is $CH_3$, $CF_3$ or halogen;
$R^7$ is phenyl or 2-pyridinyl, each, optionally substituted; and
p is 0, 1 or 2.
Preferred 3. A compound of Preferred 2 wherein $R^3$ is $C_1$-$C_4$ alkyl and $R^6$ is $CF_3$.

Preferred 4. A compound of Preferred 2 wherein $R^3$ is $C_1$-$C_4$ alkyl and $R^6$ is Cl or Br.

As noted above, $R^7$ is (among others) a phenyl, a benzyl, a 5- or 6-membered heteroaromatic ring, a naphthyl ring system or an aromatic 8-, 9- or 10-membered fused heterobicyclic ring system, each ring or ring system optionally substituted with one to three substituents independently selected from $R^9$. The term, "optionally substituted" in connection with these $R^7$ groups refers to groups which are unsubstituted or have at least one non-hydrogen substituent that does not extinguish the invertebrate pest control activity possessed by the unsubstituted analog. Note also that J-1 through J-4 below denote 5- or 6-membered heteroaromatic rings. An example of a phenyl ring optionally substituted with 1 to 3 $R^9$ is the ring illustrated as J-5 in Exhibit 1, wherein r is an integer from 0 to 3. An example of a benzyl ring optionally substituted with 1 to 3 $R^9$ is the ring illustrated as J-6 in Exhibit 1, wherein r is an integer from 0 to 3. An example of a naphthyl ring system optionally substituted with 1 to 3 $R^9$ is illustrated as J-59 in Exhibit 1, wherein r is an integer from 0 to 3. Examples of a 5- or 6-membered heteroaromatic ring optionally substituted with 1 to 3 $R^9$ include the rings J-7 through J-58 illustrated in Exhibit 1 wherein r is an integer from 0 to 3. Note that J-7 through J-26 are examples of J-1, J-27 through J-41 are examples of J-2, and J-46 through J-58 are examples of J-3 and J-4. The nitrogen atoms that require substitution to fill their valence are substituted with H or $R^9$. Note that some J groups can only be substituted with less than 3 $R^9$ groups (e.g. J-19, J-20, J-23 through J-26 and J-37 through J-40 can only be substituted with one $R^9$). Examples of aromatic 8-, 9- or 10-membered fused heterobicyclic ring systems optionally substituted with 1 to 3 $R^9$ include J-60 through J-90 illustrated in Exhibit 1 wherein r is art integer from 0 to 3. Although $R^9$ groups are shown in the structures J-5 through J-90, it is noted that they do not need to be present since they are optional substituents. Note that when the attachment point between $(R^9)_r$ and the J group is illustrated, as floating, $(R^9)_r$ can be attached to any available carbon atom of the J group. Note that when the attachment point on the J group is illustrated as floating, the J group can be attached to the remainder of Formula I through any available carbon of the J group by replacement of a hydrogen atom.

Exhibit 1

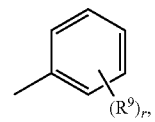
J-5

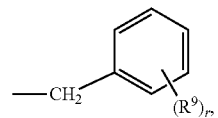
J-6

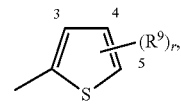
J-7

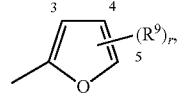
J-8

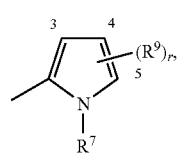 J-9
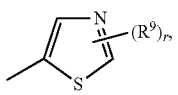 J-10
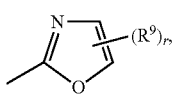 J-11
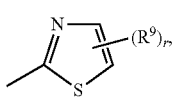 J-12
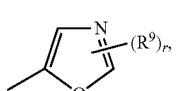 J-13
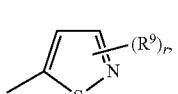 J-14
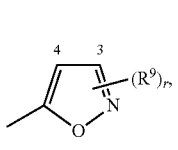 J-15
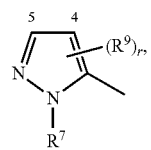 J-16
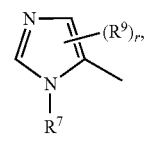 J-17
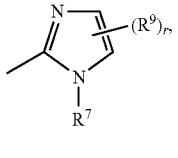 J-18
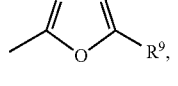 J-19
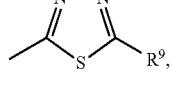 J-20
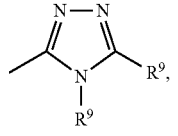 J-21
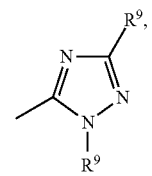 J-22
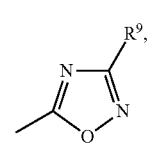 J-23
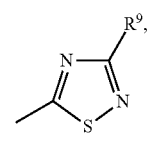 J-24
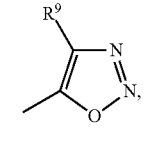 J-25
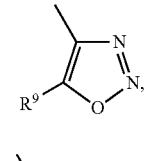 J-26
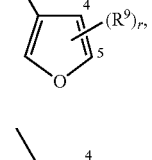 J-27
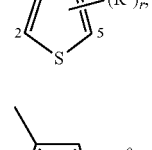 J-28
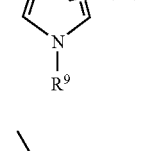 J-29
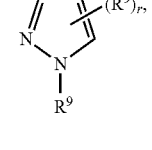 J-30
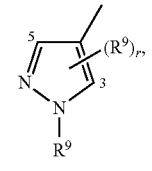 J-31

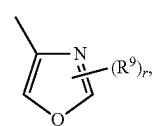 J-32
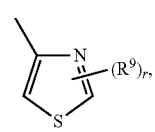 J-33
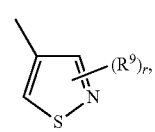 J-34
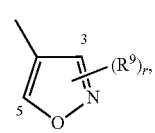 J-35
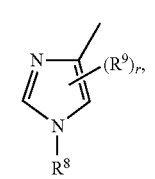 J-36
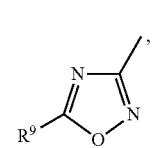 J-37
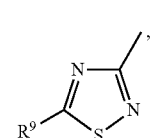 J-38
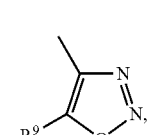 J-39
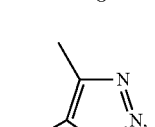 J-40
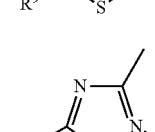 J-41
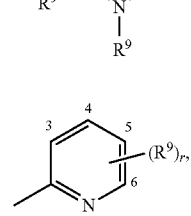 J-46
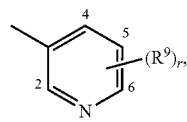 J-47
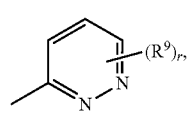 J-48
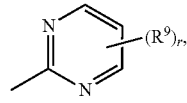 J-49
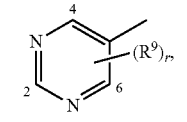 J-50
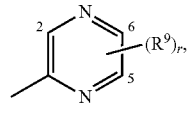 J-51
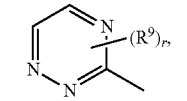 J-52
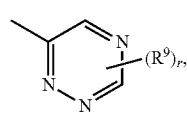 J-53
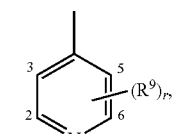 J-54
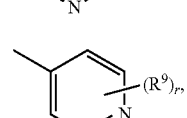 J-55
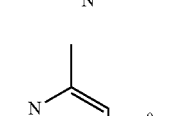 J-56
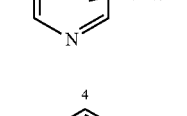 J-57
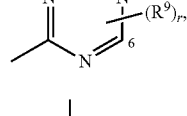 J-58
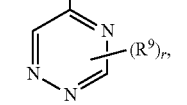

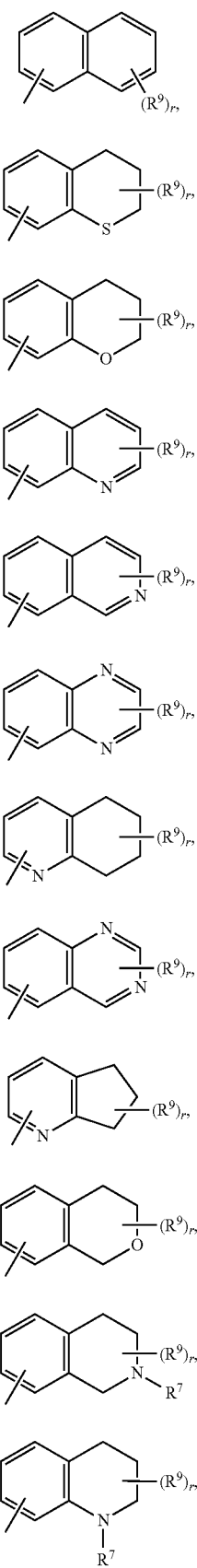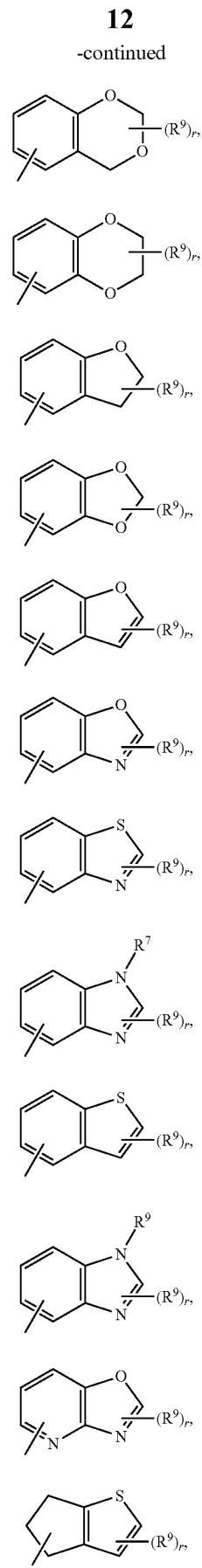

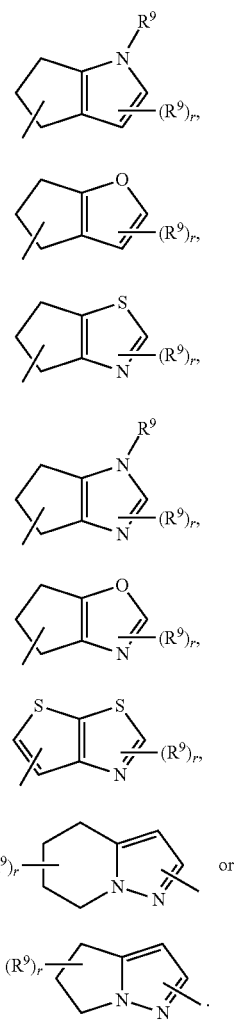

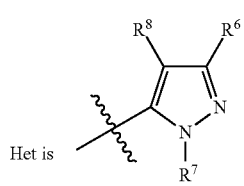

One or more of the following methods and variations as described in Schemes 1-22 can be used to prepare the compounds of Formula I. The definitions of A, B and $R^1$ through $R^9$ in the compounds of Formulae 2-40 below are as defined above in the Summary of the Invention unless indicated otherwise. Compounds of Formulae Ia-d, 2a-d, 3a, 4a-d, 5a-b, 17a-c, 18a and 32a-b are various subsets of the compounds of Formula I, 2, 3, 4, 17, 18 and 32. In the schemes, Het is the moiety shown below:

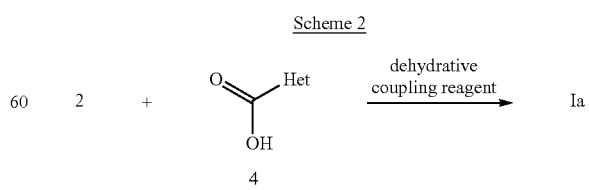

A typical method for preparation of a compound of Formula Ia is described in Scheme 1.

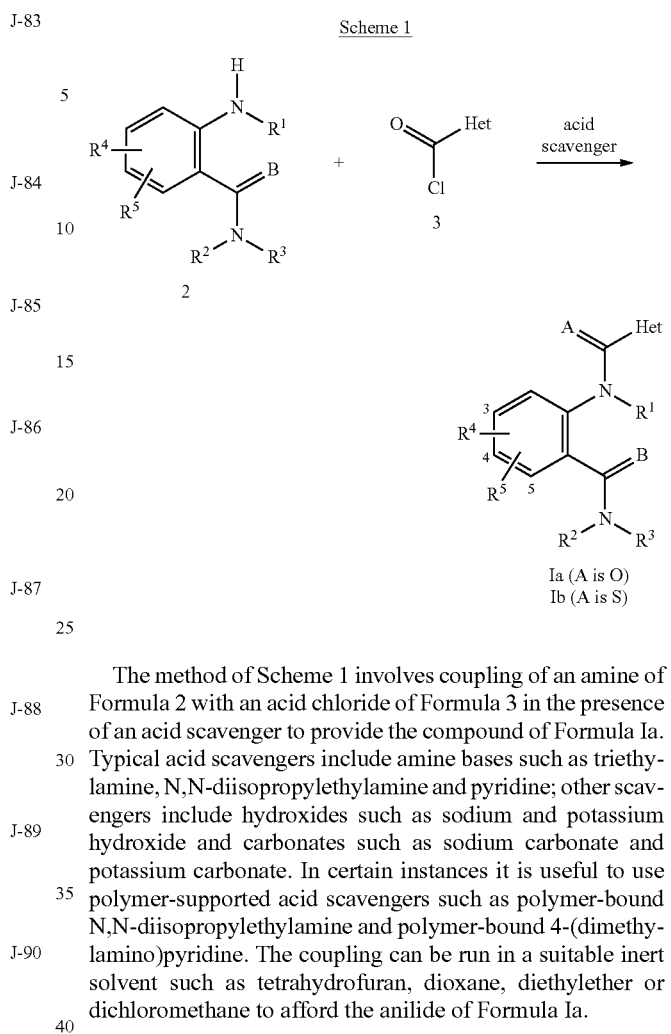

The method of Scheme 1 involves coupling of an amine of Formula 2 with an acid chloride of Formula 3 in the presence of an acid scavenger to provide the compound of Formula Ia. Typical acid scavengers include amine bases such as triethylamine, N,N-diisopropylethylamine and pyridine; other scavengers include hydroxides such as sodium and potassium hydroxide and carbonates such as sodium carbonate and potassium carbonate. In certain instances it is useful to use polymer-supported acid scavengers such as polymer-bound N,N-diisopropylethylamine and polymer-bound 4-(dimethylamino)pyridine. The coupling can be run in a suitable inert solvent such as tetrahydrofuran, dioxane, diethylether or dichloromethane to afford the anilide of Formula Ia.

A thioamide of Formula Ib can be obtained in a subsequent step from the corresponding amide of Formula Ia by treatment with one of a variety of standard thio transfer reagents including phosphorus pentasulfide and Lawesson's reagent (2,4-bis(4-methoxyphenyl)-1,3-dithia-2,4-diphosphetane-2,4-disulfide).

As shown in Scheme 2, an alternate procedure for the preparation of compounds of Formula Ia involves coupling of an amine of Formula 2 with an acid of Formula 4 in the presence of a dehydrating agent such as dicyclohexylcarbodiimide (DCC), 1,1'-carbonyl-diimidazole, bis(2-oxo-3-oxazolidinyl)phosphinic chloride or benzotriazol-1-yloxy-tris-(dimethylamino)phosphonium hexafluorophosphate.

Polymer-supported reagents are again useful here, such as polymer-bound cyclohexylcarbodiimide. The coupling can be run in a suitable inert solvent such as dichloromethane or N,N-dimethylformamide. The synthetic methods of Schemes 1 and 2 are just representative examples of a wide variety of coupling methods useful for the preparation of Formula I compounds; the synthetic literature is extensive for this type of coupling reaction.

One skilled in the art will also realize that acid chlorides of Formula 3 may be prepared from acids of Formula 4 by numerous well-known methods. For example, acid chlorides of Formula 3 are readily made from carboxylic acids of Formula 4 by reacting the carboxylic acid 4 with thionyl chloride or oxalyl chloride in an inert solvent such as toluene or dichloromethane in the presence of a catalytic amount of N,N-dimethylformamide.

As shown in Scheme 3, amines of Formula 2a are typically available from the corresponding 2-nitrobenzamides of Formula 5 via catalytic hydrogenation of the nitro group.

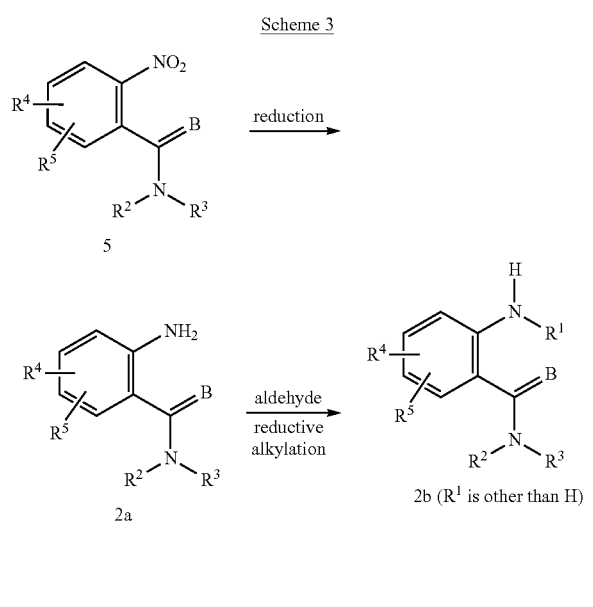

Typical procedures involve reduction with hydrogen in the presence of a metal catalyst such as palladium on carbon or platinum oxide and in hydroxylic solvents such as ethanol and isopropanol. Amines of Formula 2a can also be prepared by reduction with zinc in acetic acid. These procedures are well documented in the chemical literature. $R^1$ substituents such as $C_1$-$C_6$ alkyl can be introduced at this stage through well known methodologies including either direct alkylation or through the generally preferred method of reductive alkylation of the amine. As is further shown in Scheme 3, a commonly employed procedure is to combine the amine 2a with an aldehyde in the presence of a reducing agent such as sodium cyanoborohydride to produce the Formula 2b compounds where $R^1$ is $C_1$-$C_6$ alkyl.

Scheme 4 shows that compounds of Formula Ic can be alkylated or acylated with a suitable alkylating or acylating agent such as an alkyl halide, alkyl chloroformate or acyl chloride in the presence of a base such as sodium hydride or n-butyllithium in an inert solvent such as tetrahydrofuran or N,N-dimethylformamide to afford anilides of Formula Id wherein $R^1$ is other than, hydrogen.

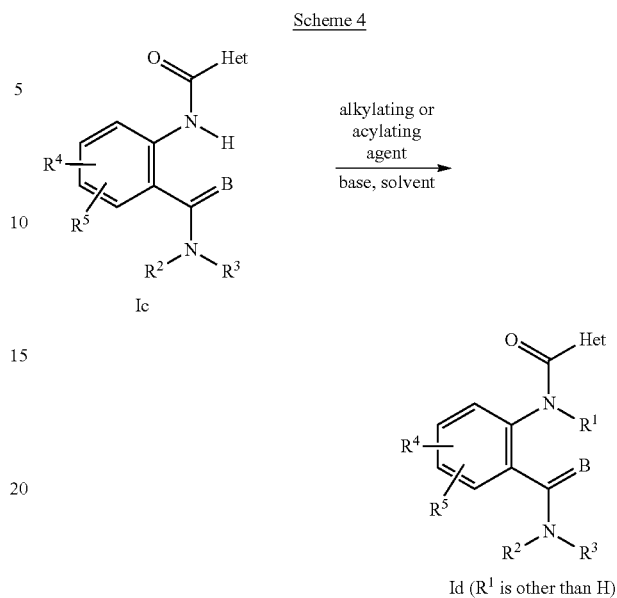

The intermediate amides of Formula 5a are readily prepared from commercially available 2-nitrobenzoic acids. Typical methods for amide formation can be used. As shown in Scheme 5, these methods include direct dehydrative coupling of acids of Formula 6 with amines of Formula 7 using for example DCC, and conversion of the acids to activated forms such as the acid chlorides or anhydrides and subsequent coupling with amines to form amides of Formula 5a.

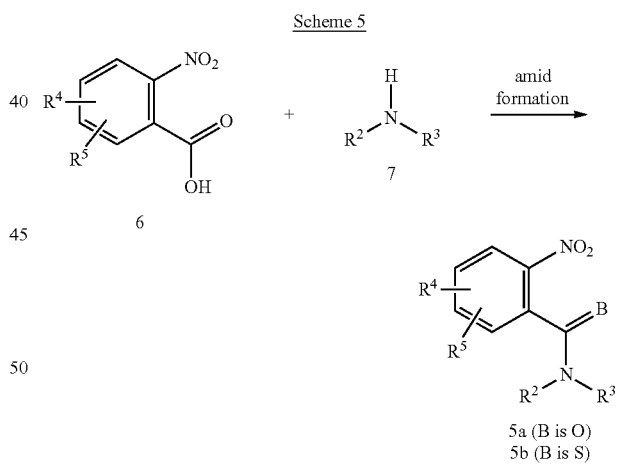

Alkyl chloroformates, such as ethyl chloroformate or isopropyl chloroformate, are especially useful reagents for this type of reaction involving activation of the acid. The chemical literature is extensive regarding methods for amide formation. Amides of Formula 5a are readily converted to thioamides of Formula 5b by using commercially available thio transfer reagents such as phosphorus pentasulfide and Lawesson's reagent.

Intermediate anthranilic amides of Formula 2c or 2d may also be prepared from isatoic anhydrides of Formula 8 or 9 respectively, as shown in Scheme 6.

Scheme 6

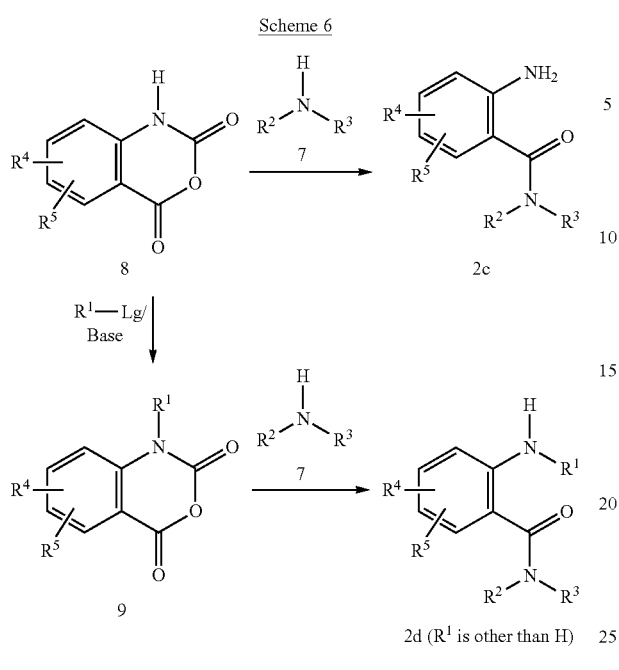

Typical procedures involve combination of equimolar amounts of the amine 7 with the isatoic anhydride in polar aprotic solvents such as pyridine and N,N-dimethylformamide at temperatures ranging from room temperature to 100° C. $R^1$ substituents such as alkyl and substituted alkyl may be introduced by the base-catalyzed alkylation of isatoic anhydride 8 with known alkylating reagents $R^1$-Lg (wherein Lg is a nucleophilic displaceable leaving group such as halide, alkyl or aryl sulfonates or alkyl sulfates) to provide the alkyl substituted intermediate 9. Isatoic anhydrides of Formula 8 may be made by methods described in Coppola, *Synthesis* 1980, 505-36.

As shown in Scheme 7, an alternate procedure for the preparation of specific compounds of Formula Ic involves reaction of an amine 7 with a bensoxazinone of Formula 10.

Scheme 7

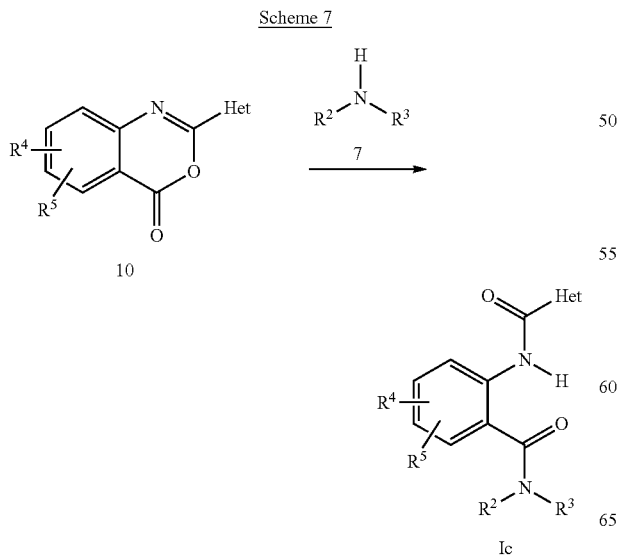

The reaction of Scheme 7 can be run neat or in a variety of suitable solvents including tetrahydrofuran, diethyl ether, pyridine, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 2095-2103 and references cited therein. See also Coppola, *J. Heterocyclic Chemistry* 1999, 36, 563-588.

Benzoxazinones of Formula 10 can be prepared by a variety of procedures. Two procedures that are especially useful are detailed in Schemes 8-9. In Scheme 8, a benzoxazinone of Formula 10 is prepared directly via coupling of a pyrazolicarboxylic acid of Formula 4a with an anthranilic acid of Formula 11.

Scheme 8

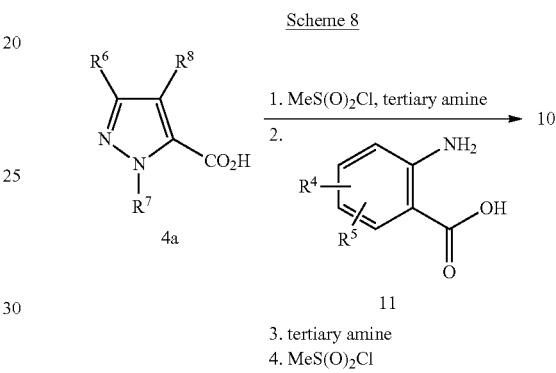

3. tertiary amine
4. MeS(O)$_2$Cl

This involves sequential addition of methanesulfonyl chloride in the presence of a tertiary amine such as triethylamine or pyridine to a pyrazolecarboxylic acid of Formula 4a, followed by the addition of an anthranilic acid of Formula 11, followed by a second addition of tertiary amine and methanesulfonyl chloride. This procedure generally affords good yields of the benzoxazinone and is illustrated with greater detail in Examples 6 and 8.

Scheme 9 depicts an alternate preparation for benzoxazinones of Formula 10 involving coupling of a pyrazole acid chloride of Formula 3a with an isatoic anhydride of Formula 8 to provide the Formula 10 benzoxazinone directly.

Scheme 9

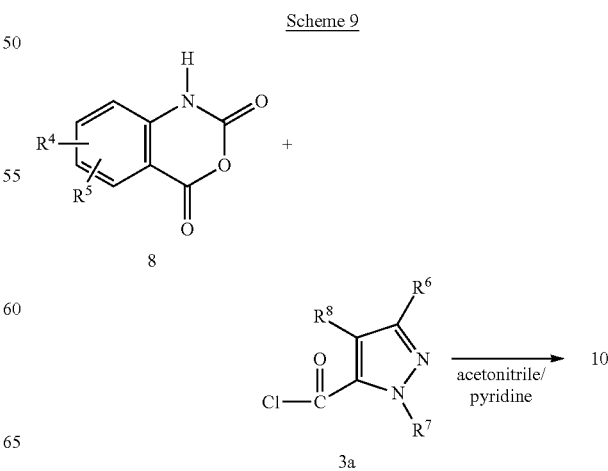

Solvents such as pyridine or pyridine/acetonitrile are suitable for this reaction. The acid chlorides of Formula 3a are available from the corresponding acids of Formula 4a by a variety of synthetic methods such as chlorination with thionyl chloride or oxalyl chloride.

Isatoic anhydrides of Formula 8 can be prepared from isatins of Formula 13 as outlined in Scheme 10.

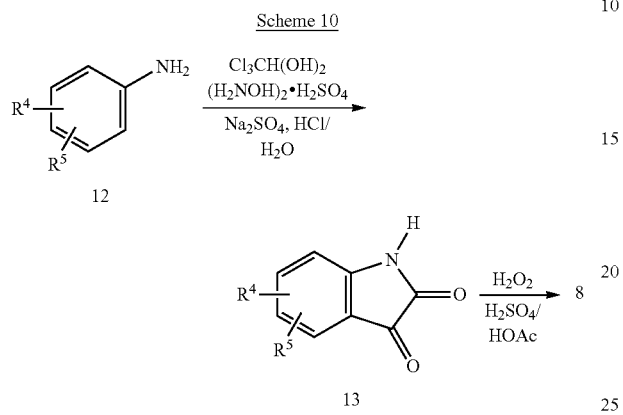

Isatins of Formula 13 are obtained from aniline derivatives of Formula 12 using methods known in the literature. Oxidation of isatin 13 with hydrogen peroxide generally affords good yields of the corresponding isatoic anhydride 8 (*Angew. Chem. Int. Ed. Engl.* 19, 222-223). Isatoic anhydrides are also available from the anthranilic acids 11 via many known procedures involving reaction of 11 with phosgene or a phosgene, equivalent.

The syntheses of representative acids of Formula 4 are depicted in Schemes 11-16. Syntheses of pyrazoles of Formula 4a are shown in Scheme 11.

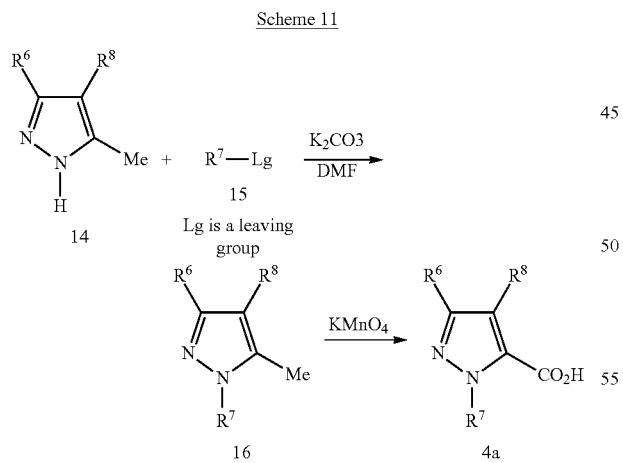

The synthesis of compounds of Formula 4a in Scheme 11 involves as the key step introduction of the $R^7$ substituent via alkylation or arylation of the pyrazole of Formula 14 with compounds of Formula 15 (wherein Lg is a leaving group as defined above). Oxidation of the methyl group affords the pyrazole carboxylic acid. Some of the more preferred $R^6$ groups include haloalkyl.

Synthesis of pyrazoles of Formula 4a is also shown in Scheme 12.

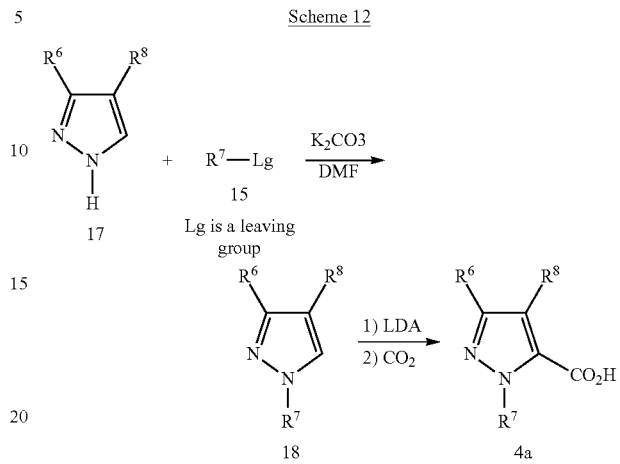

These acids may be prepared via metallation and carboxylation of compounds of Formula 18 as the key step. The $R^7$ group is introduced in a manner similar to that of Scheme 11, i.e. via alkylation or arylation with a compound of Formula 15. Representative $R^6$ groups include e.g. cyano, haloalkyl and halogen.

This procedure is particularly useful for preparing 1-(2-pyridinyl)pyrazolecarboxylic acids of Formula 4b as shown in Scheme 13.

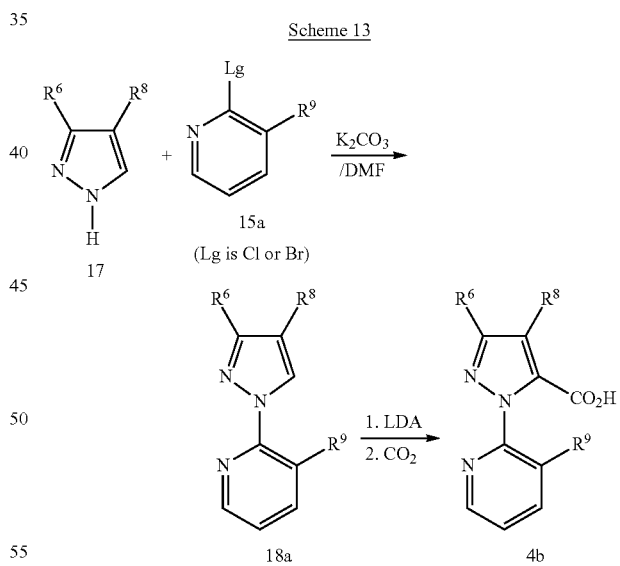

Reaction of a pyrazole of Formula 17 with a 2,3-dihalopyridine of Formula 15a affords good yields of the 1-pyridylpyrazole of Formula 18a with good specificity for the desired regiochemistry. Metallation of 18a with lithium diisopropylamide (LDA) followed by quenching of the lithium salt with carbon dioxide affords the 1-(2-pyridinyl)pyrazolecarboxylic acid of Formula 4b. Additional details for these procedures are provided in Examples 1, 3, 6, 8 and 10.

The synthesis of pyrazoles of Formula 4c is described, in Scheme 14.

Scheme 14

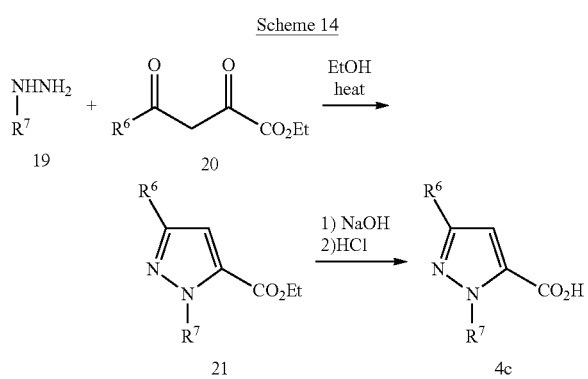

Scheme 14 involves reaction of an optionally substituted phenyl hydrazine of Formula 19 with a ketopyruvate of Formula 20 to yield pyrazole esters of Formula 21. Hydrolysis of the esters affords the pyrazole acids of Formula 4c. This procedure is particularly useful for the preparation of compounds in which $R^7$ is optionally substituted phenyl and $R^6$ is haloalkyl.

An alternate synthesis of pyrazole acids of Formula 4c is described in Scheme 15.

Scheme 15

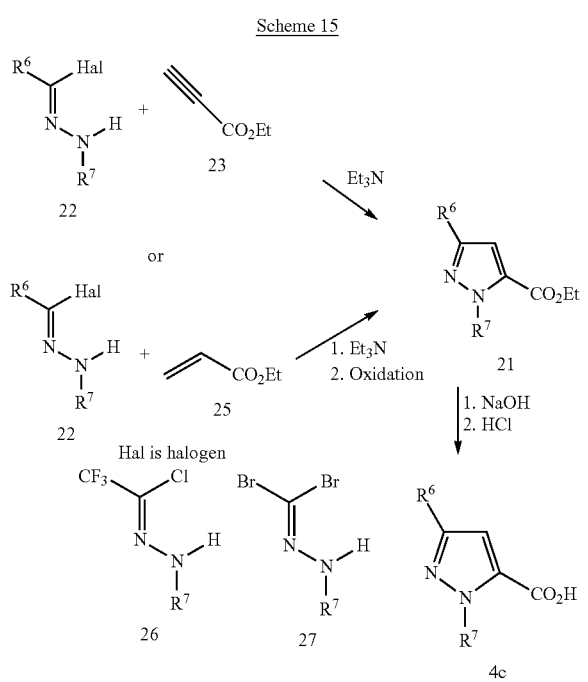

The method of Scheme 15 involves 3+2 cycloaddition of an appropriately substituted iminohalide 22 with either substituted propiolates of Formula 23 or acrylates of Formula 25. Cycloaddition with an acrylate requires additional oxidation of the intermediate pyrazoline to the pyrazole. Hydrolysis of the esters affords the pyrazole acids of Formula 4c. Preferred iminohalides for this reaction include the trifluoromethyl iminochloride of Formula 26 and the iminodibromide of Formula 27. Compounds such as 26 are known (*J. Heterocycl. Chem.* 1985, 22(2), 565-8). Compounds such as 27 are available by known methods (*Tetrahedron Letters* 1990, 40, 2605). These procedures are particularly useful for the preparation of compounds where $R^7$ is optionally substituted phenyl and $R^6$ is haloalkyl or bromo.

The starting pyrazoles of Formula 17 are known compounds or can be prepared according to known methods. The pyrazole of Formula 17a (the compound of Formula 17 wherein $R^6$ is $CF_3$ and $R^8$ is H) can be prepared by literature procedures (*J. Fluorine Chem.* 1991, 53(1), 61-70). The pyrazoles of Formula 17c (compounds of Formula 17 wherein $R^6$ is Cl or Br and $R^8$ is H) can also be prepared by literature procedures (*Chem. Ber.* 1966, 99(10), 3350-7). A useful alternative method for the preparation of compound 17c is depicted in Scheme 16.

Scheme 16

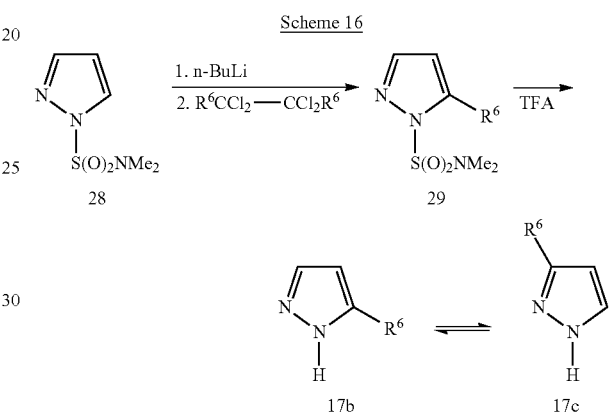

($R^6$ is Cl or Br)

In the method of Scheme 16, metallation of the sulfamoyl pyrazole of Formula 28 with n-butyllithium followed by direct halogenation of the anion with either hexachloroethane (for $R^6$ being Cl) or 1,2-dibromotetrachloroethane (for $R^6$ being Br) affords the halogenated derivatives of Formula 29. Removal of the sulfamoyl group with trifluoreacetic acid (TFA) at room temperature proceeds cleanly and in good yield to afford the pyrazoles of Formula 17c. One skilled in the art will recognize that Formula 17c is a tautomer of Formula 17b. Further experimental details for these procedures are described in Examples 8 and 10.

Pyrazolecarboxylic acids of Formula 4d wherein $R^6$ is H, $C_1$-$C_6$ alkyl or $C_1$-$C_6$ haloalkyl can be prepared by the method outlined in Scheme 17.

Scheme 17

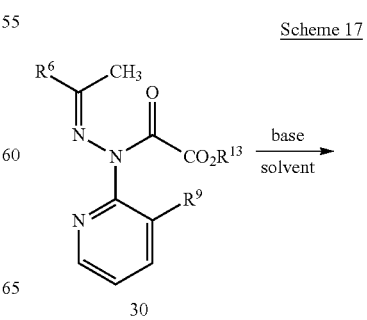

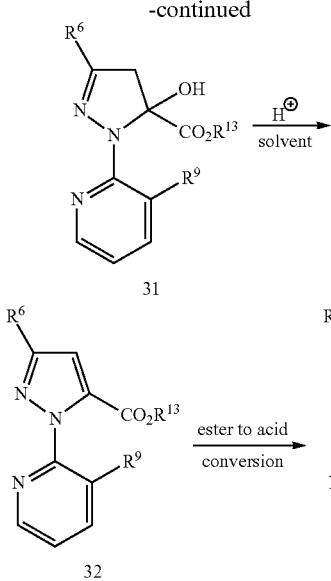

31

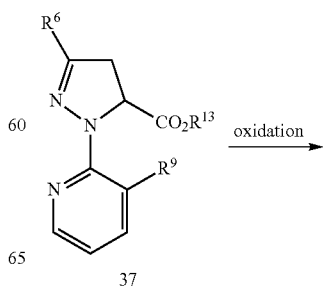

32 → 4d (ester to acid conversion)

Reaction of a compound of Formula 30 wherein $R^{13}$ is $C_1$-$C_4$ alkyl with a suitable base in a suitable organic solvent affords the cyclized product of Formula 31 after neutralization with an acid such as acetic acid. The suitable base can be, for example but not limitation, sodium hydride, potassium t-butoxide, dimsyl sodium ($CH_3S(O)CH_2^-Na^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine. The suitable organic solvent can be, for example but not limitation, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride.

Dehydration of the compound of Formula 31 to give the compound of Formula 32, followed by converting the carboxylic ester function to carboxylic acid, affords the compound of Formula 4d. The dehydration is effected by treatment with a catalytic amount of a suitable acid. This catalytic acid can be for example but not limitation, sulfuric acid. The reaction is generally conducted using an organic solvent. As one skilled in the art will realize, dehydration reactions may be conducted in a wide variety of solvents in a temperature range generally between about 0 and 200° C. more preferably between about 0 and 100° C. For the dehydration in the method of Scheme 17, a solvent comprising acetic acid and temperatures of about 65° C. are preferred. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis*, 2nd ed., John Wiley & Sons, Inc., New York, 1991, pp. 224-269 for a review of methods). For the method of Scheme 17, base-catalyzed hydrolyic methods are preferred. Suitable bases include alkali metal (such as lithium, sodium or potassium) hydroxides. For example, the ester can be dissolved in a mixture of water and an alcohol such as ethanol. Upon treatment with, sodium hydroxide or potassium hydroxide, the ester is saponified to provide the sodium or potassium, salt of the carboxylic acid. Acidification with a strong acid, such as hydrochloric acid or sulfuric acid, yields the carboxylic acid of Formula 4d. The carboxylic acid can be isolated by methods known to those skilled in the art, including crystallization, extraction and distillation.

Compounds of Formula 30 can be prepared by the method outlined in Scheme 18.

Scheme 18

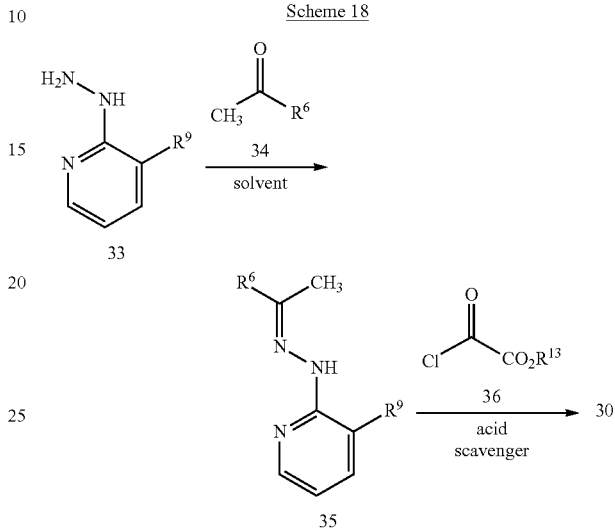

wherein $R^6$ is H, $C_1$-$C_6$ alkyl or $C_1$-$C_6$ haloalkyl and $R^{13}$ is $C_1$-$C_4$ alkyl.

Treatment of a hydrazine compound of Formula 33 with a ketone of Formula 34 in a solvent such, as water, methanol or acetic acid gives the hydrazone of Formula 35. One skilled in the art will recognize that this reaction may require catalysis by an optional acid and may also require elevated temperatures depending on the molecular substitution pattern of the hydrazine of Formula 35. Reaction of the hydrazone of Formula 35 with the compound of Formula 36 in a suitable organic solvent such as, for example but not limitation, dichloromethane or tetrahydrofuran in the presence of an acid scavenger such as triethylamine provides the compound of Formula 30. The reaction is usually conducted at a temperature between about 0 and 100° C. Further experimental details for the method of Scheme 18 are illustrated in Example 17. Hydrazine compounds of Formula 33 can be prepared by standard methods, such as by contacting the corresponding halo compound of Formula 15a with hydrazine.

Pyrazolecarboxylic acids of Formula 4d wherein $R^6$ is halogen can be prepared by the method outlined in Scheme 19.

Scheme 19

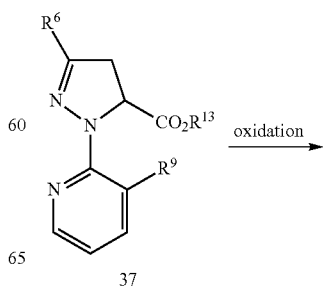

37

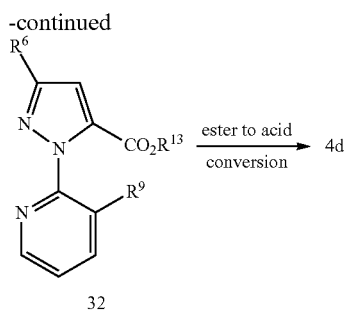

wherein $R^{13}$ is $C_1$-$C_4$ alkyl.

Oxidization of the compound of Formula 37 optionally in the presence of acid to give the compound of Formula 32 followed by conversion of the carboxylic ester function to the carboxylic acid provides the compound of Formula 4d. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 37 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula 37. To obtain complete conversion, one to five equivalents of acid can be used. The preferred oxidant is potassium persulfate and the oxidation is preferably carried out in the presence of sulfuric acid. The reaction can be carried out by mixing the compound of Formula 37 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 32 can be isolated by methods known to those skilled in the art, including crystallization, extraction and distillation. Methods suitable for converting the ester of Formula 32 to the carboxylic acid of Formula 44 are already described for Scheme 17. Further experimental details for the method of Scheme 19 are illustrated in Examples 12 and 13.

Compounds of Formula 37 can be prepared from corresponding compounds of Formula 38 as shown in Scheme 20.

Scheme 20

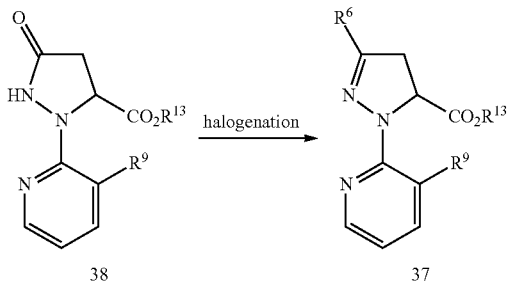

wherein $R^{13}$ is $C_3$-$C_4$ alkyl and $R^6$ is halogen.

Treatment of a compound of Formula 38 with a halogenating reagent, usually in the presence of a solvent, affords the corresponding halo compound of Formula 37. Halogenating reagents that can be used include phosphorus oxyhalides, phosphorus trihalides, phosphorus pentahalides, thionyl chloride, dihalotrialkylphosphoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 38 (i.e. the mole reatio of phosphorus oxyhalide to Formula 18 is at least 0.33) should be used, preferably between about 0.33 and 1.2 equivalents. To obtain complete conversion, at least 0.20 equivalents of phosphorus pentahalide versus the compound of Formula 38 should be used, preferably between about 0.20 and 1.0 equivalents. Compounds of Formula 38 wherein $R^{13}$ is $C_1$-$C_4$ alkyl are preferred for this reaction. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 38 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 37, can be isolated by methods known to those skilled in the art, including crystallization, extraction and distillation.

Alternatively, compounds of Formula 37 wherein $R^6$ is halogen can be prepared by treating the corresponding compounds of Formula 37 wherein is a different halogen (e.g., Cl for making Formula 37 wherein $R^3$ is Br) or a sulfonate group such as p-toluenesulfonate, benzenesulfonate and methanesulfonate with the appropriate hydrogen halide. By this method the halogen or sulfonate substituent on the Formula 37 starting compound is replaced with, for example, Br or Cl from hydrogen bromide or hydrogen chloride, respectively. The reaction is conducted in a suitable solvent such as dibromomethane, dichloromethane or acetonitrile. The reaction can be conducted at or near atmospheric pressure or above atmospheric pressure in a pressure vessel. When $R^6$ in the starting compound of Formula 37 is a halogen such as Cl, the reaction is preferably conducted in such a way that the hydrogen halide generated from the reaction is removed by sparging or other suitable means. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 37 wherein $R^6$ is Br) can facilitate the reaction. The product of Formula 37 is isolated by the usual methods known to those skilled in the art, including extraction, distillation and crystallization. Further details for this process are illustrated in Example 14.

Starting compounds of Formula 37 wherein $R^6$ is Cl or Br can be prepared from corresponding compounds of Formula 38 as already described. Starting compounds of Formula 37 wherein $R^6$ is a sulfonate group can likewise be prepared from corresponding compounds of Formula 38 by standard methods such as treatment with a sulfonyl chloride (e.g., p-toluenesulfonyl chloride) and base such as a tertiary amine (e.g., triethylamine) in a suitable solvent such as dichloromethane; further details for this process are illustrated in Example 15.

Pyrazolecarboxylic acids of Formula 4d wherein $R^6$ is $C_1$-$C_4$ alkoxy or $C_1$-$C_4$ haloalkoxy can also be prepared by the method outlined in Scheme 21.

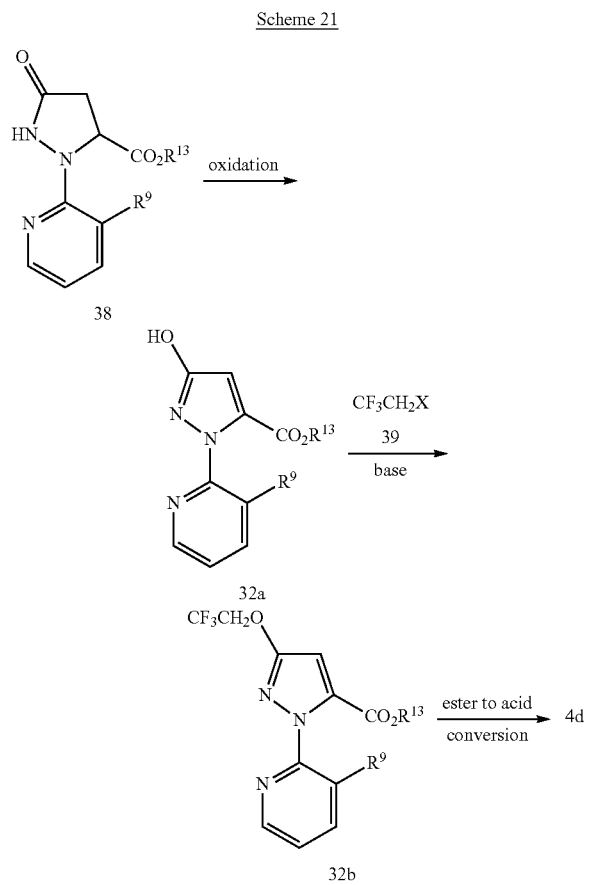

wherein $R^3$ is $C_1$-$C_4$ alkyl, and X is a leaving group.

In this method, instead of being halogenated as shown in Scheme 20, the compound of Formula 38 is oxidized to the compound of Formula 32a. The reaction conditions for this oxidation are as already described for the conversion of the compound, of Formula 37 to the compound of Formula 32 in Scheme 19.

The compound of Formula 32a is then alkylated to form the compound of Formula 32b by contact with an alkylating agent $CF_3CH_2X$ (39) in the presence of a base. In the alkylating agent 39, X is a nucleophilic reaction leaving group such as halogen (e.g., Br, I), $OS(O)_2CH_3$ (methanesulfonate), $OS(O)_2CF_3$, $OS(O)_2Ph$-$p$-$CH_3$ (p-tolunenesulfonate), and the like; methanesulfonate works well. The reaction is conducted in the presence of at least one equivalent of a base. Suitable bases include inorganic bases, such as alkali metal (such as lithium, sodium or potassium) carbonates and hydroxides, and organic bases, such as triethylamine, diisopropylethylamine and 1,8-diazabicyclo[5.4.0]undec-7-ene. The reaction is generally conducted in a solvent which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as acetonitrile, such as such as acetonitrile, N,N-dimethylformamide, and the like. Alcohols and polar aprotic solvents are preferred for use with inorganic bases. Potassium carbonate as base and acetonitrile as solvent are preferred. The reaction is generally conducted between about 0 and 150° C., with most typically between ambient temperature and 100° C. The product of Formula 32b can be isolated by conventional techniques such as extraction. The ester of Formula 32b can then be converted to the carboxylic acid of Formula 4d by the methods already described for the conversion of Formula 32 to Formula 4d in Scheme 17. Further experimental details for the method of Scheme 21 are illustrated in Example 16.

Compounds of Formula 38 can be prepared from compounds of Formula 33 as outlined in Scheme 22.

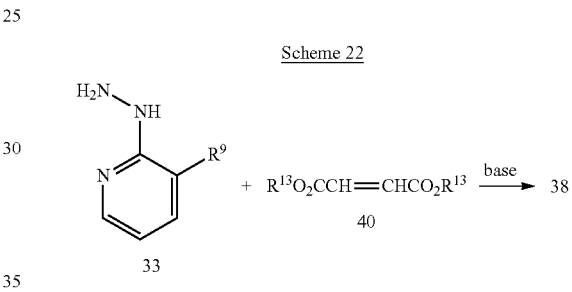

wherein $R^{13}$ is $C_1$-$C_4$ alkyl.

In this method, a hydrazine compound of Formula 33 is contacted with a compound of Formula 40 (a fumarate ester or maleate ester or a mixture thereof may be used) in the presence of a base and a solvent. The base is typically a metal alkoxide salt, such as sodium methoxide, potassium methoxide, sodium epoxide, potassium epoxide, potassium tert-butoxide, lithium tert-butoxide, and the like. Greater than 0.5 equivalents of base versus the compound of Formula 33 should be used, preferably between 0.9 and 1.3 equivalents. Greater than 1.0 equivalents of the compound of Formula 40 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 33 and the base in the solvent. The mixture can be heated or cooled to a desired temperature and the compound of Formula 40 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 33 and Formula 40. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid, and the like, or an inorganic acid, such as hydrochloric acid, sulfuric acid and the like. Depending on the reaction conditions and the means of isolation, the —CO$_2$R$^{13}$ function on the compound of Formula 38 may be hydrolyzed to —CO$_2$H; for example, the presence of water in the reaction, mixture can promote such hydrolysis. If the carboxylic acid (—CO$_2$H) is formed, it can be converted back to —CO$_2$R$^{13}$ wherein R$^{13}$ is C$_1$-C$_4$ alkyl using esterification methods well-known in the art. The desired product, a compound of Formula 38, can be isolated by methods known to those skilled in the art, such as crystallization, extraction or distillation.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

It is believed that one skilled in the art using the preceding description can prepare compounds of Formula I of the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s means singlet, d means doublet, t means triplet, q means quartet, m means multiplet, dd means doublet of doublets, dt means doublet of triplets, br s means broad singlet.

Example 1

Preparation of 2-[1-Ethyl-3-trifluoromethylpyrazol-5-yl carbamoyl]-3-methyl-N-(1-methylethyl)benzamide Step A: Preparation of 3-Methyl-N-(1-methylethyl)-2-nitrobenzamide A solution of 3-methyl-2-nitrobenzoic acid (2.00 g, 11.0 mmol) and triethylamine (1.22 g, 12.1 mmol) in 25 mL of methylene chloride was cooled to 10° C. Ethyl chloroformate was carefully added and a solid precipitate formed. After stirring for 30 minutes isopropylamine (0.94 g, 16.0 mmol) was added and a homogeneous solution resulted. The reaction was stirred for an additional hour, poured into water and extracted with ethyl acetate. The organic extracts were washed with water, dried over magnesium sulfate and evaporated under reduced pressure to afford 1.96 g of the desired intermediate as a white solid melting at 126-128° C.

$^1$H NMR (CDCl$_3$) δ 1.24 (d, 6H), 2.38 (s, 3H), 4.22 (m, 1H), 5.80 (br s, 1H), 7.4 (m, 3H).

Step B: Preparation of 2-Amino-3-methyl-N-(1-methylethyl)benzamide

The 2-nitrobenzamide of Step A (1.70 g, 7.6 mmol) was hydrogenated over 5% Pd/C in 40 mL of ethanol at 50 psi. When the uptake of hydrogen ceased the reaction was filtered through Celite® diatomaceous filter aid and the Celite® was washed with ether. The filtrate was evaporated under reduced pressure to afford 1.41 g of the title compound as a solid melting at 149-151° C.

$^1$H NMR (CDCl$_3$) δ 1.24 (dd, 6H), 2.16 (s, 3H), 4.25 (m, 1H) 5.54 (br s, 2H), 5.85 (br s, 1H), 6.59 (t, 1H), 7.13 (d, 1H), 7.17 (d, 1H).

Step C: Preparation of 1-Ethyl-3-trifluoromethylpyrazol-5-yl carboxylic acid

To a mixture of 3-trifluoromethylpyrazole (5 g, 37 mmol) and powdered potassium carbonate (10 g, 72 mmol) stirring in 30 mL of N,N-dimethylformamide, iodoethane (8 g, 51 mmol) was added dropwise. After a mild exotherm, the reaction was stirred overnight at room temperature. The reaction mixture was partitioned between 100 mL of diethyl ether and 100 mL of water. The ether layer was separated, washed with water (3×) and brine, and dried over magnesium, sulfate. Evaporation of solvent vacuo gave 4 g of oil.

To 3.8 g of this oil stirring in 40 mL of tetrahydrofuran under nitrogen in a dry ice/acetone bath, 17 mL of a 2.5 M solution of n-butyllithium. In tetrahydrofuran (43 mmol) was added dropwise and the solution stirred for 20 minutes at –78° C. An excess of gaseous carbon dioxide was babbled into the stirred solution, at a moderate rate for 10 minutes. After addition of carbon dioxide, the reaction was allowed to slowly reach room temperature and stirred overnight. The reaction mixture was partitioned between diethyl ether (100 mL) and 0.5 N aqueous sodium hydroxide (100 mL). The basic layer was separated and acidified with concentrated hydrochloric acid to a pH of 2-3. The aqueous mixture was extracted with ethyl acetate (100 mL) and the organic extract washed with water and brine and dried over magnesium sulfate. The oily residue, which remained after evaporating the solvent in vacuo, was triturated to a solid from a small amount of 1-chlorobutane. After filtering and drying, a slightly impure sample of 1-ethyl-3-trifluoromethyl-pyrazol-5-yl carboxylic acid (1.4 g) was obtained as a broad-melting solid.

$^1$H NMR(CDCl$_3$) δ 1.51 (t, 3H), 4.68 (q, 2H), 7.23 (s, 1H), 9.85 (br s, 1H).

Step D: Preparation of 2-[1-Ethyl-3-trifluoromethylpyrazol-5-yl carbamoyl]-3-methyl-N-(1-methylethyl)benzamide To a solution of 1-ethyl-3-trifluoromethyl-pyrazol-5-yl carboxylic acid (i.e. the product of Step C) (0.5 g, 2.4 mmol) stirring in 20 mL of methylene chloride, oxalyl chloride (1.2 mL, 14 mmol) was added. Upon addition of 2 drops of N,N-dimethylformamide, foaming and bubbling occurred. The reaction mixture was heated at reflux for 1 hr as a yellow solution. After cooling, the solvent was removed in vacuo and the resulting residue dissolved in 20 mL of tetrahydrofuran. To the stirred solution, 2-amino-3-methyl-N-(1-methylethyl)

benzamide (i.e. the product of Step B) (0.7 g, 3.6 mmol) was added followed by the dropwise addition of N,N-diisopropylethylamine (3 mL, 17 mmol). After stirring at room temperature overnight, the reaction mixture was partitioned between ethyl acetate (100 mL) and 1N aqueous hydrochloric acid (75 mL). The separated organic layer was washed with water and brine and dried over magnesium sulfate. Evaporating in vacuo gave a white solid residue, which on purification by flash column chromatography on silica gel (2:1 hexanes/ethyl acetate) afforded 0.5 g of the title compound, a compound of the present invention, melting at 223-226° C.

$^1$H NMR (DMSO-d$_6$) δ 1.06 (d, 6H), 1.36 (t, 3H), 2.45 (s, 3H), 3.97 (m, 1H), 4.58 (q, 2H), 7.43-7.25 (m, 3H), 7.45 (s, 1H), 8.05 (d, 1H), 10.15 (s, 1H).

Example 2

Preparation of N-[2-Methyl-6-[[(1-methylethyl)amino]carbonyl]phenyl]-1-phenyl-3-(trifluoromethyl)-1H-pyrazole-5-carboxamide Step A: Preparation of 2-Methyl-1-phenyl-4-(trifluoromethyl)-1H-pyrazole A solution of 1,1,1-trifluoropentane-2,4-dione (20.0 g, 0.130 mole) in glacial acetic acid (60 mL) was cooled to 7° C. using an ice/water bath. Phenylhydrazine (14.1 g, 0.130 mole) was added dropwise over a period of 60 minutes. The reaction mass temperature increased, to 15° C. during the addition. The resulting orange solution was held under ambient conditions for 60 minutes. The bulk of the acetic acid was removed by stripping on a rotary evaporator at a bath temperature of 65° C. The residue was dissolved in methylene chloride (150 mL). The solution was washed with aqueous sodium bicarbonate (3 g in 50 mL of water). The purple-red organic layer was separated, treated with activated charcoal (2 g) and MgSO$_4$, then filtered. Volatiles were removed on a rotary evaporator. The crude product consisted of 28.0 g of a rose-colored oil, which contained ~89% the desired product and 11% 1-phenyl-5-(trifluoromethyl)-3-methylpyrazole.

$^1$H NMR (DMSO-d$_6$) δ 2.35 (s, 3H), 6.76 (s, 1H), 7.6-7.5 (m, 5H).

Step B: Preparation of 1-Phenyl-3-(trifluoromethyl)-1H-pyrazole-5-carboxylic acid A sample of crude 2-methyl-1-phenyl-4-(trifluoromethyl)-1H-pyrazole (i.e. the product of Step A) (~89%, 50.0 g, 0.221 mole) was mixed with water (400 mL) and cetyltrimethylammonium chloride (4.00 g, 0.011 mole). The mixture was heated to 95° C. Potassium permanganate was added in 10 equal portions, spaced at ~8 minute intervals. The reaction mass was maintained at 95-100° C. during this period. After the last portion was added, the mixture was held for ~15 minutes at 95-100° C., whereupon the purple, permanganate color had been discharged. The reaction mass was filtered while hot (~75° C.) through a 1-cm bed of Celite® diatomaceous filter aid in a 150-mL coarse glass frit funnel. The filter cake was washed with warm (~50° C.) water (3×100 mL). The combined filtrate and washings were extracted with ether (2×100 mL) to remove a small amount of yellow, water-insoluble material. The aqueous layer was purged with nitrogen to remove residual ether. The clear, colorless alkaline solution was acidified by adding concentrated hydrochloric acid dropwise until the pH reached ~1.3 (28 g, 0.28 mole). Gas evolution was vigorous during the first two-thirds of the addition. The product was collected via filtration, washed with water (3×40 mL), then dried overnight at 55° C. in vacuo. The product consisted of 11.7 g of a white, crystalline powder, which was essentially pure based upon $^1$H NMR.

$^1$H NMR (CDCl$_3$) δ 7.33 (s, 1H), 7.4-7.5 (m, 5H).

Step C: Preparation of 1-Phenyl-3-(trifluoromethyl)-1H-pyrazole-5-carbonyl chloride A sample of crude 1-phenyl-3-(trifluoromethyl)pyrazole-5-carboxylic acid (i.e. the product of Step B) (4.13 g, 16.1 mmol) was dissolved in methylene chloride (45 mL). The solution was treated with oxalyl chloride (1.80 mL, 20.6 mmol), followed by N,N-dimethylformamide (0.010 mL, 0.13 mmol). Off-gassing began shortly after adding the N,N-dimethylformamide catalyst. The reaction mixture was stirred for ~20 minutes under ambient conditions, then was heated to reflux for a period of 35 minutes. Volatile were removed by stripping the reaction mixture on a rotary evaporator at a bath temperature of 55° C. The product consisted of 4.43 g of a light-yellow oil. The only impurity observed by $^1$H NMR was N,N-dimethylformamide.

$^1$H NMR (CDCl$_3$) δ 7.40 (m, 1H), 7.42 (s, 1H), 7.50-7.53 (m, 4H).

Step D: Preparation of N-[2-Methyl-6-[[(1-methylethyl)amino]carbonyl]phenyl]-1-phenyl-3-(trifluoromethyl)-1H-pyrazole-5-carboxamide A sample of 3-methylisatoic anhydride (0.30 g, 1.7 mmol) partially dissolved in pyridine (4.0 mL) was treated with 1-phenyl-3-trifluoromethylpyrazole)-5-carboxyl chloride (i.e. the product of Step C) (0.55 g, 1.9 mmol). The mixture was heated to ~95° C. for a period of 2 hours. The resulting orange solution was cooled to 29° C., then was treated with isopropylamine (1.00 g, 16.9 mmol). The reaction mass exothermically warmed to 39° C. It was further heated to 55° C. for a period of 30 minutes, whereupon much precipitate formed. The reaction mass was dissolved in dichloromethane (150 mL). The solution was washed with aqueous acid (5 mL of conc. HCl in 45 mL of water), then with aqueous base (2 g sodium carbonate in 50 mL of water). The organic layer was dried over MgSO$_4$, filtered, then concentrated on a rotary evaporator. Upon reduction to ~4 mL, product crystals had formed. The slurry was diluted with ~10 mL of ether, whereupon more product precipitated. The product was isolated by filtration, washed with ether (2×10 mL), then washed with water (2×50 mL). The wet cake was dried for 30 minutes at 70° C. in vacuo. The product, a compound of the present invention, consisted of 0.52 g of an off-white powder melting at 260-262° C.

$^1$H NMR (DMSO-d$_6$) δ 1.07 (d, 6H), 2.21 (s, 3H), 4.02 (octet, 1H), 7.2-7.4 (m, 3H), 7.45-7.6 (m, 6H), 8.10 (d, 1H), 10.31 (s, 1H).

Example 3

Preparation of N-[2-Methyl-6-[[(1-methylethyl)amino]carbonyl]phenyl]-3-(trifluoromethyl)-1-[3-(trifluoromethyl)-2-pyridinyl]-1H-pyrazole-5-carboxamide Step A: Preparation of 3-Trifluoromethyl-2-[3-(trifluoromethyl)-1H-pyrazol-1-yl]pyridine A mixture of 2-chloro-3-trifluoromethylpyridine (3.62 g, 21 mmol), 3-trifluoromethylpyrazole (2.7 g, 20 mmol), and potassium carbonate (6.0 g, 43 mmol) were heated at 100° C.

for 18 h. The cooled reaction mixture was added to ice/water (100 mL). The mixture was extracted twice with ether (100 mL) and the combined ether extracts were washed twice with water (100 mL). The organic layer was dried with magnesium sulfate and concentrated to an oil. Chromatography on silica gel with hexanes:ethyl acetate 8:1 to 4:1 as eluent gave the title compound (3.5 g) as as oil.

$^1$H NMR (CDCl$_3$) δ 6.75 (m, 1H), 7.5 (m, 1H), 8.2 (m, 2H), 8.7 (m, 1H).

Step B: Preparation of 3-(Trifluoromethyl)-1-[3-(trifluoromethyl)-2-pyridinyl]-1H-pyrazole-5-carboxylic acid A mixture of the title compound of Example 3, Step A (3.4 g, 13 mmol) was dissolved in tetrahydrofuran (30 mL) and cooled to −70° C. Lithium diisopropylamide (2N in heptane/tetrahydrofuran, (Aldrich) 9.5 mL, 19 mmol) was added and the resulting dark mixture was stirred for 10 minutes. Dry carbon dioxide was bubbled through the mixture for 15 minutes. The mixture was allowed to warm to 23° C. and treated with water (50 mL) and 1N sodium hydroxide (10 mL). The aqueous mixture was extracted with ether (100 mL) and then ethyl acetate (100 mL). The aqueous layer was acidified with 6N hydrochloric acid to pH 1-2 and extracted twice with dichloromethane. The organic layer was dried with magnesium sulfate and concentrated to give the title compound (1.5 g).

$^1$H NMR (CDCl$_3$) δ 7.6 (m, 1H), 7.95 (m, 1H), 8.56 (m, 1H), 8.9 (m, 1H), 14.2 (br, 1H)

Step C: Preparation of N-[2-Methyl-6-[[(1-methylethyl)amino]carbonyl]phenyl]-3-(trifluoromethyl)-1-[3-(trifluoromethyl)-2-pyridinyl]-1H-pyrazole-5-carboxamide A mixture of the title compound of Example 3, Step B (0.54 g, 1.1 mmol), the title compound from Example 1, Step B (0.44 g, 2.4 mmol) and BOP chloride (bis(2-oxo-oxazolidinyl)phosphinyl chloride, 0.54 g, 2.1 mmol) in acetonitrile (1.3 mL) was treated with triethylamine (0.9 mL). The mixture was shaken in a closed scintillation vial for 18 h. The reaction was partitioned between ethyl acetate (100 mL) and 1N hydrochloric acid. The ethyl acetate layer was washed successively with 1N hydrochloric acid (50 mL), 1N sodium hydroxide (50 mL) and saturated sodium chloride solution (50 mL). The organic layer was dried over magnesium sulfate and concentrated. The residue was subjected to column chromatography on silica gel with hexanes/ethyl acetate (5:1 to 3:1) as eluent. The title compound (0.43 g) a compound of the present invention, was isolated as a white solid. m.p. 227-230° C.

$^1$H NMR (CDCl$_3$) δ 1.2 (m, 6H), 4.15 (m, 1H), 5.9 (br d, 1H), 7.1 (m, 1H), 7.2 (m, 2H), 7.4 (s, 1H), 7.6 (m, 1H), 8.15 (m, 1H), 8.74 (m, 1H), 10.4 (br, 1H).

Example 4

Preparation of 1-(3-Chloro-2-pyridinyl)-N-[2-methyl-6-[[(1-methylethyl)amino]carbonyl]-phenyl]-3-(trifluoromethyl)-1H-pyrazole-5-carboxamide Step A: Preparation of 3-Chloro-2-[3-trifluoromethyl)-1H-pyrazol-1-yl]pyridine To a mixture of 2,3-dichloropyridine (99.0 g, 0.67 mmol) and 3-(trifluoromethyl)-pyrazole (83 g, 0.61 mmol) in dry N,N-dimethylformamide (300 mL) was added potassium carbonate (166.0 g, 1.2 mol) and the reaction was then heated to 110-125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139-141° C., 7 mm) afforded the desired intermediate as a clear yellow oil (113.4 g).

$^1$H NMR(CDCl$_3$) δ 6.78 (s, 1H), 7.36 (t, 1H), 7.93 (d, 1H), 8.15 (s, 1H), 8.45 (d, 1H).

Step B: Preparation of 1-(3-Chloro-2-pyridinyl)-3-(trifluoromethyl)-1H-pyrazole-5-carboxylic acid To a solution of 3-chloro-2-[3-(trifluoroethyl)-1H-pyrazol-1-yl]pyridine (i.e. the product of Step A) (105.0 g, 425 mmol) in dry tetrahydrofuran (700 mL) at −75° C. was added via cannula a −30° C. solution of lithium diisopropylamide (425 mmol) in dry tetrahydrofuran (300 mL). The deep red solution was stirred for 15 minutes, after which time carbon dioxide was bubbled through at −63° C. until the solution became pale yellow and the exothermicity ceased. The reaction was stirred for an additional 20 minutes and then quenched with water (20 mL). The solvent was removed under reduced pressure, and the reaction mixture partitioned between ether and 0.5N aqueous sodium hydroxide solution. The aqueous extracts were washed with ether (3×), filtered through Celite® diatomaceous filter aid to remove residual solids, and then acidified to a pH of approximately 4, at which point an orange oil formed. The aqueous mixture was stirred vigorously and additional acid was added to lower the pH to 2.5-3. The orange oil congealed into a granular solid, which was filtered, washed successively with water and 1N hydrochloric acid, and dried under vacuum, at 50° C. to afford the title product as as off-white solid (130 g). (Product from another run following similar procedures melted at 175-176° C.)

$^1$H NMR (DMSO-d$_6$) δ 7.61 (s, 1H), 7.76 (dd, 1H), 8.31 (d, 1H), 8.60 (d, 1H).

Step C: Preparation of 8-Methyl-2H-3,1-benzoxazine-2,4(1H)-dione

To a solution of 2-amino-3-methylbenzoic acid (6 g) in dry 1,4-dioxane (50 mL) was added dropwise a solution of trichloromethyl chloroformate (8 mL) in dry 1,4-dioxane (25 mL), with ice-water cooling to keep the reaction temperature below 25° C. A white precipitate began to form during the addition. The reaction mixture was stirred at room temperature overnight. The precipitated solids were removed by filtration and washed with 1,4-dioxane (2×20 mL) and hexane (2×15 mL) and air-dried to yield 6.51 g of off-white solid.

$^1$H NMR (DMSO-d$_6$) δ 2.33 (s, 3H), 7.18 (t, 1H), 7.59 (d, 1H), 7.78 (d, 1H), 11.0 (br s, 1H).

Step D: Preparation of 2-[1-(3-Chloro-2-pyridinyl)-3-(trifluoromethyl)-1H-pyrazol-5-yl]-8-methyl-4H-3,1-benzoxazin-4-one To a suspension of the carboxylic acid product prepared as in Step B (146 g, 500 mmol) in dichloromethane (approximately 2 L) was added N,N-dimethylformamide (20 drops) and oxalyl chloride (67 mL, 750 mmol) in approximately 5-mL portions over approximately 2 h. Vigorous gas evolution occurred during the addition. The reaction mixture was stirred at room temperature overnight. The reaction mixture was concentrated in vacuo to provide the crude acid chloride as an opaque orange mixture. This material was taken up in dichloromethane, filtered to remove some solids and then reconcentrated and used without further purification. The crude acid chloride was dissolved in acetonitrile (250 mL) and added to a suspension of the product from Step C in acetonitrile (400 mL). Pyridine (250 mL) was added, the mixture was stirred for 15 min at room temperature, then warmed to reflux for 3 h. The resulting mixture was cooled to room temperature and stirred overnight to provide a solid mass. Additional acetonitrile was added and the mixture was mixed to form a thick slurry. The solids were collected and washed with cold acetonitrile. The solids were air-dried and the dried in vacuo at 90° C. for 5 h to yield 144.8 g of fluffy white solid.

$^1$H NMR (CDCl$_3$) δ 1.84 (s, 3H), 7.4 (t, 1H), 7.6 (m, 3H), 8.0 (dd, 1H), 8.1 (s, 1H), 8.6 (d, 1H).

Step E: Preparation of 1-(3-Chloro-2-pyridinyl)-N-[2-methyl-6-[[(1-methylethyl)-amino]carbonyl]phenyl]-3-(trifluoromethyl)-1H-pyrazole-5-carboxamide To a suspension of the benzoxazinone product of Step D (124 g, 300 mmol) in dichloromethane (500 mL) was added dropwise isopropylamine (76 mL, 900 mmol) at room temperature. The temperature of the reaction mixture rose and the suspension thinned during the addition. The reaction mixture was then warmed to reflux for 1.5 h. A new suspension formed. The reaction, mixture was cooled to room temperature and diethyl ether (1.3 L) was added and the mixture stirred at room temperature overnight. The solids were collected and washed with ether. The solids were air-dried and then dried in vacuo at 90° C. for 5 h to yield 122 g of the title compound, a compound of the present invention, as a fluffy white solid, melting at 194-196° C.

$^1$H NMR (CDCl$_3$) δ 1.23 (d, 6H), 2.21 (s, 3H), 4.2 (m, 1H), 5.9 (d, 1H), 7.2 (t, 1H), 7.3 (m, 2H), 7.31 (s, 1H), 7.4 (m, 1H), 7.8 (d, 1H), 8.5 (d, 1H), 10.4 (s, 1H).

Example 5

Alternate preparation of 1-(3-chloro-2-pyridinyl)-N-[2-methyl-6-[[(1-methylethyl)amino]-carbonyl]phenyl]-3-(trifluoromethyl)-1H-pyrazole-5-carboxamide To a solution of the carboxylic acid product prepared as in Example 4, Step B (28 g, 96 mmol) in dichloromethane (240 mL) was added N,N-dimethylformamide (1.2 drops) and oxalyl chloride (15.8 g, 124 mmol). The reaction mixture was stirred at room temperature until gas evolution ceased (approximately 1.5 h). The reaction mixture was concentrated in vacuo to provide the crude acid chloride as an oil that was used without further purification. The crude acid chloride was dissolved in acetonitrile (95 mL) and added to a solution of the benzoxazin-2,4-dione prepared as in Example 4, Step C in acetonitrile (95 mL). The resulting mixture was stirred at room temperature (approximately 30 min). Pyridine (95 mL) was added and the mixture heated to about 90° C. (approximately 1 h). The reaction mixture was cooled to about 35° C. and isopropylamine (25 mL) was added. The reaction mixture exothermically warmed during the addition and then was maintained at about 50° C. (approximately 1 h). The reaction mixture was then poured into ice water and stirred. The resulting precipitate was collected by filtration, washed with water and dried in vacuo overnight to provide 37.5 g of the title compound, a compound of the present invention, as a tan solid.

$^1$H NMR (CDCl$_3$) δ 1.23 (d, 6H), 2.21 (s, 3H), 4.2 (m, 1H), 5.9 (d, 1H), 7.2 (t, 1H), 7.3 (m, 2H), 7.31 (s, 1H), 7.4 (m, 1H), 7.8 (d, 1H), 8.5 (d, 1H), 10.4 (s, 1H).

Example 6

Preparation of N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide Step A: Preparation of 2-Amino-3-methyl-5-chlorobenzoic acid To a solution of 2-amino-3-methylbenzoic acid (Aldrich, 15.0 g, 99.2 mmol) in N,N-dimethylformamide (50 mL) was added N,N-chlorosuccimide (13.3 g, 99.2 mmol) and the reaction mixture was heated to 100° C. for 30 minutes. The heat was removed, the reaction was cooled to room temperature and let stand overnight. The reaction mixture was then slowly poured into ice-water (250 mL) to precipitate a white solid. The solid was filtered and washed four times with water and then taken up in ethyl acetate (900 mL). The ethyl acetate solution was dried over magnesium sulfate, evaporated under reduced pressure and the residual solid was washed with either to afford the desired intermediate as a white solid (13.9 g).

$^1$H NMR (DMSO-d$_6$) δ 2.11 (s, 3H), 7.22 (s, 1H), 7.55 (s, 1H).

Step B: Preparation of 3-chloro-2-[3-trifluoromethyl)-1H-pyrazol-1-yl]pyridine

To a mixture of 2,3-dichloropyridine (99.0 g, 0.67 mol) and 3-trifluoromethyl pyrazole (83 g, 0.61 mol) in dry N,N-dimethylformamide (300 mL) was added potassium carbonate (166.0 g, 1.2 mol) and the reaction was then heated to 110-125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139-141° C., 7 mm) afforded the title compound as a clear yellow oil (113.4 g).

$^1$H NMR (CDCl$_3$) δ 6.78 (s, 1H), 7.36 (t, 1H), 7.93 (d, 1H), 8.15 (s, 1H), 8.45 (d, 1H).

Step C: Preparation of 1-(3-Chloro-2-pyridinyl)-3-(trifluoromethyl)-1H-pyrazole-5-carboxylic acid To a solution of the pyrazole product from Step B (105.0 g, 425 mmol) in dry tetrahydrofuran (700 mL) at −75° C. was added via cannula a −30° C. solution of lithium diisopropylamide (425 mmol) in dry tetrahydrofuran (300 mL). The deep red solution was stirred for 15 minutes, after which time carbon dioxide was bubbled through at −63° C. until the solution became pale yellow and the exothermicity ceased. The reaction was stirred for an additional 20 minutes and then quenched with water (20 mL). The solvent was removed under reduced pressure, and the reaction mixture was partitioned between ether and 0.5 N aqueous sodium hydroxide solution. The aqueous extracts were washed with ether (3×), filtered through Celite® diatomaceous filter aid to remove residual solids, and then acidified to a pH of approximately 4, at which point an orange oil formed. The aqueous mixture was stirred vigorously and additional, acid was added to lower the pH to 2.5-3. The orange oil congealed into a granular solid, which was filtered, washed successively with water and 1N hydrochloric acid, and dried under vacuum at 50° C. to afford the title product as an off-white solid (130 g). (Product from another run following similar procedure melted at 175-176° C.) $^1$H NMR (DMSO-d$_6$) δ 7.61 (s, 1H), 7.76 (dd, 1H), 8.31 (d, 1H), 8.60 (d, 1H).

Step D: Preparation of 6-chloro-2-[1-(3-chloro-2-pyridinyl)-3-(trifluoromethyl)-1H-pyrazol-5-yl]-8-methyl-4H-3,1-benzoxazin-4-one To a solution of methanesulfonyl chloride (2.2 mL, 28.3 mmol) in acetonitrile (75 mL) was added dropwise a mixture of the carboxylic acid product from Step C (7.5 g, 27.0 mmol) and triethylamine (3.75 mL, 27.0 mmol) in acetonitrile (75 mL) at 0-5° C. The reaction temperature was then maintained at 0° C. throughout successive addition of reagents. After stirring for 20 minutes, 2-amino-3-methyl-5-chlorobenzoic acid from Step A (5.1 g, 27.0 mmol) was added and stirring was continued for an additional 5 minutes. A solution of triethylamine (7.5 mL, 54.0 mmol) in acetonitrile (15 mL) was then added dropwise, and the reaction mixture was stirred 45 minutes, followed by the addition of methanesulfonyl chloride (2.2 mL, 28.3 mmol). The reaction mixture was then warmed to room temperature and stirred overnight. Approximately 75 mL of water was then added to precipitate 3.8 g of a yellow solid. An additional 1 g of product was isolated by extraction front the filtrate to provide a total of 6.8 g of the title compound as a yellow solid.

$^1$H NMR (CDCl$_3$) δ 1.83 (s, 3H), 7.50 (s, 1H), 7.53 (m, 2H), 7.99 (m, 2H), 8.58 (d, 1H).

Step E: Preparation of N-[4-Chloro-2-methyl-6-[[(1-methyl)amino]carbonyl]-phenyl]-1-(3-chloro-2-pyridinyl)-3-(trifluoromethyl)-1H-pyrazole-5-carboxamide To a solution of the benzoxazinone product of Step D (5.0 g, 11.3 mmol) in tetrahydrofuran (35 mL) was added dropwise isopropylamine (2.9 mL, 34.0 mmol) in tetrahydrofuran (10 mL) at room temperature. The reaction mixture was then warmed until ail solids had dissolved and stirred an additional five minutes, at which point thin layer chromatography on silica gel confirmed completion of the reaction. The tetrahydrofuran solvent was evaporated under reduced pressure, and the residual solid was purified by chromatography on silica gel, followed by trituration with ether/hexane to afford the title compound, a compound of the present invention, as a solid (4.6 g), melting at 195-196° C.

$^1$H NMR (CDCl$_3$) δ 1.21 (d, 6H), 2.17 (s, 3H), 4.16 (m, 1H), 5.95 (br d, 1H), 7.1-7.3 (m, 2H), 7.39 (s, 1H), 7.4 (m, 1H), 7.84 (d, 1H), 8.50 (d, 1H), 10.24 (br s, 1H).

Example 7

Preparation of N-[4-Chloro-2-methyl-6-[(methylamino)carbonyl]phenyl]-1-(3-chloro-2-pyridinyl)-3-(trifluoromethyl)-1H-pyrazole-5-carboxamide To a solution of the benzoxazinone product of Example 6, Step D (4.50 g, 10.18 mmol) in tetrahydrofuran (THF; 70 mL) was added methylamine (2.0 M solution in THF, 15 mL, 30.0 mmol) dropwise and the reaction mixture was stirred at room temperature for 5 minutes. The tetrahydrofuran solvent was evaporated under reduced pressure and the residual solid was purified by chromatography on silica gel to afford 4.09 g of the title compound, a compound of the present invention, as a white solid melting at 185-186° C.

$^1$H NMR (DMSO-d$_6$) δ 1.17 (s, 3H), 2.65 (d, 3H), 7.35 (dd, 1H), 7.46 (dd, 1H), 7.65 (dd, 1H), 7.74 (s, 1H), 8.21 (d, 1H), 8.35 (br q, 1H), 8.74 (d, 1H), 10.39 (s, 1H).

Example 8

Preparation of 3-Chloro-N-[4-chloro-2-methyl-6-[[(1-methylethyl)amino]carbonyl]phenyl]-1-(3-chloro-2-pyridinyl)-1H-pyrazole-5-carboxamide Step A: Preparation of 3-Chloro-N,N-dimethyl-1H-pyrazole-1-sulfonamide To a solution of N,N-dimethylsulfamoylpyrazole (188.0 g, 1.07 mol) in dry tetrahydrofuran (1500 mL) at −78° C. was added dropwise a solution of 2.5 M n-butyllithium. (472 mL, 1.18 mol) in hexane while maintaining the temperature below −65° C. Upon completion of the addition the reaction mixture was maintained at −78° C. for an additional 45 minutes, after which time a solution of hexachloroethane (279 g, 1.18 mol) in tetrahydrofuran (120 mL) was added dropwise. The reaction mixture was maintained for an hour at −78° C., warmed to −20° C. and then quenched with water (1 L). The reaction mixture was extracted with methylene chloride (4×500 mL); the organic extracts were dried over magnesium sulfate and concentrated. The crude product was further purified by chromatography on silica gel using methylene chloride as eluent to afford the title product compound as a yellow oil (160 g).

$^1$H NMR (CDCl$_3$) δ 3.07 (d, 6H), 6.33 (s, 1H), 7.61 (s, 1H).

Step B: Preparation of 3-Chloropyrazole

To trifluoroacetic acid (290 mL) was added dropwise the chloropyrazole product (160 g) from Step A, and the reaction mixture was stirred at room temperature for 1.5 hours and then concentrated at reduced pressure. The residue was taken up in hexane, insoluble solids were filtered off, and the hexane was concentrated to afford the crude product as an oil. The crude product was further purified by chromatography on silica gel using ether/hexane (40:60) as eluent to afford the title product as a yellow oil (64.44 g).

$^1$H NMR (CDCl$_3$) δ 6.39 (s, 1H), 7.66 (s, 1H), 9.6 (br s, 1H).

Step C: Preparation of 3-Chloro-2-(3-chloro-1H-pyrazol-1-yl)pyridine

To a mixture of 2,3-dichloropyridine (92.60 g, 0.629 mol) and 3-chloropyrazole (i.e. the product of Step B) (64.44 g, 0.629 mol) in N,N-dimethylformamide (400 mL) was added potassium, carbonate (147.78 g, 1.06 mol), and the reaction mixture was then heated to 100° C. for 36 hours. The reaction mixture was cooled to room temperature and slowly poured into ice water. The precipitated solids were altered and washed with water. The solid filter cake was taken up in ethyl acetate, dried over magnesium sulfate and concentrated. The crude solid was chromatographed on silica gel using 20% ethyl acetate/hexane as eluent to afford the title product as a white solid (39.75 g).

$^1$H NMR (CDCl$_3$) δ 6.43 (s, 1H), 7.26 (m, 1H), 7.90 (d, 1H), 8.09 (s, 1H), 8.41 (d, 1H).

Step D: Preparation of 3-Chloro-1-(3-chloro-2-pyridinyl)-1H-pyrazole-5-carboxylic acid To a solution of the pyrazole product from Step C (39.75 g, 186 mmol) in dry tetrahydrofuran (400 mL) at −78° C. was added dropwise a solution of 2.0 M lithium diisopropylamide (93 mL, 186 mmol) in tetrahydrofuran. Carbon dioxide was bubbled through the another solution for 14 minutes, after which time the solution became pale brownish-yellow. The reaction was made basic with 1N aqueous sodium hydroxide solution and extracted with ether (2×500 mL). The aqueous extracts were acidified with 6N hydrochloric acid and extracted with ethyl acetate 2×500 mL). The ethyl acetate extracts were dried over magnesium sulfate and concentrated to afford the title product as an off-white solid (42.96 g). (Product from another run following similar procedure melted at 198-199° C.)

$^1$H NMR (DMSO-$d_6$) δ 6.99 (s, 1H), 7.45 (m, 1H), 7.93 (d, 1H), 8.51 (d, 1H).

Step E: Preparation of 6-Chloro-2-[3-chloro-1-(3-chloro-2-pyridinyl)-1H-pyrazol-5-yl]-8-methyl-4H-3,1-benzoxazin-4-one To a solution of methanesulfonyl chloride (6.96 g, 61.06 mmol) in acetonitrile (150 mL) was added dropwise a mixture of the carboxylic acid product from Step D (15.0 g, 58.16 mmol) and triethylamine (5.88 g, 58.16 mmol) in acetonitrile (150 mL) at −5° C. The reaction mixture was then stirred for 30 minutes at 0° C. Then, 2-amino-3-methyl-5-chlorobenzoic acid from Example 6, Step A (10.79 g, 58.16 mmol) was added, and stirring was continued for an additional 10 minutes. A solution of triethylamine (11.77 g, 116.5 mmol) in acetonitrile was then added dropwise while keeping the temperature below 10° C. The reaction mixture was stirred 60 minutes at 0° C., and then methanesulfonyl chloride (6.96 g, 61.06 mmol) was added. The reaction mixture was then warmed to room temperature and stirred for an additional 2 hours. The reaction mixture was then concentrated, and the crude product was chromatographed on silica gel using methylene chloride as eluent to afford the title product as a yellow solid (9.1 g).

$^1$H NMR (CDCl$_3$) δ 1.81 (s, 3H), 7.16 (s, 1H), 7.51 (m, 2H) 7.98 (d, 2H) 8.56 (d, 1H).

Step F: Preparation of 3-chloro-N-[4-chloro-2-methyl-6-[[(1-methylethyl)amino]-carbonyl]phenyl]-1-(3-chloro-2-pyridinyl)-1H-pyrazole-5-carboxamide To a solution of the benzoxazinone product of Step E (6.21 g, 15.21 mmol) in tetrahydrofuran (100 mL) was added isopropylamine (4.23 g, 72.74 mmol) and the reaction mixture was then heated to 60° C., stirred for 1 hour and then cooled to room temperature. The tetrahydrofuran solvent was evaporated under reduced pressure, and the residual solid was purified by chromatography on silica gel to afford the title compound, a compound of the present invention, as a white solid (5.05 g) melting at 173-175° C.

$^1$H NMR (CDCl$_3$) δ 2.23 (d, 6H), 2.18 (s, 3H), 4.21 (m, 1H), 5.97 (d, 1H), 7.01 (m, 1H), 7.20 (s, 1H), 7.24 (s, 1H), 7.41 (d, 1H) 7.83 (d, 1H), 8.43 (d, 1H), 10.15 (br s, 1H).

Example 9

Preparation of 3-Chloro-N-[4-chloro-2-methyl-6-[(methylamino)carbonyl]phenyl]-1-(3-chloro-2-pyridinyl)-1H-pyrazole-5-carboxamide To a solution of the benzoxazinone product of Example 8, Step E (6.32 g, 15.47 mmol) in tetrahydrofuran (50 mL) was added methylamine (2.0 M solution in THF, 38 mL, 77.38 mmol), and the reaction mixture was heated to 60° C., stirred for 1 hour and then cooled to room temperature. The tetrahydrofuran solvent was evaporated under reduced pressure, and the residual solid was purified by chromatography on silica gel to afford the title compound, a compound of the present invention, as a white solid (4.57 g) melting at 225-226° C.

$^1$H NMR (CDCl$_3$) δ 2.15 (s, 3H), 2.93 (s, 3H), 6.21 (d, 1H), 7.06 (s, 1H), 7.18 (s, 1H), 7.20 (s, 1H), 7.42 (m, 1H), 7.83 (d, 1H), 8.42 (d, 1H), 10.08 (br s, 1H).

Example 10

Preparation of 3-Bromo-N-[4-chloro-2-methyl-6-[[(1-methylethyl)amino]carbonyl]phenyl]-1-(3-chloro-2-pyridinyl)-1H-pyrazole-5-carboxamide

Step A: Preparation of 3-Bromo-N,N-dimethyl-1H-pyrazole-1-sulfonamide

To a solution of N,N-dimethylsulfamoylpyrazole (44.0 g, 0.251 mol) in dry tetrahydrofuran (500 mL) at −78° C. was added dropwise a solution of n-butyllithium (2.5 M in hexane, 105.5 mL, 0.264 mol) while maintaining the temperature below −60° C. A thick solid formed during the addition. Upon completion of the addition, the reaction mixture was maintained for an additional 15 minutes, after which time a solution of 1,2-dibromotetrachloroethane (90 g, 0.276 mol) in tetrahydrofuran (150 mL) was added dropwise while maintaining the temperature below −70° C. The reaction mixture turned a clear orange; stirring was continued for an additional 15 minutes. The −78° C. bath was removed and the reaction was quenched with water (600 mL). The reaction, mixture was extracted with methylene chloride (4×), and the organic extracts were dried over magnesium sulfate and concentrated. The crude product, was further purified by chromatography on silica gel using methylene chloride/hexane (50:50) as eluent to afford the title product as a clear colorless oil (57.04 g).

$^1$H NMR (CDCl$_3$) δ 3.07 (d, 6H), 6.44 (m, 1H), 7.62 (m, 1H).

Step B: Preparation of 3-Bromopyrazole

To trifluoroacetic acid (70 mL) was slowly added the bromopyrazole product (57.04 g) from Step A. The reaction mixture was stirred at room temperature for 30 minutes and then concentrated at reduced pressure. The residue was taken up in hexane, insoluble solids were filtered off, and the hexane was evaporated to afford the crude product as as oil. The crude product was wither purified by chromatography on silica gel using ethyl acetate/dichloromethane (10:90) as eluent to afford an oil. The oil was taken up in dichloromethane, neutralized with aqueous sodium bicarbonate solution, extracted with methylene chloride (3×), dried over magnesium sulfate and concentrated to afford the title product as a white solid (25.9 g), m.p, 61-64° C.

$^1$H NMR (CDCl$_3$) δ 6.37 (d 1H), 7.59 (d, 1H), 12.4 (br s, 1H).

Step C: Preparation of 2-(3-Bromo-1H-pyrazol-1-yl)-3-chloropyridine

To a mixture of 2,3-dichloropyridine (27.4 g, 185 mmol) and 3-bromopyrazole (i.e. the product of Step B) (25.4 g, 176 mmol) in dry N,N-dimethylformamide (88 mL) was added potassium carbonate (48.6 g, 352 mmol), and the reaction mixture was heated to 125° C. for 18 hours. The reaction mixture was cooled to room temperature and poured into ice water (800 mL). A precipitate formed. The precipitated solids were stirred for 1.5 hrs, filtered and washed with water (2×100 mL). The solid filter cake was taken up in methylene chloride and washed sequentially with water, 1N hydrochloric acid, saturated aqueous sodium bicarbonate solution, and brine. The organic extracts were then dried over magnesium sulfate and concentrated to afford 39.9 g of a pink solid. The crude solid was suspended in hexane and stirred vigorously for 1 hr. The solids were filtered, washed with hexane and dried to afford the title product as an off-white powder (30.4 g) determined to be <94% pure by NMR. This material was used without further purification in Step D. $^1$H NMR (CDCl$_3$) δ 6.52 (s, 1H), 7.30 (d, 1H), 7.92 (d, 1H), 8.05 (s, 1H), 8.43 (d, 1H).

Step D: Preparation of 3-Bromo-1-(3-chloro-2-pyridinyl)-1H-pyrazole-5-carboxylic acid To a solution of the pyrazole product from Step C (30.4 g, 118 mmol) in dry tertahydrofuran (250 mL) at −76° C. was added dropwise a solution of lithium diisopropylamide (138 mmol) in tetrahydrofuran at such a rate as to maintain the temperature below −71° C. The reaction mixture was stirred for 15 minutes at −76° C. and carbon dioxide was then bubbled through for 10 minutes, causing warming to −57° C. The reaction mixture was warmed to −20° C. and quenched with water. The reaction mixture was concentrated and then taken up in water (1 L) and ether (500 mL), and then aqueous sodium hydroxide solution (1 N, 20 mL) was added. The aqueous extracts were washed with ether and acidified with hydrochloric acid. The precipitated solids were filtered, washed with water and dried to afford the title product as a tan solid (27.7 g). (Product from another run following similar procedure melted at 200-201° C.)
$^1$H NMR (DMSO-d$_6$) δ 7.25 (s, 1H), 7.68 (dd, 1H), 8.24 (d, 1H), 8.56 (d, 1H).

Step E: Preparation of 2-[(3-Bromo-1-(3-chloro-2-pyridinyl)-1H-pyrazol-5-yl]-6-chloro-8-methyl-4H-3,1-benzoxazin-4-one A procedure analogous to that of Example 6, Step D was used to convert the pyrazolecarboxylic acid product from Example 10, Step D (1.5 g, 4.96 mmol) and 2-amino-3-methyl-5-chlorobenzoic acid (0.92 g, 4.96 mmol) to the title product as a solid (1.21 g).
$^1$H NMR (CDCl$_3$) δ 2.01 (s, 3H), 7.29 (s, 1H), 7.42 (d, 1H), 7.95 (d, 1H), 8.04 (m, 1H), 8.25 (s, 1H), 8.26 (d, 1H).

Step F: Preparation of 3-Bromo-N-[4-chloro-2-methyl-6[[(1-methylethyl)amino]-carbonyl]phenyl]-1-(3-chloro-2-pyridinyl)-1H-pyrazole-5-carboxamide To a solution of the bensoxazinone product of Step E (0.20 g, 0.44 mmol) in tetrahydrofuran was added isopropylamine (0.122 mL, 1.42 mmol), and the reaction mixture was heated to 60° C. for 90 minutes and then cooled to room temperature. The tetrahydrofuran solvent was evaporated under reduced pressure, and the residual solid was triturated with ether, filtered, and dried to afford the title compound, a compound of the present invention, as a solid (150 mg), m.p. 159-161° C.
$^1$H NMR (CDCl$_3$) δ 1.22 (d, 6H), 2.19 (s, 3H), 4.21 (m, 1H), 5.99 (m, 1H), 7.05 (m, 1H), 7.22 (m, 2H), 7.39 (m, 1H), 7.82 (d, 1H), 8.41 (d, 1H).

Example 11

Preparation of 3-Bromo-N-[4-chloro-2-methyl-6-[(methylamino)carbonyl]phenyl]-1-(3-chloro-2-pyridinyl)-1H-pyrazole-5-carboxamide To a solution of the benzoxazinone product of Example 10, Step E (0.20 g, 0.44 mmol) in tetrahydrofuran was added methylamine (2.0 M solution in THF, 0.514 mL, 1.02 mmol), and the reaction mixture was heated to 60° C. for 90 minutes and then cooled to room temperature. The tetrahydrofuran solvent was evaporated under reduced pressure, and the residual solid was triturated with ether, filtered, and dried to afford the title compound, a compound of the present invention, as a solid (40 mg), m.p. 162-154° C.
$^1$H NMR (CDCl$_3$) δ 2.18 (s, 3H), 2.95 (s, 3H), 6.21 (m, 1H), 7.10 (s, 1H), 7.24 (m, 2H), 7.39 (m, 1H), 7.80 (d, 1H), 8.45 (d, 1H).

The following Example 12 illustrates an alternative preparation of 3-chloro-1-(3-chloro-2-pyridinyl)-1H-pyrazole-5-carboxylic acid, which can be used to prepare, for example, 3-chloro-N-[4-chloro-2-methyl-6-[[(1-methylethyl)amino] carbonyl]phenyl]-1-(3-chloro-2-pyridinyl)-1H-pyrazole-5-carboxamide and 3-chloro-N-[4-chloro-2-methyl-6-[(methylamino)carbonyl]phenyl]-1-(3-chloro-2-pyridinyl)-1H-pyrazole-5-carboxamide, by further steps illustrated in Examples 8 and 9.

Example 12

Preparation, of 3-chloro-1-(3-chloro-2-pyridinyl)-1H-pyrazole-5-carboxylic acid

Step A: Preparation of Ethyl 2-(3-chloro-2-pyridinyl)-5-oxo-3-pyrazolidinecarboxylate (alternatively named ethyl 1-(3-chloro-2-pyridinyl)-3-pyrazilidinone-5-carboxylate)

A 2-L four-necked flask equipped with a mechanical stirrer, thermometer, addition funnel, reflux condenser, and nitrogen inlet was charged with absolute ethanol (250 mL) and an ethanolic solution of sodium ethoxide (21%, 190 mL, 0.504 mol). The mixture was heated to reflux at about 83° C. It was then treated with 3-chloro-2(1H)-pyridinone hydrazone (68.0 g, 0.474 mol). The mixture was re-heated to reflux over a period of 5 minutes. The yellow slurry was then treated dropwise with diethyl maleate (88.0 mL, 0.544 mol) over a period of 5 minutes. The reflux rate increased markedly during the addition. By the end of the addition all of the starting material had dissolved. The resulting orange-red solution was held at reflux for 10 minutes. After being cooled to 65° C., the reaction mixture was treated with glacial acetic acid (50.0 mL, 0.873 mol). A precipitate formed. The mixture was diluted with water (650 mL), causing the precipitate to dissolve. The orange solution was cooled in an ice bath. Product began to precipitate at 28° C. The slurry was held at about 2° C. for 2 hours. The product was isolated via filtration, washed with aqueous ethanol (40%, 3×50 mL), and then air-dried, on the filter for about 1 hour. The title product compound was obtained as a highly crystalline, light orange powder (70.3 g, 55% yield). No significant impurities were observed by $^1$H NMR.
$^1$H NMR (DMSO-d$_6$) δ 1.22 (t, 3H), 2.35 (d, 1H), 2.91 (dd, 1H), 4.20 (q, 2H), 4.84 (d, 1H), 7.20 (dd, 1H), 7.92 (d, 1H), 8.27 (d, 1H), 10.18 (s, 1H).

Step B: Preparation of Ethyl 3-chloro-1-(3-chloro-2-pyridinyl)-4,5-dihydro-1H-pyrazole-5-carboxylate (alternatively named ethyl 1-(3-chloro-2-pyridinyl)-3-chloro-2-pyrazoline-5-carboxylate To a 2-L four-necked flask equipped with a mechanical stirrer, thermometer, reflux condenser, and nitrogen inlet was charged acetonitrile (1000 mL), ethyl 2-(3-chloro-2-pyridinyl)-5-oxo-3-pyrazolidinecarboxylate (i.e. the product of Step A) (91.0 g, 0.337 mol) and phosphorus oxychloride (35.0 mL, 0.375 mol). Upon adding the phosphorus oxychloride, the mixture self-heated from 22 to 25° C. and a precipitate formed. The light-yellow slurry was heated to reflux at 83° C. over a period of 35 minutes, whereupon the precipitate dissolved. The resulting orange solution was held at reflux for 45 minutes, whereupon it had become black-green. The reflux condenser was replaced with a distillation head, and 650 mL of solvent was removed by distillation. A second 2-L four-necked flask equipped with a mechanical stirrer was charged with sodium bicarbonate (130 g, 1.55 mol) and water (400 mL). The concentrated reaction mixture was added to the sodium bicarbonate slurry over a period of 15 minutes. The resulting, two-phase mixture was stirred vigorously for 29 minutes, at which time gas evolution had ceased. The mixture was diluted with dichloromethane (250 mL) and then was stirred for 50 minutes. The mixture was treated with Celite® 545 diatomaceous earth filter aid (11 g) and then filtered to remove a black, tarry substance that inhibited phase separation. Since the filtrate was slow to separate into distinct phases, it was diluted with dichloromethane (200 mL) and water (200 mL) and treated with more Celite® 545 (15 g). The mixture was filtered, and the filtrate was transferred to a separatory funnel. The heavier, deep green organic layer was separated. A rag layer (50 mL) was refiltered and then added to the organic layer. The organic solution (800 mL) was treated with magnesium sulfate (30 g) and silica gel (12 g), and the slurry was stirred magnetically for 30 minutes. The slurry was filtered to remove the magnesium sulfate and silica gel, which had become deep blue-green. The filter cake was washed with dichloromethane (100 mL). The filtrate was concentrated on a rotary evaporator. The product consisted of dark amber oil (92.0 g, 93% yield). The only appreciable impurities observed by $^1$H NMR were 1% starting material and 0.7% acetonitrile.

$^1$H NMR (DMSO-$d_6$) δ 1.15 (t, 3H), 3.26 (dd, 1H), 3.58 (dd, 1H), 4.11 (q, 2H), 5.25 (dd, 1H), 7.00 (dd, 1H), 7.84 (d, 1H), 8.12 (d, 1H).

Step C: Preparation of Ethyl 3-chloro-1-(3-chloro-2-pyridinyl)-1H-pyrazole-5-carboxylate (alternatively named ethyl 1-(3-chloro-2-pyridinyl)-3-chloropyrazole-5-carboxylate)

A 2-L four-necked flask equipped with a mechanical stirrer, thermometer, reflux condenser, and nitrogen inlet was charged with ethyl 3-chloro-1-(3-chloro-2-pyridinyl)-4,5-dihydro-1H-pyrazole-5-carboxylate (i.e. the product of Step B) (95% pure, 99.5 g, 0.328 mol), acetonitrile (1000 mL) and sulfuric acid (98%, 35.0 mL, 0.661 mol). The mixture self-heated from 22 to 35° C. upon adding the sulfuric acid. After being stirred for several minutes, the mixture was treated with potassium persulfate (140 g, 0.518 mol). The slurry was heated to reflux at 84° C. for 4.5 hours. The resulting orange slurry while still warm (50-65° C.) was filtered to remove a fine, white precipitate. The filter cake was washed with acetonitrile (50 mL). The filtrate was concentrated to about 500 mL on a rotary evaporator. A second 2-L four-necked flask equipped with a mechanical stirrer was charged with water (1250 mL). The concentrated reaction mass was added to the water over a period of about 5 minutes. The product was isolated via filtration, washed with aqueous acetonitrile (25%, 3×125 mL), washed once with water (100 mL), and men dried overnight in vacuo at room temperature. The product consisted of a crystalline, orange powder (79.3 g, 82% yield). The only appreciable impurities observed by $^1$H NMR were about 1.9% water and 0.6% acetonitrile.

$^1$H NMR (DMSO-$d_6$) δ 1.09 (t, 3H), 4.16 (q, 2H), 7.31 (s, 1H), 7.71 (dd, 1H), 8.38 (d, 1H), 8.59 (d, 1H).

Step B: Preparation of 3-Chloro-1-(3-chloro-2-pyridinyl)-1H-pyrazole-5-carboxylic acid (alternatively named 1-(3-chloro-2-pyridinyl)-3-chloropyrazole-5-carboxylic acid)

A 1-L four-necked flask equipped with a mechanical stirrer, thermometer, and nitrogen inlet was charged with ethyl 3-chloro-1-(3-chloro-2-pyridinyl)-1H-pyrazole-5-carboxylate (i.e. the product of Step C) (97.5% pure, 79.3 g, 0.270 mol), methanol (260 mL), water (140 mL) and sodium hydroxide pellets (13.0 g, 0.325 mol). Upon adding the sodium hydroxide the mixture self-heated from 22 to 35° C., and the starting material began to dissolve. After being stirred for 45 minutes under ambient conditions, all of the starting material had dissolved. The resulting deep orange-brown solution was concentrated to about 250 mL on a rotary evaporator. The concentrated reaction mixture was then diluted with water (400 mL). The aqueous solution, was extracted with ether (200 mL). Then the aqueous layer was transferred to a 1-L Erlenmeyer flask equipped with a magnetic stirrer. The solution was treated dropwise with concentrated hydrochloric acid (36.0 g, 0.355 mol) over a period of about 10 minutes. The product was isolated via filtration, reslurried with water (2×200 mL), cover washed once with water (100 mL) and then air-dried on the filter for 1.5 hours. The product consisted of a crystalline, light brown powder (58.1 g, 83% yield). About 0.7% ether was the only appreciable impurity observed by $^1$H NMR.

$^1$H NMR (DMSO-$d_6$) δ 7.20 (s, 1H), 7.68 (dd, 1H), 8.25 (d, 1H), 8.56 (d, 1H), 13.95 (br s, 1H).

The following Example 13 illustrates an alternative preparation of 3-bromo-1-(3-chloro-2-pyridinyl)-1H-pyrazole-5-carboxylic acid, which can be used to prepare, for example, 3-bromo-N-[4-chloro-2-methyl-6-[[(1-methylethyl)amino]carbonyl]phenyl]-1-(3-chloro-2-pyridinyl)-1H-pyrazole-5-carboxamide and 3-bromo-N-[4-chloro-2-methyl-6-[(methylamino)carbonyl]phenyl]-1-(3-chloro-2-pyridinyl)-1H-pyrazole-5-carboxamide, by further steps illustrated in Examples 10 and 11.

Example 13

Preparation of 3-Bromo-1-(3-chloro-2-pyridinyl)-1H-pyrazole-5-carboxylic acid

Step A1: Preparation of Ethyl 3-bromo-1-(3-chloro-2-pyridinyl)-4,5-dihydro-1H-pyrazole-5-carboxylate (alternatively named ethyl 1-(3-chloro-2-pyridinyl)-3-bromo-2-pyrazoline-5-carboxylate) using phosphorus oxybromide A 1-L four-necked flask equipped with a mechanical stirrer, thermometer, reflux condenser, and nitrogen inlet was charged with acetonitrile (400 mL), ethyl 2-(3-chloro-2-pyridinyl)-5-oxo-3-pyrazolidinecarboxylate (i.e. the product of Example 12, Step A) (50.0 g, 0.185 mol) and phosphorus oxybromide (34.0 g, 0.119 mol). The orange slurry was heated to reflux at 83° C. over a period of 20 minutes. The resulting turbid, orange solution was held at reflux for 75 minutes, at which time a dense, tan, crystalline precipitate had formed. The reflux condenser was replaced with a distillation head, and a cloudy, colorless distillate (300 mL) was collected. A second 1-L four-necked flask equipped with a mechanical stirrer was changed with sodium bicarbonate (45 g, 0.54 mol) and water (200 mL). The concentrated reaction mixture was added to the sodium bicarbonate slurry over a period of 5 minutes. The resulting two-phase mixture was stirred vigorously for 5 minutes, at which time gas evolution had ceased. The mixture was diluted with dichloromethane (200 mL) and then was stirred for 75 minutes. The mixture was treated with 5 g of Celite® 545 diatomaceous filter aid and then filtered to remove a brown, tarry substance. The filtrate was transferred to a separatory funnel. The brown organic layer (400 mL) was separated and then was treated with magnesium sulfate (1.5 g) and Darco® G360 activated charcoal (2.0 g). The resulting slurry was stirred magnetically for 15 minutes and then filtered to remove the magnesium sulfate and charcoal. The green filtrate was treated with silica gel (3 g) and stirred for several minutes. The deep blue-green silica get was removed by filtration, and the filtrate was concentrated on a rotary evaporator. The product consisted of a light amber oil (58.6 g, 95% yield), which crystallized upon standing. The only appreciable impurity observed by $^1$H NMR was 0.3% acetonitrile.

$^1$H NMR (DMSO-$d_6$) δ 1.15 (t, 3H), 3.29 (dd, 1H), 3.60 (dd, 1H), 4.11 (q, 2H), 5.20 (dd, 1H), 6.99 (dd, 1H), 7.84 (d, 1H), 8.12 (d, 1H).

Step A2: Preparation of Ethyl 3-bromo-1-(3-chloro-2-pyridinyl)-4,5-dihydro-1H-pyrazole-5-carboxylate using phosphorus pentabromide A 1-L four-necked flask equipped with a mechanical stirrer, thermometer, reflux, condenser, and nitrogen inlet was charged with acetonitrile (330 mL), ethyl 2-(3-chloro-2-pyridinyl)-5-oxo-3-pyrazolidinecarboxylate (i.e. the product of Example 12, Step A) (52.0 g, 0.193 mol), and phosphorus pentabromide (41.0 g, 0.0952 mol). The orange slurry was heated to reflux at 84° C. over a period of 20 minutes. The resulting brick-red mixture was held at reflux for 90 minutes, at which time a dense tan crystalline precipitate had formed. The reflux condenser was replaced with a distillation head, and a cloudy, colorless distillate (220 mL) was collected. A second 1-L four-necked flask equipped with a mechanical stirrer was charged with sodium bicarbonate (40 g, 0.48 mol) and water (200 mL). The concentrated reaction-mixture was added to the sodium bicarbonate slurry over a period of 5 minutes. The resulting, two-phase mixture was stirred vigorously for 10 minutes, at which time gas evolution had ceased. The mixture was diluted with dichloromethane (200 mL) and then was stirred for 10 minutes. The mixture was treated with Celite® 545 diatomaceous filter aid (5 g) and then filtered to remove a purple, tarry substance. The filter cake was washed with dichloromethane (50 mL). The filtrate was transferred to a separatory funnel. The purple-red organic layer (400 mL) was separated and then was treated with magnesium sulfate (15 g) and Darco® G60 activated charcoal (2.2 g). The slurry was stirred magnetically for 40 minutes. The slurry was filtered to remove the magnesium sulfate and charcoal. The filtrate was concentrated on a rotary evaporator. The product consisted of a dark amber oil (61.2 g, 95% yield), which crystallized upon standing. The only appreciable impurity observed by $^1$H NMR was 0.7% acetonitrile.

$^1$H NMR (DMSO-$d_6$) δ 1.15 (t, 3H), 3.29 (dd, 1H), 3.60 (dd, 1H), 4.11 (q, 2H), 5.20 (dd, 1H), 6.99 (dd, 1H), 7.84 (d, 1H), 8.12 (d, 1H).

Step B: Preparation of Ethyl 3-bromo-1-(3-chloro-2-pyridinyl)-1H-pyrazole-5-carboxylate (alternatively named ethyl 1-(3-chloro-2-pyridinyl)-3-bromopyrazole-5-carboxylate)

A 1-L four-necked flask equipped with a mechanical stirrer, thermometer, reflux condenser, and nitrogen inlet was charged with ethyl 3-bromo-1-(3-chloro-2-pyridinyl)-4,5-dihydro-1H-pyrazole-5-carboxylate (i.e. the product of Steps A1 and A2) (40.2 g, 0.121 mol), acetonitrile (300 mL) and sulfuric acid (98%, 13.0 mL, 0.245 mol). The mixture self-heated from 22 to 36° C. upon adding the sulfuric acid. After being stirred for several minutes, the mixture was treated with potassium persulfate (48.0 g, 0.178 mol). The slurry was heated to reflux at 84° C. for 2 hours. The resulting orange slurry while still warm (50-65° C.) was filtered to remove a white precipitate. The filter cake was washed with acetonitrile (2×50 mL). The filtrate was concentrated to about 200 mL on a rotary evaporator. A second 1-L four-necked flask equipped with a mechanical stirrer was charged with water (400 mL). The concentrated reaction mass was added to the water over a period of about 5 minutes. The product was isolated via filtration, washed sequentially with aqueous acetonitrile (20%, 100 mL) and water (75 mL), and was then air-dried on the filter for 1 hour. The product consisted of a crystalline, orange powder (36.6 g, 90% yield). The only appreciable impurities observed by $^1$H NMR were about 1% of an unknown and 0.5% acetonitrile.

$^1$H NMR (DMSO-$d_6$) δ 1.09 (t, 3H), 4.16 (q, 2H), 7.35 (s, 1H), 7.72 (dd, 1H), 8.39 (d, 1H), 8.59 (d, 1H).

Step C: Preparation of 3-Bromo-1-(3-chloro-2-pyridinyl)-1H-pyrazole-5-carboxylic acid (alternatively named 1-(3-chloro-2-pyridinyl)-3-bromopyrazole-5-carboxylic acid)

A 300-mL four-necked flask equipped with a mechanical stirrer, thermometer, and nitrogen inlet was charged with ethyl 3-bromo-1-(3-chloro-2-pyridinyl)-1H-pyrazole-5-carboxylate (i.e. the product of Step B) (98.5% pure, 25.0 g, 0.0756 mol), methanol (75 mL), water (50 mL), and sodium hydroxide pellets (3.30 g, 0.0825 mol). Upon adding the sodium hydroxide the mixture self-heated from 29 to 34° C. and the starting material began to dissolve. After being stirred for 90 minutes under ambient conditions, all of the starting material had dissolved. The resulting dark orange solution was concentrated to about 90 mL on a rotary evaporator. The concentrated reaction mixture was then diluted with water (100 mL). The aqueous solution was extracted with ether (100 mL). Then the aqueous layer was transferred to a 500-mL Erlenmeyer flask equipped with a magnetic stirrer. The solution was treated dropwise with concentrated hydrochloric acid (8.50 g, 0.0839 mol) over a period of about 10 minutes. The product was isolated via filtration, reslurried with water (2×40 mL), cover washed once with water (25 mL), and then air-dried on the filter for 2 hours. The product consisted of a crystalline, tan powder (20.9 g, 91% yield). The only appreciable impurities observed by $^1$H NMR were about 0.8% of an unknown and 0.7% ether.

$^1$H NMR (DMSO-$d_6$) δ 7.25 (s, 1H), 13.95 (br s, 1H), 8.56 (d, 1H), 8.25 (d, 1H), 7.68 (dd, 1H).

The following Example 14 illustrates an alternative preparation of ethyl 3-bromo-1-(3-chloro-2-pyridinyl)-4,5-dihydro-1H-pyrazole-5-carboxylate, which can be used to prepare, for example, ethyl 3-bromo-1-(3-chloro-2-pyridinyl)-1H-pyrazole-5-carboxylate (i.e. product of Example 13, Step B).

Example 14

Preparation of Ethyl 3-bromo-1-(3-chloro-2-pyridinyl)-4,5-dihydro-1H-pyrazole-5-carboxylate from ethyl 3-chloro-1-(3-chloro-2-pyridinyl)-4,5-dihydro-1H-pyrazole-5-carboxylate using hydrogen bromide Hydrogen bromide was passed through a solution of ethyl 3-chloro-1-(3-chloro-2-pyridinyl)-4,5-dihydro-1H-pyrazole-5-carboxylate (i.e. product of Example 12, Step B) (8.45 g, 29.3 mmol) in dibromomethane (85 mL). After 90 minutes the gas flow was terminated, and the reaction mixture was washed with aqueous sodium bicarbonate solution (100 mL). The organic phase was dried and evaporated under reduced pressure to give the title product as an oil (9.7 g, 99% yield), which crystallized on standing. $^1$H NMR (CDCl$_3$) δ 1.19 (t, 3H), 3.24 (½ of AB in ABX pattern, J=9.3, 17.3 Hz, 1H), 3.44 (½ of AB in ABX pattern, J=11.7, 17.3 Hz, 1H), 4.18 (q, 2H), 5.25 (X of ABX, 1H, J=9.3, 11.9 Hz), 6.85 (dd, J=4.7, 7.7 Hz, 1H), 7.65 (dd, J=1.6, 7.8 Hz, 1H), 8.07 (dd, J=1.6, 4.8 Hz, 1H).

The following Example 15 illustrates the preparation of ethyl 1-(3-chloro-2-pyridinyl)-4,5-dihydro-3-[[(4-methylphenyl)sulfonyl]oxy]-1H-pyrazole-5-carboxylate, which can be used to prepare ethyl 3-bromo-1-(3-chloro-2-pyridinyl)-4,5-dihydro-1H-pyrazole-5-carboxylate by procedures similar to that described in Example 14.

Example 15

Preparation of ethyl 1-(3-chloro-2-pyridinyl)-4,5-dihydro-3-[[(4-methylphenyl)sulfonyl]oxy]-1H-pyrazole-5-carboxylate Triethylamine (3.75 g, 37.1 mmol) was added dropwise to a mixture of ethyl 2-(3-chloro-2-pyridinyl)-5-oxo-3-pyrazolidinecarboxylate (i.e. the product of Example 12, Step A) (10.0 g, 37.1 mmol) and p-toluenesulfonyl chloride (7.07 g, 37.1 mmol) in dichloromethane (100 mL) at 0° C. Further portions of p-toluenesulfonyl chloride (0.35 g, 1.83 mmol) and triethylamine (0.19 g, 1.88 mmol) were added. The reaction mixture was then allowed to warm to room temperature and was stirred overnight. The mixture was then diluted with dichloromethane (200 mL) and washed with water (3×70 mL). The organic phase was dried and evaporated to leave the title product as an oil (13.7 g, 87% yield), which slowly formed crystals. Product recrystallized from ethyl acetate/hexanes melted at 99.5-100° C.

IR (nujol) v 1740, 1638, 1576, 1446, 1343, 1296, 1228, 1191, 1178, 1084, 1027, 948, 969, 868, 845 cm$^{-1}$.

$^1$H NMR (CDCl$_3$) δ 1.19 (t, 3H), 2.45 (s, 3H), 3.12 (½ of AB in ABX pattern, J=17.3, 9 Hz, 1H), 3.33 (½ of AB in ABX pattern, J=17.5, 11.8 Hz, 1H), 4.16 (q, 2H), 5.72 (X of ABX, J=9, 11.8 Hz, 1H), 6.79 (dd, J=4.6, 7.7 Hz, 1H), 7.36 (d, J=8.4 Hz, 2H), 7.56 (dd, J=1.6, 7.8 Hz, 1H), 7.95 (d, J=8.4 Hz, 2H), 8.01 (dd, J=1.4, 4.6 Hz, 1H).

Example 16

Preparation of N-[4-Chloro-2-methyl-6-[(methylamino)carbonyl]phenyl]-1-(3-chloro-2-pyridinyl)-3-(2,2,2-trifluoroethoxy)-1H-pyrazole-5-carboxamide Step A: Preparation of Ethyl 1-(3-chloro-2-pyridinyl)-2,3-dihydro-3-oxo-1H-pyrazole-5-carboxylate To a suspension of ethyl 2-(3-chloro-2-pyridinyl)-5-oxo-3-pyrazolidinecarboxylate (i.e. product of Example 12, Step A) (27 g, 100 mmol) stirred in dry acetonitrile (200 mL) was added sulfuric acid (20 g, 200 mmol) in one portion. The reaction mixture thinned to form a pale green, nearly clear solution before thickening again to form a pale yellow suspension. Potassium persulfate (33 g, 120 mmol) was added in one portion, and then the reaction mixture was heated at gentle reflux for 3.5 hours. After cooling using an ice bath, a precipitate of white solid was removed by filtration and discarded. The filtrate was diluted with water (400 mL) and then extracted three times with ethyl ether (700 mL total). Concentration of the combined ether extracts to a reduced volume (75 mL) caused precipitation of an off-white solid (3.75 g), which was collected by filtration. The ether mother liquor was further concentrated to yield a second crop of an off-white precipitate (4.2 g), which was also collected by filtration. An off-white solid also precipitated from the aqueous phase; this solid (4.5 g) was collected by filtration to provide a combined total of 12.45 g of the title compound.

$^1$H NMR (DMSO-d$_6$) δ 1.06 (t, 3H), 4.11 (q, 2H), 6.34 (s, 1H), 7.6 (t, 1H), 8.19 (d, 1H), 8.5 (d, 1H), 10.6 (s, 1H).

Step B: Preparation of Ethyl 1-(3-chloro-2-pyridinyl)-3-(2,2,2-trifluoroethoxy)-1H-pyrazole-5-carboxylate To a suspension of ethyl 1-(3-chloro-2-pyridinyl)-2,3-dihydro-3-oxo-1H-pyrazole-5-carboxylate (i.e. product of Step A) (0.8 g, 3 mmol) stirred in dry acetonitrile (15 mL) at −5° C. was added potassium carbonate (0.85 g, 6.15 mmol). The suspension was stirred for 15 minutes at 20° C. The stirred suspension was then cooled to 5° C., and 2,2,2-trifluoroethyl trifluoromethanesulfate (0.8 g, 3.45 mmol) was added dropwise. The reaction mixture was warmed to room temperature and then heated to reflux, at which time thin layer chromatography showed the reaction to be complete. Water (25 mL) was added to the reaction mixture, which was then extracted with ethyl ether. The ether extract was dried over magnesium sulfate and concentrated to yield the title product compound (1.05 g) as a pale yellow oil.

$^1$H NMR (CDCl$_3$) δ 1.21 (t, 3H), 4.20 (q, 2H), 4.63 (q, 2H), 6.53 (s, 1H), 7.4 (t, 1H), 7.9 (d, 1H), 8.5 (d, 1H).

Step C: Preparation of 1-(3-Chloro-2-pyridinyl)-3-(2,2,2-trifluoroethoxy)-1H-pyrazole-5-carboxylic acid To a stirred solution of ethyl 1-(3-chloro-2-pyridinyl-3-(2,2,2-trifluoroethoxy)-1H-pyrazole-5-carboxylate (i.e. product of Step B) (0.92 g, 2.8 mmol) in methanol (15 mL) was added water (5 mL), which caused the reaction mixture to become cloudy. An aqueous solution of sodium hydroxide (50%, 1.5 g. 19.2 mmol) was added, dropwise, and the reaction mixture was stirred at room temperature for 30 minutes, during which time the reaction mixture became again clear. Water (20 mL) was added and the reaction mixture was extracted with ethyl ether, which was discarded. The aqueous phase was acidified to pH 2 using concentrated hydrochloric acid and then extracted with ethyl acetate (50 mL). The ethyl acetate extract, which was washed with water (20 mL) and brine (20 mL), dried over magnesium sulfate and concentrated to give the title compound, isolated as a white solid (0.8 g).

$^1$H NMR (DMSO-d$_6$) δ 4.9 (q, 2H), 6.75 (s, 1H), 7.6 (t, 1H), 8.2 (d 1H), 8.55 (d, 1H), 13.7 (bs, 1H).

Step D: Preparation of 6-Chloro-8-methyl-2H-3,1-benzoxazine-2,4(1H)-dione

To a suspension of 2-amino-3-methyl-5-chlorobenzoic acid (i.e. product of Example 6, Step A) (97 g, 520 mmol) stirred, in dry dioxane (750 mL) at room temperature, trichloromethyl chloroformate (63 g, 320 mmol) was added dropwise. The reaction mixture exothermically warmed slowly to 42° C., and the solid almost completely dissolved before a thick suspension formed again. After the suspension was stirred at ambient temperature for 2.5 hours, the title compound was isolated by filtration, washed with ethyl ether, and dried to yield the title product compound, obtained as a white solid (98 g). $^1$H NMR (DMSO-d$_6$) δ 2.3 (s, 3H), 7.70 (s, 1H), 7.75 (s, 1H), 11.2 (s, 1H).

Step E: Preparation of 6-Chloro-2-[1-(3-chloro-2-pyridinyl)-3-(2,2,2-trifluoroethoxy)-1H-pyrazol-5-yl]-8-methyl-4H-3,1-benzoxazin-4-one To a suspension of 1-(3-chloro-2-pyridinyl)-3-(2,2,2-trifluoroethoxy)-1H-pyrazole-5-carboxylic acid (i.e. product of Step C) (7.9 g, 24 mmol) stirred in dichloromethane (100 mL) was added N,N-dimethylformamide (4 drops). Oxalyl chloride (4.45 g, 35 mmol) was added dropwise over a period of 45 minutes. The resulting solution was stirred at room temperature for 4 hours and then concentrated under vacuum. The isolated acid chloride was dissolved in dry acetonitrile (10 mL) and added to a suspension of 6-chloro-8-methyl-2H-3,1-benzoxazine-2,4-(1H)-dione (i.e. product of Step D) (4.9 g, 23 mmol) stirred in dry acetonitrile (1.4 mL). Pyridine (10 mL) was added, and the solution heated at reflux 6 hours. After cooling using an ice bath, a precipitate of white solid (9.15 g) was collected. The $^1$H NMR spectrum of the collected precipitate showed peaks consistent with the title compound and residual 6-chloro-8-methyl-2H-3,1-benzoxazine-2,4(1H)-dione starting material. A small portion of the collected precipitate was recrystallized from acetonitrile to yield the pure title product melting at 178-180° C.

$^1$H NMR (DMSO-D$_6$) δ 1.72 (s, 3H), 4.96 (q, 2H), 7.04 (s, 1H), 7.7 (t, 1H), 7.75 (s, 1H), 7.9 (s, 1H), 8.3 (d, 1H), 8.6 (d, 1H).

Step F: Preparation of N-[4-chloro-2-methyl-6-[(methylamino)carbonyl]phenyl]-1-(3-chloro-2-pyridinyl)-3-(2,2,2-trifluoroethoxy)-1H-pyrazole-5-carboxamide To a suspension of the 6-chloro-2-[1-(3-chloro-2-pyridinyl)-3-(2,2,2-trifluoroethoxy)-1H-pyrazol-5-yl]-8-methyl-4H-3,1-benzoxazin-4-one (i.e. precipitate product of Step E) (3.53 g, 7.5 mmol) in tetrahydrofuran (15 mL), methylamine (2.0 M solution in THF, 11 mL, 22 mmol) was added dropwise, and the resulting solution, was stirred at room temperature for 45 minutes. Thin layer chromatography then showed the reaction to be complete. Ethyl ether (100 mL) was added, and the reaction, mixture was stirred for 2 hours while a precipitate formed. The precipitate was collected by filtration and then recrystallized from acetonitrile to yield a white solid (0.82 g). A second crop of white solid (0.35 g) precipitated from, the acetonitrile mother liquor and was collected by filtration. The initial ether/tetrahydrofuran mother liquor was concentrated to dryness, and the residual solid was recrystallized from acetonitrile to yield a third crop of white solid (0.95 g). The three crops were combined, totaling 2.12 g (after drying) of the title compound, a compound of the present invention, isolated as a white solid, melting at 195-197° C.

$^1$H NMR (CDCl$_3$) δ 2.18 (s, 3H), 2.92 (d, 3H), 4.66 (q, 2H), 6.15 (q, 1H), 6.6 (s, 1H), 7.2 (s, 1H), 7.25 (s, 1H), 7.35 (t, 1H), 7.8 (d, 1H), 8.45 (d, 1H), 10.0 (s, 1H).

The following Example 17 illustrates an alternative preparation of 1-(3-chloro-2-pyridinyl)-3-(trifluoromethyl)-1H-pyrazole-5-carboxylic acid, which can be used to prepare, for example, 1-(3-chloro-2-pyridinyl)-N-[2-methyl-6-[[1-methylethyl)amino]carbonyl]-phenyl]-3-(trifluoromethyl)-1H-pyrazole-5-carboxamide, by further steps illustrated in Examples 4.

Example 17

Preparation of 1-(3-chloro-2-pyridinyl)-3-(trifluoromethyl)-1-carboxylic acid

Step A: Preparation of 3-chloro-2(1H)-pyridinone-(2,2,2-trifluoro-1-methylethylidene)hydrazone 1,1,1-Trifluoroacetone (7.80 g, 69.6 mmol) was added to 3-chloro-2(1H)-pyridinone hydrazone (alternatively named (3-chloro-pyridin-2-yl)-hydrazine) (10 g, 69.7 mmol) at 20-25° C. After the addition was complete, the mixture was stirred for about 10 minutes. The solvent was removed under reduced pressure and the mixture partitioned between ethyl acetate (100 mL) and saturated aqueous sodium carbonate solution (100 mL). The organic layer was dried and evaporated. Chromatography on silica gel (eluted with ethyl acetate) gave the product as an off-white solid (11 g, 66% yield), m.p. 64-64.5° C. (after crystallization from ethyl acetate/hexanes).

IR (nujol) ν 1629, 1590, 1518, 1403, 1365, 1309, 1240, 1196, 1158, 1100, 1032, 992, 800 cm$^{-1}$.

$^1$H NMR (CDCl$_3$) δ 2.12 (s, 3H), 6.91-4.86 (m, 1H), 7.64-7.61 (m, 1H), 8.33-8.32 (m, 2H).

MS m/z 237 (M$^+$).

Step B: Preparation of ethyl hydrogen ethanedioate (3-chloro-2-pyridinyl)(2,2,2-trifluoro-1-methylethylidene)hydrazide (alternatively named ethyl hydrogen ethanedioate (3-chloro-2-pyridinyl)(2,2,2-trifluoro-1-methylethylidene)hydrazine Triethylamine (20.81 g, 0.206 mol) was added to 3-chloro-2(1H)-pyridinone (2,2,2-trifluoro-1-methylethylidene)hydrazone (i.e. the product of Step A) (32.63 g, 0.1.37 mol) in dichloromethane (68 mL) at 0° C. Ethyl chlorooxoacetate (18.75 g, 0.137 mol) in dichloromethane (69 mL) was added dropwise to the mixture at 0° C. The mixture was allowed to warm to 25° C. over about 2 hours. The mixture was cooled to 0° C. and a further portion of ethyl chlorooxoacetate (3.75 g, 27.47 mmol) in dichloromethane (14 mL) was added dropwise. After about an additional 1 hour, the mixture was diluted with dichloromethane (about 450 mL), and the mixture was washed with water (2×150 mL). The organic layer was dried and evaporated. Chromatography on silica gel (eluted with 1:1 ethyl acetate-hexanes) gave the product as a solid (42.06 g, 90% yield), m.p. 73.0-73.5° C. (after crystallization from ethyl acetate/hexanes).

IR (nujol) ν 1751, 1720, 1664, 1572, 1417, 1361, 1330, 1202, 1214, 1184, 1137, 1110, 1004, 1043, 1013, 942, 807, 836 cm$^{-1}$.

$^1$H NMR (DMSO-d$_6$, 115° C.) 1.19 (t, 3H), 1.72 (br s, 3H), 4.25 (q, 2H), 7.65 (dd, J=8.3, 4.7 Hz, 1H), 8.20 (dd, J=7.6, 1.5 Hz, 1H), 8.55 (d, J=3.6 Hz, 1H).

MS m/z 337 (M$^+$).

Step C: Preparation of ethyl 1-(3-chloro-2-pyridinyl)-4,5-dihydro-5-hydroxy-3-(trifluoroethyl)-1H-pyrazole-5-carboxylate Ethyl hydrogen ethanedioate (3-chloro-2-pyridinyl)(2,2,2-trifluoro-1-methyl-ethylidene)hydrazide (i.e. the product of Step B) (5 g, 14.8 mmol) in dimethyl sulfoxide (25 mL) was added to tetrabutylammonium fluoride hydrate (10 g) in dimethyl sulfoxide (25 mL) over 8 hours. When the addition was complete, the mixture was poured into acetic acid (3.25 g) in water (25 mL). After stirring at 25° C. overnight, the mixture was then extracted with toluene (4×25 mL), and the combined toluene extracts were washed with water (50 mL), dried and evaporated to give a solid. Chromatography on silica gel (eluted with 1:2 ethyl acetate-hexanes) gave the product as a solid (2.91 g, 50% yield, containing about 5% of 3-chloro-2 (1H)-pyridinone (2,2,2-trifluoro-1-methylethylidene)hydrazone, m.p. 78-78.5° C. (after recrystallization from ethyl acetate/hexanes).

IR (nujol) ν 3403, 1726, 1618, 1582, 1407, 1320, 1293, 1260, 1217, 1187, 1150, 1122, 1100, 1067, 1013, 873, 829 $cm^{-1}$.

$^1$H NMR (CDCl$_3$) δ 1.19 (s, 3H), 3.20 (½ of ABZ pattern, J=18 Hz, 1H), 3.42 (½ of ABZ pattern, J=18 Hz, 1H), 4.24 (q, 2H), 6.94 (dd, J=7.9, 4.9 Hz, 1H), 7.74 (dd, 7.7, 1.5 Hz, 1H), 8.03 (dd, J=4.7, 1.5 Hz, 1H).

MS m/z 319 (M$^+$).

Step D: Preparation of ethyl 1-(3-chloro-2-pyridinyl-3-(trifluoromethyl)-1H-pyrazole-5-carboxylate Sulfuric acid (concentrated, 2 drops) was added to ethyl 1-(3-chloro-2-pyridinyl)-4,5-dihydro-5-hydroxy-3-(trifluoromethyl)-1H-pyrazole-5-carboxylate (i.e. the product of Step C) (1 g, 2.96 mmol) in acetic acid (10 mL) and the mixture was warmed to 65° C. for about 1 hour. The mixture was allowed to cool to 25° C. and most of the acetic acid was removed under reduced pressure. The mixture was partitioned between saturated aqueous sodium carbonate solution (100 mL) and ethyl acetate (100 mL). The aqueous layer was further extracted with ethyl acetate (100 mL). The combined organic extracts were dried and evaporated to give the product as an oil (0.66 g, 77% yield).

IR (neat) ν 3147, 2986, 1734, 1577, 1547, 1466, 1420, 1367, 1277, 1236, 1135, 1082, 1031, 973, 842, 802 $cm^{-1}$.

$^1$H NMR (CDCl$_3$) δ 1.23 (t, 3H), 4.25 (q, 2H), 7.21 (s, 1H), 7.48 (dd, J=8.1, 4.7 Hz, 1H), 7.94 (dd, J=6.6, 2 Hz, 1H), 8.53 (dd, J=4.7, 1.5 Hz, 1H).

MS m/z 319 (M$^+$).

Step E: Preparation of 1-(3-chloro-2-pyridinyl)-3-trifluoromethyl)-1H-pyrazole-5-carboxylic acid Potassium hydroxide (0.5 g, 85%, 2.28 mmol) in water (1 mL) was added to ethyl 1-(3-chloro-2-pyridinyl)-3-(trifluoromethyl)-1H-pyrazole-5-carboxylate (i.e. product of Step D) (0.66 g, 2.07 mmol) in ethanol (3 mL). After about 30 minutes, the solvent was removed under reduced pressure, and the mixture was dissolved in water (40 mL). The solution was washed with ethyl acetate (20 mL). The aqueous layer was acidified with concentrated hydrochloric acid and was extracted with ethyl acetate (3×2.0 mL). The combined extracts were dried and evaporated to give the product as a solid (0.53 g, 93% yield), m.p. 178-179° C. (after crystallization from hexanes-ethyl acetate).

IR (nujol) ν 1711, 1586, 1565, 1550, 1440, 1425, 1292, 1247, 1249, 1170, 1135, 1087, 1059, 1031, 972, 843, 816 $cm^{-1}$.

$^1$H NMR (DMSO-d$_6$) δ 7.61 (s, 1H), 7.77 (m, 1H), 8.30 (d, 1H), 8.60 (s, 1H).

Examples 18 and 19 illustrate alternatives to reaction conditions described in Example 10, Step E and Example 8, Step E, respectively.

Example 18

Preparation of 2-[3-bromo-1-(3-chloro-2-pyridinyl)-1H-pyrazol-5yl]-6-chloro-8-methyl-4H-3,1-benzoxazin-4-one Methanesulfonyl chloride (1.0 mL, 1.5 g, 13 mmol) was dissolved in acetonitrile (10 mL), and the mixture was cooled to −5° C. A solution of 3-bromo-1-(3-chloro-2-pyridinyl)-1H-pyrazole-5-carboxylic acid (i.e. the pyrazolecarboxylic acid product of Example 10, Step D) (3.02 g, 10 mmol) and pyridine (1.4 ml, 1.4 g. 17 mmol) in acetonitrile (10 mL) was added dropwise over 5 minutes at −5 to 0° C. A slurry formed during the addition. The mixture was stirred 5 minutes at this temperature, and then a mixture of 2-amino-3-methyl-5-chlorobenzoic acid (i.e. the product of Example 6 Step A) (1.86 g, 10 mmol) and pyridine (2.8 mL, 2.7 g, 35 mmol) in acetonitrile (10 mL) was added, rinsing with more acetonitrile (5 mL). The mixture was stirred 15 minutes at −5 to 0° C. and then methanesulfonyl chloride (1.0 mL, 1.5 mL, 13 mmol) in acetonitrile (5 mL) was added dropwise over 5 minutes at a temperature of −5 to 0° C. The reaction mixture was stirred 15 minutes more at this temperature, then allowed to warm slowly to room temperature, and stirred 4 h. Water (20 mL) was added dropwise, and the mixture was stirred 15 minutes. Then the mixture was filtered, and the solids were washed with 2:1 acetonitrile-water (3×3 mL), then with acetonitrile (2×3 mL), and dried under nitrogen to afford the title product as a light yellow powder, 4.07 g (90.2% crude yield), melting at 203-205° C. HPLC of the product using a Zorbax® RX-C8 chromatography column (4.6 mm×25 cm, element 25-95% acetonitrile/pH 3 water) showed a major peak corresponding to the title compound and having 95.7% of total chromatogram peak area.

$^1$H NMR (DMSO-d$_6$) δ 1.72 (s, 3H) 7.52 (s, 1H), 7.72-7.78 (m, 2H), 7.88 (m, 1H), 8.37 (dd, 1H), 8.62 (dd, 1H).

Example 19

Preparation of 6-chloro-2-[3-chloro-1-(3-chloro-2-pyridinyl)-1H-pyrazol-5-yl]-8-methyl-4H-3,1-benzoxazin-4-one Methanesulfonyl chloride (1.0 mL, 1.5 g 13 mmol) was dissolved in acetonitrile (10 mL) and the mixture was cooled to −5° C. A solution of 5-chloro-1-(3-chloro-2-pyridinyl)-1H-pyrazole-5-carboxylic acid (i.e. the carboxylic acid product of Example 8, Step D) (2.58 g, 10 mmol) and pyridine (1.4 mL, 1.4 g, 17 mmol) in acetonitrile (10 mL) was added dropwise over 5 minutes at −5 to 0° C. A slurry formed during the addition. The mixture was stirred 5 minutes at this temperature, and then 2-amino-3-methyl-5-chlorobenzoic acid (i.e. the product from Example 6, Step A) (1.86 g, 10 mmol) was added all at once. Then a solution of pyridine (2.8 mL, 2.7 g, 35 mmol) in acetonitrile (10 mL) was added dropwise in 5 min at −5 to 0° C. The mixture was stirred 15 minutes at −5 to 0° C., and then methanesulfonyl chloride (1.0 mL, 1.5 mL, 13 mmol) in acetonitrile (5 mL) was added dropwise in 5 min at −5 to 0° C. The reaction mixture was stirred 15 minutes at this temperature, then allowed to warm slowly to room temperature, and stirred 4 h. Water (15 mL) was added dropwise, and the mixture was stirred 15 minutes. Then the mixture was filtered, and the solids were washed with 2:1 acetonitrile-water (3×3 mL), then with acetonitrile 2×5 mL), and dried under nitrogen to afford the title product as a pale yellow powder, 3.83 g (94.0% crude yield), melting at 199-201° C. HPLC or the product using a Zorbax® RX-C8 chromatography column (4.5 mm×25 cm, eluent 25-95% acetonitrile/pH 3 water) showed a major peak corresponding to the title compound and having 97.8% of total chromatogram peak area.

$^1$H NMR (DMSO-d$_6$) δ 1.72 (s, 3H), 7.48 (s, 1H), 7.74-7.80 (m, 2H), (m, 1H), 8.37 (dd, 1H), 8.62 (dd, 1H).

By the procedures described herein together with methods known in the art, the following compounds of Tables 1-6 can be prepared. The following abbreviations are used in the Tables which follow: t means tertiary, s means secondary, n means normal, i means iso, Me means methyl, Et means ethyl, Pr means propyl, i-Pr means isopropyl, and Bu means butyl.

TABLE 1

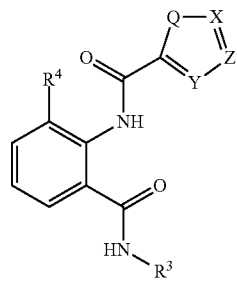

| R³ | R⁴ | O | X | Y | Z | R³ | R⁴ | O | X | Y | Z |
|---|---|---|---|---|---|---|---|---|---|---|---|
| i-Pr | Me | NMe | N | CH | CCF₃ | i-Pr | Me | NMe | N | CH | CC₂F₅ |
| i-Pr | Cl | NMe | N | CH | CCF₃ | i-Pr | Cl | NMe | N | CH | CC₂F₅ |
| i-Pr | Br | NMe | N | CH | CCF₃ | i-Pr | Br | NMe | N | CH | CC₂F₅ |
| i-Pr | I | NMe | N | CH | CCF₃ | i-Pr | I | NMe | N | CH | CC₂F₅ |
| i-Pr | F | NMe | N | CH | CCF₃ | i-Pr | F | NMe | N | CH | CC₂F₅ |
| i-Pr | H | NMe | N | CH | CCF₃ | i-Pr | H | NMe | N | CH | CC₂F₅ |
| i-Pr | Et | NMe | N | CH | CCF₃ | i-Pr | Et | NMe | N | CH | CC₂F₅ |
| i-Pr | Me | NEt | N | CH | CCF₃ | t-Bu | Me | NMe | N | CH | CCF₃ |
| i-Pr | Cl | NEt | N | CH | CCF₃ | t-Bu | Cl | NMe | N | CH | CCF₃ |
| i-Pr | Br | NEt | N | CH | CCF₃ | t-Bu | Br | NMe | N | CH | CCF₃ |
| i-Pr | I | NEt | N | CH | CCF₃ | t-Bu | I | NMe | N | CH | CCF₃ |
| i-Pr | F | NEt | N | CH | CCF₃ | t-Bu | F | NMe | N | CH | CCF₃ |
| i-Pr | H | NEt | N | CH | CCF₃ | t-Bu | H | NMe | N | CH | CCF₃ |
| i-Pr | Et | NEt | N | CH | CCF₃ | t-Bu | Et | NMe | N | CH | CCF₃ |

TABLE 2

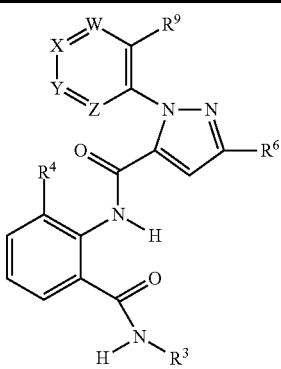

| W | X | Y | Z | R³ | R⁴ | R⁶ | R⁹ |
|---|---|---|---|---|---|---|---|
| CH | CH | CH | CH | i-Pr | Me | CF₃ | Me |
| CH | CH | CH | CH | t-Bu | Me | CF₃ | Me |
| CH | CH | CH | CH | i-Pr | Cl | CF₃ | Me |
| CH | CH | CH | CH | t-Bu | Cl | CF₃ | Me |
| CH | CH | CH | CH | i-Pr | Br | CF₃ | Me |
| CH | CH | CH | CH | t-Bu | Br | CF₃ | Me |
| CH | CH | CH | CH | i-Pr | Me | Cl | Me |
| CH | CH | CH | CH | t-Bu | Me | Cl | Me |
| CH | CH | CH | CH | i-Pr | Cl | Cl | Me |
| CH | CH | CH | CH | t-Bu | Cl | Cl | Me |
| CH | CH | CH | CH | i-Pr | Br | Cl | Me |
| CH | CH | CH | CH | t-Bu | Br | Cl | Me |
| CH | CH | CH | CH | i-Pr | Me | Br | Me |
| CH | CH | CH | CH | t-Bu | Me | Br | Me |
| CH | CH | CH | CH | i-Pr | Cl | Br | Me |
| CH | CH | CH | CH | t-Bu | Cl | Br | Me |
| CH | CH | CH | CH | i-Pr | Br | Br | Me |
| CH | CH | CH | CH | t-Bu | Br | Br | Me |
| CH | CH | CH | CH | i-Pr | Me | CN | Me |

TABLE 2-continued

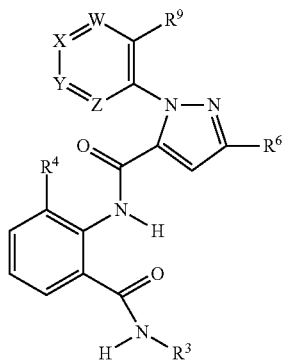

| W | X | Y | Z | R³ | R⁴ | R⁶ | R⁹ |
|---|---|---|---|---|---|---|---|
| CH | CH | CH | CH | t-Bu | Me | CN | Me |
| CH | CH | CH | CH | i-Pr | Cl | CN | Me |
| CH | CH | CH | CH | t-Bu | Cl | CN | Me |
| CH | CH | CH | CH | i-Pr | Br | CN | Me |
| CH | CH | CH | CH | t-Bu | Br | CN | Me |
| CH | CH | CH | CH | i-Pr | Me | CF₃ | F |
| CH | CH | CH | CH | t-Bu | Me | CF₃ | F |
| CH | CH | CH | CH | i-Pr | Cl | CF₃ | F |
| CH | CH | CH | CH | t-Bu | Cl | CF₃ | F |
| CH | CH | CH | CH | i-Pr | Br | CF₃ | F |
| CH | CH | CH | CH | t-Bu | Br | CF₃ | F |
| CH | CH | CH | CH | i-Pr | Me | Cl | F |
| CH | CH | CH | CH | t-Bu | Me | Cl | F |
| CH | CH | CH | CH | i-Pr | Cl | Cl | F |
| CH | CH | CH | CH | t-Bu | Cl | Cl | F |
| CH | CH | CH | CH | i-Pr | Br | Cl | F |
| CH | CH | CH | CH | t-Bu | Br | Cl | F |
| CH | CH | CH | CH | i-Pr | Me | Br | F |
| CH | CH | CH | CH | t-Bu | Me | Br | F |
| CH | CH | CH | CH | i-Pr | Cl | Br | F |
| CH | CH | CH | CH | t-Bu | Cl | Br | F |
| CH | CH | CH | CH | i-Pr | Br | Br | F |
| CH | CH | CH | CH | t-Bu | Br | Br | F |
| CH | CH | CH | CH | i-Pr | Me | CN | F |
| CH | CH | CH | CH | t-Bu | Me | CN | F |
| CH | CH | CH | CH | i-Pr | Cl | CN | F |
| CH | CH | CH | CH | t-Bu | Cl | CN | F |
| CH | CH | CH | CH | i-Pr | Br | CN | F |
| CH | CH | CH | CH | t-Bu | Br | CN | F |
| CH | CH | CH | CH | i-Pr | Me | CF₃ | Cl |
| CH | CH | CH | CH | t-Bu | Me | CF₃ | Cl |
| CH | CH | CH | CH | i-Pr | Cl | CF₃ | Cl |
| CH | CH | CH | CH | t-Bu | Cl | CF₃ | Cl |
| CH | CH | CH | CH | i-Pr | Br | CF₃ | Cl |
| CH | CH | CH | CH | t-Bu | Br | CF₃ | Cl |
| CH | CH | CH | CH | i-Pr | Me | Cl | Cl |
| CH | CH | CH | CH | t-Bu | Me | Cl | Cl |
| CH | CH | CH | CH | i-Pr | Cl | Cl | Cl |
| CH | CH | CH | CH | t-Bu | Cl | Cl | Cl |
| CH | CH | CH | CH | i-Pr | Br | Cl | Cl |
| CH | CH | CH | CH | t-Bu | Br | Cl | Cl |
| CH | CH | CH | CH | i-Pr | Me | Br | Cl |
| CH | CH | CH | CH | t-Bu | Me | Br | Cl |
| CH | CH | CH | CH | i-Pr | Cl | Br | Cl |
| CH | CH | CH | CH | t-Bu | Cl | Br | Cl |
| CH | CH | CH | CH | i-Pr | Br | Br | Cl |
| CH | CH | CH | CH | t-Bu | Br | Br | Cl |
| CH | CH | CH | CH | i-Pr | Me | CN | Cl |
| CH | CH | CH | CH | t-Bu | Me | CN | Cl |
| CH | CH | CH | CH | i-Pr | Cl | CN | Cl |
| CH | CH | CH | CH | t-Bu | Cl | CN | Cl |
| CH | CH | CH | CH | i-Pr | Br | CN | Cl |
| CH | CH | CH | CH | t-Bu | Br | CN | Cl |
| CH | CH | CH | CH | i-Pr | Me | CF₃ | Br |
| CH | CH | CH | CH | t-Bu | Me | CF₃ | Br |
| CH | CH | CH | CH | i-Pr | Cl | CF₃ | Br |
| CH | CH | CH | CH | t-Bu | Cl | CF₃ | Br |
| CH | CH | CH | CH | i-Pr | Br | CF₃ | Br |
| CH | CH | CH | CH | t-Bu | Br | CF₃ | Br |
| CH | CH | CH | CH | i-Pr | Me | Cl | Br |

TABLE 2-continued

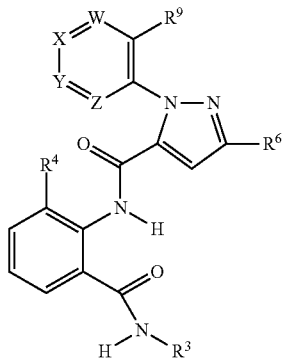

| W | X | Y | Z | R³ | R⁴ | R⁶ | R⁹ |
|---|---|---|---|----|----|----|----|
| CH | CH | CH | CH | t-Bu | Me | Cl | Br |
| CH | CH | CH | CH | i-Pr | Cl | Cl | Br |
| CH | CH | CH | CH | t-Bu | Cl | Cl | Br |
| CH | CH | CH | CH | i-Pr | Br | Cl | Br |
| CH | CH | CH | CH | t-Bu | Br | Cl | Br |
| CH | CH | CH | CH | i-Pr | Me | Br | Br |
| CH | CH | CH | CH | t-Bu | Me | Br | Br |
| CH | CH | CH | CH | i-Pr | Cl | Br | Br |
| CH | CH | CH | CH | t-Bu | Cl | Br | Br |
| CH | CH | CH | CH | i-Pr | Br | Br | Br |
| CH | CH | CH | CH | t-Bu | Br | Br | Br |
| CH | CH | CH | CH | i-Pr | Me | CN | Br |
| CH | CH | CH | CH | t-Bu | Me | CN | Br |
| CH | CH | CH | CH | i-Pr | Cl | CN | Br |
| CH | CH | CH | CH | t-Bu | Cl | CN | Br |
| CH | CH | CH | CH | i-Pr | Br | CN | Br |
| CH | CH | CH | CH | t-Bu | Br | CN | Br |
| CH | CH | CH | CH | i-Pr | Me | CF₃ | CN |
| CH | CH | CH | CH | t-Bu | Me | CF₃ | CN |
| CH | CH | CH | CH | i-Pr | Cl | CF₃ | CN |
| CH | CH | CH | CH | t-Bu | Cl | CF₃ | CN |
| CH | CH | CH | CH | i-Pr | Br | CF₃ | CN |
| CH | CH | CH | CH | t-Bu | Br | CF₃ | CN |
| CH | CH | CH | CH | i-Pr | Me | Cl | CN |
| CH | CH | CH | CH | t-Bu | Me | Cl | CN |
| CH | CH | CH | CH | i-Pr | Cl | Cl | CN |
| CH | CH | CH | CH | t-Bu | Cl | Cl | CN |
| CH | CH | CH | CH | i-Pr | Br | Cl | CN |
| CH | CH | CH | CH | t-Bu | Br | Cl | CN |
| CH | CH | CH | CH | i-Pr | Me | Br | CN |
| CH | CH | CH | CH | t-Bu | Me | Br | CN |
| CH | CH | CH | CH | i-Pr | Cl | Br | CN |
| CH | CH | CH | CH | t-Bu | Cl | Br | CN |
| CH | CH | CH | CH | i-Pr | Br | Br | CN |
| CH | CH | CH | CH | t-Bu | Br | Br | CN |
| CH | CH | CH | CH | i-Pr | Me | CN | CN |
| CH | CH | CH | CH | t-Bu | Me | CN | CN |
| CH | CH | CH | CH | i-Pr | Cl | CN | CN |
| CH | CH | CH | CH | t-Bu | Cl | CN | CN |
| CH | CH | CH | CH | i-Pr | Br | CN | CN |
| CH | CH | CH | CH | t-Bu | Br | CN | CN |
| CH | CH | CH | N | i-Pr | Me | CF₃ | Me |
| CH | CH | CH | N | t-Bu | Me | CF₃ | Me |
| CH | CH | CH | N | i-Pr | Cl | CF₃ | Me |
| CH | CH | CH | N | t-Bu | Cl | CF₃ | Me |
| CH | CH | CH | N | i-Pr | Br | CF₃ | Me |
| CH | CH | CH | N | t-Bu | Br | CF₃ | Me |
| CH | CH | CH | N | i-Pr | Me | Cl | Me |
| CH | CH | CH | N | t-Bu | Me | Cl | Me |
| CH | CH | CH | N | i-Pr | Cl | Cl | Me |
| CH | CH | CH | N | t-Bu | Cl | Cl | Me |
| CH | CH | CH | N | i-Pr | Br | Cl | Me |
| CH | CH | CH | N | t-Bu | Br | Cl | Me |
| CH | CH | CH | N | i-Pr | Me | Br | Me |
| CH | CH | CH | N | t-Bu | Me | Br | Me |
| CH | CH | CH | N | i-Pr | Cl | Br | Me |
| CH | CH | CH | N | t-Bu | Cl | Br | Me |
| CH | CH | CH | N | i-Pr | Br | Br | Me |
| CH | CH | CH | N | t-Bu | Br | Br | Me |
| CH | CH | CH | N | i-Pr | Me | CN | Me |

TABLE 2-continued

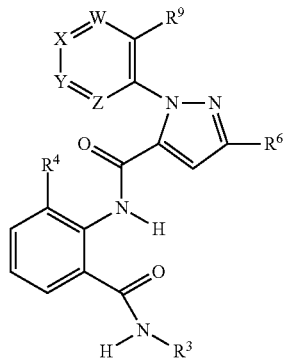

| W | X | Y | Z | R³ | R⁴ | R⁶ | R⁹ |
|---|---|---|---|----|----|----|----|
| CH | CH | CH | N | t-Bu | Me | CN | Me |
| CH | CH | CH | N | i-Pr | Cl | CN | Me |
| CH | CH | CH | N | t-Bu | Cl | CN | Me |
| CH | CH | CH | N | i-Pr | Br | CN | Me |
| CH | CH | CH | N | t-Bu | Br | CN | Me |
| CH | CH | CH | N | i-Pr | Me | CF₃ | F |
| CH | CH | CH | N | t-Bu | Me | CF₃ | F |
| CH | CH | CH | N | i-Pr | Cl | CF₃ | F |
| CH | CH | CH | N | t-Bu | Cl | CF₃ | F |
| CH | CH | CH | N | i-Pr | Br | CF₃ | F |
| CH | CH | CH | N | t-Bu | Br | CF₃ | F |
| CH | CH | CH | N | i-Pr | Me | Cl | F |
| CH | CH | CH | N | t-Bu | Me | Cl | F |
| CH | CH | CH | N | i-Pr | Cl | Cl | F |
| CH | CH | CH | N | t-Bu | Cl | Cl | F |
| CH | CH | CH | N | i-Pr | Br | Cl | F |
| CH | CH | CH | N | t-Bu | Br | Cl | F |
| CH | CH | CH | N | i-Pr | Me | Br | F |
| CH | CH | CH | N | t-Bu | Me | Br | F |
| CH | CH | CH | N | i-Pr | Cl | Br | F |
| CH | CH | CH | N | t-Bu | Cl | Br | F |
| CH | CH | CH | N | i-Pr | Br | Br | F |
| CH | CH | CH | N | t-Bu | Br | Br | F |
| CH | CH | CH | N | i-Pr | Me | CN | F |
| CH | CH | CH | N | t-Bu | Me | CN | F |
| CH | CH | CH | N | i-Pr | Cl | CN | F |
| CH | CH | CH | N | t-Bu | Cl | CN | F |
| CH | CH | CH | N | i-Pr | Br | CN | F |
| CH | CH | CH | N | t-Bu | Br | CN | F |
| CH | CH | CH | N | i-Pr | Me | CF₃ | Cl |
| CH | CH | CH | N | t-Bu | Me | CF₃ | Cl |
| CH | CH | CH | N | i-Pr | Cl | CF₃ | Cl |
| CH | CH | CH | N | t-Bu | Cl | CF₃ | Cl |
| CH | CH | CH | N | i-Pr | Br | CF₃ | Cl |
| CH | CH | CH | N | t-Bu | Br | CF₃ | Cl |
| CH | CH | CH | N | i-Pr | Me | Cl | Cl |
| CH | CH | CH | N | t-Bu | Me | Cl | Cl |
| CH | CH | CH | N | i-Pr | Cl | Cl | Cl |
| CH | CH | CH | N | t-Bu | Cl | Cl | Cl |
| CH | CH | CH | N | i-Pr | Br | Cl | Cl |
| CH | CH | CH | N | t-Bu | Br | Cl | Cl |
| CH | CH | CH | N | i-Pr | Me | Br | Cl |
| CH | CH | CH | N | t-Bu | Me | Br | Cl |
| CH | CH | CH | N | i-Pr | Cl | Br | Cl |
| CH | CH | CH | N | t-Bu | Cl | Br | Cl |
| CH | CH | CH | N | i-Pr | Br | Br | Cl |
| CH | CH | CH | N | t-Bu | Br | Br | Cl |
| CH | CH | CH | N | i-Pr | Me | CN | Cl |
| CH | CH | CH | N | t-Bu | Me | CN | Cl |
| CH | CH | CH | N | i-Pr | Cl | CN | Cl |
| CH | CH | CH | N | t-Bu | Cl | CN | Cl |
| CH | CH | CH | N | i-Pr | Br | CN | Cl |
| CH | CH | CH | N | t-Bu | Br | CN | Cl |
| CH | CH | CH | N | i-Pr | Me | CF₃ | Br |
| CH | CH | CH | N | t-Bu | Me | CF₃ | Br |
| CH | CH | CH | N | i-Pr | Cl | CF₃ | Br |
| CH | CH | CH | N | t-Bu | Cl | CF₃ | Br |
| CH | CH | CH | N | i-Pr | Br | CF₃ | Br |
| CH | CH | CH | N | t-Bu | Br | CF₃ | Br |
| CH | CH | CH | N | i-Pr | Me | Cl | Br |

TABLE 2-continued

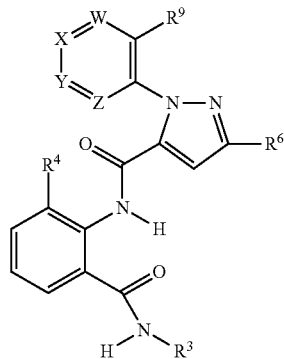

| W | X | Y | Z | R³ | R⁴ | R⁶ | R⁹ |
|---|---|---|---|---|---|---|---|
| CH | CH | CH | N | t-Bu | Me | Cl | Br |
| CH | CH | CH | N | i-Pr | Cl | Cl | Br |
| CH | CH | CH | N | t-Bu | Cl | Cl | Br |
| CH | CH | CH | N | i-Pr | Br | Cl | Br |
| CH | CH | CH | N | t-Bu | Br | Cl | Br |
| CH | CH | CH | N | i-Pr | Me | Br | Br |
| CH | CH | CH | N | t-Bu | Me | Br | Br |
| CH | CH | CH | N | i-Pr | Cl | Br | Br |
| CH | CH | CH | N | t-Bu | Cl | Br | Br |
| CH | CH | CH | N | i-Pr | Br | Br | Br |
| CH | CH | CH | N | t-Bu | Br | Br | Br |
| CH | CH | CH | N | i-Pr | Me | CN | Br |
| CH | CH | CH | N | t-Bu | Me | CN | Br |
| CH | CH | CH | N | i-Pr | Cl | CN | Br |
| CH | CH | CH | N | t-Bu | Cl | CN | Br |
| CH | CH | CH | N | i-Pr | Br | CN | Br |
| CH | CH | CH | N | t-Bu | Br | CN | Br |
| CH | CH | CH | N | i-Pr | Me | CF₃ | CN |
| CH | CH | CH | N | t-Bu | Me | CF₃ | CN |
| CH | CH | CH | N | i-Pr | Cl | CF₃ | CN |
| CH | CH | CH | N | t-Bu | Cl | CF₃ | CN |
| CH | CH | CH | N | i-Pr | Br | CF₃ | CN |
| CH | CH | CH | N | t-Bu | Br | CF₃ | CN |
| CH | CH | CH | N | i-Pr | Me | Cl | CN |
| CH | CH | CH | N | t-Bu | Me | Cl | CN |
| CH | CH | CH | N | i-Pr | Cl | Cl | CN |
| CH | CH | CH | N | t-Bu | Cl | Cl | CN |
| CH | CH | CH | N | i-Pr | Br | Cl | CN |
| CH | CH | CH | N | t-Bu | Br | Cl | CN |
| CH | CH | CH | N | i-Pr | Me | Br | CN |
| CH | CH | CH | N | t-Bu | Me | Br | CN |
| CH | CH | CH | N | i-Pr | Cl | Br | CN |
| CH | CH | CH | N | t-Bu | Cl | Br | CN |
| CH | CH | CH | N | i-Pr | Br | Br | CN |
| CH | CH | CH | N | t-Bu | Br | Br | CN |
| CH | CH | CH | N | i-Pr | Me | CN | CN |
| CH | CH | CH | N | t-Bu | Me | CN | CN |
| CH | CH | CH | N | i-Pr | Cl | CN | CN |
| CH | CH | CH | N | t-Bu | Cl | CN | CN |
| CH | CH | CH | N | i-Pr | Br | CN | CN |
| CH | CH | CH | N | t-Bu | Br | CN | CN |
| CH | CH | CH | CH | Me | Me | CF₃ | F |
| CH | CH | CH | CH | Et | Me | CF₃ | F |
| CH | CH | CH | CH | CH(CH₃)CH₂OCH₃ | Me | CF₃ | F |
| CH | CH | CH | CH | CH(CH₃)CH₂SCH₃ | Me | CF₃ | F |
| CH | CH | CH | CH | propargyl | Me | CF₃ | F |
| CH | CH | CH | CH | Me | Me | CF₃ | Cl |
| CH | CH | CH | CH | Et | Me | CF₃ | Cl |
| CH | CH | CH | CH | CH(CH₃)CH₂OCH₃ | Me | CF₃ | Cl |
| CH | CH | CH | CH | CH(CH₃)CH₂SCH₃ | Me | CF₃ | Cl |
| CH | CH | CH | CH | propargyl | Me | CF₃ | Cl |
| CH | CH | CH | CH | Me | Me | Br | F |
| CH | CH | CH | CH | Et | Me | Br | F |
| CH | CH | CH | CH | CH(CH₃)CH₂OCH₃ | Me | Br | F |
| CH | CH | CH | CH | CH(CH₃)CH₂SCH₃ | Me | Br | F |
| CH | CH | CH | CH | propargyl | Me | Br | F |
| CH | CH | CH | CH | Me | Me | Br | Cl |
| CH | CH | CH | CH | Et | Me | Br | Cl |
| CH | CH | CH | CH | CH(CH₃)CH₂OCH₃ | Me | Br | Cl |
| CH | CH | CH | CH | CH(CH₃)CH₂SCH₃ | Me | Br | Cl |

TABLE 2-continued

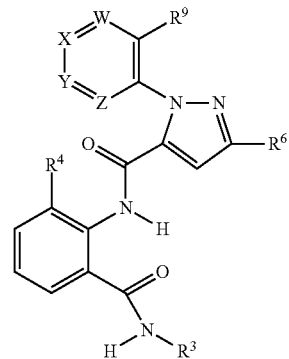

| W | X | Y | Z | R³ | R⁴ | R⁶ | R⁹ |
|---|---|---|---|---|---|---|---|
| CH | CH | CH | CH | propargyl | Me | Br | Cl |
| CH | CH | CH | CH | Me | Cl | CF₃ | F |
| CH | CH | CH | CH | Et | Cl | CF₃ | F |
| CH | CH | CH | CH | CH(CH₃)CH₂OCH₃ | Cl | CF₃ | F |
| CH | CH | CH | CH | CH(CH₃)CH₂SCH₃ | Cl | CF₃ | F |
| CH | CH | CH | CH | propargyl | Cl | CF₃ | F |
| CH | CH | CH | CH | Me | Cl | CF₃ | Cl |
| CH | CH | CH | CH | Et | Cl | CF₃ | Cl |
| CH | CH | CH | CH | CH(CH₃)CH₂OCH₃ | Cl | CF₃ | Cl |
| CH | CH | CH | CH | CH(CH₃)CH₂SCH₃ | Cl | CF₃ | Cl |
| CH | CH | CH | CH | propargyl | Cl | CF₃ | Cl |
| CH | CH | CH | CH | Me | Cl | Br | F |
| CH | CH | CH | CH | Et | Cl | Br | F |
| CH | CH | CH | CH | CH(CH₃)CH₂OCH₃ | Cl | Br | F |
| CH | CH | CH | CH | CH(CH₃)CH₂SCH₃ | Cl | Br | F |
| CH | CH | CH | CH | propargyl | Cl | Br | F |
| CH | CH | CH | CH | Me | Cl | Br | Cl |
| CH | CH | CH | CH | Et | Cl | Br | Cl |
| CH | CH | CH | CH | CH(CH₃)CH₂OCH₃ | Cl | Br | Cl |
| CH | CH | CH | CH | CH(CH₃)CH₂SCH₃ | Cl | Br | Cl |
| CH | CH | CH | CH | propargyl | Cl | Br | Cl |
| CH | CH | CH | N | Me | Me | CF₃ | F |
| CH | CH | CH | N | Et | Me | CF₃ | F |
| CH | CH | CH | N | CH(CH₃)CH₂OCH₃ | Me | CF₃ | F |
| CH | CH | CH | N | CH(CH₃)CH₂SCH₃ | Me | CF₃ | F |
| CH | CH | CH | N | propargyl | Me | CF₃ | F |
| CH | CH | CH | N | Me | Me | CF₃ | Cl |
| CH | CH | CH | N | Et | Me | CF₃ | Cl |
| CH | CH | CH | N | CH(CH₃)CH₂OCH₃ | Me | CF₃ | Cl |
| CH | CH | CH | N | CH(CH₃)CH₂SCH₃ | Me | CF₃ | Cl |
| CH | CH | CH | N | propargyl | Me | CF₃ | Cl |
| CH | CH | CH | N | Me | Me | Br | F |
| CH | CH | CH | N | Et | Me | Br | F |
| CH | CH | CH | N | CH(CH₃)CH₂OCH₃ | Me | Br | F |
| CH | CH | CH | N | CH(CH₃)CH₂SCH₃ | Me | Br | F |
| CH | CH | CH | N | propargyl | Me | Br | F |
| CH | CH | CH | N | Me | Me | Br | Cl |
| CH | CH | CH | N | Et | Me | Br | Cl |
| CH | CH | CH | N | CH(CH₃)CH₂OCH₃ | Me | Br | Cl |
| CH | CH | CH | N | CH(CH₃)CH₂SCH₃ | Me | Br | Cl |
| CH | CH | CH | N | propargyl | Me | Br | Cl |
| CH | CH | CH | N | Me | Cl | CF₃ | F |
| CH | CH | CH | N | Et | Cl | CF₃ | F |
| CH | CH | CH | N | CH(CH₃)CH₂OCH₃ | Cl | CF₃ | F |
| CH | CH | CH | N | CH(CH₃)CH₂SCH₃ | Cl | CF₃ | F |
| CH | CH | CH | N | propargyl | Cl | CF₃ | F |
| CH | CH | CH | N | Me | Cl | CF₃ | Cl |
| CH | CH | CH | N | Et | Cl | CF₃ | Cl |
| CH | CH | CH | N | CH(CH₃)CH₂OCH₃ | Cl | CF₃ | Cl |
| CH | CH | CH | N | CH(CH₃)CH₂SCH₃ | Cl | CF₃ | Cl |
| CH | CH | CH | N | propargyl | Cl | CF₃ | Cl |
| CH | CH | CH | N | Me | Cl | Br | F |
| CH | CH | CH | N | Et | Cl | Br | F |
| CH | CH | CH | N | CH(CH₃)CH₂OCH₃ | Cl | Br | F |
| CH | CH | CH | N | CH(CH₃)CH₂SCH₃ | Cl | Br | F |
| CH | CH | CH | N | propargyl | Cl | Br | F |
| CH | CH | CH | N | Me | Cl | Br | Cl |
| CH | CH | CH | N | Et | Cl | Br | Cl |
| CH | CH | CH | N | CH(CH₃)CH₂OCH₃ | Cl | Br | Cl |
| CH | CH | CH | N | CH(CH₃)CH₂SCH₃ | Cl | Br | Cl |

TABLE 2-continued

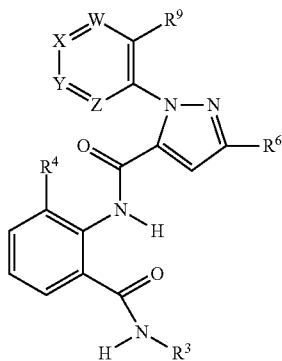

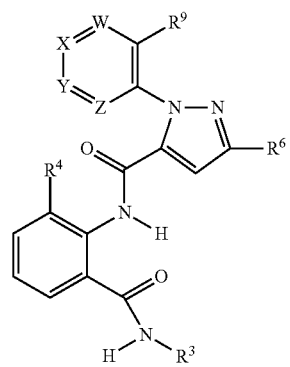

| W | X | Y | Z | R³ | R⁴ | R⁶ | R⁹ |
|---|---|---|---|---|---|---|---|
| CH | CH | CH | N | propargyl | Cl | Br | Cl |
| C—Cl | CH | CH | CH | i-Pr | Me | CF₃ | Cl |
| C—F | CH | CH | CH | i-Pr | Me | CF₃ | F |
| CH | CH | CH | CH | i-Pr | Me | CF₃ | C≡CH |
| CH | CH | CH | CH | i-Pr | Me | CF₃ | I |
| CH | CH | CH | CH | i-Pr | Me | CF₃ | SO₂Me |
| C—Cl | CH | CH | CH | i-Pr | Cl | CF₃ | Cl |
| C—F | CH | CH | CH | i-Pr | Cl | CF₃ | F |
| CH | CH | CH | CH | i-Pr | Cl | CF₃ | C≡CH |
| CH | CH | CH | CH | i-Pr | Cl | CF₃ | I |
| CH | CH | CH | CH | i-Pr | Cl | CF₃ | SO₂Me |
| C—Cl | CH | CH | CH | i-Pr | Me | Br | Cl |
| C—F | CH | CH | CH | i-Pr | Me | Br | F |
| CH | CH | CH | CH | i-Pr | Me | Br | C≡CH |
| CH | CH | CH | CH | i-Pr | Me | Br | I |
| CH | CH | CH | CH | i-Pr | Me | Br | SO₂Me |
| C—Cl | CH | CH | CH | i-Pr | Cl | Br | Cl |
| C—F | CH | CH | CH | i-Pr | Cl | Br | F |
| CH | CH | CH | CH | i-Pr | Cl | Br | C≡CH |
| CH | CH | CH | CH | i-Pr | Cl | Br | I |
| CH | CH | CH | CH | i-Pr | Cl | Br | SO₂Me |
| C—Cl | CH | CH | N | i-Pr | Me | CF₃ | Cl |
| C—F | CH | CH | N | i-Pr | Me | CF₃ | F |
| CH | CH | CH | N | i-Pr | Me | CF₃ | C≡CH |
| CH | CH | CH | N | i-Pr | Me | CF₃ | I |
| CH | CH | CH | N | i-Pr | Me | CF₃ | SO₂Me |
| C—Cl | CH | CH | N | i-Pr | Cl | CF₃ | Cl |
| C—F | CH | CH | N | i-Pr | Cl | CF₃ | F |
| CH | CH | CH | N | i-Pr | Cl | CF₃ | C≡CH |
| CH | CH | CH | N | i-Pr | Cl | CF₃ | I |
| CH | CH | CH | N | i-Pr | Cl | CF₃ | SO₂Me |
| C—Cl | CH | CH | N | i-Pr | Me | Br | Cl |
| C—F | CH | CH | N | i-Pr | Me | Br | F |
| CH | CH | CH | N | i-Pr | Me | Br | C≡CH |
| CH | CH | CH | N | i-Pr | Me | Br | I |
| CH | CH | CH | N | i-Pr | Me | Br | SO₂Me |
| C—Cl | CH | CH | N | i-Pr | Cl | Br | Cl |
| C—F | CH | CH | N | i-Pr | Cl | Br | F |
| CH | CH | CH | N | i-Pr | Cl | Br | C≡CH |
| CH | CH | CH | N | i-Pr | Cl | Br | I |
| CH | CH | CH | N | i-Pr | Cl | Br | SO₂Me |
| CH | N | CH | N | i-Pr | Me | CF₃ | H |
| CH | N | CH | N | i-Pr | Me | CF₃ | Me |
| CH | N | CH | N | i-Pr | Me | CF₃ | Cl |
| CH | N | CH | N | i-Pr | Cl | CF₃ | H |
| CH | N | CH | N | i-Pr | Cl | CF₃ | Me |
| CH | N | CH | N | i-Pr | Cl | CF₃ | Cl |
| CH | N | CH | N | i-Pr | Me | CN | H |
| CH | N | CH | N | i-Pr | Me | CN | Me |
| CH | N | CH | N | i-Pr | Me | CN | Cl |
| CH | N | CH | N | i-Pr | Cl | CN | H |
| CH | N | CH | N | i-Pr | Cl | CN | Me |
| CH | N | CH | N | i-Pr | Cl | CN | Cl |
| CH | N | CH | N | i-Pr | Me | Br | H |
| CH | N | CH | N | i-Pr | Me | Br | Me |
| CH | N | CH | N | i-Pr | Me | Br | Cl |
| CH | N | CH | N | i-Pr | Cl | Br | H |
| CH | N | CH | N | i-Pr | Cl | Br | Me |
| CH | N | CH | N | i-Pr | Cl | Br | Cl |
| CH | N | CH | N | t-Bu | Me | CF₃ | H |
| CH | N | CH | N | t-Bu | Me | CF₃ | Me |
| CH | N | CH | N | t-Bu | Me | CF₃ | Cl |
| CH | N | CH | N | t-Bu | Cl | CF₃ | H |
| CH | N | CH | N | t-Bu | Cl | CF₃ | Me |
| CH | N | CH | N | t-Bu | Cl | CF₃ | Cl |
| CH | N | CH | N | t-Bu | Me | CN | H |
| CH | N | CH | N | t-Bu | Me | CN | Me |
| CH | N | CH | N | t-Bu | Me | CN | Cl |
| CH | N | CH | N | t-Bu | Cl | CN | H |
| CH | N | CH | N | t-Bu | Cl | CN | Me |
| CH | N | CH | N | t-Bu | Cl | CN | Cl |
| CH | N | CH | N | t-Bu | Me | Br | H |
| CH | N | CH | N | t-Bu | Me | Br | Me |
| CH | N | CH | N | t-Bu | Me | Br | Cl |
| CH | N | CH | N | t-Bu | Cl | Br | H |
| CH | N | CH | N | t-Bu | Cl | Br | Me |
| CH | N | CH | N | t-Bu | Cl | Br | Cl |
| CH | CH | N | N | i-Pr | Me | CF₃ | H |
| CH | CH | N | N | i-Pr | Me | CF₃ | Me |
| CH | CH | N | N | i-Pr | Me | CF₃ | Cl |
| CH | CH | N | N | i-Pr | Cl | CF₃ | H |
| CH | CH | N | N | i-Pr | Cl | CF₃ | Me |
| CH | CH | N | N | i-Pr | Cl | CF₃ | Cl |
| CH | CH | N | N | i-Pr | Me | CN | H |
| CH | CH | N | N | i-Pr | Me | CN | Me |
| CH | CH | N | N | i-Pr | Me | CN | Cl |
| CH | CH | N | N | i-Pr | Cl | CN | H |
| CH | CH | N | N | i-Pr | Cl | CN | Me |
| CH | CH | N | N | i-Pr | Cl | CN | Cl |
| CH | CH | N | N | i-Pr | Me | Br | H |
| CH | CH | N | N | i-Pr | Me | Br | Me |
| CH | CH | N | N | i-Pr | Me | Br | Cl |
| CH | CH | N | N | i-Pr | Cl | Br | H |
| CH | CH | N | N | i-Pr | Cl | Br | Me |
| CH | CH | N | N | i-Pr | Cl | Br | Cl |
| CH | CH | N | N | i-Pr | Me | CF₃ | H |
| CH | CH | N | N | i-Pr | Me | CF₃ | Me |
| CH | CH | N | N | i-Pr | Me | CF₃ | Cl |
| CH | CH | N | N | i-Pr | Cl | CF₃ | H |
| CH | CH | N | N | i-Pr | Cl | CF₃ | Me |
| CH | CH | N | N | i-Pr | Cl | CF₃ | Cl |
| CH | CH | N | N | i-Pr | Me | CN | H |
| CH | CH | N | N | i-Pr | Me | CN | Me |
| CH | CH | N | N | i-Pr | Me | CN | Cl |
| CH | CH | N | N | i-Pr | Cl | CN | H |
| CH | CH | N | N | i-Pr | Cl | CN | Me |
| CH | CH | N | N | i-Pr | Cl | CN | Cl |
| CH | CH | N | N | i-Pr | Me | Br | H |
| CH | CH | N | N | i-Pr | Me | Br | Me |
| CH | CH | N | N | i-Pr | Me | Br | Cl |
| CH | CH | N | N | i-Pr | Cl | Br | H |
| CH | CH | N | N | i-Pr | Cl | Br | Me |
| CH | CH | N | N | i-Pr | Cl | Br | Cl |

TABLE 3

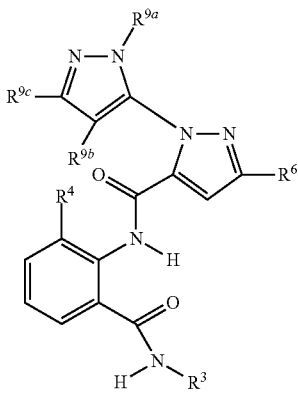

| R⁴ | R⁶ | R³ | R⁹ᵃ | R⁹ᵇ | R⁹ᶜ | R⁴ | R⁶ | R³ | R⁹ᵃ | R⁹ᵇ | R⁹ᶜ |
|---|---|---|---|---|---|---|---|---|---|---|---|
| Me | CF₃ | i-Pr | Me | H | H | Me | CF₃ | t-Bu | Me | H | H |
| Me | CF₃ | i-Pr | Me | H | Me | Me | CF₃ | t-Bu | Me | H | Me |
| Me | CF₃ | i-Pr | Me | Cl | H | Me | CF₃ | t-Bu | Me | Cl | H |
| Me | CF₃ | i-Pr | Me | Cl | Me | Me | CF₃ | t-Bu | Me | Cl | Me |
| Me | CF₃ | i-Pr | Me | Me | Me | Me | CF₃ | t-Bu | Me | Me | Me |
| Cl | CF₃ | i-Pr | Me | H | H | Cl | CF₃ | t-Bu | Me | H | H |
| Cl | CF₃ | i-Pr | Me | H | Me | Cl | CF₃ | t-Bu | Me | H | Me |
| Cl | CF₃ | i-Pr | Me | Cl | H | Cl | CF₃ | t-Bu | Me | Cl | H |
| Cl | CF₃ | i-Pr | Me | Cl | Me | Cl | CF₃ | t-Bu | Me | Cl | Me |
| Cl | CF₃ | i-Pr | Me | Me | Me | Cl | CF₃ | t-Bu | Me | Me | Me |

TABLE 4

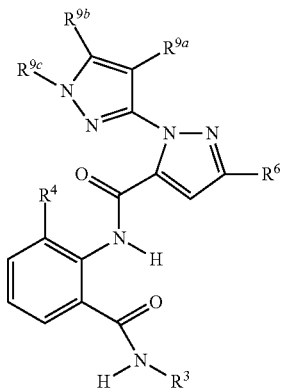

| R⁴ | R⁶ | R³ | R⁹ᵃ | R⁹ᵇ | R⁹ᶜ | R⁴ | R⁶ | R³ | R⁹ᵃ | R⁹ᵇ | R⁹ᶜ |
|---|---|---|---|---|---|---|---|---|---|---|---|
| Me | CF₃ | i-Pr | Me | H | Me | Me | CF₃ | t-Bu | Me | H | Me |
| Me | CF₃ | i-Pr | Me | Me | Me | Me | CF₃ | t-Bu | Me | Me | Me |
| Me | CF₃ | i-Pr | Cl | H | Me | Me | CF₃ | t-Bu | Cl | H | Me |
| Me | CF₃ | i-Pr | Cl | Me | Me | Me | CF₃ | t-Bu | Cl | Me | Me |
| Cl | CF₃ | i-Pr | Me | H | Me | Cl | CF₃ | t-Bu | Me | H | Me |
| Cl | CF₃ | i-Pr | Me | Me | Me | Cl | CF₃ | t-Bu | Me | Me | Me |
| Cl | CF₃ | i-Pr | Cl | H | Me | Cl | CF₃ | t-Bu | Cl | H | Me |
| Cl | CF₃ | i-Pr | Cl | Me | Me | Cl | CF₃ | t-Bu | Cl | Me | Me |

TABLE 5

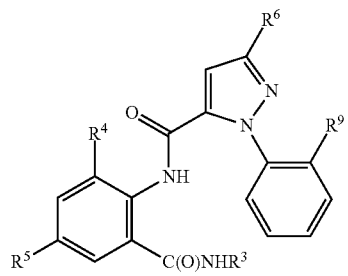

| R⁴ | R⁵ | R⁶ | R³ | R⁹ | R⁴ | R⁵ | R⁶ | R³ | R⁹ |
|---|---|---|---|---|---|---|---|---|---|
| CH₃ | F | CF₃ | Me | Cl | Cl | Br | Cl | Me | Br |
| CH₃ | F | CF₃ | Et | Cl | Cl | Br | Cl | Et | Br |
| CH₃ | F | CF₃ | i-Pr | Cl | Cl | Br | Cl | i-Pr | Br |
| CH₃ | F | CF₃ | t-Bu | Cl | Cl | Br | Cl | t-Bu | Br |
| CH₃ | F | CF₃ | Me | Br | Cl | Br | Br | Me | Cl |
| CH₃ | F | CF₃ | Et | Br | Cl | Br | Br | Et | Cl |
| CH₃ | F | CF₃ | i-Pr | Br | Cl | Br | Br | i-Pr | Cl |
| CH₃ | F | CF₃ | t-Bu | Br | Cl | Br | Br | t-Bu | Cl |
| CH₃ | F | Cl | Me | Cl | Cl | Br | Br | Me | Br |
| CH₃ | F | Cl | Et | Cl | Cl | Br | Br | Et | Br |
| CH₃ | F | Cl | i-Pr | Cl | Cl | Br | Br | i-Pr | Br |
| CH₃ | F | Cl | t-Bu | Cl | Cl | Br | Br | t-Bu | Br |
| CH₃ | F | Cl | Me | Br | Cl | I | CF₃ | Me | Cl |
| CH₃ | F | Cl | Et | Br | Cl | I | CF₃ | Et | Cl |
| CH₃ | F | Cl | i-Pr | Br | Cl | I | CF₃ | i-Pr | Cl |
| CH₃ | F | Cl | t-Bu | Br | Cl | I | CF₃ | t-Bu | Cl |
| CH₃ | F | Br | Me | Cl | Cl | I | CF₃ | Me | Br |
| CH₃ | F | Br | Et | Cl | Cl | I | CF₃ | Et | Br |
| CH₃ | F | Br | i-Pr | Cl | Cl | I | CF₃ | i-Pr | Br |
| CH₃ | F | Br | t-Bu | Cl | Cl | I | CF₃ | t-Bu | Br |
| CH₃ | F | Br | Me | Br | Cl | I | Cl | Me | Cl |
| CH₃ | F | Br | Et | Br | Cl | I | Cl | Et | Cl |
| CH₃ | F | Br | i-Pr | Br | Cl | I | Cl | i-Pr | Cl |
| CH₃ | F | Br | t-Bu | Br | Cl | I | Cl | t-Bu | Cl |
| CH₃ | Cl | CF₃ | Me | Cl | Cl | I | Cl | Me | Br |
| CH₃ | Cl | CF₃ | Et | Cl | Cl | I | Cl | Et | Br |
| CH₃ | Cl | CF₃ | i-Pr | Cl | Cl | I | Cl | i-Pr | Br |
| CH₃ | Cl | CF₃ | t-Bu | Cl | Cl | I | Cl | t-Bu | Br |
| CH₃ | Cl | CF₃ | Me | Br | Cl | I | Br | Me | Cl |
| CH₃ | Cl | CF₃ | Et | Br | Cl | I | Br | Et | Cl |
| CH₃ | Cl | CF₃ | i-Pr | Br | Cl | I | Br | i-Pr | Cl |
| CH₃ | Cl | CF₃ | t-Bu | Br | Cl | I | Br | t-Bu | Cl |
| CH₃ | Cl | Cl | Me | Cl | Cl | I | Br | Me | Br |
| CH₃ | Cl | Cl | Et | Cl | Cl | I | Br | Et | Br |
| CH₃ | Cl | Cl | i-Pr | Cl | Cl | I | Br | i-Pr | Br |
| CH₃ | Cl | Cl | t-Bu | Cl | Cl | I | Br | t-Bu | Br |
| CH₃ | Cl | Cl | Me | Br | Cl | CF₃ | CF₃ | Me | Br |
| CH₃ | Cl | Cl | Et | Br | Cl | CF₃ | CF₃ | Et | Cl |
| CH₃ | Cl | Cl | i-Pr | Br | Cl | CF₃ | CF₃ | i-Pr | Cl |
| CH₃ | Cl | Cl | t-Bu | Br | Cl | CF₃ | CF₃ | t-Bu | Cl |
| CH₃ | Cl | Br | Me | Cl | Cl | CF₃ | CF₃ | Me | Br |
| CH₃ | Cl | Br | Et | Cl | Cl | CF₃ | CF₃ | Et | Cl |
| CH₃ | Cl | Br | i-Pr | Cl | Cl | CF₃ | CF₃ | i-Pr | Cl |
| CH₃ | Cl | Br | t-Bu | Cl | Cl | CF₃ | CF₃ | t-Bu | Br |
| CH₃ | Cl | Br | Me | Br | Cl | CF₃ | Cl | Me | Cl |
| CH₃ | Cl | Br | Et | Br | Cl | CF₃ | Cl | Et | Cl |
| CH₃ | Cl | Br | i-Pr | Br | Cl | CF₃ | Cl | i-Pr | Cl |
| CH₃ | Cl | Br | t-Bu | Br | Cl | CF₃ | Cl | t-Bu | Cl |
| CH₃ | Br | CF₃ | Me | Cl | Cl | CF₃ | Cl | Me | Br |
| CH₃ | Br | CF₃ | Et | Cl | Cl | CF₃ | Cl | Et | Br |
| CH₃ | Br | CF₃ | i-Pr | Cl | Cl | CF₃ | Cl | i-Pr | Br |
| CH₃ | Br | CF₃ | t-Bu | Cl | Cl | CF₃ | Cl | t-Bu | Br |
| CH₃ | Br | CF₃ | Me | Br | Cl | CF₃ | Br | Me | Cl |
| CH₃ | Br | CF₃ | Et | Br | Cl | CF₃ | Br | Et | Cl |
| CH₃ | Br | CF₃ | i-Pr | Br | Cl | CF₃ | Br | i-Pr | Cl |
| CH₃ | Br | CF₃ | t-Bu | Br | Cl | CF₃ | Br | t-Bu | Cl |
| CH₃ | Br | Cl | Me | Cl | Cl | CF₃ | Br | Me | Br |
| CH₃ | Br | Cl | Et | Cl | Cl | CF₃ | Br | Et | Br |
| CH₃ | Br | Cl | i-Pr | Cl | Cl | CF₃ | Br | i-Pr | Br |
| CH₃ | Br | Cl | t-Bu | Cl | Cl | CF₃ | Br | t-Bu | Br |
| CH₃ | Br | Cl | Me | Br | Cl | Cl | Br | Me | Br |
| CH₃ | Br | Cl | Et | Br | Cl | Cl | Br | Et | Br |
| CH₃ | Br | Cl | i-Pr | Br | Cl | Cl | Br | i-Pr | Br |
| CH₃ | Br | Cl | t-Bu | Br | Cl | Cl | Br | t-Bu | Br |
| CH₃ | Br | Cl | Me | Cl | Cl | Cl | Br | n-Pr | Cl |
| CH₃ | Br | Cl | Et | Cl | Cl | Cl | Br | n-Bu | Cl |
| CH₃ | Br | Cl | i-Pr | Cl | Cl | Cl | Br | s-Bu | Cl |
| CH₃ | Br | Cl | t-Bu | Cl | Cl | Cl | Br | i-Pr | Cl |

TABLE 5-continued

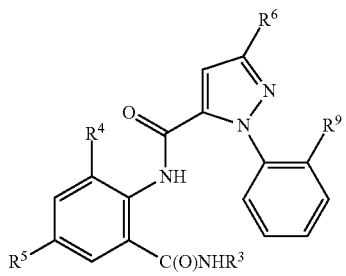

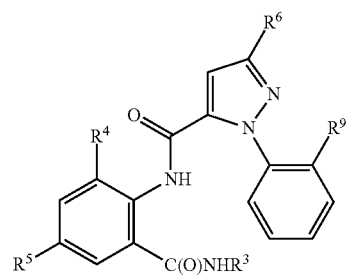

| R⁴ | R⁵ | R⁶ | R³ | R⁹ | R⁴ | R⁵ | R⁶ | R³ | R⁹ |
|---|---|---|---|---|---|---|---|---|---|
| CH₃ | Br | Br | Me | Cl | Br | F | CF₃ | Me | Cl |
| CH₃ | Br | Br | Et | Cl | Br | F | CF₃ | Et | Cl |
| CH₃ | Br | Br | i-Pr | Cl | Br | F | CF₃ | i-Pr | Cl |
| CH₃ | Br | Br | t-Bu | Cl | Br | F | CF₃ | t-Bu | Cl |
| CH₃ | Br | Br | Me | Br | Br | F | CF₃ | Me | Br |
| CH₃ | Br | Br | Et | Br | Br | F | CF₃ | Et | Br |
| CH₃ | Br | Br | i-Pr | Br | Br | F | CF₃ | i-Pr | Br |
| CH₃ | Br | Br | t-Bu | Br | Br | F | CF₃ | t-Bu | Br |
| CH₃ | I | CF₃ | Me | Cl | Br | F | Cl | Me | Cl |
| CH₃ | I | CF₃ | Et | Cl | Br | F | Cl | Et | Cl |
| CH₃ | I | CF₃ | i-Pr | Cl | Br | F | Cl | i-Pr | Cl |
| CH₃ | I | CF₃ | t-Bu | Cl | Br | F | Cl | t-Bu | Cl |
| CH₃ | I | CF₃ | Me | Br | Br | F | Cl | Me | Br |
| CH₃ | I | CF₃ | Et | Br | Br | F | Cl | Et | Br |
| CH₃ | I | CF₃ | i-Pr | Br | Br | F | Cl | i-Pr | Br |
| CH₃ | I | CF₃ | t-Bu | Br | Br | F | Cl | t-Bu | Br |
| CH₃ | I | Cl | Me | Cl | Br | F | Br | Me | Cl |
| CH₃ | I | Cl | Et | Cl | Br | F | Br | Et | Cl |
| CH₃ | I | Cl | i-Pr | Cl | Br | F | Br | i-Pr | Cl |
| CH₃ | I | Cl | t-Bu | Cl | Br | F | Br | t-Bu | Cl |
| CH₃ | I | Cl | Me | Br | Br | F | Br | Me | Br |
| CH₃ | I | Cl | Et | Br | Br | F | Br | Et | Br |
| CH₃ | I | Cl | i-Pr | Br | Br | F | Br | i-Pr | Br |
| CH₃ | I | Cl | t-Bu | Br | Br | F | Br | t-Bu | Br |
| CH₃ | I | Br | Me | Cl | Br | Cl | CF₃ | Me | Cl |
| CH₃ | I | Br | Et | Cl | Br | Cl | CF₃ | Et | Cl |
| CH₃ | I | Br | i-Pr | Cl | Br | Cl | CF₃ | i-Pr | Cl |
| CH₃ | I | Br | t-Bu | Cl | Br | Cl | CF₃ | t-Bu | Cl |
| CH₃ | I | Br | Me | Br | Br | Cl | CF₃ | Me | Br |
| CH₃ | I | Br | Et | Br | Br | Cl | CF₃ | Et | Br |
| CH₃ | I | Br | i-Pr | Br | Br | Cl | CF₃ | i-Pr | Br |
| CH₃ | I | Br | t-Bu | Br | Br | Cl | CF₃ | t-Bu | Br |
| CH₃ | CF₃ | CF₃ | Me | Cl | Br | Cl | Cl | Me | Cl |
| CH₃ | CF₃ | CF₃ | Et | Cl | Br | Cl | Cl | Et | Cl |
| CH₃ | CF₃ | CF₃ | i-Pr | Cl | Br | Cl | Cl | i-Pr | Cl |
| CH₃ | CF₃ | CF₃ | t-Bu | Cl | Br | Cl | Cl | t-Bu | Cl |
| CH₃ | CF₃ | CF₃ | Me | Br | Br | Cl | Cl | Me | Br |
| CH₃ | CF₃ | CF₃ | Et | Br | Br | Cl | Cl | Et | Br |
| CH₃ | CF₃ | CF₃ | i-Pr | Br | Br | Cl | Cl | i-Pr | Br |
| CH₃ | CF₃ | CF₃ | t-Bu | Br | Br | Cl | Cl | t-Bu | Br |
| CH₃ | CF₃ | Cl | Me | Cl | Br | Cl | Br | Me | Cl |
| CH₃ | CF₃ | Cl | Et | Cl | Br | Cl | Br | Et | Cl |
| CH₃ | CF₃ | Cl | i-Pr | Cl | Br | Cl | Br | i-Pr | Cl |
| CH₃ | CF₃ | Cl | t-Bu | Cl | Br | Cl | Br | t-Bu | Cl |
| CH₃ | CF₃ | Cl | Me | Br | Br | Cl | Br | Me | Br |
| CH₃ | CF₃ | Cl | Et | Br | Br | Cl | Br | Et | Br |
| CH₃ | CF₃ | Cl | i-Pr | Br | Br | Cl | Br | i-Pr | Br |
| CH₃ | CF₃ | Cl | t-Bu | Br | Br | Cl | Br | t-Bu | Br |
| CH₃ | CF₃ | Br | Me | Cl | Br | Br | CF₃ | Me | Cl |
| CH₃ | CF₃ | Br | Et | Cl | Br | Br | CF₃ | Et | Cl |
| CH₃ | CF₃ | Br | i-Pr | Cl | Br | Br | CF₃ | i-Pr | Cl |
| CH₃ | CF₃ | Br | t-Bu | Cl | Br | Br | CF₃ | t-Bu | Cl |
| CH₃ | CF₃ | Br | Me | Br | Br | Br | CF₃ | Me | Br |
| CH₃ | CF₃ | Br | Et | Br | Br | Br | CF₃ | Et | Br |
| CH₃ | CF₃ | Br | i-Pr | Br | Br | Br | CF₃ | i-Pr | Br |
| CH₃ | CF₃ | Br | t-Bu | Br | Br | Br | CF₃ | t-Bu | Br |
| CH₃ | Cl | Cl | n-Pr | Cl | Br | Br | Cl | Me | Cl |
| CH₃ | Cl | Cl | n-Bu | Cl | Br | Br | Cl | Et | Cl |
| CH₃ | Cl | Cl | s-Bu | Cl | Br | Br | Cl | i-Pr | Cl |
| CH₃ | Cl | Cl | i-Bu | Cl | Br | Br | Cl | t-Bu | Cl |
| Cl | F | CF₃ | Me | Br | Br | Br | Cl | Me | Br |
| Cl | F | CF₃ | Et | Br | Br | Br | Cl | Et | Br |
| Cl | F | CF₃ | i-Pr | Br | Br | Br | Cl | i-Pr | Br |
| Cl | F | CF₃ | t-Bu | Br | Br | Br | Cl | t-Bu | Br |

| R⁴ | R⁵ | R⁶ | R³ | R⁹ | R⁴ | R⁵ | R⁶ | R³ | R⁹ |
|---|---|---|---|---|---|---|---|---|---|
| Cl | F | CF₃ | Me | Br | Br | Br | Br | Me | Cl |
| Cl | F | CF₃ | Et | Br | Br | Br | Br | Et | Cl |
| Cl | F | CF₃ | i-Pr | Br | Br | Br | Br | i-Pr | Cl |
| Cl | F | CF₃ | t-Bu | Br | Br | Br | Br | t-Bu | Cl |
| Cl | F | Cl | Me | Cl | Br | Br | Br | Me | Br |
| Cl | F | Cl | Et | Cl | Br | Br | Br | Et | Br |
| Cl | F | Cl | i-Pr | Cl | Br | Br | Br | i-Pr | Br |
| Cl | F | Cl | t-Bu | Cl | Br | Br | Br | t-Bu | Br |
| Cl | F | Cl | Me | Br | Br | I | CF₃ | Me | Cl |
| Cl | F | Cl | Et | Br | Br | I | CF₃ | Et | Cl |
| Cl | F | Cl | i-Pr | Br | Br | I | CF₃ | i-Pr | Cl |
| Cl | F | Cl | t-Bu | Br | Br | I | CF₃ | t-Bu | Cl |
| Cl | F | Br | Me | Cl | Br | I | CF₃ | Me | Br |
| Cl | F | Br | Et | Cl | Br | I | CF₃ | Et | Br |
| Cl | F | Br | i-Pr | Cl | Br | I | CF₃ | i-Pr | Br |
| Cl | F | Br | t-Bu | Cl | Br | I | CF₃ | t-Bu | Br |
| Cl | F | Br | Me | Br | Br | I | Cl | Me | Cl |
| Cl | F | Br | Et | Br | Br | I | Cl | Et | Cl |
| Cl | F | Br | i-Pr | Br | Br | I | Cl | i-Pr | Cl |
| Cl | F | Br | t-Bu | Br | Br | I | Cl | t-Bu | Cl |
| Cl | Cl | CF₃ | Me | Cl | Br | I | Cl | Me | Br |
| Cl | Cl | CF₃ | Et | Cl | Br | I | Cl | Et | Br |
| Cl | Cl | CF₃ | i-Pr | Cl | Br | I | Cl | i-Pr | Br |
| Cl | Cl | CF₃ | t-Bu | Cl | Br | I | Cl | t-Bu | Br |
| Cl | Cl | CF₃ | Me | Br | Br | I | Br | Me | Cl |
| Cl | Cl | CF₃ | Et | Br | Br | I | Br | Et | Cl |
| Cl | Cl | CF₃ | i-Pr | Br | Br | I | Br | i-Pr | Cl |
| Cl | Cl | CF₃ | t-Bu | Br | Br | I | Br | t-Bu | Cl |
| Cl | Cl | Cl | Me | Cl | Br | I | Br | Me | Br |
| Cl | Cl | Cl | Et | Cl | Br | I | Br | Et | Br |
| Cl | Cl | Cl | i-Pr | Cl | Br | I | Br | i-Pr | Br |
| Cl | Cl | Cl | t-Bu | Cl | Br | I | Br | t-Bu | Br |
| Cl | Cl | Cl | Me | Br | Br | CF₃ | CF₃ | Me | Cl |
| Cl | Cl | Cl | Et | Br | Br | CF₃ | CF₃ | Et | Cl |
| Cl | Cl | Cl | i-Pr | Br | Br | CF₃ | CF₃ | i-Pr | Cl |
| Cl | Cl | Cl | t-Bu | Br | Br | CF₃ | CF₃ | t-Bu | Cl |
| Cl | Cl | Br | Me | Cl | Br | CF₃ | CF₃ | Me | Br |
| Cl | Cl | Br | Et | Cl | Br | CF₃ | CF₃ | Et | Br |
| Cl | Cl | Br | i-Pr | Cl | Br | CF₃ | CF₃ | i-Pr | Br |
| Cl | Cl | Br | t-Bu | Cl | Br | CF₃ | CF₃ | t-Bu | Br |
| Cl | Cl | Br | Me | Br | Br | CF₃ | Cl | Me | Cl |
| Cl | Cl | Br | Et | Br | Br | CF₃ | Cl | Et | Cl |
| Cl | Cl | Br | i-Pr | Br | Br | CF₃ | Cl | i-Pr | Cl |
| Cl | Cl | Br | t-Bu | Br | Br | CF₃ | Cl | t-Bu | Cl |
| Cl | Br | CF₃ | Me | Cl | Br | CF₃ | Cl | Me | Br |
| Cl | Br | CF₃ | Et | Cl | Br | CF₃ | Cl | Et | Br |
| Cl | Br | CF₃ | i-Pr | Cl | Br | CF₃ | Cl | i-Pr | Br |
| Cl | Br | CF₃ | t-Bu | Cl | Br | CF₃ | Cl | t-Bu | Br |
| Cl | Br | CF₃ | Me | Br | Br | CF₃ | Br | Me | Cl |
| Cl | Br | CF₃ | Et | Br | Br | CF₃ | Br | Et | Cl |
| Cl | Br | CF₃ | i-Pr | Br | Br | CF₃ | Br | i-Pr | Cl |
| Cl | Br | CF₃ | t-Bu | Br | Br | CF₃ | Br | t-Bu | Cl |
| Cl | Br | Cl | Me | Cl | Br | CF₃ | Br | Me | Br |
| Cl | Br | Cl | Et | Cl | Br | CF₃ | Br | Et | Br |
| Cl | Br | Cl | i-Pr | Cl | Br | CF₃ | Br | i-Pr | Br |
| Cl | Br | Cl | t-Bu | Cl | Br | CF₃ | Br | t-Bu | Br |

TABLE 6

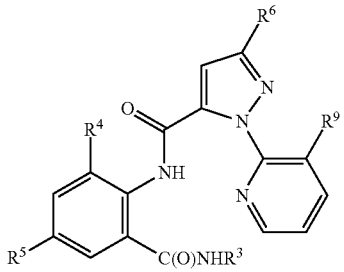

| R⁴ | R⁵ | R⁶ | R³ | R⁹ | R⁴ | R⁵ | R⁶ | R³ | R⁹ |
|---|---|---|---|---|---|---|---|---|---|
| CH₃ | F | CF₃ | Me | Cl | Cl | Br | Cl | Me | Br |
| CH₃ | F | CF₃ | Et | Cl | Cl | Br | Cl | Et | Br |
| CH₃ | F | CF₃ | i-Pr | Cl | Cl | Br | Cl | i-Pr | Br |
| CH₃ | F | CF₃ | t-Bu | Cl | Cl | Br | Cl | t-Bu | Br |
| CH₃ | F | CF₃ | Me | Br | Cl | Br | Br | Me | Cl |
| CH₃ | F | CF₃ | Et | Br | Cl | Br | Br | Et | Cl |
| CH₃ | F | CF₃ | i-Pr | Br | Cl | Br | Br | i-Pr | Cl |
| CH₃ | F | CF₃ | t-Bu | Br | Cl | Br | Br | t-Bu | Cl |
| CH₃ | F | Cl | Me | Cl | Cl | Br | Br | Me | Br |
| CH₃ | F | Cl | Et | Cl | Cl | Br | Br | Et | Br |
| CH₃ | F | Cl | i-Pr | Cl | Cl | Br | Br | i-Pr | Br |
| CH₃ | F | Cl | t-Bu | Cl | Cl | Br | Br | t-Bu | Br |
| CH₃ | F | Cl | Me | Br | Cl | I | CF₃ | Me | Cl |
| CH₃ | F | Cl | Et | Br | Cl | I | CF₃ | Et | Cl |
| CH₃ | F | Cl | i-Pr | Br | Cl | I | CF₃ | i-Pr | Cl |
| CH₃ | F | Cl | t-Bu | Br | Cl | I | CF₃ | t-Bu | Cl |
| CH₃ | F | Br | Me | Cl | Cl | I | CF₃ | Me | Br |
| CH₃ | F | Br | Et | Cl | Cl | I | CF₃ | Et | Br |
| CH₃ | F | Br | i-Pr | Cl | Cl | I | CF₃ | i-Pr | Br |
| CH₃ | F | Br | t-Bu | Cl | Cl | I | CF₃ | t-Bu | Br |
| CH₃ | F | Br | Me | Br | Cl | I | Cl | Me | Cl |
| CH₃ | F | Br | Et | Br | Cl | I | Cl | Et | Cl |
| CH₃ | F | Br | i-Pr | Br | Cl | I | Cl | i-Pr | Cl |
| CH₃ | F | Br | t-Bu | Br | Cl | I | Cl | t-Bu | Cl |
| CH₃ | Cl | CF₃ | Me | Cl | Cl | I | Cl | Me | Br |
| CH₃ | Cl | CF₃ | Et | Cl | Cl | I | Cl | Et | Br |
| CH₃ | Cl | CF₃ | i-Pr | Cl | Cl | I | Cl | i-Pr | Br |
| CH₃ | Cl | CF₃ | t-Bu | Cl | Cl | I | Cl | t-Bu | Br |
| CH₃ | Cl | CF₃ | Me | Br | Cl | I | Br | Me | Cl |
| CH₃ | Cl | CF₃ | Et | Br | Cl | I | Br | Et | Cl |
| CH₃ | Cl | CF₃ | i-Pr | Br | Cl | I | Br | i-Pr | Cl |
| CH₃ | Cl | CF₃ | t-Bu | Br | Cl | I | Br | t-Bu | Cl |
| CH₃ | Cl | Cl | Me | Cl | Cl | I | Br | Me | Br |
| CH₃ | Cl | Cl | Et | Cl | Cl | I | Br | Et | Br |
| CH₃ | Cl | Cl | i-Pr | Cl | Cl | I | Br | i-Pr | Br |
| CH₃ | Cl | Cl | t-Bu | Cl | Cl | I | Br | t-Bu | Br |
| CH₃ | Cl | Cl | Me | Br | CF₃ | CF₃ | CF₃ | Me | Cl |
| CH₃ | Cl | Cl | Et | Br | CF₃ | CF₃ | CF₃ | Et | Cl |
| CH₃ | Cl | Cl | i-Pr | Br | CF₃ | CF₃ | CF₃ | i-Pr | Cl |
| CH₃ | Cl | Cl | t-Bu | Br | CF₃ | CF₃ | CF₃ | t-Bu | Cl |
| CH₃ | Cl | Br | Me | Cl | CF₃ | CF₃ | CF₃ | Me | Br |
| CH₃ | Cl | Br | Et | Cl | CF₃ | CF₃ | CF₃ | Et | Br |
| CH₃ | Cl | Br | i-Pr | Cl | CF₃ | CF₃ | CF₃ | i-Pr | Br |
| CH₃ | Cl | Br | t-Bu | Cl | CF₃ | CF₃ | CF₃ | t-Bu | Br |
| CH₃ | Cl | Br | Me | Br | CF₃ | CF₃ | Cl | Me | Cl |
| CH₃ | Cl | Br | Et | Br | CF₃ | CF₃ | Cl | Et | Cl |
| CH₃ | Cl | Br | i-Pr | Br | CF₃ | CF₃ | Cl | i-Pr | Cl |
| CH₃ | Cl | Br | t-Bu | Br | CF₃ | CF₃ | Cl | t-Bu | Cl |
| CH₃ | Br | CF₃ | Me | Cl | CF₃ | CF₃ | Cl | Me | Br |
| CH₃ | Br | CF₃ | Et | Cl | CF₃ | CF₃ | Cl | Et | Br |
| CH₃ | Br | CF₃ | i-Pr | Cl | CF₃ | CF₃ | Cl | i-Pr | Br |
| CH₃ | Br | CF₃ | t-Bu | Cl | CF₃ | CF₃ | Cl | t-Bu | Br |
| CH₃ | Br | CF₃ | Me | Br | CF₃ | CF₃ | Br | Me | Cl |
| CH₃ | Br | CF₃ | Et | Br | CF₃ | CF₃ | Br | Et | Cl |
| CH₃ | Br | CF₃ | i-Pr | Br | CF₃ | CF₃ | Br | i-Pr | Cl |
| CH₃ | Br | CF₃ | t-Bu | Br | CF₃ | CF₃ | Br | t-Bu | Cl |
| CH₃ | Br | Cl | Me | Cl | CH₃ | Cl | Cl | n-Pr | Cl |
| CH₃ | Br | Cl | Et | Cl | CH₃ | Cl | Cl | n-Bu | Cl |
| CH₃ | Br | Cl | i-Pr | Cl | CH₃ | Cl | Cl | s-Bu | Cl |
| CH₃ | Br | Cl | t-Bu | Cl | CH₃ | Cl | Cl | i-Bu | Cl |
| CH₃ | Br | Cl | Me | Br | Cl | F | CF₃ | Me | Cl |
| CH₃ | Br | Cl | Et | Br | Cl | F | CF₃ | Et | Cl |
| CH₃ | Br | Cl | i-Pr | Br | Cl | F | CF₃ | i-Pr | Cl |
| CH₃ | Br | Cl | t-Bu | Br | Cl | F | CF₃ | t-Bu | Cl |

TABLE 6-continued

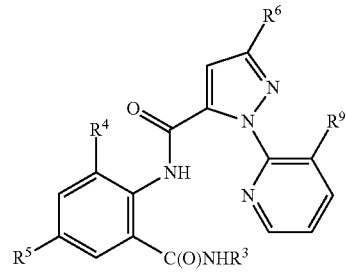

| R⁴ | R⁵ | R⁶ | R³ | R⁹ | R⁴ | R⁵ | R⁶ | R³ | R⁹ |
|---|---|---|---|---|---|---|---|---|---|
| CH₃ | Br | Br | Me | Cl | Br | F | CF₃ | Me | Cl |
| CH₃ | Br | Br | Et | Cl | Br | F | CF₃ | Et | Cl |
| CH₃ | Br | Br | i-Pr | Cl | Br | F | CF₃ | i-Pr | Cl |
| CH₃ | Br | Br | t-Bu | Cl | Br | F | CF₃ | t-Bu | Cl |
| CH₃ | Br | Br | Me | Br | Br | F | CF₃ | Me | Br |
| CH₃ | Br | Br | Et | Br | Br | F | CF₃ | Et | Br |
| CH₃ | Br | Br | i-Pr | Br | Br | F | CF₃ | i-Pr | Br |
| CH₃ | Br | Br | t-Bu | Br | Br | F | CF₃ | t-Bu | Br |
| CH₃ | I | CF₃ | Me | Cl | Br | F | Cl | Me | Cl |
| CH₃ | I | CF₃ | Et | Cl | Br | F | Cl | Et | Cl |
| CH₃ | I | CF₃ | i-Pr | Cl | Br | F | Cl | i-Pr | Cl |
| CH₃ | I | CF₃ | t-Bu | Cl | Br | F | Cl | t-Bu | Cl |
| CH₃ | I | CF₃ | Me | Br | Br | F | Cl | Me | Br |
| CH₃ | I | CF₃ | Et | Br | Br | F | Cl | Et | Br |
| CH₃ | I | CF₃ | i-Pr | Br | Br | F | Cl | i-Pr | Br |
| CH₃ | I | CF₃ | t-Bu | Br | Br | F | Cl | t-Bu | Br |
| CH₃ | I | Cl | Me | Cl | Br | F | Br | Me | Cl |
| CH₃ | I | Cl | Et | Cl | Br | F | Br | Et | Cl |
| CH₃ | I | Cl | i-Pr | Cl | Br | F | Br | i-Pr | Cl |
| CH₃ | I | Cl | t-Bu | Cl | Br | F | Br | t-Bu | Cl |
| CH₃ | I | Cl | Me | Br | Br | F | Br | Me | Br |
| CH₃ | I | Cl | Et | Br | Br | F | Br | Et | Br |
| CH₃ | I | Cl | i-Pr | Br | Br | F | Br | i-Pr | Br |
| CH₃ | I | Cl | t-Bu | Br | Br | F | Br | t-Bu | Br |
| CH₃ | I | Br | Me | Cl | Cl | CF₃ | Me | Cl |
| CH₃ | I | Br | Et | Cl | Cl | CF₃ | Et | Cl |
| CH₃ | I | Br | i-Pr | Cl | Cl | CF₃ | i-Pr | Cl |
| CH₃ | I | Br | t-Bu | Cl | Cl | CF₃ | t-Bu | Cl |
| CH₃ | I | Br | Me | Br | Cl | CF₃ | Me | Br |
| CH₃ | I | Br | Et | Br | Cl | CF₃ | Et | Br |
| CH₃ | I | Br | i-Pr | Br | Cl | CF₃ | i-Pr | Br |
| CH₃ | I | Br | t-Bu | Br | Cl | CF₃ | t-Bu | Br |
| CH₃ | CF₃ | CF₃ | Me | Cl | Cl | Cl | Me | Cl |
| CH₃ | CF₃ | CF₃ | Et | Cl | Cl | Cl | Et | Cl |
| CH₃ | CF₃ | CF₃ | i-Pr | Cl | Cl | Cl | i-Pr | Cl |
| CH₃ | CF₃ | CF₃ | t-Bu | Cl | Cl | Cl | t-Bu | Cl |
| CH₃ | CF₃ | CF₃ | Me | Br | Cl | Cl | Me | Br |
| CH₃ | CF₃ | CF₃ | Et | Br | Cl | Cl | Et | Br |
| CH₃ | CF₃ | CF₃ | i-Pr | Br | Cl | Cl | i-Pr | Br |
| CH₃ | CF₃ | CF₃ | t-Bu | Br | Cl | Cl | t-Bu | Br |
| CH₃ | CF₃ | Cl | Me | Cl | Br | Me | Cl |
| CH₃ | CF₃ | Cl | Et | Cl | Br | Et | Cl |
| CH₃ | CF₃ | Cl | i-Pr | Cl | Br | i-Pr | Cl |
| CH₃ | CF₃ | Cl | t-Bu | Cl | Br | t-Bu | Cl |
| CH₃ | CF₃ | Cl | Me | Br | Br | Me | Br |
| CH₃ | CF₃ | Cl | Et | Br | Br | Et | Br |
| CH₃ | CF₃ | Cl | i-Pr | Br | Br | i-Pr | Br |
| CH₃ | CF₃ | Cl | t-Bu | Br | Br | t-Bu | Br |
| CH₃ | CF₃ | Br | Me | Cl | Br | CF₃ | Me | Cl |
| CH₃ | CF₃ | Br | Et | Cl | Br | CF₃ | Et | Cl |
| CH₃ | CF₃ | Br | i-Pr | Cl | Br | CF₃ | i-Pr | Cl |
| CH₃ | CF₃ | Br | t-Bu | Cl | Br | CF₃ | t-Bu | Cl |
| CH₃ | CF₃ | Br | Me | Br | Br | CF₃ | Me | Br |
| CH₃ | CF₃ | Br | Et | Br | Br | CF₃ | Et | Br |
| CH₃ | CF₃ | Br | i-Pr | Br | Br | CF₃ | i-Pr | Br |
| CH₃ | CF₃ | Br | t-Bu | Br | Br | CF₃ | t-Bu | Br |

TABLE 6-continued

| R⁴ | R⁵ | R⁶ | R³ | R⁹ | R⁴ | R⁵ | R⁶ | R³ | R⁹ |
|---|---|---|---|---|---|---|---|---|---|
| Cl | F | CF₃ | Me | Br | Br | Br | Br | Me | Cl |
| Cl | F | CF₃ | Et | Br | Br | Br | Br | Et | Cl |
| Cl | F | CF₃ | i-Pr | Br | Br | Br | Br | i-Pr | Cl |
| Cl | F | CF₃ | t-Bu | Br | Br | Br | Br | t-Bu | Cl |
| Cl | F | Cl | Me | Cl | Br | Br | Br | Me | Br |
| Cl | F | Cl | Et | Cl | Br | Br | Br | Et | Br |
| Cl | F | Cl | i-Pr | Cl | Br | Br | Br | i-Pr | Br |
| Cl | F | Cl | t-Bu | Cl | Br | Br | Br | t-Bu | Br |
| Cl | F | Cl | Me | Br | Br | I | CF₃ | Me | Cl |
| Cl | F | Cl | Et | Br | Br | I | CF₃ | Et | Cl |
| Cl | F | Cl | i-Pr | Br | Br | I | CF₃ | i-Pr | Cl |
| Cl | F | Cl | t-Bu | Br | Br | I | CF₃ | t-Bu | Cl |
| Cl | F | Br | Me | Cl | Br | I | CF₃ | Me | Br |
| Cl | F | Br | Et | Cl | Br | I | CF₃ | Et | Br |
| Cl | F | Br | i-Pr | Cl | Br | I | CF₃ | i-Pr | Br |
| Cl | F | Br | t-Bu | Cl | Br | I | CF₃ | t-Bu | Br |
| Cl | F | Br | Me | Br | Br | I | Cl | Me | Cl |
| Cl | F | Br | Et | Br | Br | I | Cl | Et | Cl |
| Cl | F | Br | i-Pr | Br | Br | I | Cl | i-Pr | Cl |
| Cl | F | Br | t-Bu | Br | Br | I | Cl | t-Bu | Cl |
| Cl | Cl | CF₃ | Me | Cl | Br | I | Cl | Me | Br |
| Cl | Cl | CF₃ | Et | Cl | Br | I | Cl | Et | Br |
| Cl | Cl | CF₃ | i-Pr | Cl | Br | I | Cl | i-Pr | Br |
| Cl | Cl | CF₃ | t-Bu | Cl | Br | I | Cl | t-Bu | Br |
| Cl | Cl | CF₃ | Me | Br | I | Br | Me | Cl |
| Cl | Cl | CF₃ | Et | Br | I | Br | Et | Cl |
| Cl | Cl | CF₃ | i-Pr | Br | I | Br | i-Pr | Cl |
| Cl | Cl | CF₃ | t-Bu | Br | I | Br | t-Bu | Cl |
| Cl | Cl | Cl | Me | Cl | Br | I | Br | Me | Br |
| Cl | Cl | Cl | Et | Cl | Br | I | Br | Et | Br |
| Cl | Cl | Cl | i-Pr | Cl | Br | I | Br | i-Pr | Br |
| Cl | Cl | Cl | t-Bu | Cl | Br | I | Br | t-Bu | Br |
| Cl | Cl | Cl | Me | Br | Br | CF₃ | CF₃ | Me | Cl |
| Cl | Cl | Cl | Et | Br | Br | CF₃ | CF₃ | Et | Cl |
| Cl | Cl | Cl | i-Pr | Br | Br | CF₃ | CF₃ | i-Pr | Cl |
| Cl | Cl | Cl | t-Bu | Br | Br | CF₃ | CF₃ | t-Bu | Cl |
| Cl | Cl | Br | Me | Cl | Br | CF₃ | CF₃ | Me | Br |
| Cl | Cl | Br | Et | Cl | Br | CF₃ | CF₃ | Et | Br |
| Cl | Cl | Br | i-Pr | Cl | Br | CF₃ | CF₃ | i-Pr | Br |
| Cl | Cl | Br | t-Bu | Cl | Br | CF₃ | CF₃ | t-Bu | Br |
| Cl | Cl | Br | Me | Br | Br | CF₃ | Cl | Me | Cl |
| Cl | Cl | Br | Et | Br | Br | CF₃ | Cl | Et | Cl |
| Cl | Cl | Br | i-Pr | Br | Br | CF₃ | Cl | i-Pr | Cl |
| Cl | Cl | Br | t-Bu | Br | Br | CF₃ | Cl | t-Bu | Cl |
| Cl | Br | CF₃ | Me | Cl | Br | CF₃ | Cl | Me | Br |
| Cl | Br | CF₃ | Et | Cl | Br | CF₃ | Cl | Et | Br |
| Cl | Br | CF₃ | i-Pr | Cl | Br | CF₃ | Cl | i-Pr | Br |
| Cl | Br | CF₃ | t-Bu | Cl | Br | CF₃ | Cl | t-Bu | Br |
| Cl | Br | CF₃ | Me | Br | Br | CF₃ | Br | Me | Cl |
| Cl | Br | CF₃ | Et | Br | Br | CF₃ | Br | Et | Cl |
| Cl | Br | CF₃ | i-Pr | Br | Br | CF₃ | Br | i-Pr | Cl |
| Cl | Br | CF₃ | t-Bu | Br | Br | CF₃ | Br | t-Bu | Cl |
| Cl | Br | Cl | Me | Cl | Br | CF₃ | Br | Me | Br |
| Cl | Br | Cl | Et | Cl | Br | CF₃ | Br | Et | Br |
| Cl | Br | Cl | i-Pr | Cl | Br | CF₃ | Br | i-Pr | Br |
| Cl | Br | Cl | t-Bu | Cl | Br | CF₃ | Br | t-Bu | Br |

Formulation/Utility

Compounds of Formula I have bees discovered to not only have excellent activity controlling phytophagous invertebrate pests, but also have favorable residual patterns and plant translocation to provide protection of a plant developing from a plant propagule such as a seed, bulb, rhizome, tuber, corm, or stem or leaf cutting. (In the context of this disclosure "invertebrate pest control" means inhibition of invertebrate pest development (including mortality) that causes significant reduction in feeding or other injury or damage caused by the pest; related expressions are defined analogously.) This invention thus provides a method for protecting a plant propagule from phytophagous invertebrate pests by contacting the propagule or the locus of the propagule with a biologically effective amount of a compound of Formula I. The method of this invention using a sufficient amount of the Formula I compound has also been discovered to protect not only the propagule itself but also new growth developing from the propagule.

As described herein, "treating" a propagule or locus of a propagule means applying a Compound of Formula I or composition containing the compound to the propagule or locus of the propagule so that the compound of Formula I is brought in contact with the propagule; related terms such as "treatment" are defined analogously. When a propagule is thus brought into contact with a biologically effective amount of a Formula I compound, the compound protects it against injury by phytophagous invertebrate pests. Not only does the Formula I compound protect the external surface of the propagule, but it will be absorbed by the propagule to produce a propagule comprising the Formula I compound. If the propagule is contacted with sufficient amount of Formula I compound, enough will be absorbed to produce a biologically effective concentration of Formula I compound inside the propagule, and hence a propagule comprising a biologically effective amount of the Formula I compound. If a sufficient amount of the Formula I compound is applied to raise the concentration of Formula I compound in the propagule to a concentration greater than the minimum for biological effectiveness then translocation can move a biologically effective concentration of the Formula I compound to the developing shoot and root to protect them as well.

As referred to in this disclosure, the term "invertebrate pest" includes arthropods, gastropods and nematodes of economic importance as pests. The term "phytophagous invertebrate pest" refers to invertebrate pests causing injury to plants by feeding upon them, such as by eating foliage, stem, leaf, fruit or seed tissue or by sucking the vascular juices of plants. The term "arthropod" includes insects, mites, centipedes, millipedes, pill bugs and symphylans. The term "gastropod" includes snails, slugs and other Stylommatophora. The term "nematode" includes the phytophagous nematodes (Phylum or Class Nematoda). Economically important phytophagous invertebrate pests include: larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelos transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* L. (L. means Linnaeus)), grape berry moth (*Endopiza viteana* Clemens), oriental fruit moth (*Grapholita molesta* Busck)); and many other economically important lepidoptera (e.g., diamondback moth (*Phutella xylostella* L.), pink bollworm (*Pectinophora gossypiella* Saunders), gypsy moth (*Lymantria dispar* L.)); foliar feeding larvae and adults of the order Coleoptera including weevils from the families Anthribidae, Bruchidae, and Curculiomdae (e.g., boll weevil (*Anthonomus grandis* Boheman), rice water weevil (*Lissorhoptrus oryzophilus* Kuschel), rice weevil (*Sitophilus oryzae* L.)); flea beetles, cucumber beetles, rootworms, leaf beetles, potato beetles, and leafminers in the family Chrysomelidae (e.g., Colorado potato beetle (*Leptinotarsa decemlineta* Say), western corn rootworm (*Diabrotica virgifera virgifera* LeConte)); chafers and other beetles from the family Scaribaeidae (e.g., Japanese beetle (*Popillia japonica* Newman) and European, chafer (*Rhizotrogus majalis* Razoumowsky)); wireworms from the family Elateridae and bark beetles from the family Scolytidae; adults and larvae of the order Dermaptera including earwigs from the family Forficulidae (e.g., European earwig (*Forficula auricularia* L.), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudoccidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from, the family Cercopidae squash bugs from, the family Coreidae, and red bugs and cotton stainers from the family Pyrrhocoridae; adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites; adults and immatures of the order Orthoptera including grasshoppers, locusts and crickets (e.g., migratory grasshoppers (e.g., *Melanophus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* L.), mole crickets (*Gryllotalpa* spp.)); adults and immatures of the order Diptera including leafminers, midges, fruit flies (Tephritidae), frit flies (e.g., *Oscinella frit* L.), soil maggots and other Nematocera; adults and immatures of the order Thysanoptera including onion thrips (*Thrips tabaci* Lindeman) and other foliar feeding thrips; and centipedes in the order Scutigeromorpha; and members of the Phylum or Class Nematoda including such important agricultural pests as root knot nematodes in the genus *Meloidogyne*, lesion nematodes in the genus *Pratylenchus*, stubby root nematodes in the genus *Trichodorus*, etc.

Those skilled in the art will recognize that not all compounds are equally effective against all pests. Compounds of the invention show particularly high activity against pests in the order Lepidoptera (e.g., *Alabama argillacea* Hübner (cotton leaf worm), *Archips argyrospila* Walker (fruit tree leaf roller), *A. rosana* L. (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomenella* L. (codling moth), *Earias insulana* Boisduval (spiny bollworm), *Earias vitella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophra gossypiella* Saunders (pink bollworm), *Phyllocnistis citrella* Stainton (citrus leafminer), *Pieris brassicae* L. (large white butterfly), *Pieris rapae* L, (small white butterfly), *Plutella xylostella* L. (diamondback moth), *Spodoptera exigua* Hübner (beet army worm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid). *Aphis gossypi* Glover (cotton aphid, melon aphid), *Aphis pomi* De Geer (apple aphid), *Aphis spiraecola* Patch, (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmaan (woolly apple aphid), *Hyalopterus pruni* Geoffrey (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* L. (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citrtida* Kirkaldy (brown citrus aphid); *Adelges* spp, (adelgids); *Phylloxera devastatrix* Pergande (pecan phylloxera); *Bemisia tabaci* Gennadius (tobacco whitefly, sweetpotato whitefly), *Bemisia argentifolii* Bellows & Peering (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stäl (rice leafhopper), *Nilaparvata lugens* Stäl (brown, planthopper), *Peregrinus maidis* Ashmead (corn planthopper), *Sogatella furcifera* Horvath (white-backed planthopper), *Sogatodes orizicola* Muir (rice delphacid), *Typhlocya pomaria* McAtee white apple leafhopper, *Erythroneoura* spp. (grape leafhoppers); *Magicidada septendecim* L. (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylia), *Trioza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus* leucopterus Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* L. (southern green stink bug), *Oebalus pugnax* Fabricius (rice stink bug), *Oncopeltus fasciatus* Dallas (large milkweed bug), *Pseudatomoscelis seriatus* Renter (cotton fleahopper). Other insect orders controlled by compounds of the invention include Thysanoptera (e.g., *Franklin-*

*iella occidenitalis* Pergande (western flower thrip), *Scirtothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agroptes, Athous* or *Limonius*).

The method of this invention is applicable to virtually all plant species. Seeds that can be treated, include for example, wheat (*Triticum aestivum* L.), durum wheat (*Triticum durum* Desf.), barley (*Hordeum vulgare* L.) oat (*Avena sativa* L.), rye (*Secale cereale* L.), maize (*Zea mays* L.), sorghum (*Sorghum vulgare* Pers.), rice (*Oryza sativa* L.), wild rice (*Zizania aquatica* L.), cotton (*Gossypium barbadense* L. and *G. hirsutum* L.), flax (*Linum usitatissimum* L.), sunflower (*Helianthus annuus* L.), soybean (*Glycine max* Merr.), garden bean (*Phaseolus vulgaris* L.), lima bean (*Phasealus limensis* Macf.), broad bean (*Vicia faba* L.), garden pea (*Pisum sativum* L.), peanut (*Arachis hypogaea* L.), alfalfa (*Medicago sativa* L.), beet (*Beta vulgaris* L.), garden lettuce (*Lactuca sativa* L.), rapeseed (*Brassica rapa* L. and *B. napus* L.), cole crops such as cabbage, cauliflower and broccoli (*Brassica oleracea* L.), turnip (*Brassica rapa* L.), leaf (oriental) mustard (*Brassica juncea* Coss.), black mustard (*Brassica nigra* Koch), tomato (*Lycopersicon esculentum* Mill.), potato (*Solatium tuberosum* L.), pepper (*Capsicum frutescens* L.), eggplant (*Solanum melongena* L.), tobacco (*Nicotiana tabacum*), cucumber (*Cucumis sativus* L.), muskmelon (*Cucumis melo* L.), watermelon (*Citrullus vulgaris* Schrad.), squash (*Curcurbita pepo* L.), *C. moschata* Duchesne, and *C. maxima* Duchesne.), carrot (*Daucus carota* L.), zinnia (*Zinnia elegans* Jacq.), cosmos (e.g., *Cosmos bipinnatus* Cav.), chrysanthemum (*Chrysanthemum* spp.), sweet scabious (*Scabiosa atropurpurea* L.), snapdragon (*Antirrhinum majus* L.), gerbera (*Gerbera jamesonii* Bolus), babys-breath (*Gypsophila paniculata* L., *G. repens* L., and *G. elegans* Bieb.), statice (e.g., *Limonium sinuatum* Mill., *L. sinense* Kuntze), blazing star (e.g., *Liatris spicata* Willd., *L. pycnostachya* Michx., *L. scariosa* Willd.), lisianthus (e.g., *Eustoma grandiflorum* (Raf.) Shinn), yarrow (e.g., *Achillea filipendulina* Lam., *A. millefolium* L.), marigold (e.g., *Tagetes patula* L., *T. erecta* L.), pansy (e.g., *Viola cornuta* L., *V. tricolor* L.), impatiens (e.g., *Impatiens balsamina* L.) petunia (*Petunia* spp.), geranium (*Geranium* spp.) and coleus (e.g., *Solenostemon scutellarioides* (L.) Codd). Not only seeds, but also rhizomes, tubers, bulbs or corms, including viable cuttings thereof, can be treated according to the invention from, for example, potato (*Solanum tuberosum* L.), sweet potato (*Ipomoea batatas* L.), yam (*Dioscorea cayenemis* Lam. and *D. rotundata* Poir.), garden onion (e.g., *Allium cepa* L.), tulip (*Tulipa* spp.), gladiolus (*Gladiolus* spp.), lily (*Lilium* spp.), narcissus (*Narcissus* spp.), dahlia (e.g., *Dahlia pinnata* Cav.), iris (*Iris germancia* L. and other species), crocus (*Crocus* spp.), anemone (*Anemone* spp.), hyacinth (*Hyacinth* spp.), grape-hyacinth (*Muscari* spp.), freesia (e.g., *Freesia refracta* Klatt., *F. armstrongii* W. Wats), ornamental onion (*Allium* spp.), woodsorrel (*Oxalis* spp.), squill (*Scilla peruviana* L. and other species), cyclamen (*Cyclamen persicum* Mill. and other species), glory-of-the-snow (*Chionodoxa luciliae* Boiss. and other species), striped squill (*Puschkinia scilloides* Adams), calla lily (*Zantedeschia aethiopica* Spreng., *Z. elliottiana* Engler and other species), gloxinia (*Sinnigia speciosa* Benth. & Hook.) and tuberous begonia (*Begonia tuberhybrida* Voss.). Stem cuttings can be treated according to this invention include those from such plants as sugarcane (*Saccharum officinarum* L.), carnation (*Dianthus caryophyllus* L.), florists chrysanthemum (*Chrysanthemum mortifolium* Ramat.), begonia (*Begonia* spp.), geranium (*Geranium* spp.), coleus (e.g., *Solenostemon scutellariodes* (L.) Codd) and poinsettia (*Euphorbia pulcherrima* Willd.). Leaf cuttings which can be treated according to this invention include those from begonia (*Begonia* spp.), african-vioiet (e.g., *Saintpaulia ionantha* Wendl.) and sedum (*Sedum* spp.). The above recited cereal, vegetable, ornamental (including flower) and fruit crops are illustrative, and should not be considered limiting in any way. For reason of invertebrate pest control spectrum and economic importance, seed treatments of cotton, maize, soybean and rice, and tuber and bulb treatments of potato, sweet potato, garden onion, tulip, daffodil, crocus and hyacinth are preferred embodiments of the invention.

The locus of the propagules can be treated with a Formula I compound by many different methods. All that is needed is for a biologically effective amount of a Formula I compound to be applied on or sufficiently close to the propagule so that it can be absorbed by the propagule. The Formula I compound can be applied by such methods as drenching the growing medium including a propagule with a solution or dispersion of a Formula I compound, mixing a Formula I compound with growing medium and planting a propagule in the treated growing medium (e.g., nursery box treatments), or various forms of propagule treatments whereby a Formula I compound is applied to a propagule before it is planted in a growing medium.

In these methods the Formula I compound will generally be used as a formulation or composition with an agriculturally suitable carrier comprising at least one of a liquid diluent, a solid diluent or a surfactant. A wide variety of formulations are suitable for this invention, the most suitable types of formulations depend upon the method of application. As is well known to those skilled in the art, the purpose of formulation is to provide a safe and convenient means of transporting, measuring and dispensing the crop protection chemical and also to optimize its bioefficacy.

Depending on the method of application useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro) encapsulated and further formed into a suspension or solid formulation; alternatively the entire formulation of active ingredient can be encapsulated (or "over-coated"). Encapsulation can control or delay release of the active ingredient. Sprayable formulations can be extended in suitable media and used at spray volumes from about one to several hundred liters per hectare. High-strength compositions ate primarily used as intermediates for further formulation.

The formulations will typically contain effective amounts of active ingredient, diluent and surfactant within the following approximate ranges that add up to 100 percent by weight.

|  | Weight Percent | | |
| --- | --- | --- | --- |
|  | Active Ingredient | Diluent | Surfactant |
| Water-Disersible and Water-soluble Granules, Tablets and Powders. | 5-90 | 0-94 | 1-15 |

|  | Weight Percent | | |
|---|---|---|---|
|  | Active Ingredient | Diluent | Surfactant |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Stremgth Compositions | 90-99 | 0-10 | 0-2 |

Typical solid diluents are described in Watkins et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Emulsifiers and Detergents and McCutcheon's Functional Materials* (*North America and International Editions*, 2001). The Manufacturing Confection Publ. Co., Glen Rock, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, ethoxylated alcohols, ethoxylated alkylphenols, ethoxylated sorbitan fatty acid esters, ethoxylated amines, ethoxylated fatty acids, esters and oils, dialkyl sulfosuccinates, alkyl sulfates, alkylaryl sulfonates, organosilicones, N,N-dialkyltaurates, glycol esters, phosphate esters, lignin sulfonates, naphthalene sulfonate formaldehyde condensates, polycarboxylates, and block polymers including polyoxyethylene/polyoxypropylene block copolymers. Solid diluents include, for example, clays such as bentonite, montmorillonite, attapulgite and kaolin, starch, sugar, silica, talc, diatomaceous earth, urea, calcium, carbonate, sodium carbonate and bicarbonate, and sodium sulfate. Liquid diluents include, for example, water, N,N-dimethylformamide, dimethyl sulfoxide, N-alkylpyrrolidione, ethylene glycol, polypropylene glycol, propylene carbonate, dibasic esters, paraffins, alkylbenzenes, alkylnaphthalenes, oils of olive, castor, linseed, rung, sesame, corn, peanut, cotton-seed, soybean, rape-seed and coconut, fatty acid esters, ketones such, as cyclohexanone, 2-heptanone, isophorone and 4-hydroxy-4-methyl-2-pentanone, and alcohols such as methanol, cyclohexanol, decanal, benzyl and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods. "The Formulator's Toolbox—Product Forms for Modern Agriculture" in *Pesticide Chemistry and Bioscience, The Food-Envimnment Challenge*, T. Brooks and T. R. Roberts. Eds., Proceedings of the 9th International Congress on Pesticide Chemistry, The Royal Society of Chemistry, Cambridge, 1999, pp. 120-133. See also U.S. Pat. No. 3,235,361, Col 6, line 16 through Col. 7, line 19 and Examples 10-41; U.S. Pat. No. 3,309,192, Col. 5, line 43 through Col 7, line 62 and Examples 8, 12, 15, 39, 41, 52, 53, 58, 132, 138-140, 162-164, 166, 167 and 169-182; U.S. Pat. No. 2,891,855, Col. 3, line 66 through. Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989.

A propagule or a plant grown therefrom can be protected from an invertebrate pest according to this invention by a method comprising contacting the propagule or the locus of the propagule with a composition comprising a biologically effective amount of a compound of Formula I, an N-oxide thereof or an agriculturally suitable salt thereof. The invention includes a propagule contacted with a composition comprising a biologically effective amount a compound of Formula I, its N-oxide or an agriculturally suitable salt thereof and an effective amount of at least one other biologically active compound or agent. The compositions used for treating propagules (or plant grown therefrom) according to this invention can also comprise (besides the Formula I component) an effective amount of one or more other biologically active compounds or agents. Suitable additional compounds or agents include insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Examples of stack biologically active compounds or agents with, which compounds of this invention can be formulated are: insecticides such as abamectin, acephate, acetamiprid, amidoflumet (S1955), avermectin, azadirachtin, azinphos-methyl, bifenthrin, binfenazate, buprofezin, carbofuran, chlorfenapyr, chlorfluazuron, chlorpyrifos, chloorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxurom fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-

(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imaidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), floquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC 375839), myclobutanil, neoasozin (ferric methanearsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki, Bacillus thuringienis* delta endotoxin, baculovirus, and entomopathogenic bacteria, virus and fungi.

A general reference for these agricultural protectants is *The Pesticide Manual,* 12*th Edition*, C. D, 8. Tomlin, Ed., British Crop Protection Council, Farnham, Surrey, U.K., 2000.

Preferred insecticides and acaricides for mixing with Formula I compounds include pyrethroids such as cypermethrin, cyhalothrin, cyfluthrin and beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb, insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta, endotoxin as well as naturally occurring and genetically modified viral insecticides including members of the family Baculoviridae as well as entomophagous fungi.

Preferred plant growth regulants for mixing with the Formula I compounds in compositions for treating stem cuttings are 1H-indole-3-acetic acid, 1H-indole-3-butanoic acid and 1-naphthaleneacetic acid and their agriculturally suitable salt, ester and amide derivatives, such as 1-naphthaleneacetamide. Preferred fungicides for mixing with the Formula I compounds include fungicides useful as seed treatments such as thiram, maneb, mancozeb and captan.

In the following Examples, all percentages are by weight and all formulations are prepared in conventional ways. Compound numbers refer to compounds in Index Table A.

Example A

| Wettable Powder | |
|---|---|
| Compound 208 | 65.0% |
| dodecylphenol polyethylene glycol ether | 2.0% |
| sodium ligninsulfonate | 4.0% |
| sodium silicoaluminute | 6.0% |
| montmorillonite (calcined) | 23.0% |

Example B

| Granule | |
|---|---|
| Compound 486 | 10.0% |
| attapulgite granules (low volatile matter, 0.71/0.30 mm; U.S.S. No. 25-50 sieves) | 90.0% |

Example C

| Extruded Pellet | |
|---|---|
| Compound 509 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example D

| Emulsifiable Concentrate | |
|---|---|
| Compound 516 | 20.0% |
| blend of oil soluble sulfonates and polyoxyethylene ethers | 10.0% |
| isophorone | 70.0% |

For growing-medium drenches, the formulation needs to provide the Formula I compound, generally after dilution with water, in solution or as particles small enough to remain dispersed in the liquid. Water-dispersible or soluble powders, granules, tablets, emulsifiable concentrates, aqueous suspension concentrates and the like are formulations suitable for aqueous drenches of growing media. Drenches are most satisfactory for treating growing media that have relatively high porosity, such as light soils or artificial growing medium comprising porous materials such as peat moss, perlite, vermiculite and the like. The drench liquid comprising the Formula I compound can also be added to a liquid growing medium (i.e. hydroponics), which causes the Formula I compound to become part of the liquid growing medium. One skilled the art will appreciate mat the amount of Formula I compound needed m the drench liquid for invertebrate pest control efficacy (i.e. biologically effective amount) will vary with the type, of propagate, the Formula I compound, the duration and extent of plant protection desired, the invertebrate pests to be controlled and environmental factors. The concentration of Formula I compound in the drench liquid is generally between about 0.01 ppm and 10,000 ppm, more typically between about 1 ppm and 100 ppm. One skilled in the art can easily determine the biologically effective concentration necessary for the desired level of phytophagous invertebrate pest control.

For treating a growing medium a Formula I compound can also be applied by mixing it as a dry powder or granule formulation with the growing medium. Because this method of application does not require first dispersing or dissolving in water, the dry powder or granule formulations need not be highly dispersible or soluble. While in a nursery box the entire body of growing medium may be treated, in an agricultural field only the soil in the vicinity of the propagule is typically treated for environmental and cost reasons. To minimize application effort and expense, a formulation, of Formula I compound is most efficiently applied concurrently with propagule planting (e.g., seeding). For in-furrow application, the Formula I formulation (most conveniently a granule formulation) is applied directly behind the planter shoe. For T-band application, the Formula I formulation is applied in a band over the row behind the planter shoe and behind or usually in front of the press wheel. One skilled the art will appreciate that the amount of Formula I compound needed in the growing medium locus for invertebrate pest control efficacy (i.e. biologically effective amount) will vary with the type of propagule, the Formula I compound, the duration and extent of plant protection desired, the invertebrate pests to be controlled and environmental factors. The concentration of Formula I compound in the growing medium locus of the propagule is generally between about 0.0001 ppm and 100 ppm, more typically between about 0.01 ppm and 10 ppm. One skilled in the art can easily determine the biologically effective amount necessary for the desired level of phytophagous invertebrate pest control.

A propagule can be directly treated by soaking it in a solution or dispersion of a Formula I compound. Although this application method is useful for propagules of all types, treatment of large seeds (e.g., having a mean diameter of at least 3 mm) is more effective than treatment of small seeds for providing invertebrate pest control protection to the developing plant. Treatment of propagules such as tubers, bulbs, corms, rhizomes and stem and leaf cuttings also can provide effective treatment of the developing plant in addition to the propagule. The formulations useful for growing-medium drenches are generally also useful for soaking treatments. The soaking medium comprises a nonphytotoxic liquid, generally water-based although it may contain nonphytotoxic amounts of other solvents such as methanol, ethanol, isopropanol, ethylene glycol, propylene glycol, propylene carbonate, benzyl alcohol, dibasic esters, acetone, methyl acetate, ethyl acetate, cyclohexanone, dimethylsulfoxide and N-methylpyrrolidone, which may be useful for enhancing solubility of the Formula I compound and penetration into the propagule. A surfactant can facilitate wetting of the propagule and penetration of the Formula I compound. One skilled the art will appreciate that the amount of Formula I compound needed in the soaking medium for invertebrate pest control efficacy (i.e. biologically effective amount) will vary with the type of propagule, the Formula I compound, the duration and extent of plant protection desired, the invertebrate pests to be controlled and environmental factors. The concentration of Formula I compound in the soaking liquid is generally between about 0.01 ppm and 10,000 ppm, more typically between about 1 ppm and 100 ppm. One skilled in the art can easily determine the biologically effective concentration necessary for the desired level of phytophagous invertebrate pest control. The soaking time can vary from 1 minute to 1 day or even longer. Indeed the propagule can remain in the treatment liquid while it is germinating or sprouting (e.g., sprouting of rice seeds prior to direct seeding). As shoot and root emerge through the testa (seed coat), the shoot and root directly contact the solution comprising the Formula I compound. For treatment of sprouting seeds of large-seeded crops such as rice, treatment times of about 8 to 48 hours, e.g., about 24 hours, is typical. Shorter times are most useful for treating small seeds.

A propagule can also be coated with a composition comprising a biologically effective amount of a Formula I compound. The coatings of the invention are capable of effecting a slow release of a Formula I compound by diffusion into the propagule and surrounding medium. Coatings include dry dusts or powders adhering to the propagule by action of a sticking agent such as methylcellulose or gum arabic. Coatings can also be prepared from suspension concentrates, water-dispersible powders or emulsions that are suspended in water, sprayed on the propagule in a tumbling device and then dried. Formula I compounds that are dissolved in the solvent can be sprayed on the tumbling propagule and the solvent then evaporated. Such compositions preferably include ingredients promoting adhesion, of the coating to the propagule. The compositions may also contain surfactants promoting wetting of the propagule. Solvents used must not be phytotoxic to the propagule; generally water is used, but other volatile solvents with low phytotoxicity such as methanol, ethanol, methyl acetate, ethyl acetate, acetone, etc. may be employed alone or in combination. Volatile solvents are those with a normal boiling point less than about 100° C. Drying must be conducted in a way not to injure the propagule or induce premature germination or sprouting.

The thickness of coatings can vary from adhering dusts to thin films to pellet layers about 0.5 to 5 mm thick. Propagule coatings of this invention can comprise more than one adhering layers, only one of which need comprise a Formula I compound. Generally pellets are most satisfactory for small seeds, because their ability to provide a biologically effective amount of a Formula I compound is not limited by the surface area of the seed, and pelleting small seeds also facilitates seed transfer and planting operations. Because of their larger size and surface area, large seeds and bulbs, tubers, corms and rhizomes and their viable cuttings are generally not pelleted, but instead coated with powders or thin, films.

Propagules contacted with compounds of Formula I in a accordance to this invention include seeds. Suitable seeds Include seeds of wheat, durum wheat, barley, oat, rye, maize, sorghum, rice, wild rice, cotton, flax, sunflower, soybean, garden bean, lima bean, broad bean, garden pea, peanut, alfalfa, beet, garden, lettuce, rape-seed, cole crop, turnip, leaf mustard, black mustard, tomato, potato, pepper, eggplant, tobacco, cucumber, muskmelon, watermelon, squash, carrot, zinnia, cosmos, chrysanthemum, sweet scabious, snapdragon, gerbera, babys-breath, statice, blazing star, lislanthus, yarrow, marigold, pansy, impatiens, petunia, geranium and coleus. Of note are seeds of cotton, maize, soybean and rice. Propagules contacted with compounds of Formula I in accordance to this invention also include rhizomes, tubers, bulbs or corms, or viable divisions thereof. Suitable rhizomes, tubers, bulbs and corms, or viable divisions thereof include those of potato, sweet potato, yam, garden onion, tulip, gladiolus, lily, narcissus, dahlia, iris, crocus, anemone, hyacinth, grape-hyacinth, freesia, ornamental onion, wood-sorrel, squill, cyclamen, glory-of-the-snow, striped squill, calla lily, gloxinia and tuberous begonia. Of note are rhizomes, tubers, bulbs and corms, or viable division thereof of potato, sweet potato, garden onion, tulip, daffodil, crocus and hyacinth. Propagules contacted with compounds of Formula I in accordance to this invention, also include stems and leaf cuttings.

One embodiment of a propagule contacted with a Formula I compound is a propagule coated with a composition comprising a compound of Formula I, its N-oxide or an agriculturally suitable salt thereof and a film former or adhesive agent. Compositions of this invention which comprise a biologically effective amount of a compound of Formula I, its N-oxide or an agriculturally suitable salt thereof and a film former or adhesive agent, can further comprise an effective amount of at least one additional biologically active compound or agent. Of note are compositions comprising (in addition to the Formula I component and the film former or adhesive agent) an athropodicides of the group consisting of pyrethroids, carbamates, neonicotinoids, neuronal sodium channel blockers, insecticidal macrocyclic lactones, γ-aminobutyric acid (GABA) antagonists, insecticidal ureas and juvenile hormone mimics. Also of note are compositions comprising (in addition to the Formula I component and the film former or adhesive agent) at least one additional biologically active compound, or agent selected from the group consisting of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben, tebufenpyrad; and biological agents such as *Bacillus thuringiensis* including ssp. *aizawai* and *kurstaki, Bacillus thuringiensis* delta endotoxin, baculovirus, and entomopathogenic bacteria, virus and fungi. Also of note are compositions comprising (in addition to the Formula I component and the film former or adhesive agent) at least one additional biologically active compound or agent selected from fungicides of the group consisting of acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salt, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC S725), fluquinconazole, flusilazole, flutolanil, flutriafol, folpet, fosetyl-aluminium, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC 375839), myclobutanil, neoasozin (ferric methanearsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl thiram, tiadinil, triadimefon, triadimenol, tricyclazole, trifloxystrobin, triticonazole, validamycin and vinclozolin (especially compositions wherein the at least one additional biologically active compound or agent is selected from fungicides in the group consisting of thiram, maneb, mancozeb and captan).

Generally a propagule coating of the invention comprises a compound of Formula I, a film former or sticking agent. The coating may further comprise formulation aids such as a dispersant, a surfactant, a carrier and optionally an antifoam and dye. One skilled the art will appreciate that the amount of Formula I compound needed In the coating for invertebrate pest control efficacy (i.e. biologically effective amount) will vary with the type of propagule, the Formula I compound, the duration and extent of plant protection desired, the invertebrate pests to be controlled and environmental factors. The coating needs to not inhibit germination or sprouting of the propagule and should be consistently efficacious in reducing plant injury during the plant-injury-causing phase of the target invertebrate pest's life cycle. A coating comprising sufficient Formula I compound can provide invertebrate pest control protection for op to about 120 days or even longer. Generally the amount of Formula I compound ranges from about 0.001 to 50% of the weight of the propagule, for seeds more often in the range of about 0.01 to 50% of the seed weight, and most typically for large seeds in the range of about 0.1 to 10% of the seed weight. However, larger amounts up to about 100% or more are useful, particularly for pelleting small seed for extended invertebrate pest control protection. For propagules such as bulbs, tubers, corms and rhizomes and their viable cuttings, and stem and leaf cuttings, generally the amount of Formula I compound ranges from about 0.001 to 5% of the propagule weight, with the higher percentages used for smaller propagate. One skilled in the art can easily determine the biologically effective amount necessary for the desired level of phytophagous invertebrate pest control.

The film former or adhesive agent component of the propagule coating is composed preferably of an adhesive polymer that may be natural or synthetic and is without phytotoxic effect on the propagule to be coated. The film former or sticking agent may be selected from polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxymethylcelluloses, hydroxypropylcellulose, hydroxymethylpropylcelluloses, polyvinylpyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof. Preferred film formers and adhesive agents include polymers and copolymers of vinyl acetate, polyvinylpyrrolidone-vinyl acetate copolymer and water-soluble waxes. Particularly preferred are polyvinylpyrrolidone-vinyl acetate copolymers and water-soluble waxes. The above-identified polymers include those known in the art and for example some are identified as Agrimer® VA 6 and Licowax® KST. The amount of film former or sticking agent in the formulation is generally in the range of about 0.001 to 100% of the weight of the propagule. For large seeds the amount of film former or sticking agent is typically in the range of about 0.05 to 5% of the seed weight; for small seeds the amount is typically in the range of about 1 to 100%, but can be greater than 100% of seed weight in pelleting. For other propagules the amount of film former or sticking agent is typically in foe range of 0.001 to 2% of the propagule weight.

Materials known as formulation aids may also be used in propagule treatment coatings of the invention for the invertebrate pest control and are well known to those skilled in the art. Formulation aids assist in the production or process of propagate treatment and include but are not limited to dispersants, surfactants, carriers, antifoams and dyes. Useful dispersants can include highly water-soluble anionic surfactants like Borresperse® CA, Morwet® D425 and the like. Useful surfactants can include highly water-soluble nonionic surfactants like Pluronic® F108, Brij® 78 and the like. Useful carriers can include liquids like water and oils which are water soluble such as alcohols. Useful carriers can also include fillers like woodflours, clays, activated carbon, diatomaceous earth, fine-grain inorganic solids, calcium carbonate and the like. Clays and inorganic solids which may be used include calcium bentonite, kaolin, china clay, talc, perlite, mica, vermiculite, silicas, quartz powder, montmorillonite and mixtures thereof. Antifoams can include water dispersible liquids comprising polyorganic siloxanes like Rhodorsil® 416. Dyes can include water dispersible liquid colorant compositions like Pro-lzed® Colorant Red. One skilled in the art will appreciate that this is a non-exhaustive list of formulation aids and that other recognized materials may be used depending on the propagule to be coated and the compound of Formula I used in the coating. Suitable examples of formulation aids include those listed herein and those listed in McCutcheon's 2001, Volume 2: Functional Materials, published by MC Publishing Company. The amount of formulation aids used may vary, but generally the weight of the components will be in the range of about 0.001 to 10000% of the propagule weight, with the percentages above 100% being mainly used for pelleting small seed. For nonpelleted seed generally the amount of formulating aids is about 0.01 to 45% of the seed weight and typically about 0.1 to 15% of the seed weight. For propagules other than seeds, the amount of formulation aids generally is about 0.00 to 10% of the propagule weight.

Conventional means of applying seed coatings may be used to carry out the coating of the invention. Dusts or powders may be applied by tumbling the propagule with a formulation comprising a Formula I compound and a sticking agent to cause the dust or powder to adhere to the propagule and not fall off during packaging or transportation. Dusts or powders can also be applied by adding the dust or powder directly to the tumbling bed of propagules, followed by spraying a carrier liquid onto the seed and drying. Dusts and powders comprising a Formula I compound can also be applied by treating (e.g., dipping) a least a portion of the propagule with a solvent such as water, optionally comprising a sticking agent, and dipping the treated portion into a supply of the dry dust or powder. This method can be particularly useful for coating stem cuttings. Propagules can also be dipped into compositions comprising Formula I formulations of wetted powders, solutions, suspoemulsions, emulfiable concentrates and emulsions in water, and then dried or directly planted in the growing medium. Propagules such as bulbs, tubers, corms and rhizomes typically need only a single coating layer to provide a biologically effective amount of a Formula I compound.

Propagules may also be coated by spraying a suspension concentrate directly into a tumbling bed of propagules and then drying the propagules. Alternatively, other formulation type like wetted powders, solutions, suspoemulsions, emulsifiable concentrates and emulsions in water may be sprayed on the propagules. This process is particularly useful for applying film coatings to seeds. Various coating machines and processes are available to one skilled in the art. Suitable processes include those listed in P. Kosters et al., *Seed Treatment: Progress and Prospects,* 1994 BCPC Monograph No. 57 and the references listed therein. Three well-known techniques include the use of drum coaters, fluidized bed techniques and spouted beds. Propagules such as seeds may be presided prior to coating. After coating the propagules are dried and then optionally sized by transfer to a sizing machine. These machines are known in the art for example, a typical machine used when sizing corn (maize) seed in the industry.

For coating seed, the seed and coating material are mixed in any variety of conventional seed coating apparatus. The rate of rolling and application of coating depends upon the seed. For large oblong seeds such as that of cotton, a satisfactory seed coating apparatus comprises a rotating type pan with lifting vanes turned sufficient rpm to maintain a rolling action of the seed, facilitating uniform coverage. For seed coating formulations applied as liquids, the seed coating must be applied over sufficient time to allow drying to minimize clumping of the seed. Using forced air or heated forced air can allow increasing the rate in application. One skilled in the art will also recognize that this process may be a batch or continuous process. As the name implies, a continuous process allows the seeds to flow continuously throughout the product run. New seeds enter the pan in a steady stream to replace coated seeds exiting the pan.

The seed coating process of the present invention is not limited to thin film coating and may also include seed pelleting. The pelleting process typically increases the seed weight from 2 to 100 times and can be used to also improve the shape of the seed for use in mechanical seeders. Pelleting compositions generally contain a solid diluent, which is typically an insoluble particulate material, such as clay, ground limestone, powdered silica, etc. to provide bulk in addition to a binder such as an artificial polymer (e.g., polyvinyl alcohol, hydrolyzed polyvinyl acetates, polyvinyl methyl ether, polyvinyl methyl ether-maleic anhydride copolymer, and polyvinylpyrrolidinone) or natural polymer (e.g., alginates, karaya gum, jaguar gum, tragacanth gum, polysaccharide gum, mucilage). After sufficient layers have been built up, the coat is dried and the pellets graded. A method for producing pellets is described in Agrow, *The Seed Treatment Market*, Chapter 3, PJB Publications Ltd., 1994.

For further description of composition components and processes suitable for the coating a propagule with a Formula I compound, see U.S. Pat. Nos. 4,443,637, 5,494,700, 5,527, 760, 5,834,006, 5,849,320, 5,876,739, 6,150,699, 6,199,318, 6,202,346 and 6,230,438 and European Patent Publication EP-1,078,563-A1.

The following Examples E-H illustrate the process of coating seeds. Compound numbers refer to compounds in Index Table A.

Example E

Preparation of cottonseed batches coated with composition comprising Compound 208

Step 1: Preparation of Flowable Suspension comprising Compound 208

A flowable suspension containing the ingredients listed in Table 7 was prepared.

TABLE 7

Amounts of Ingredients in Flowable Suspension

| Ingredient | Wt. % including water | Wt. % excluding water |
| --- | --- | --- |
| Compound 208 | 15.60 | 52.28 |
| Agrimer ® VA 6 | 5.00 | 16.76 |
| Licowax ® KST | 5.00 | 16.76 |
| Borresperse ™ CA | 1.00 | 3.35 |
| Pluronic ® F-108 | 1.00 | 3.35 |
| Brij ® 78 | 2.00 | 6.70 |
| Rhodorsil ® 416 | 0.20 | 0.67 |
| Pro-Ized ® Colorant Red | 0.04 | 0.13 |
| Water | 70.16 | ~ |

Agrimer® VA 6 is a highly water-soluble, film-forming adhesive having a softening point of 106° C. comprising a polyvinylpyrrolidone-vinyl acetate copolymer and marketed by International Specialty Products (ISP). Licowax® KST is a highly water-soluble, film-forming adhesive having a drop forming point of 59° C. comprising montan wax acid, polyethylene glycol ester and marketed by Clariant. Borresperse™ CA is a highly water-soluble anionic dispersant having a softening point of 132° C. comprising de-sugared calcium lignosulfonate and marketed by Borregaard Ligno-Tech. Pluronic® F-108 is a highly water-soluble, nonionic dispersant having a melting point of 57° C. comprising polyoxypropylene-polyoxyethylene block copolymer and marketed by BASF. Brij® 78 is a highly water-soluble, nonionic dispersant having a pour point of 38° C. comprising stearyl alcohol (POE 20) and marketed by Uniqema. Rhodorsil® 416 is a water-dispersible liquid antifoam agent comprising polyorganosiloxanes and emulsifying agent and marketed by Rhodia. Pro-Ized® Colorant Red is a water-dispersible liquid colorant composition comprising a red colorant, kaolin clay and a nonionic surfactant and marketed by Gustafson.

A suspension carrier (253.20 g) was prepared by first dissolving Brij® 78 (6.00 g) in warm water (210.48 g), followed by vigorously mixing in Agrimer® VA 6 (15.00 g), Licowax® KST (15.00 g), Borresperse™ CA (3.00 g), Pluronic® F-108 (3.00 g), Brij® 78 (6.00 g), Rhodorsil® 416 (0.6 g) and Pro-lzed® Colorant Red (0.12 g). Compound 208 (15.6 g) was added to a beaker, followed by a portion of the thoroughly mixed suspension carrier (84.4 g), and a spatula was used to fold Compound 208 into the suspension carrier. The mixture was then further homogenized using a Polytron high-speed rotor stator disperser (marketed by Brinkman Instruments Inc., Cantiague Rd., Westbury, N.Y. 11590 U.S.A.) with, a 10 mm generator probe, which disintegrated aggregates of Compound 208.

The resulting slurry was then transferred to a running mill charged to 80% capacity with 0.5-mm, mono-sized, high-density ceramic milling media, and cooled by passing a chilled aqueous 33% ethylene glycol solution through the cooling jacket of the milling chamber. The slurry was recirculated through the milling chamber for 13 minutes with the agitator spinning at 4300 rpm. The circulation pipe end was then moved from the mill feed funnel to a collection bottle to obtain the finished pink, highly pourable flowable suspension (89.5 g).

The diameters of the micronized (milled) particles in the suspension were analyzed using a laser diffraction instrument. Using the average of two measurements, the arithmetic mean particle diameter was 2.03 μm, 90% of the particles were less than 5.21 μm diameter, 10% of the particles were less than 0.30 μm diameter, and the median particle diameter was 1.0 μm.

Step 2: Coating cottonseed with composition comprising Compound 208

Cottonseed (Stoneville 4793 RR, 122.5 g) were added to a stainless-steel pot (12 cm i.d., 11 cm depth) containing two counter-opposing lifting vanes to lift the seed as the pot turns. The pot was oriented at a 40 to 45° angle from horizontal and mechanically rotated at 640 rpm, which caused good mixing and tumbling action inside the pot.

The flowable prepared in Step 1 was sprayed directly on the tumbling bed of seed with a supply air pressure of 10-11 psi (69-76 kPa) to produce fine droplets. By measuring the weight of the reservoir, the amount of flowable suspension, sprayed on the seeds could be determined. With the seeds tumbling, the hand-held atomizer was pointed inside the pot to direct spray at the center of the tumbling bed of seed. Spraying was continued until the seed surfaces became tacky, causing the seeds to clump together. The atomizer was then shut off, and the seed coating was quickly dried by blowing on the seed low-pressure air at room temperature from a nozzle mounted to direct airflow inside the pot. The increasing sound of tumbling seeds provided an audible signal that the seed coating was sufficiently dry. The drying airflow was then shut off, and spraying using the hand-held atomizer was resumed. The cycle of spraying and drying was repeated until the desired amount of flowable suspension had been applied to the seeds. The drying of the seed coating was then completed by exposure to a low flow of ambient air for 60 hours.

The weights of Compound 208 applied to each of ten seeds from each batch was determined by macerating each seed in a bead mill and men adding acetonitrile-extraction solvent. The extracts were centrifuged and aliquots of the supernate (supernatant liquid) were diluted 10,000:1 and then analyzed by LC/MS. The analysis results are listed in Table 8.

TABLE 8

Measurements for Cottonseed Coated with Compound 208 Composition

| Measurement | Nominal 1% batch | Nominal 2% batch | Nominal 3% batch |
|---|---|---|---|
| Weight of flowable suspension sprayed on 122.5 g batch of seed | 9.20 g | 18.94 g | 30.21 g |
| Weight of treated seed batch after drying | 124.76 g | 127.10 g | 129.87 g |
| Weight of dried coating on batch of treated seed | 2.26 g | 4.60 g | 7.37 g |
| Average weight of one treated seed* | 94 mg | 101 mg | 115 mg |
| Average weight of Compound 208 per seed* | 1.2 mg | 2.6 mg | 4.4 mg |
| Average weight % of Compound 208 on coated seed* | 1.3% | 2.6% | 3.8% |

*based on 10 replicates

TABLE 9

Amounts of Ingredients in Flowable Suspensions

| Ingredient | Wt. % including water | Wt. % excluding water |
|---|---|---|
| Compounds 208, 484, 486, 502, 509 or 515 | 15.00 | 51.3 |
| Agrimer ® VA 6 | 5.00 | 17.1 |
| Licowax ® KST | 5.00 | 17.1 |
| Borresperse ™ CA | 1.00 | 3.42 |
| Pluronic ® F-108 | 1.00 | 3.42 |
| Brij ® 78 | 2.00 | 6.84 |
| Rhodorsil ® 416 | 0.20 | 0.68 |
| Pro-Ized ® Colorant Red | 0.04 | 0.14 |
| Water | 70.76 | ~ |

All the ingredients other than the active ingredient compounds are described in Example E.

A flowable suspension of each compound was prepared by the method as described, in. Example E, Step 1. The diameters (i.e. Dia. in Table 10) of the particles in the suspension were analyzed by the method also described in Example E, Step 1. The particle diameter distribution achieved after wet milling are shown in Table 10.

TABLE 10

Particle Sizes of the 6 Flowable Suspensions

| | Comound 208 | Compound 484 | Compound 486 | Compound 509 | Compound 502 | Compound 515 |
|---|---|---|---|---|---|---|
| Mean Particle Dia. =* | 1.54 μm | 1.17 μm | 0.92 μm | 2.24 μm | 1.03 μm | 0.68 μm |
| 90% of Particle Dia. <* | 3.08 μm | 2.37 μm | 2.04 μm | 4.87 μm | 2.30 μm | 1.36 μm |
| Median Particle Dia. | 1.27 μm | 0.92 μm | 0.59 μm | 1.47 μm | 0.67 μm | 0.50 μm |
| 10% of Particle Dia. <* | 0.35 μm | 0.30 μm | 0.27 μm | 0.34 μm | 0.27 μm | 0.26 μm |

*the average of two measurements
"<" means less than

Example F

Preparation of cornseed batches coated with composition comprising compounds 208, 484, 486, 502, 509 or 515

Step 1: Preparation of 6 Flowable Suspensions comprising Compounds 208, 484, 486, 502, 509 or 515

Six flowable suspensions, each containing one of the six active ingredient compounds above, were prepared using fee recipe as shown in Table 9 below.

Step 2: Coating Corn seed with separate compositions comprising Compounds 208, 484, 486, 502, 509 or 515

Corn (maize) seed (Pioneer 3146 Lot #C92FA (Parent), 65 g) were added to a stainless-steel pot (8.5 cm i.d., 8.3 cm depth) containing two counter-opposing lifting vanes to lift the seed as the pot turns. The pot was oriented at a 40 to 45° angle from horizontal and mechanically rotated at 110 rpm, which gave good mixing and tumbling action, inside the pot.

The 6 flowables prepared in Step 1 were each sprayed directly on a tumbling bed of corn seed following the general procedure described in Example E, Step 2. The drying of the seed coating was then completed by allowing seeds to dry overnight in a chemical fume hood. Nominal 3% by weight coatings of each micronized compound on corn seed were achieved as shown in Table 11.

TABLE 11

Measurements for Corn Seed Coated with Separate Compound Compositions

| Measurement | Compound 208 | Compound 484 | Compound 486 | Compound 509 | Compound 502 | Compound 515 |
|---|---|---|---|---|---|---|
| Weight of Corn Seed Batch | 65 g | 65 g | 65.15 g | 65 g | 65.04 g | 64.02 g |
| Weight of flowable suspension sprayed on seed | 15.28 g | 14.46 g | 15.49 g | 15.25 g | 15.25 g | 15.31 g |
| % of flowable suspension delivered on seed | 91.82% | 88.62% | 95.74% | 92.96% | 92.82% | 91.78% |
| Weight of treated seed batch after drying | 68.03 g | 67.88 g | 68.48 g | 68.31 g | 68.66 g | 67.93 g |
| Average weight of compounds per seed* | 2.1 mg | 1.92 mg | 2.21 mg | 2.13 mg | 2.12 mg | 2.11 mg |
| Average weight % of compounds on coated seed* | 3.14% | 2.87% | 3.28% | 3.17% | 3.16% | 3.19% |

*based on 10 replicates

Example G

Preparation of cottonseed batches coated with compositions comprising Compounds 208, 276 or 483

Step 1: Preparation of 3 Flowable Suspensions comprising compounds 208, 276 or 483

Three flowable suspensions, each containing one of the three compounds above, were prepared, using the same recipe as shown in Table 9 of Example F. A flowable suspension of each compound was prepared by the method as described in Example E, Step 1. The diameters (i.e. Dia. in Table 10) of the particles in the suspension were analyzed by the method also described in Example E, Step 1. The particle diameter distribution achieved after wet milling are shown in Table 12.

TABLE 12

Particle Sizes of the 3 Flowable Suspensions

| | Compound 483 | Compound 502 | Compound 276 |
|---|---|---|---|
| Mean Particle Dia. =* | 1.5 μm | 1.01 μm | 1.17 μm |
| 9% of Particle Dia. <* | 3.23 μm | 2.23 μm | 2.37 μm |
| Median Particle Dia. | 1.11 μm | 0.69 μm | 0.92 μm |
| 10% of Particle Dia. <* | 0.33 μm | 0.28 μm | 0.3 μm |

*the average of two measurements
"<" means less than

Step 2: Coating Cottonseed with separate compositions comprising Compounds 208, 276 or 483

Cottonseed (Stoneville 4793 RR, 33 g) were added to a stainless-steel pot (6.5 cm i.d., 7.5 cm. depth) containing two counter-opposing lifting vanes to lift the seed as the pot turns. The pot was oriented at a 40 to 45° angle from horizontal and mechanically rotated at 100 rpm, gave good mixing and tumbling action inside the pot.

The 3 flowables prepared in Step 1, were sprayed directly on separate batches of tumbling cottonseed following the general procedure described in Example E, Step 2. The drying of the seed coating was then completed by allowing seeds to dry overnight in a chemical fume hood. Nominal 3% by weight coatings of each micronized compound on cottonseed were achieved as shown in Table 13.

TABLE 13

Measurements for Cottonseed Coated with Separate Compound Compositions

| Measurement | Compound 483 | Compound 502 | Compound 276 |
|---|---|---|---|
| Weight of Cottonseed Batch | 33 g | 33 g | 33 g |
| Weight of flowable suspension sprayed on seed | 7.35 g | 7.31 g | 7.25 g |
| % of flowable suspension delivered on seed | 91.9% | 95.77% | 92.72% |
| Weight of treated seed batch after drying | 34.93 g | 35.05 g | 34.91 g |
| Average weight of compounds per seed* | 1.01 mg | 1.05 mg | 1.01 mg |
| Average weight % of compounds on coated seed* | 2.9% | 3% | 2.89% |

*based on 10 replicates

Example M

Preparation of cornseed batches coated with composition comprising Compound 502

Step 1: Preparation of Flowable Suspension comprising 15% w/w Compound 502

A 15% flowable suspension of Compound 502 containing the same ingredients other than the compounds listed in Table 9, Example F was prepared. The flowable suspension of compound 502 was prepared by the method as described In Example E, Step 1. The diameters (i.e. Dia. in Table 10) of the particles in the suspension were analyzed by the method also described In Example E, Step 1. The resultant particle diameter distribution achieved after wet milling is shown in Table 14.

TABLE 14

Particle Sizes of the Flowable Suspension

| | Compound 502 |
|---|---|
| Mean Particle Dia. =* | 0.89 μm |
| 90% of Particle Dia. <* | 1.96 μm |

TABLE 14-continued

Particle Sizes of the Flowable Suspension

| | Compound 502 |
|---|---|
| Median Particle Dia. | 0.58 μm |
| 10% of Particle Dia. <* | 0.27 μm |

*the average of two measurements
"<" means less than

Step 2: Coating corn seed with composition comprising Compound 502

Corn (maize) seed (Pioneer 34M94 Hybrid Field Corn, 575 g) were added to a stainless-steel pot (17 cm i.d. 16 cm depth) containing two counter-opposing lifting vanes to lift the seed as the pot turns. The pot was oriented at a 40 to 45° angle from horizontal and mechanically rotated at 200 rpm, giving good mixing and tumbling action inside the pot.

The 15% w/w flowable prepared in Step 1, was sprayed directly on separate batches of tumbling corn seed following the general procedure described in Example E, Step 2. The drying of the seed coating was then completed by allowing seeds to dry overnight in a chemical fume hood. Nominal 0.15, 0.29, 0.58, 1.09, 1.75% by weight coatings of micronized Compound 502 on cornseed were achieved as shown in Table 15. The average Wt. % of Compound 502 on coated seed was measured by LC/MS following the method in Step 2 of Example E.

TABLE 15

Measurements for Cottonseed Coated with Compound 502 Composition

| Measurement | Nominal 1.75% batch | Nominal 1.09% batch | Nominal 0.58% batch | Nominal 0.29% batch | Nominal 0.15% batch |
|---|---|---|---|---|---|
| Weight of Cornseed Batch | 575 g | 575 g | 575.22 g | 575.28 g | 575 g |
| Weight of flowable suspension sprayed on seed | 71.17 g | 44.56 g | 22.79 g | 11.94 g | 5.95 g |
| % of flowable suspension delivered on target | 96.11 g | 95.18% | 97.38% | 93.42% | 97.21% |
| Weight of treated seed batch after drying | 592.31 g | 577.92 g | 572.15 g | 578.12 g | 576.74 g |
| Calculated weight of compound delivered on seed | 10.26 g | 6.36 g | 3.33 g | 1.67 g | 0.87 g |
| Nominal Wt. % Seed Coating | 1.75% | 1.09% | 0.58% | 0.29% | 0.15% |
| Average Wt. % of Compound 502 on coated seed * | 1.35% | ~ | 0.42% | ~ | 0.13% |

* based on 10 replicates

The following Tests in the Biological Examples of the Invention demonstrate the efficacy of methods and compositions of the invention for protecting plants from specific arthropod pests. The pest control protection afforded by the compounds is not limited, however, to these species. See Index Table A for compound descriptions. The following abbreviations are used in the Index Table which follows: t is tertiary, n is normal, i is iso, s is secondary, c is cyclo, Me is methyl, Et is ethyl, Br is propyl and Bu is butyl; accordingly i-Pr is isopropyl, s-Bu is secondary butyl, etc. The abbreviation "Ex." stands for "Example" and is followed by a number indicating in which example the compound is prepared.

INDEX TABLE A

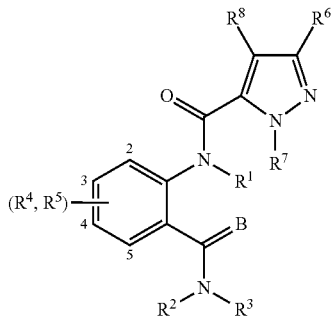

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 1 | i-Pr | H | 2-Me | $CF_3$ | $CH_3$ | 200-204 |
| 2 (Ex. 1) | i-Pr | H | 2-Me | $CF_3$ | Et | 123-126 |
| 3 | i-Pr | H | 2-Cl | $CF_3$ | $CH_3$ | 233-235 |

INDEX TABLE A-continued

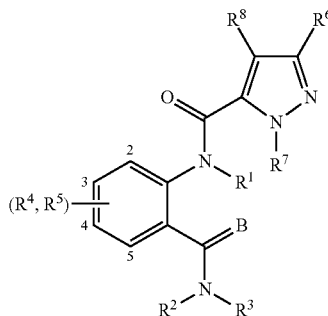

R¹, R⁵, and R⁸ are H, except where indicated; B is O, except where indicated. "CN" is bonded through carbon, not nitrogen; for example "CN—Ph" specifies cyanophenyl, not isocyanophenyl.

| Compound | R³ | R² | R⁴, R⁵ | R⁶ | R⁷ | m.p. (° C.) |
|---|---|---|---|---|---|---|
| 4 | t-Bu | H | 2-Me | CF₃ | Et | 215-218 |
| 5 | i-Pr | H | 2-Me | CH₃ | Ph | 238-239 |
| 6 | i-Pr | H | 2-Me | CH₃ | CH₃ | 206-208 |
| 7 | i-Pr | H | 2-Me | CH₃ | CH₂CF₃ | 246-248 |
| 8 | i-Pr | H | 2-Cl | Et | CF₃ | 235-237 |
| 9 | i-Pr | H | 2-Me | CH₃ | CH₃, R⁸ is Cl | 205-207 |
| 10 | i-Pr | H | 2-Me | CH₃ | 4-CF₃—Ph | 256-258 |
| 11 | i-Pr | H | 2-Me | CH₃ | 2-CF₃—Ph | 204-206 |
| 12 | t-Bu | H | 2-Me | CH₃ | Ph | 236-238 |
| 13 | i-Pr | H | 2-F | CH₃ | Ph | 227-229 |
| 14 | i-Pr | H | 5-F | CH₃ | Ph | 209-211 |
| 15 | i-Pr | H | 2-Cl | CH₃ | Ph | 233-234 |
| 16 | i-Pr | H | H | CH₃ | Ph | 215-217 |
| 17 | i-Pr | H | 2-NO₂ | CH₃ | Ph | 236-237 |
| 18 | i-Pr | H | 2-Cl | CF₃ | Ph | 240-242 |
| 19 (Ex. 2) | i-Pr | H | 2-Me | CF₃ | Ph | 260-262 |
| 20 | i-Pr | H | 2-I | CH₃ | Ph | 250-251 |
| 21 | i-Pr | H | 2-I | CH₃ | 2-CF₃—Ph | 251-253 |
| 22 | H | H | 2-Me | CH₃ | Ph | 253-255 |
| 23 | Et | Et | 2-Me | CH₃ | Ph | 182-184 |
| 24 | t-Bu | H | 2-Cl | CF₃ | Ph | 232-234 |
| 25 | i-Pr | H | 2-I | CF₃ | Ph | 271-273 |
| 26 | t-Bu | H | 2-I | CF₃ | Ph | 249-250 |
| 27 | i-Pr | H | 2-Me | CH₃ | t-Bu | 210-211 |
| 28 | i-Pr | H | 2-Br | CF₃ | Ph | 257-259 |
| 29 | i-Pr | H | 2-Br | CH₃ | Ph | 246-247 |
| 30 | i-Pr | H | 2-Me | CF₃ | 2-pyridinyl | 237-238 |
| 31 | i-Pr | H | 2,5-di-Cl | CF₃ | Ph | >250 |
| 32 | B is S, i-Pr | H | 2-Me | CF₃ | Ph | 169-172 |
| 33 | i-Pr | H | 2-Me | CF₃ | 2-Cl—Ph | 208-209 |
| 34 | i-Pr | H | 2-Cl | CF₃ | 2-Cl—Ph | 234-235 |
| 35 | i-Pr | H | 2-Me | CF₃ | 4-Cl—Ph | 289-290 |
| 36 | i-Pr | H | 2-Cl | CF₃ | 4-Cl—Ph | 276-278 |
| 37 | i-Pr | H | 2-Cl | CF₃ | 2-pyridinyl | 239-240 |
| 38 | i-Pr | H | 2-Me | CF₃ | 2-pyrimidinyl | 205-208 |
| 39 | i-Pr | H | 2-Me | CF₃ | 2-(3-CH₃-pyridinyl) | 183-187 |
| 40 | i-Pr | H | 2-Me | CF₂CF₃ | Ph | 231-232 |
| 41 | i-Pr | H | 2-Cl | CF₂CF₃ | Ph | 206-207 |
| 42 | t-Bu | H | 2-Cl | CF₂CF₃ | Ph | 212-213 |
| 43 | i-Pr | H | 2-Br | CF₂CF₃ | Ph | 219-222 |
| 44 | i-Pr | H | 2-Me | CF₃ | 3-Cl—Ph | 278-280 |
| 45 | i-Pr | H | 2-Cl | CF₃ | 3-Cl—Ph | 272-273 |
| 46 | i-Pr | H | 2-Me | CF₃ | 2-F—Ph | 217-218 |
| 47 | i-Pr | H | 2-Cl | CF₃ | 2-F—Ph | 220-221 |
| 48 | i-Pr | H | 2-Me | CF₃ | 4-F—Ph | 269-270 |
| 49 | i-Pr | H | 2-Cl | CF₃ | 4-F—Ph | 279-280 |
| 50 | i-Pr | H | 2-CF₃ | CF₃ | Ph | 247-249 |
| 51 | i-Pr | H | 2-Cl | CF₃ | i-Pr | 255-258 |
| 52 | i-Pr | H | 2-Me | CF₃ | 3-F—Ph | 277-278 |
| 53 | i-Pr | H | 2-Cl | CF₃ | 3-F—Ph | 256-257 |
| 54 | i-Pr | H | 2-Me | CF₃ | 2-CF₃—Ph | 215-216 |
| 55 | i-Pr | H | 2-Cl | CF₃ | 2-CF₃—Ph | 230-231 |
| 56 | i-Pr | H | 2-Me | CF₃ | 2-Br—Ph | 207-208 |
| 57 | i-Pr | H | 2-Cl | CF₃ | 2-Br—Ph | 239-240 |
| 58 | i-Pr | H | 2-OCH₃ | CF₃ | Ph | 215-216 |
| 59 | i-Pr | H | 5-Cl | CF₃ | 2-(3-CH₃-pyridinyl) | 224-225 |
| 60 | i-Pr | H | 5-Me | CF₃ | 2-(3-Cl-pyridinyl) | 179-181 |
| 61 | s-Bu | H | 2-Cl | CF₃ | Ph | >240 |

INDEX TABLE A-continued

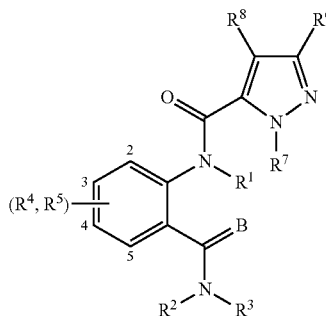

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4$, $R^5$ | $R^6$ | $R^7$ | m.p. (° C.) |
|---|---|---|---|---|---|---|
| 62 | c-Pr | H | 2-Cl | $CF_3$ | Ph | >240 |
| 63 | Et | H | 2-Cl | $CF_3$ | Ph | >240 |
| 64 | t-Bu | H | 2-$CF_3$ | $CF_3$ | Ph | 230-233 |
| 65 | Et | H | 2-$CF_3$ | $CF_3$ | Ph | 246-249 |
| 66 | $CH(CH_3)CH_2SCH_3$ | H | 2-$CF_3$ | $CF_3$ | Ph | 215-217 |
| 67 | $CH(CH_3)CH_2OCH_3$ | H | 2-$CF_3$ | $CF_3$ | Ph | 220-223 |
| 68 | i-Pr | H | 5-Cl | $CF_3$ | 2-(3-Cl-pyridinyl) | 230-233 |
| 69 | i-Pr | H | 5-Me | $CF_3$ | 2-thiazolyl | 201-203 |
| 70 | i-Pr | H | 5-Me | $CF_3$ | 2-pyrazinyl | 252-253 |
| 71 | i-Pr | H | 5-Me | $CF_3$ | 4-pyrazinyl | 224-228 |
| 72 | i-Pr | H | 2-Me | $CF_3$ | i-Pr | 236-243 |
| 73 | i-Pr | H | 2-Me | $CF_3$ | 2-$CH_3$—Ph | 211-212 |
| 74 | i-Pr | H | 2-Cl | $CF_3$ | 2-$CH_3$—Ph | 232-234 |
| 75 | i-Pr | H | 2-Br | $CF_3$ | 2-Cl—Ph | 247-248 |
| 76 | t-Bu | H | 2-Me | $CF_3$ | 2-Cl—Ph | 216-217 |
| 77 (Ex. 3) | i-Pr | H | 2-Me | $CF_3$ | 2-(3-$CF_3$-pyridinyl) | 227-230 |
| 78 | $CH_2CH_2Cl$ | H | 2-Cl | $CF_3$ | Ph | 237-242 |
| 79 | $CH_2CH_2CH_2Cl$ | H | 2-Cl | $CF_3$ | Ph | 233-239 |
| 80 | $CH(CH_3)CO_2CH_3$ | H | 2-Cl | $CF_3$ | Ph | 221-222 |
| 81 | $CH(i-Pr)CO_2CH_3$ (S configuration) | H | 2-Cl | $CF_3$ | Ph | 212-213 |
| 82 | i-Pr | H | 2-Me | $CF_3$ | 2,6-di-Cl—Ph | 267-268 |
| 83 | i-Pr | H | 2-Cl | $CF_3$ | 2,6-di-Cl—Ph | 286-287 |
| 84 | i-Pr | H | 2-Me | Br | Ph | 253-255 |
| 85 | i-Pr | H | 2-Cl | Br | Ph | 247-248 |
| 86 | i-Pr | H | 2-Me | $CF_3$ | i-Bu | 205-210 |
| 87 | i-Pr | H | 2-Me | $CF_3$ | $CH_2Ph$ | 235-237 |
| 88 | i-Pr | H | 2-Me | $CF_3$ | 2-(3-$CH_3O$-pyridinyl) | 221-222 |
| 89 | i-Pr | H | 2-Me | $CF_3$ | 3-pyridinyl | 260-261 |
| 90 | i-Pr | H | 2-Me | $CF_3$ | 4-quinolinyl | >260 |
| 91 | i-Pr | H | 2-Me | CN | 2-(3-Cl-pyridinyl) | 203-204 |
| 92 | i-Pr | H | 2-Me | $CF_3$ | 2,4-di-F—Ph | 245-246 |
| 93 | i-Pr | H | 2-Cl | $CF_3$ | 2,4-di-F—Ph | 252-253 |
| 94 | i-Pr | H | 2-Me | $CF_3$ | 2-Et—Ph | 207-209 |
| 95 | i-Pr | H | 2-Cl | $CF_3$ | 2-Et—Ph | 221-222 |
| 96 | i-Pr | H | H | $CF_3$ | 2-Cl—Ph | 206-207 |
| 97 | t-Bu | H | H | $CF_3$ | 2-Cl—Ph | 197-198 |
| 98 | $CH(CH_3)CH_2OCH_3$ | H | H | $CF_3$ | 2-Cl—Ph | 145-148 |
| 99 | $CH(CH_3)CH_2SCH_3$ | H | H | $CF_3$ | 2-Cl—Ph | 158-160 |
| 100 | $CH(CH_3)CH_2SCH_3$ | H | 2-Cl | $CF_3$ | Ph | 184-186 |
| 101 | $CH(CH_3)CH_2OCH_3$ | H | 2-Cl | $CF_3$ | Ph | 217-218 |
| 102 | n-Pr | H | 2-Cl | $CF_3$ | Ph | 247-248 |
| 103 | i-Bu | H | 2-Cl | $CF_3$ | Ph | 244-245 |
| 104 | $CH_3$ | H | 2-Cl | $CF_3$ | Ph | >250 |
| 105 | i-Pr | Me | 2-Cl | $CF_3$ | Ph | 193-194 |
| 106 | $CH_2C\equiv CH$ | H | 2-Cl | $CF_3$ | Ph | >250 |
| 107 | $CH_2CH=CH_2$ | H | 2-Cl | $CF_3$ | Ph | 248-249 |
| 108 | $CH_2$(2-furanyl) | H | 2-Cl | $CF_3$ | Ph | 246-247 |
| 109 | i-Pr | H | 2-Me | $CF_3$ | 4-(3,5-di-Cl-pyridinyl) | 239-242 |
| 110 | i-Pr | H | 2-Cl | $CF_3$ | 4-(3,5-di-Cl-pyridinyl) | 229-231 |
| 111 | $CH(CH_3)CH_2SCH_3$ | H | 2-Me | $CF_3$ | 2-Cl—Ph | 194-195 |
| 112 | $CH(CH_3)CH_2OCH_3$ | H | 2-Me | $CF_3$ | 2-Cl—Ph | 181-183 |
| 113 | s-Bu | H | 2-Me | $CF_3$ | 2-Cl—Ph | 199-200 |
| 114 | c-Pr | H | 2-Me | $CF_3$ | 2-Cl—Ph | 234-235 |
| 115 | n-Pr | H | 2-Me | $CF_3$ | 2-Cl—Ph | 222-223 |
| 116 | i-Bu | H | 2-Me | $CF_3$ | 2-Cl—Ph | 235-237 |
| 117 | Me | H | 2-Me | $CF_3$ | 2-Cl—Ph | 242-243 |
| 118 | i-Pr | Me | 2-Me | $CF_3$ | 2-Cl—Ph | 90-93 |

INDEX TABLE A-continued

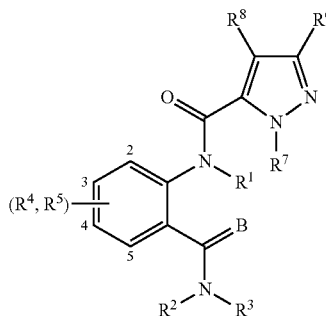

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 119 | $CH_2C{\equiv}CH$ | H | 2-Me | $CF_3$ | 2-Cl—Ph | 215-216 |
| 120 | Et | H | 2-Me | $CF_3$ | 2-Cl—Ph | 228-229 |
| 121 | $CH_2CH{=}CH_2$ | H | 2-Me | $CF_3$ | 2-Cl—Ph | 227-228 |
| 122 | $CH_2$(2-furanyl) | H | 2-Me | $CF_3$ | 2-Cl—Ph | 218-219 |
| 123 | $CH(CH_3)CH_2SCH_3$ | H | 2-Me | $CF_3$ | Ph | 179-180 |
| 124 | $CH(CH_3)CH_2OCH_3$ | H | 2-Me | $CF_3$ | Ph | 219-220 |
| 125 | s-Bu | H | 2-Me | $CF_3$ | Ph | 244-245 |
| 126 | c-Pr | H | 2-Me | $CF_3$ | Ph | >250 |
| 127 | n-Pr | H | 2-Me | $CF_3$ | Ph | 238-239 |
| 128 | i-Bu | H | 2-Me | $CF_3$ | Ph | 237-238 |
| 129 | Me | H | 2-Me | $CF_3$ | Ph | 263-265 |
| 130 | i-Pr | Me | 2-Me | $CF_3$ | Ph | 178-179 |
| 131 | $CH_2C{\equiv}CH$ | H | 2-Me | $CF_3$ | Ph | 253-254 |
| 132 | Et | H | 2-Me | $CF_3$ | Ph | 244-245 |
| 133 | $CH_2CH{=}CH_2$ | H | 2-Me | $CF_3$ | Ph | 240-241 |
| 134 | $CH_2$(2-furanyl) | H | 2-Me | $CF_3$ | Ph | 245-246 |
| 135 | i-Pr | H | 2-$OCHF_2$ | $CF_3$ | 2-Cl—Ph | 200-201 |
| 136 | i-Pr | H | 2-$OCH_3$ | $CF_3$ | 2-Cl—Ph | 206-207 |
| 137 | i-Pr | H | 2-I | $CF_3$ | 2-Cl—Ph | 253-256 |
| 138 | i-Pr | H | 2-Me | Br | 2-Cl—Ph | 147-150 |
| 139 | i-Pr | H | 2-Cl | Br | 2-Cl—Ph | 246-247 |
| 140 | i-Pr | H | 2-Me | $CF_3$ | 2-$CH_3O$—Ph | 218-219 |
| 141 | i-Pr | H | 2-Cl | $CF_3$ | 2-$CH_3O$—Ph | 243-244 |
| 142 | i-Pr | H | 2-Me | $CF_3$ | 1-isoquinolinyl | 252-253 |
| 143 | $CH(CH_3)CH_2SCH_3$ | H | 2-Cl | $CF_3$ | 2-Cl—Ph | 217-218 |
| 144 | $CH(CH_3)CH_2OCH_3$ | H | 2-Cl | $CF_3$ | 2-Cl—Ph | 207-208 |
| 145 | s-Bu | H | 2-Cl | $CF_3$ | 2-Cl—Ph | 216-217 |
| 146 | c-Pr | H | 2-Cl | $CF_3$ | 2-Cl—Ph | 261-262 |
| 147 | n-Pr | H | 2-Cl | $CF_3$ | 2-Cl—Ph | 231-232 |
| 148 | i-Bu | H | 2-Cl | $CF_3$ | 2-Cl—Ph | 255-256 |
| 149 | Me | H | 2-Cl | $CF_3$ | 2-Cl—Ph | 233-235 |
| 150 | i-Pr | Me | 2-Cl | $CF_3$ | 2-Cl—Ph | 127-128 |
| 151 | $CH_2C{\equiv}CH$ | H | 2-Cl | $CF_3$ | 2-Cl—Ph | 226-227 |
| 152 | Et | H | 2-Cl | $CF_3$ | 2-Cl—Ph | 244-246 |
| 153 | $CH_2CH{=}CH_2$ | H | 2-Cl | $CF_3$ | 2-Cl—Ph | 235-236 |
| 154 | $CH_2$(2-furanyl) | H | 2-Cl | $CF_3$ | 2-Cl—Ph | 207-208 |
| 155 | i-Pr | H | C≡CH | $CF_3$ | 2-Cl—Ph | 228-230 |
| 156 | i-Pr | H | 2-Cl | C≡CH | 2-Cl—Ph | 219-222 |
| 157 | i-Pr | H | 2-Me | H | H, $R^8$ is $CH_3$ | 220-223 |
| 158 | i-Pr | H | 2-Me | $CH_3$ | Ph, $R^8$ is Cl | 209-210 |
| 159 | B is S, i-Pr | H | 2-Cl | $CF_3$ | Ph | 169-174 |
| 160 | i-Pr | H | 2-Me | $CF_3$ | 2,6-di-F—Ph | 223-225 |
| 161 | i-Pr | H | 2-Me | $CF_3$ | 2-Cl-6-F—Ph | 203-206 |
| 162 | i-Pr | H | 2-Cl | $CF_3$ | 2-Cl-6-F—Ph | 218-221 |
| 163 | i-Pr | H | 2-Me-4-Br | $CF_3$ | 2-F—Ph | 232-233 |
| 164 | t-Bu | H | 2-Cl | $CF_3$ | 2-(3-Cl-pyridinyl) | 250-251 |
| 165 | Me-cyclopropyl | H | 2-Cl | $CF_3$ | 2-(3-Cl-pyridinyl) | >250 |
| 166 | Et | Et | 2-Cl | $CF_3$ | 2-Cl—Ph | 243-247 |
| 167 | Me | Me | 2-Cl | $CF_3$ | 2-Cl—Ph | 234-235 |
| 168 | Et | Et | 2-Me | $CF_3$ | 2-Cl—Ph | 237-238 |
| 169 | Me | Me | 2-Me | $CF_3$ | 2-Cl—Ph | 225-226 |
| 170 | i-Pr | H | 2-Cl | $CF_3$ | 2-pyrazinyl | 242-243 |
| 171 | t-Bu | H | 2-Me-4-Br | $CF_3$ | 2-Cl—Ph | >260 |
| 172 | $CH(CH_3)CH_2OCH_3$ | H | 2-Me | $CF_3$ | 2-(3-Cl-pyridinyl) | 176-177 |

INDEX TABLE A-continued

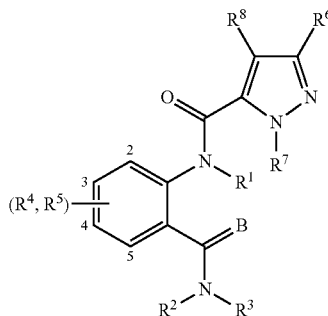

R$^1$, R$^5$, and R$^8$ are H, except where indicated; B is O, except where indicated. "CN" is bonded through carbon, not nitrogen; for example "CN—Ph" specifies cyanophenyl, not isocyanophenyl.

| Compound | R$^3$ | R$^2$ | R$^4$, R$^5$ | R$^6$ | R$^7$ | m.p. (° C.) |
|---|---|---|---|---|---|---|
| 173 | CH(CH$_3$)CH$_2$SCH$_3$ | H | 2-Me | CF$_3$ | 2-(3-Cl-pyridinyl) | 196-197 |
| 174 | CH(CH$_3$)CH$_2$OCH$_3$ | H | 2-Cl | CF$_3$ | 2-(3-Cl-pyridinyl) | 197-198 |
| 175 | CH(CH$_3$)CH$_2$SCH$_3$ | H | 2-Cl | CF$_3$ | 2-(3-Cl-pyridinyl) | 202-203 |
| 176 | i-Pr | H | 2-Me | CF$_3$ | 2-I—Ph | 221-222 |
| 177 | i-Pr | H | 2-Cl | CF$_3$ | 2-I—Ph | 238-240 |
| 178 | i-Pr | H | 2-Me | CF$_3$ | 2-(HC≡C)—Ph | 215-217 |
| 179 | i-Pr | H | 2-Cl | CF$_3$ | 2-(HC≡C)—Ph | 244-246 |
| 180 | i-Pr | H | 2-Me | CF$_3$ | 2-Cl-4-F—Ph | 203-205 |
| 181 | i-Pr | H | 2-Cl | CF$_3$ | 2-Cl-4-F—Ph | 218-219 |
| 182 | Et | Et | 2-Me | CF$_3$ | 2-Cl—Ph | 243-247 |
| 183 | i-Pr | H | 2-Me | CF$_3$ | 2,6-di-Me—Ph | 259-260 |
| 184 | i-Pr | H | 2-Cl | CF$_3$ | 2,6-di-Me—Ph | 268-269 |
| 185 | i-Pr | H | 2-Me | CF$_3$ | 2,6-di-Cl-4-CN—Ph | * |
| 186 | i-Pr | H | 2-Me | CF$_3$ | 2-CN—Ph | 225-235 |
| 187 | i-Pr | H | 2-Me | CF$_3$ | 2-(CF$_3$O)—Ph | 214-215 |
| 188 | i-Pr | H | 2-Cl | CF$_3$ | 2-(CF$_3$O)—Ph | 223-224 |
| 189 | i-Pr | H | 2-Me | CF$_3$ | 2-Br-4-F—Ph | 202-203 |
| 190 | i-Pr | H | 2-Cl | CF$_3$ | 2-Br-4-F—Ph | 222-223 |
| 191 | i-Pr | H | 2-Me | CF$_3$ | 2-(3-Me-pyrazinyl) | 205-207 |
| 192 | Me | H | 2-Cl | CF$_3$ | 2-(3-Cl-pyridinyl) | 215-220 |
| 193 | CH$_2$C≡CH | H | 2-Cl | CF$_3$ | 2-(3-Cl-pyridinyl) | 197-198 |
| 194 | Me | H | 2-Me | CF$_3$ | 2-(3-Cl-pyridinyl) | 193-196 |
| 195 | Et | H | 2-Me | CF$_3$ | 2-(3-Cl-pyridinyl) | 204-206 |
| 196 | CH$_2$C≡CH | H | 2-Me | CF$_3$ | 2-(3-Cl-pyridinyl) | 177-178 |
| 197 | i-Pr | H | 2-Me | CF$_3$ | 4-(8-Cl-quinolinyl) | >250 |
| 198 | i-Pr | H | 2-Me | CF$_3$ | 4-(2-Me-quinolinyl) | >250 |
| 199 | i-Pr | H | 2-Cl | CF$_3$ | 4-(2-Me-quinolinyl) | >250 |
| 200 | i-Pr | H | 2-Me | CF$_3$ | 4-(7-Cl-quinolinyl) | >250 |
| 201 | i-Pr | H | 2,4-Br$_2$ | CF$_3$ | 2-Cl—Ph | 233-234 |
| 202 | i-Pr | H | 2-Br | Br | 2-Cl—Ph | 255-258 |
| 203 | Me | H | 2-Me | Br | 2-Cl—Ph | 236-237 |
| 204 | t-Bu | H | 2-Cl | Br | 2-Cl—Ph | 260-261 |
| 205 | Et | H | 2-Me | Br | 2-Cl—Ph | 254-255 |
| 206 | t-Bu | H | 2-Me | Br | 2-Cl—Ph | 259-260 |
| 207 | c-Bu | H | 2-Cl | CN | 2-(3-Cl-pyridinyl) | 177-180 |
| 208 (Ex. 4, 5) | i-Pr | H | 2-Me | CF$_3$ | 2-(3-Cl-pyridinyl) | 237-239 |
| 209 | i-Pr | H | 2-Me | CF$_3$ | 4-(6-Cl-quinolinyl) | >250 |
| 210 | Me | Me | 2-Me | CF$_3$ | 4-(6-Cl-quinolinyl) | >250 |
| 211 | i-Pr | H | 2-Cl | CN | 2-(3-Cl-pyridinyl) | 195-200 |
| 212 | t-Bu | H | 2-Cl | CN | 2-(3-Cl-pyridinyl) | >250 |
| 213 | Et | H | 2-Cl | CN | 2-(3-Cl-pyridinyl) | 200-205 |
| 214 | i-Pr | H | 2-Cl | CF$_3$ | 2-(3-Me-pyrazinyl) | 225-230 |
| 215 | t-Bu | H | 2-Cl | CF$_3$ | 2-(3-Me-pyrazinyl) | 235-240 |
| 216 | Et | H | 2-Cl | CF$_3$ | 2-(3-Me-pyrazinyl) | 210-220 |
| 217 | i-Pr | H | 2-Me | CF$_3$ | 3-(2-Cl-pyridinyl) | * |
| 218 | i-Pr | H | 2-Cl | CF$_3$ | 2,3-di-Cl—Ph | 217-219 |
| 219 | t-Bu | H | 2-Cl | CF$_3$ | 2,3-di-Cl—Ph | 254-256 |
| 220 | i-Pr | H | 2-Me | CF$_3$ | 2,3-di-Cl—Ph | 208-209 |
| 221 | t-Bu | H | 2-Me | CF$_3$ | 2,3-di-Cl—Ph | 232-233 |
| 222 | t-Bu | H | 2-Me-4-Br | Br | 2-Cl—Ph | 239-241 |
| 223 | Me | H | 2-Me-4-Br | Br | 2-Cl—Ph | 150-152 |
| 224 | Et | H | 2-Me-4-Br | Br | 2-Cl—Ph | 223-225 |
| 225 | i-Pr | H | 2-Me-4-Br | Br | 2-Cl—Ph | 197-198 |
| 226 | Me | H | 2-Me | CF$_3$ | 2-F—Ph | 245-247 |
| 227 | CH$_2$C≡CH | H | 2-Me | CF$_3$ | 2-F—Ph | 222-227 |
| 228 | Me | Me | 2-Cl | CF$_3$ | 2-Cl—Ph | 234-236 |
| 229 | CH$_2$C≡CH | H | 2-Me-4-Br | Br | 2-Cl—Ph | 187-188 |
| 230 | i-Pr | H | 2-Cl | CF$_3$ | 2-(3-Me-pyridinyl) | 224-225 |

INDEX TABLE A-continued

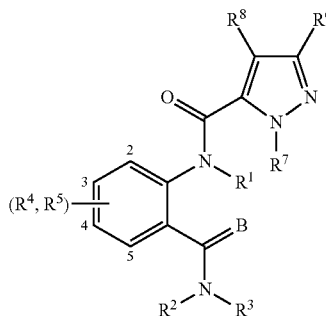

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 231 | i-Pr | H | 2-Cl | $CF_3$ | 2-(3-Cl-pyridinyl) | 230-233 |
| 232 | i-Pr | H | 2-Me | $CF_3$ | 2-pyrazinyl | 252-253 |
| 233 | i-Pr | H | 2-Me | $CF_3$ | 2-thiazolyl | 201-203 |
| 234 | i-Pr | H | 2-Me | $CF_3$ | 4-pyridinyl | 224-228 |
| 235 | i-Pr | H | 2-Me | $CF_3$ | 2-(3-Cl-pyridinyl) | 249-250 |
| 236 | i-Pr | H | 2-Me | $CF_3$ | Ph, $R^8$ is $CH_3$ | 246-248 |
| 237 | Me | Me | 2-Me | $CF_3$ | 2-Cl—Ph | 234-235 |
| 238 | i-Pr | H | 2-Me | $CF_3$ | $CH{=}CHCH_3$ | 225-228 |
| 239 | i-Pr | H | 2-Me | $CF_3$ | 2-Cl-6-Me—Ph | |
| 240 | i-Pr | H | 2-Cl | $CF_3$ | 2-Cl-6-Me—Ph | |
| 241 | i-Pr | H | 2-Cl | $CF_3$ | 4-CN—Ph | * |
| 242 | i-Pr | H | 2-Cl | $CF_3$ | 2,6-di-Cl-4-CN—Ph | * |
| 243 | i-Pr | H | 2-Cl | $CF_3$ | 2-Cl-4-CN—Ph | * |
| 244 | i-Pr | H | 2-Cl | CN | Ph | * |
| 245 | i-Pr | H | 2-Me | $CF_3$ | 4-CN—Ph | 271-272 |
| 246 | i-Pr | H | 2-Me | $CF_3$ | 3-CN—Ph | 263-264 |
| 247 | i-Pr | H | 2-Me | $CF_3$ | 2-Cl-4-CN—Ph | * |
| 248 | i-Pr | H | 2-Me | CN | Ph | * |
| 249 | i-Pr | H | 2-Cl | $CF_3$ | 3-CN—Ph | * |
| 250 | i-Pr | H | 2-Me | $CF_3$ | 2-Me-4-F—Ph | 204-206 |
| 251 | i-Pr | H | 2-Cl | $CF_3$ | 2-Me-4-F—Ph | 212-213 |
| 252 | i-Pr | H | 2-Me | $CF_3$ | 2,4-di-Me—Ph | 189-190 |
| 253 | t-Bu | H | 2-Me | $CF_3$ | 2,4-di-Me—Ph | 197-198 |
| 254 | t-Bu | H | 2-Cl | $CF_3$ | 2,4-di-Me—Ph | 234-235 |
| 255 | i-Pr | H | 2-Me | $CF_3$ | n-Bu, $R^8$ is Cl | 95-98 |
| 256 | Me | H | 2-Cl | $CF_3$ | 4-(7-Cl-quinolinyl) | >250 |
| 257 | Et | H | 2-Cl | $CF_3$ | 4-(7-Cl-quinolinyl) | >250 |
| 258 | $CH_2CH{=}CH_2$ | H | 2-Cl | $CF_3$ | 4-(7-Cl-quinolinyl) | >250 |
| 259 | i-Pr | H | 2-Cl | $CF_3$ | 4-(8-Cl-quinolinyl) | >250 |
| 260 | i-Pr | H | 2-Me | $CF_3$ | 2-(3-CN-pyridinyl) | 237-239 |
| 261 | i-Pr | H | 2-Me | $CF_3$ | 1-(6-Cl-isoquinolinyl) | >250 |
| 262 | t-Bu | H | 2-Me | $CF_3$ | 1-(6-Cl-isoquinolinyl) | 227-229 |
| 263 | Me | Me | 2-Me | $CF_3$ | 1-(6-Cl-isoquinolinyl) | >250 |
| 264 | i-Pr | H | 2-Me | $CF_3$ | 2-Cl-4-CN-6-Me—Ph | * |
| 265 | i-Pr | H | 2-Me-4-Br | Br | 2-Cl—Ph | 187-188 |
| 266 | $CH_2CH(OCH_3)_2$ | H | 2-Me | $CF_3$ | 2-Cl—Ph | 205-207 |
| 267 | $CH_2CH(OCH_3)_2$ | Me | 2-Me | $CF_3$ | 2-Cl—Ph | 185-190 |
| 268 | $CH_2CH_2CH(OCH_3)_2$ | H | 2-Me | $CF_3$ | 2-Cl—Ph | 85-90 |
| 269 | Me | H | 2-Me | $CF_3$ | 2,6-di-Cl—Ph | 280-282 |
| 270 | Et | H | 2-Me | $CF_3$ | 2,6-di-Cl—Ph | 274-275 |
| 271 | t-Bu | H | 2-Me | $CF_3$ | 2,6-di-Cl—Ph | 285-286 |
| 272 | t-Bu | H | 2-Cl | $CF_3$ | 2,6-di-Cl—Ph | 290-291 |
| 273 | i-Pr | H | 2-Me | H | 2-Cl—Ph | * |
| 274 | i-Pr | H | 2-Me | H | 2-Me—Ph | * |
| 275 | i-Pr | H | 2-Me | H | 2-F—Ph | * |
| 276 | i-Pr | H | 2-Me | Br | 2-(3-Cl-pyridinyl) | 206-209 |
| 277 | $CH_2CH_2CN$ | H | 2-Me | $CF_3$ | 2-Cl—Ph | 189-195 |
| 278 | i-Pr | H | 2-Me | CN | 2-Cl—Ph | * |
| 279 | i-Pr | H | 2-Me | $CF_3$ | 2-(3-$CH_3$O-pyrazinyl) | 195-200 |
| 280 | i-Pr | H | 2-Me | Br | 2,6-di-Cl—Ph | 265-267 |
| 281 | t-Bu | H | 2-Me | Br | 2,6-di-Cl—Ph | 282-284 |
| 282 | i-Pr | H | 2-Cl | Br | 2,6-di-Cl—Ph | 277-279 |
| 283 | t-Bu | H | 2-Cl | Br | 2,6-di-Cl—Ph | 296-298 |
| 284 | i-Pr | H | 2-Me | Br | 2-Cl-4-F—Ph | 236-238 |
| 285 | t-Bu | H | 2-Me | Br | 2-Cl-4-F—Ph | 249-250 |
| 286 | i-Pr | H | 2-Cl | Br | 2-Cl-4-F | 176-177 |
| 287 | t-Bu | H | 2-Cl | Br | 2-Cl-4-F—Ph | 257-258 |
| 288 | i-Pr | H | 2-I | Br | 2-Cl-4-F | 227-229 |
| 289 | c-Bu | H | 2-Cl | $CF_3$ | 2-(3-Cl-pyridinyl) | 230-231 |

INDEX TABLE A-continued

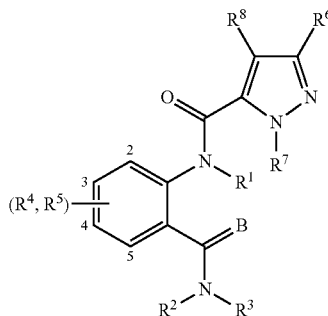

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 290 | i-Pr | H | 2-Cl | Br | 2-(3-Cl-pyridinyl) | 231-234 |
| 291 | t-Bu | H | 2-Cl | Br | 2-(3-Cl-pyridinyl) | 245-248 |
| 292 | Et | H | 2-Cl | Br | 2-(3-Cl-pyridinyl) | 219-222 |
| 293 | Et | H | 2-Me | Br | 2-(3-Cl-pyridinyl) | 217-220 |
| 294 | t-Bu | H | 2-Me | Br | 2-(3-Cl-pyridinyl) | 237-240 |
| 295 | CH$_2$CN | H | 2-Me | Br | 2-(3-Cl-pyridinyl) | 227-229 |
| 296 | t-Bu | H | 2-Me | CN | 2-(3-Cl-pyridinyl) | 215-225 |
| 297 | c-Bu | H | 2-Me | CN | 2-(3-Cl-pyridinyl) | 105-115 |
| 298 | c-Bu | H | 2-Me | CF$_3$ | 2-(3-Cl-pyridinyl) | 187-190 |
| 299 | c-pentyl | H | 2-Me | CF$_3$ | 2-(3-Cl-pyridinyl) | 190-195 |
| 300 | s-Bu | H | 2-Me | CF$_3$ | 2-(3-Cl-pyridinyl) | 170-180 |
| 301 | c-pentyl | H | 2-Cl | CF$_3$ | 2-(3-Cl-pyridinyl) | 215-222 |
| 302 | s-Bu | H | 2-Cl | CF$_3$ | 2-(3-Cl-pyridinyl) | 210-220 |
| 306 | i-Pr | H | 2-Me | Cl | 2-(3-Cl-pyridinyl) | 204-206 |
| 307 | t-Bu | H | 2-Me | Cl | 2-(3-Cl-pyridinyl) | 210-213 |
| 308 | t-Bu | H | 2-Cl | Cl | 2-(3-Cl-pyridinyl) | 237-239 |
| 309 | i-Pr | H | 2-Cl | Cl | 2-(3-Cl-pyridinyl) | 159-162 |
| 310 | CH(CH$_3$)$_2$CH$_2$CH$_3$ | H | 2-Me | CN | 2-(3-Cl-pyridinyl) | 165-175 |
| 311 | c-hexyl | H | 2-Cl | CF$_3$ | 2-(3-Cl-pyridinyl) | 250-260 |
| 312 | CH(CH$_3$)$_2$CH$_2$CH$_3$ | H | 2-Cl | CF$_3$ | 2-(3-Cl-pyridinyl) | 200-210 |
| 313 | i-Pr | H | 2,4-di-Me | CF$_3$ | 2-Cl—Ph | 239-240 |
| 314 | i-Pr | H | 2-Me | CF$_3$ | 2-Cl-5-CN—Ph | * |
| 315 | i-Pr | H | 2-Me | H | 2-(3-Cl-pyridinyl) | 111-115 |
| 316 | i-Pr | H | 2-Me | CF$_3$ | 2-CO$_2$Me—Ph | |
| 317 | i-Pr | H | 2-Me-4-Br | CF$_3$ | 2,6-di-Cl—Ph | 230-233 |
| 318 | t-Bu | H | 2-Me-4-Br | CF$_3$ | 2,6-di-Cl—Ph | >250 |
| 319 | Me | H | 2-Me-4-Br | CF$_3$ | 2,6-di-Cl—Ph | 228-230 |
| 320 | CH$_2$CN | H | 2-Me-4-Br | CF$_3$ | 2,6-di-Cl—Ph | 228-230 |
| 321 | i-Pr | H | 2,4-di-Cl | CF3 | 2-Cl—Ph | 223-224 |
| 322 | i-Pr | H | 2-Me | CF$_3$ | 2-Cl-4-CF$_3$-6-Cl—Ph | 206-207 |
| 323 | i-Pr | H | 2-Me | CF$_3$ | 5-(1,3-di-Me-4-Cl-pyrazolyl) | |
| 324 | i-Pr | H | 2-Me | CF$_3$ | 2-(4,6-di-Me-pyrimidinyl) | 220-222 |
| 325 | i-Pr | H | 2-Cl | CF$_3$ | 2-(4,6-di-Me-pyrimidinyl) | 152-154 |
| 326 | t-Bu | H | 2-Me | CF$_3$ | 2-(4,6-di-Me-pyrimidinyl) | 124-127 |
| 327 | t-Bu | H | 2-Cl | CF$_3$ | 2-(4,6-di-Me-pyrimidinyl) | 179-182 |
| 328 | i-Pr | H | 4-I | CF$_3$ | 2-Cl—Ph | 218-219 |
| 329 | i-Pr | H | 2-Me-4-OCH$_3$ | CF$_3$ | 2-(3-Cl-pyridinyl) | 187-188 |
| 330 | i-Pr | H | 2-Me | CF$_3$ | 2-F-4-Cl-5-(i-PrO)—Ph | 214-216 |
| 331 | CH$_2$CN | H | 2-Me | Cl | 2-(3-Cl-pyridinyl) | 190-195 |
| 332 | Et | H | 2-Cl | CF$_3$ | 2-(3-Cl-pyridinyl) | 217-219 |
| 333 | i-Pr | H | 2-Me-4-Br | CF$_3$ | 2,3-di-Cl—Ph | >250 |
| 334 | i-Pr | H | 2-Me | CF$_3$ | 2,5-di-Cl—Ph | >250 |
| 335 | i-Pr | H | 2-Cl-4-Br | CF$_3$ | 2,3-di-Cl—Ph | 251-253 |
| 336 | CH$_2$CN | H | 2-Cl | CF$_3$ | 2,3-di-Cl—Ph | 185-190 |
| 337 | CH$_2$CH$_2$SCH$_2$CH$_3$ | H | 2-Me | CF$_3$ | 2-(3-Cl-pyridinyl) | 197-200 |
| 338 | CH$_2$CH$_2$CH$_2$SCH$_3$ | H | 2-Me | CF$_3$ | 2-(3-Cl-pyridinyl) | 185-190 |
| 339 | CH$_2$(2-furanyl) | H | 2-Me | CF$_3$ | 2-(3-Cl-pyridinyl) | 210-215 |
| 340 | CH$_2$C(=CH$_2$)CH$_3$ | H | 2-Me | CF$_3$ | 2-(3-Cl-pyridinyl) | 225-229 |
| 341 | CH$_2$CH$_2$OCH$_3$ | H | 2-Me | CF$_3$ | 2-(3-Cl-pyridinyl) | 215-218 |
| 342 | CH$_2$CH$_2$CH$_2$OH | H | 2-Me | CF$_3$ | 2-(3-Cl-pyridinyl) | 210-212 |
| 343 | CH$_2$CH$_2$Cl | H | 2-Me | CF$_3$ | 2-(3-Cl-pyridinyl) | 206-216 |
| 344 | CH$_2$CH$_2$OH | H | 2-Me | CF$_3$ | 2-(3-Cl-pyridinyl) | 217-220 |
| 345 | CH(CH$_3$)CH$_2$OH | H | 2-Me | CF$_3$ | 2-(3-Cl-pyridinyl) | 110-115 |
| 346 | CH$_2$CH(Br)CH$_2$Br | H | 2-Me | CF$_3$ | 2-(3-Cl-pyridinyl) | 217-220 |
| 347 | CH$_2$CO$_2$CH$_3$ | H | 2-Me | CF$_3$ | 2-(3-Cl-pyridinyl) | >250 |
| 348 | CH$_2$CH(OH)CH$_2$OH | H | 2-Me | CF$_3$ | 2-(3-Cl-pyridinyl) | >250 |
| 349 | CH$_2$CH$_2$CH$_2$Cl | H | 2-Me | CF$_3$ | 2-(3-Cl-pyridinyl) | 207-212 |
| 350 | CH(CH$_2$OH)CH$_2$CH$_3$ | H | 2-Me | CF$_3$ | 2-(3-Cl-pyridinyl) | 173-176 |
| 351 | i-Pr | H | 2-Me | CF$_3$ | 2-(5-CF$_3$-pyridinyl) | 270-275 |

INDEX TABLE A-continued

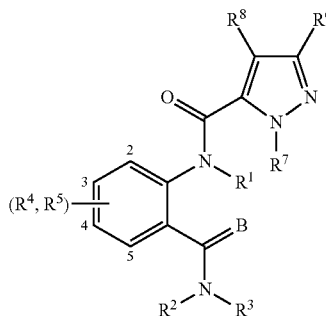

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 352 | Et | H | 2-Me | $CF_3$ | 2-(3,6-di-Me-pyrazinyl) | 210-215 |
| 353 | i-Pr | H | 2-Me | $CF_3$ | 2-(3,6-di-Me-pyrazinyl) | 215-220 |
| 354 | t-Bu | H | 2-Me | $CF_3$ | 2-(3,6-di-Me-pyrazinyl) | 265-270 |
| 355 | Et | H | 2-Cl | $CF_3$ | 2-(3,6-di-Me-pyrazinyl) | 214-217 |
| 356 | i-Pr | H | 2-Cl | $CF_3$ | 2-(3,6-di-Me-pyrazinyl) | 215-218 |
| 357 | i-Pr | H | 2-Me | $OCH_3$ | 2-Cl—Ph | 137-140 |
| 358 | i-Pr | H | 2-Cl | $OCH_3$ | 2-Cl—Ph | 155-158 |
| 359 | i-Pr | H | 2-Me | Me | 2-Cl—Ph | 151-154 |
| 360 | i-Pr | H | 2-Cl | Me | 2,6-di-Cl—Ph | 242-244 |
| 361 | $CH_2CH(OH)CH_3$ | H | 2-Me | $CF_3$ | 2-(3-Cl-pyridinyl) | 123-125 |
| 362 | $CH_2CH(OH)CH_2CH_3$ | H | 2-Me | $CF_3$ | 2-(3-Cl-pyridinyl) | 275-180 |
| 363 | $CH_2CN$ | H | 2,4-di-Br | $CF_3$ | 2-(3-Cl-pyridinyl) | 142-143 |
| 364 | c-Pr | H | 2,4-di-Br | $CF_3$ | 2-(3-Cl-pyridinyl) | 213-214 |
| 365 | $CH_2CN$ | H | 2,4-di-Cl | $CF_3$ | 2-(3-Cl-pyridinyl) | 201-202 |
| 366 | i-Pr | H | 2,6-di-Me | $CF_3$ | 2-(3-Cl-pyridinyl) | 204-205 |
| 367 | t-Bu | H | 2,6-di-Me | $CF_3$ | 2-(3-Cl-pyridinyl) | 242-243 |
| 368 | t-Bu | H | 2-Me | $CF_3$ | 2-(5-$CF_3$-pyridinyl) | 220-230 |
| 369 | $C(CH_3)_2CH_2OH$ | H | 2-Me | $CF_3$ | 2-(3-Cl-pyridinyl) | 205-210 |
| 370 | $CH_2CH_2F$ | H | 2-Me | $CF_3$ | 2-(3-Cl-pyridinyl) | 127-130 |
| 371 | i-Pr | H | 2-Me | $CF_3$ | 2-(4-Me-pyrimidinyl) | 196-197 |
| 372 | i-Pr | H | 2-Cl | $CF_3$ | 2-(4-Me-pyrimidinyl) | 208-210 |
| 373 | t-Bu | H | 2-Me | $CF_3$ | 2-(4-Me-pyrimidinyl) | 180-182 |
| 374 | t-Bu | H | 2-Cl | $CF_3$ | 2-(4-Me-pyrimidinyl) | 182-184 |
| 375 | s-Bu | H | 2-Me | $CF_3$ | 2-(3-Et-pyrazinyl) | 160-165 |
| 376 | Et | H | 2-Me | $CF_3$ | 2-(3-Et-pyrazinyl) | 185-190 |
| 377 | i-Pr | H | 2-Me | $CF_3$ | 2-(3-Et-pyrazinyl) | 180-183 |
| 378 | $CH_2CF_2CF_3$ | H | 2-Cl | $CF_3$ | 2-Cl—Ph | 258-260 |
| 379 | t-Bu | H | 2-Me | $CF_3$ | 2-(3-Et-pyrazinyl) | 180-185 |
| 380 | $CH_2CF_3$ | H | 2-Cl | $CF_3$ | 2-Cl—Ph | 262-264 |
| 381 | $CH_2CN$ | H | 2-Me-4-Br | $CF_3$ | 2-(3-Cl-pyridinyl) | 192-193 |
| 382 | $CH(CH_3)CH_2OH$ | H | 2-Me | CF3 | 2-Cl—Ph | 203-205 |
| 383 | i-Pr | H | 2-Me | Cl | 2-Cl—Ph | 207-209 |
| 384 | i-Pr | H | 2-Cl | Cl | 2-Cl—Ph | 236-237 |
| 385 | i-Pr | H | 2-Me | I | 2-Cl—Ph | 225-226 |
| 386 | i-Pr | H | 2-Cl | I | 2-Cl—Ph | 251-253 |
| 387 | $CH(CH_3)CH_2Cl$ | H | 2-Me | $CF_3$ | 2-Cl—Ph | 212-214 |
| 388 | H | H | 2-Me | $CF_3$ | 2-(3-Cl-pyridinyl) | 217-220 |
| 389 | i-Pr | H | 2-Cl | $CF_3$ | 4-(5,6-di-Me-pyrimidinyl) | 218-220 |
| 390 | t-Bu | H | 2-Cl | $CF_3$ | 4-(5,6-di-Me-pyrimidinyl) | 212-214 |
| 391 | i-Pr | H | 2-Cl | $CF_3$ | 4-(2,5,6-tri-Me-pyrimidinyl) | 162-164 |
| 392 | i-Pr | H | 2-Me | $CF_3$ | 4-(5,6-di-Me-pyrimidinyl) | 162-164 |
| 393 | $CH_2CH(OH)CH_3$ | H | 2-Me | $CF_3$ | 2-Cl—Ph | 207-209 |
| 394 | H | H | 2-Me | $CF_3$ | 2-Cl—Ph | 230-232 |
| 395 | $CH_2CH(Cl)CH_3$ | H | 2-Me | $CF_3$ | 2-Cl—Ph | 230-232 |
| 396 | $CH_2CH_2CN$ | H | 2-Cl | $CF_3$ | 2-(3-Cl-pyridinyl) | 215-217 |
| 397 | $CH_2CH_2F$ | H | 2-Cl | $CF_3$ | 2-(3-Cl-pyridinyl) | 212-214 |
| 398 | $CH_2CH_2CN$ | H | 2-Cl | $CF_3$ | 2-Cl—Ph | * |
| 399 | i-Pr | H | 2-Me-4-Br | CN | 2-(3-Cl-pyridinyl) | * |
| 400 | $CH_2CN$ | H | 2-Me-4-$CF_3$ | $CF_3$ | 2-(3-Cl-pyridinyl) | 211-213 |
| 401 | i-Pr | H | 2-Me | CF3 | 2,5-di-F—Ph | 179-181 |
| 402 | i-Pr | H | 2,4-di-Br | CN | 2-(3-Cl-pyridinyl) | * |
| 403 | t-Bu | H | 2,4-di-Br | CN | 2-(3-Cl-pyridinyl) | 145-147 |
| 404 | Me | H | 2,4-di-Br | CN | 2-(3-Cl-pyridinyl) | 165-168 |
| 405 | Et | H | 2,4-di-Br | CN | 2-(3-Cl-pyridinyl) | 179-181 |
| 406 | Me | H | 2-Me-4-Br | Me | 2-(3-Cl-pyridinyl) | 141-143 |
| 407 | t-Bu | H | 2-Me-4-Br | Me | 2-(3-Cl-pyridinyl) | 161-163 |
| 408 | i-Pr | H | 2-Me-4-Br | Me | 2-(3-Cl-pyridinyl) | 141-143 |
| 409 | Et | H | 2-Me-4-Br | Me | 2-(3-Cl-pyridinyl) | 161-163 |
| 410 | i-Pr | H | 2-Me | Me | 2-(3-Cl-pyridinyl) | 193-195 |

INDEX TABLE A-continued

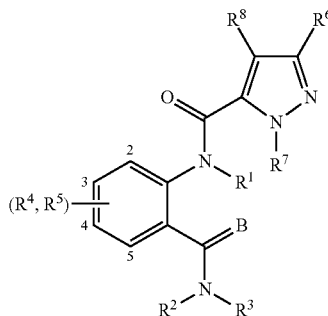

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 411 | Me | H | 2-Me | Me | 2-(3-Cl-pyridinyl) | 194-196 |
| 412 | i-Pr | H | 2-Me-4-Cl | CN | 2-(3-Cl-pyridinyl) | 188-190 |
| 413 | t-Bu | H | 2-Me-4-Cl | CN | 2-(3-Cl-pyridinyl) | 148-151 |
| 414 | Me | H | 2-Me-4-Cl | CN | 2-(3-Cl-pyridinyl) | 182-184 |
| 415 | Me | H | 2-Me | Br | 2-(3-Cl-pyridinyl) | 210-212 |
| 416 | H | H | 2-Cl | $CF_3$ | 2-Cl—Ph | 203-205 |
| 417 | H | H | 2-Me-4-Br | $CF_3$ | 2-(3-Cl-pyridinyl) | 243-245 |
| 418 | t-Bu | H | 2-Me | $CF_3$ | 5-(1,3-di-Me-4-Cl-pyrazolyl) | |
| 419 | i-Pr | H | 2-Cl | $CF_3$ | 5-(1,3-di-Me-4-Cl-pyrazolyl) | |
| 420 | t-Bu | H | 2-Cl | $CF_3$ | 5-(1,3-di-Me-4-Cl-pyrazolyl) | |
| 421 | $CH_2CN$ | H | 2-Br-4-Me | $CF_3$ | 2-(3-Cl-pyridinyl) | 149-150 |
| 422 | i-Pr | H | 2-Me-4-Cl | Cl | 2-Cl—Ph | 180-181 |
| 423 | i-Pr | H | 2-Me-4-Br | Br | 2,6-di-Cl—Ph | 238-239 |
| 424 | i-Pr | H | 2-Cl-4-Me | $CF_3$ | 2-(3-Cl-pyridinyl) | 170-171 |
| 425 | t-Bu | H | 2-Cl-4-Me | $CF_3$ | 2-(3-Cl-pyridinyl) | 167-169 |
| 426 | Me | H | 2-Cl-4-Me | $CF_3$ | 2-(3-Cl-pyridinyl) | 162-164 |
| 427 | H | H | 2-Me-4-Br | Br | 2-(3-Cl-pyridinyl) | 235-237 |
| 428 | Me | H | 5-Cl | $CF_3$ | 2-(3-Cl-pyridinyl) | 207-208 |
| 429 | $CH_2CN$ | H | 5-Cl | $CF_3$ | 2-(3-Cl-pyridinyl) | 178-179 |
| 430 | Me | H | 5-Me | $CF_3$ | 2-(3-Cl-pyridinyl) | 166-167 |
| 431 | $CH_2CN$ | H | 5-Me | $CF_3$ | 2-(3-Cl-pyridinyl) | 191-192 |
| 432 | H | H | 2-Me-4-Br | $CF_3$ | 2-(3-Cl-pyridinyl) | 243-244 |
| 433 | i-Pr | H | 2-Me | $CF_3$ | 4-pyrimidinyl | |
| 434 | i-Pr | H | 2-Cl | $CF_3$ | 4-pyrimidinyl | |
| 435 | t-Bu | H | 2-Me | $CF_3$ | 4-pyrimidinyl | |
| 436 | t-Bu | H | 2-Cl | $CF_3$ | 4-pyrimidinyl | |
| 437 | i-Pr | H | 2,3-di-Me | $CF_3$ | 2-(3-Cl-pyridinyl) | 173-175 |
| 438 | t-Bu | H | 2,3-di-Me | $CF_3$ | 2-(3-Cl-pyridinyl) | 149-150 |
| 439 | Me | H | 2,3-di-Me | $CF_3$ | 2-(3-Cl-pyridinyl) | 164-166 |
| 440 | H | H | 2,3-di-Me | $CF_3$ | 2-(3-Cl-pyridinyl) | 201-403 |
| 441 | H | H | 2-Cl-4-Br | $CF_3$ | 2-(3-Cl-pyridinyl) | 240-242 |
| 442 | H | H | 2-Cl-4-Me | $CF_3$ | 2-(3-Cl-pyridinyl) | 223-225 |
| 443 | i-Pr | H | 2-Me | $CF_3$ | 4-(5-Cl-pyrimidinyl) | |
| 444 | t-Bu | H | 2-Me | $CF_3$ | 4-(5-Cl-pyrimidinyl) | |
| 445 | t-Bu | H | 2-Cl | $CF_3$ | 4-(5-Cl-pyrimidinyl) | |
| 446 | c-Pr | H | 2-Cl | $CF_3$ | 2-(3-Cl-pyridinyl) | 224-228 |
| 447 | $CH_2CN$ | H | 2-Me-4-Br | Br | 2-(3-Cl-pyridinyl) | 232-234 |
| 448 | $CH_2CN$ | H | 2-Me-4-I | $CF_3$ | 2-(3-Cl-pyridinyl) | 221-222 |
| 449 | Me | H | 2,4-di-Cl | $CF_3$ | 2-Cl—Ph | 232-233 |
| 450 | Et | H | 2,4-di-Cl | $CF_3$ | 2-Cl—Ph | 247-248 |
| 451 | t-Bu | H | 2,4-di-Cl | $CF_3$ | 2-Cl—Ph | 223-224 |
| 452 | $CH_2CN$ | H | 2,4-di-Cl | $CF_3$ | 2-Cl—Ph | 229-231 |
| 453 | i-Pr | H | 2-Me | $CF_3$ | 5-(1-Me-pyrazolyl) | |
| 454 | t-Bu | H | 2-Me | $CF_3$ | 5-(1-Me-pyrazolyl) | |
| 455 | i-Pr | H | 2-Cl | $CF_3$ | 5-(1-Me-pyrazolyl) | |
| 456 | t-Bu | H | 2-Cl | $CF_3$ | 5-(1-Me-pyrazolyl) | |
| 457 | i-Pr | H | 2-Me | $CF_3$ | 4-(2,6-di-Me-5-Cl-pyrimidinyl) | |
| 458 | i-Pr | H | 2-Cl | $CF_3$ | 4-(2,6-di-Me-5-Cl-pyrimidinyl) | |
| 459 | t-Bu | H | 2-Me | $CF_3$ | 4-(2,6-di-Me-5-Cl-pyrimidinyl) | |
| 460 | t-Bu | H | 2-Cl | $CF_3$ | 4-(2,6-di-Me-5-Cl-pyrimidinyl) | |
| 461 | Et | H | 2-Me | Cl | 2-(3-Cl-pyridinyl) | 220-221 |
| 462 | Me | H | 2-Me | Cl | 2-(3-Cl-pyridinyl) | 217-218 |
| 463 | $CH_2C\equiv CH$ | H | 2,4-di-Br | Cl | 2-(3-Cl-pyridinyl) | 199-201 |
| 464 | $CH_2C\equiv CH$ | H | 2-Me-4-Cl | Cl | 2-(3-Cl-pyridinyl) | 219-221 |
| 465 | H | H | 2-Me-4-Cl | Cl | 2-(3-Cl-pyridinyl) | 231-233 |
| 466 | H | H | 2,4-di-Cl | Cl | 2-(3-Cl-pyridinyl) | 245-247 |
| 467 | $CH_2C\equiv CH$ | H | 2,4-di-Cl | Cl | 2-(3-Cl-pyridinyl) | 166-168 |
| 468 | H | H | 2-Me | Cl | 2-(3-Cl-pyridinyl) | 243-244 |
| 469 | H | H | 2-Me-4-I | $CF_3$ | 2-(3-Cl-pyridinyl) | 241-242 |

INDEX TABLE A-continued

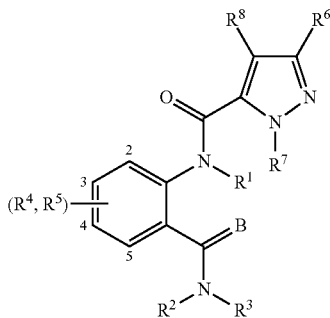

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 470 | CH$_2$CN | H | 2-Me-4-Cl | Br | 2-(3-Cl-pyridinyl) | 225-226 |
| 471 | CH$_2$C≡CH | H | 2-Me-4-Br | Cl | 2-(3-Cl-pyridinyl) | 218-220 |
| 472 | H | H | 2-Me-4-Br | Cl | 2-(3-Cl-pyridinyl) | 224-225 |
| 473 | H | H | 2,4-di-Br | Cl | 2-(3-Cl-pyridinyl) | 250-252 |
| 474 | i-Pr | H | 2-Me-4-Cl | CF$_3$ | 2-(3-Me-pyridinyl) | 228-229 |
| 475 | Me | H | 2-Me-4-Cl | CF$_3$ | 2-(3-Me-pyridinyl) | 226-227 |
| 476 | t-Bu | H | 2-Me | CF$_3$ | 5-(1-Me-4-Cl-pyrazolyl) | |
| 477 | i-Pr | H | 2-Me | CF$_3$ | 5-(1-Me-4-Cl-pyrazolyl) | |
| 478 | i-Pr | H | 2-Me-4-(HOCH$_2$) | CF$_3$ | 2-(3-Cl-pyridinyl) | 199-201 |
| 479 | CH$_2$C≡CH | H | 2-Me-4-Cl | CF$_3$ | 2-(3-Cl-pyridinyl) | 200-202 |
| 480 | B is S, i-Pr | H | 2-Me-4-Br | CF$_3$ | 2-(3-Cl-pyridinyl) | 214-217 |
| 481 | i-Pr | H | 2-Me-4-CO$_2$Me | CF$_3$ | 2-(3-Cl-pyridinyl) | 204-206 |
| 482 | i-Pr | H | 2-Me-4-CONHMe | CF$_3$ | 2-(3-Cl-pyridinyl) | 168-170 |
| 483 | i-Pr | H | 2-Me-4-Br | CF$_3$ | 2-(3-Cl-pyridinyl) | 197-198 |
| 484 (Ex. 6) | i-Pr | H | 2-Me-4-Cl | CF$_3$ | 2-(3-Cl-pyridinyl) | 195-196 |
| 485 | t-Bu | H | 2-Me-4-Cl | CF$_3$ | 2-(3-Cl-pyridinyl) | 223-225 |
| 486 (Ex. 7) | Me | H | 2-Me-4-Cl | CF$_3$ | 2-(3-Cl-pyridinyl) | 185-186 |
| 487 | i-Pr | H | 2-Br-4-Br | CF$_3$ | 2-(3-Cl-pyridinyl) | 192-193 |
| 488 | t-Bu | H | 2-Br-4-Br | CF$_3$ | 2-(3-Cl-pyridinyl) | 246-247 |
| 489 | Me | H | 2-Br-4-Br | CF$_3$ | 2-(3-Cl-pyridinyl) | 162-163 |
| 490 | Et | H | 2-Br-4-Br | CF$_3$ | 2-(3-Cl-pyridinyl) | 188-189 |
| 491 | i-Pr | H | 2,4-di-Cl | CF$_3$ | 2-(3-Cl-pyridinyl) | 200-201 |
| 492 | t-Bu | H | 2,4-di-Cl | CF$_3$ | 2-(3-Cl-pyridinyl) | 170-172 |
| 493 | Me | H | 2,4-di-Cl | CF$_3$ | 2-(3-Cl-pyridinyl) | 155-157 |
| 494 | Et | H | 2,4-di-Cl | CF$_3$ | 2-(3-Cl-pyridinyl) | 201-202 |
| 495 | t-Bu | H | 2-Me-4-Br | CF$_3$ | 2-(3-Cl-pyridinyl) | 247-248 |
| 496 | Et | H | 2-Me-4-Br | CF$_3$ | 2-(3-Cl-pyridinyl) | 192-193 |
| 477 | i-Pr | H | 2-Me-4-F | CF$_3$ | 2-(3-Cl-pyridinyl) | 179-180 |
| 498 | i-Pr | H | 2-Me-4-Br | Br | 2-(3-Cl-pyridinyl) | 185-187 |
| 499 | i-Pr | H | 2-Me-4-CF$_3$ | CF$_3$ | 2-(3-Cl-pyridinyl) | 235-236 |
| 500 | Et | H | 2-Me-4-CF$_3$ | CF$_3$ | 2-(3-Cl-pyridinyl) | 216-217 |
| 501 | i-Pr | H | 2-Me-4-I | CF$_3$ | 2-(3-Cl-pyridinyl) | 188-189 |
| 502 (Ex. 11) | Me | H | 2-Me-4-Cl | Br | 2-(3-Cl-pyridinyl) | 162-164 |
| 503 | t-Bu | H | 2-Me-4-Cl | Br | 2-(3-Cl-pyridinyl) | 159-161 |
| 504 | i-Pr | H | 2,4-di-Br | Br | 2-(3-Cl-pyridinyl) | 162-163 |
| 505 | Me | H | 2,4-di-Br | Br | 2-(3-Cl-pyridinyl) | 166-168 |
| 506 | t-Bu | H | 2,4-di-Br | Br | 2-(3-Cl-pyridinyl) | 210-212 |
| 507 | i-Pr | H | 2,4-di-Cl | Br | 2-(3-Cl-pyridinyl) | 188-190 |
| 508 | t-Bu | H | 2,4-di-Cl | Br | 2-(3-Cl-pyridinyl) | 179-180 |
| 509 (Ex. 10) | i-Pr | H | 2-Me-4-Cl | Br | 2-(3-Cl-pyridinyl) | 159-161 |
| 510 | i-Pr | H | 2,4-di-Cl | CF$_3$ | 2-(3-Cl-pyridinyl) | 200-202 |
| 511 | t-Bu | H | 2-Cl-4-Br | CF$_3$ | 2-(3-Cl-pyridinyl) | 143-145 |
| 512 | Me | H | 2-Cl-4-Br | CF$_3$ | 2-(3-Cl-pyridinyl) | 171-173 |
| 513 | Me | H | 2-Me-4-Br | Br | 2-(3-Cl-pyridinyl) | 147-149 |
| 514 | Me | H | 2-Me-4-Br | CF$_3$ | 2-(3-Cl-pyridinyl) | 222-223 |
| 515 (Ex. 8) | i-Pr | H | 2-Me-4-Cl | Cl | 2-(3-Cl-pyridinyl) | 173-475 |
| 516 (Ex. 9) | Me | H | 2-Me-4-Cl | Cl | 2-(3-Cl-pyridinyl) | 225-226 |
| 517 | t-Bu | H | 2-Me-4-Cl | Cl | 2-(3-Cl-pyridinyl) | 163-165 |
| 518 | i-Pr | H | 2-Me-4-Br | Cl | 2-(3-Cl-pyridinyl) | 152-153 |
| 519 | Me | H | 2-Me-4-Br | Cl | 2-(3-Cl-pyridinyl) | 140-141 |
| 520 | t-Bu | H | 2-Me-4-Br | Br | 2-(3-Cl-pyridinyl) | 215-221 |
| 521 | Me | H | 2-Me-4-I | CF$_3$ | 2-(3-Cl-pyridinyl) | 199-200 |
| 522 | t-Bu | H | 2-Me-4-CF$_3$ | CF$_3$ | 2-(3-Cl-pyridinyl) | 148-149 |

INDEX TABLE A-continued

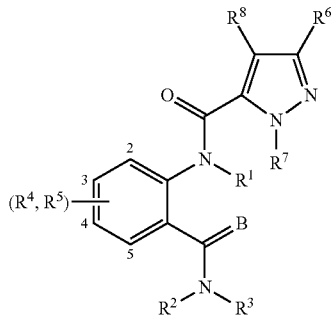

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4$, $R^5$ | $R^6$ | $R^7$ | m.p. (° C.) |
|---|---|---|---|---|---|---|
| 523 | Et | H | 2-Me-4-Cl | Cl | 2-(3-Cl-pyridinyl) | 199-200 |
| 524 | i-Pr | H | 2,4-di-Br | Cl | 2-(3-Cl-pyridinyl) | 197-199 |
| 525 | Me | H | 2,4-di-Br | Cl | 2-(3-Cl-pyridinyl) | 188-190 |
| 526 | t-Bu | H | 2,4-di-Br | Cl | 2-(3-Cl-pyridinyl) | 194-196 |
| 527 | Et | H | 2,4-di-Br | Cl | 2-(3-Cl-pyridinyl) | 192-194 |
| 528 | i-Pr | H | 2,4-di-Cl | Cl | 2-(3-Cl-pyridinyl) | 197-199 |
| 529 | Me | H | 2,4-di-Cl | Cl | 2-(3-Cl-pyridinyl) | 205-206 |
| 530 | t-Bu | H | 2,4-di-Cl | Cl | 2-(3-Cl-pyridinyl) | 172-173 |
| 531 | Et | H | 2,4-di-Cl | Cl | 2-(3-Cl-pyridinyl) | 206-208 |
| 532 | t-Bu | H | 2-Me-4-F | Br | 2-(3-Cl-pyridinyl) | 124-125 |
| 533 | Et | H | 2,4-di-Br | Br | 2-(3-Cl-pyridinyl) | 196-197 |
| 534 | Me | H | 2,4-di-Cl | Br | 2-(3-Cl-pyridinyl) | 245-246 |
| 535 | Et | H | 2,4-di-Cl | Br | 2-(3-Cl-pyridinyl) | 214-215 |
| 536 | Et | H | 2-Me-4-Br | Br | 2-(3-Cl-pyridinyl) | 194-196 |
| 537 | Me | H | 2-Me-4-I | Br | 2-(3-Cl-pyridinyl) | 229-230 |
| 538 | i-Pr | H | 2-Me-4-I | Br | 2-(3-Cl-pyridinyl) | 191-192 |
| 539 | Me | H | 2-Me-4-$CF_3$ | $CF_3$ | 2-(3-Cl-pyridinyl) | 249-250 |
| 540 | Et | H | 2-Me-4-Cl | $CF_3$ | 2-(3-Cl-pyridinyl) | 163-164 |
| 541 | Et | H | 2-Me-4-I | $CF_3$ | 2-(3-Cl-pyridinyl) | 199-200 |
| 542 | t-Bu | H | 2-Me-4-I | $CF_3$ | 2-(3-Cl-pyridinyl) | 242-243 |
| 543 | Et | H | 2-Me-4-Cl | Br | 2-(3-Cl-pyridinyl) | 194-195 |
| 544 | Me | H | 2-Me-4-F | $CF_3$ | 2-(3-Cl-pyridinyl) | 213-214 |
| 545 | Et | H | 2-Me-4-F | $CF_3$ | 2-(3-Cl-pyridinyl) | 212-213 |
| 546 | t-Bu | H | 2-Me-4-F | $CF_3$ | 2-(3-Cl-pyridinyl) | 142-143 |
| 547 | Me | H | 2-Me-4-F | Br | 2-(3-Cl-pyridinyl) | 214-215 |
| 548 | Et | H | 2-Me-4-F | Br | 2-(3-Cl-pyridinyl) | 205-205 |
| 549 | i-Pr | H | 2-Me-4-F | Br | 2-(3-Cl-pyridinyl) | 206-208 |
| 550 | i-Pr | H | 2-Me-4-F | Cl | 2-(3-Cl-pyridinyl) | 184-185 |
| 551 | Me | H | 2-Me-4-F | Cl | 2-(3-Cl-pyridinyl) | 180-182 |
| 552 | Et | H | 2-Me-4-F | Cl | 2-(3-Cl-pyridinyl) | 163-165 |
| 553 | Et | H | 2-Me-4-Br | Cl | 2-(3-Cl-pyridinyl) | 192-194 |
| 554 | Me | H | 2-Me-4-I | Cl | 2-(3-Cl-pyridinyl) | 233-234 |
| 555 | Et | H | 2-Me-4-I | Cl | 2-(3-Cl-pyridinyl) | 196-197 |
| 556 | i-Pr | H | 2-Me-4-I | Cl | 2-(3-Cl-pyridinyl) | 189-190 |
| 557 | t-Bu | H | 2-Me-4-I | Cl | 2-(3-Cl-pyridinyl) | 228-229 |
| 558 | CH($CH_3$)Ph | H | H | $CF_3$ | Me | 212-214 |
| 559 | CH($CH_3$)Ph | H | H | $CF_3$ | Et | 202-203 |
| 560 | $CH_2CH_2$N(i-Pr) | H | 2-Me | $CF_3$ | 2-Cl—Ph | 188-190 |
| 561 | $CH_2$(4-(2,2-di-Me-[1,3]-dioxolanyl)) | H | 2-Me | $CF_3$ | 2-Cl—Ph | 195-200 |
| 562 | i-Pr | H | 2-Me | $CF_3$ | 2-$CH_2$NHC(=O)$CF_3$—Ph | * |
| 563 | i-Pr | H | 2-Me | $CF_3$ | 2-$CH_2NH_2$•Ph HCl | * |
| 564 | i-Pr | H | 2-Me | $CF_3$ | 2,4-di-Cl-5-O$CH_2$C≡CH—Ph | 246-249 |
| 565 | $CH_2$(2-tetrahydrofuranyl) | H | 2-Me | $CF_3$ | 2-(3-Cl-pyridinyl) | 222-225 |
| 566 | $CH_2$(2-oxiranyl) | H | 2-Me | $CF_3$ | 2-(3-Cl-pyridinyl) | 183-185 |
| 567 | $CH_2CH_2OCH_2CH_2$OH | H | 2-Me | $CF_3$ | 2-(3-Cl-pyridinyl) | 132-135 |
| 568 | OCH($CH_3$)$_2$ | H | 2-Cl | $CF_3$ | 2-Cl—Ph | 218-219 |
| 569 | OCH($CH_3$)$_2$ | H | 2-Cl | $CF_3$ | 2-(3-Cl-pyridinyl) | 205-206 |
| 570 | OCH($CH_3$)$_2$ | H | 2-Me | $CF_3$ | 2-(3-Cl-pyridinyl) | 210-211 |
| 571 | OCH($CH_3$)$_2$ | H | 2-Me | $CF_3$ | 2-Cl—Ph | 196-198 |
| 572 | i-Pr | H | 2-Me | $CF_3$ | 2-CONHMe—Ph | * |
| 573 | Me | H | 2-Me-4-Br | $CF_3$ | 2-(3-Cl-pyridinyl) | 208-210 |
| 574 | i-Pr | H | 2-Br-4-Me | $CF_3$ | 2-(3-Cl-pyridinyl) | 127-128 |
| 575 | t-Bu | H | 2-Br-4-Me | $CF_3$ | 2-(3-Cl-pyridinyl) | 159-160 |
| 576 | Et | H | 2-Br-4-Me | $CF_3$ | 2-(3-Cl-pyridinyl) | 224-225 |
| 577 | Me | H | 2-Br-4-Me | $CF_3$ | 2-(3-Cl-pyridinyl) | 208-209 |
| 578 | t-Bu | H | 2-Me-3-Br | Cl | 2-(3-Cl-pyridinyl) | 224-225 |
| 579 | Me | H | 2-Me-4-Cl | I | 2-(3-Cl-pyridinyl) | 208-209 |
| 580 | i-Pr | H | 2-Me-4-Cl | I | 2-(3-Cl-pyridinyl) | 183-184 |

INDEX TABLE A-continued

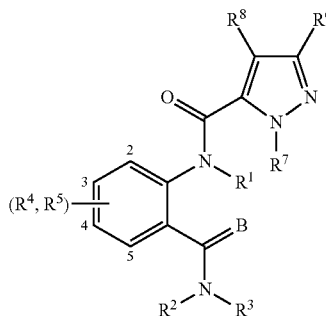

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 581 | H | H | 2-Me-4-Cl | I | 2-(3-Cl-pyridinyl) | 228-230 |
| 582 | Me | H | 2-Me-4-Cl | Br | 2-Cl-4-F—Ph | 250-251 |
| 583 | H | H | 2-Me-4-Cl | Br | 2-Cl-4-F—Ph | 229-229 |
| 584 | i-Pr | H | 2-Me-4-Cl | Br | 2-Cl-4-F—Ph | 189-190 |
| 585 | t-Bu | H | 2-Me-4-Cl | Br | 2-Cl-4-F—Ph | 247-249 |
| 586 | i-Pr | H | 2-Me-4-$NO_2$ | $CF_3$ | 2-Cl—Ph | * |
| 587 | Ph | H | 2-Me-4-Cl | $CF_3$ | 2-(3-Cl-pyridinyl) | 243-244 |
| 588 | 2-Me—Ph | H | 2-Me-4-Cl | $CF_3$ | 2-(3-Cl-pyridinyl) | 249-251 |
| 589 | i-Pr | H | 2-Me-4-$NO_2$ | $CF_3$ | 2-(3-Cl-pyridinyl) | 170-172 |
| 590 | i-Pr | H | 2-Me-4-$NO_2$ | $CF_3$ | 2-(3-Cl-pyridinyl) | * |
| 591 | Me, B is S | H | 2-Me | $CF_3$ | 2-Cl—Ph | 164-167 |
| 592 | i-Pr | H | 2-$NO_2$ | $CF_3$ | 2-Cl—Ph | * |
| 593 | i-Pr | H | 2-Me-4-Cl | $OCHF_2$ | 2-Cl—Ph | 177-179 |
| 594 | Me | Me | 2,4-di-Br | Cl | 2-(3-Cl-pyridinyl) | 151-152 |
| 595 | $CH(CH_3)CH_2OCH_3$ | H | 2,4-di-Br | Cl | 2-(3-Cl-pyridinyl) | 162-163 |
| 596 | $CH(CH_3)CH_2SCH3$ | H | 2,4-di-Br | Cl | 2-(3-Cl-pyridinyl) | 174-175 |
| 597 | $CH(CH_3)CH_2OH$ | H | 2,4-di-Br | Cl | 2-(3-Cl-pyridinyl) | 148-149 |
| 598 | i-Pr, R1 is Me | H | 2-Me | Br | 2-(3-Cl-pyridinyl) | 223-225 |
| 599 | i-Pr, R1 is Me | H | 2-Me | Cl | 2-(3-Cl-pyridinyl) | 223-225 |
| 600 | i-Pr, R1 is Me | H | 2-Me | $CF_3$ | 2-(3-Cl-pyridinyl) | 218-219 |
| 601 | i-Pr, B is S | H | 2-Me-4-Cl | Br | 2-(3-Cl-pyridinyl) | 231-235 |
| 602 | $N(CH_3)_2$ | H | 2,4-di-Br | Cl | 2-(3-Cl-pyridinyl) | 149-151 |
| 603 | $N=C(NH_2)_2$ | H | 2-Me-4-Br | $CF_3$ | 2-(3-Cl-pyridinyl) | * |
| 604 | $N(Me)_2$ | H | 2-Me-4-Cl | Br | 2-(3-Cl-pyridinyl) | 185-188 |
| 605 | i-Pr | H | 2-Cl | $CF_3$ | 5-(1-Me-4-Cl-pyrazolyl) | 221-222 |
| 606 | t-Bu | H | 2-Cl | $CF_3$ | 5-(1-Me-4-Cl-pyrazolyl) | 217-218 |
| 607 | $CH(CH_3)CH_2CO_2Et$ | H | 2,4-di-Br | Cl | 2-(3-Cl-pyridinyl) | 113-115 |
| 608 | 2-pyridinyl | H | 2-Me-4-Br | $CF_3$ | 2-(3-Cl-pyridinyl) | 244-245 |
| 609 | 2-(3-Me-pyridinyl) | H | 2-Me-4-Br | $CF_3$ | 2-(3-Me-pyridinyl) | 182-183 |
| 610 | i-Pr | H | 2-Cl-4-$NO_2$ | $CF_3$ | 2-(1-Me-3-Cl-pyridinium$^+$ $CF_3SO_3^-$) | * |
| 611 | i-Pr | H | 2-Me-4-$NO_2$ | $CF_3$ | 2-(1-Me-3-Cl-pyridinium$^+$ $CF_3SO_3^-$) | * |
| 612 | Me, B is S | H | 2-Me-4-Cl | Br | 2-(3-Cl-pyridinyl) | 110-113 |
| 613 | Me | Me | 2-Me-4-Br | $CF_3$ | 2-(3-Cl-pyridinyl) | 207-208 |
| 614 | Et | Et | 2-Me-4-Br | $CF_3$ | 2-(3-Cl-pyridinyl) | 189-190 |
| 615 | 2-pyridinyl | H | 2-Me-4-Cl | $CF_3$ | 2-(3-Cl-pyridinyl) | 233-234 |
| 616 | 2-(3-Me-pyridinyl) | H | 2-Me-4-Cl | $CF_3$ | 2-(3-Cl-pyridinyl) | 202-203 |
| 617 | Et | Et | 2,4-di-Cl | Cl | 2-(3-Cl-pyridinyl) | 197-198 |
| 618 | Me | Me | 2,4-di-Cl | Cl | 2-(3-Cl-pyridinyl) | 142-143 |
| 619 | $CH(CH_3)CH_2SCH_3$ | H | 2,4-di-Cl | Cl | 2-(3-Cl-pyridinyl) | 185-186 |
| 620 | Et | Et | 2,4-di-Br | Cl | 2-(3-Cl-pyridinyl) | 209-210 |
| 621 | i-Pr | Me | 2-Me-4-Br | $CF_3$ | 2-(3-Cl-pyridinyl) | 133-135 |
| 622 | Me | Me | 2,4-di-Br | Br | 2-(3-Cl-pyridinyl) | 185-187 |
| 623 | Et | Et | 2,4-di-Br | Br | 2-(3-Cl-pyridinyl) | 204-205 |
| 624 | $CH(CH_3)CH_2SCH_3$ | H | 2,4-di-Br | Br | 2-(3-Cl-pyridinyl) | 178-179 |
| 625 | Et | H | 2-Me-4-Cl | $OCHF_2$ | 2-(3-Cl-pyridinyl) | 209-211 |
| 626 | i-Pr | H | 2-Me-4-Cl | $OCHF_2$ | 2-(3-Cl-pyridinyl) | 179-181 |
| 627 | Me | H | 2-Me-4-Br | $OCHF_2$ | 2-Cl—Ph | 190-192 |
| 628 | Et | H | 2-Me-4-Cl | OEt | 2-Cl—Ph | 163-165 |
| 629 | i-Pr | H | 2-Me-4-Cl | OEt | 2-Cl—Ph | 173-175 |
| 630 | Me | H | 2-Me-4-Br | OEt | 2-Cl—Ph | 155-158 |
| 631 | Et | Me | 2,4-di-Br | Br | 2-(3-Cl-pyridinyl) | 181-183 |
| 632 | Et | Me | 2,4-di-Cl | Cl | 2-(3-Cl-pyridinyl) | 162-163 |
| 633 | Et | Me | 2-Me-4-Br | $CF_3$ | 2-(3-Cl-pyridinyl) | 174-175 |
| 634 | Me | Me | 2,4-di-Cl | Br | 2-(3-Cl-pyridinyl) | 216-518 |
| 635 | Et | Et | 2,4-di-Cl | Br | 2-(3-Cl-pyridinyl) | 190-191 |
| 636 | $CH(CH_3)CH_2SCH_3$ | H | 2,4-di-Cl | Br | 2-(3-Cl-pyridinyl) | 182-183 |
| 637 | Et | Me | 2,4-di-Cl | Br | 2-(3-Cl-pyridinyl) | 165-167 |

INDEX TABLE A-continued

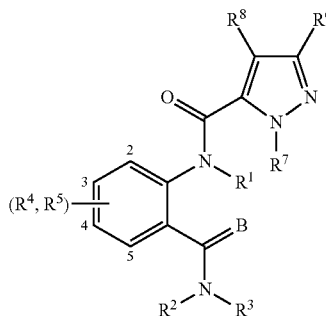

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 638 | Et | H | 2-Me-4-NO$_2$ | CF$_3$ | 2-(3-Cl-pyridinyl) | * |
| 639 | Me | Me | 2-Me-4-NO$_2$ | CF$_3$ | 2-(3-Cl-pyridinyl) | * |
| 640 | CH$_2$CH=CH$_2$ | H | 2-Me-4-NO$_2$ | CF$_3$ | 2-(3-Cl-pyridinyl) | * |
| 641 | n-Pr | H | 2-Me-4-NO$_2$ | CF$_3$ | 2-(3-Cl-pyridinyl) | * |
| 642 | CH(CH$_3$)CH$_2$SCH$_3$ | H | 2-Me-4-NO$_2$ | CF$_3$ | 2-(3-Cl-pyridinyl) | * |
| 643 | Me | H | 2-Me-4-NO$_2$ | CF$_3$ | 2-(3-Cl-pyridinyl) | * |
| 644 | t-Bu | H | 2-Me-4-NO$_2$ | CF$_3$ | 2-(3-Cl-pyridinyl) | * |
| 645 | CH$_2$CH$_2$N(Me)$_2$ | H | 2-Me-4-NO$_2$ | CF$_3$ | 2-(3-Cl-pyridinyl) | 193-195 |
| 646 | CH$_2$CH$_2$N(Me)$_3^+$I$^-$ | H | 2-Me-4-NO2 | CF$_3$ | 2-(3-Cl-pyridinyl) | >250 |
| 647 | 1-pyrrolidine | H | 2,4-di-Cl | Cl | 2-(3-Cl-pyridinyl) | 143-145 |
| 648 | N(CH$_3$)$_2$ | H | 2,4-di-Cl | Cl | 2-(3-Cl-pyridinyl) | 146-148 |
| 649 | N(CH$_3$)$_2$ | H | 2,4-di-Br | Br | 2-(3-Cl-pyridinyl) | 162-164 |
| 650 | N(CH$_3$)$_2$ | H | 2,4-di-Cl | Br | 2-(3-Cl-pyridinyl) | 208-209 |
| 651 | Et | H | 2-Me-4-Cl | OCH$_2$CF$_3$ | 2-Cl—Ph | 184-186 |
| 652 | i-Pr | H | 2-Me-4-Cl | OCH$_2$CF$_3$ | 2-Cl—Ph | 196-198 |
| 653 | Me | H | 2-Me-4-Br | OCH$_2$CF$_3$ | 2-Cl—Ph | 220-223 |
| 654 | N(CH$_3$)$_2$ | H | 2-Me-4-NO2 | CF$_3$ | 2-(3-Cl-pyridinyl) | * |
| 655 | H | H | 2-Me-4-Cl | Br | 2-(3-Cl-pyridinyl) | 240-242 |
| 656 | n-Pr | n-Pr | 2-Me-4-Br | CF$_3$ | 2-(3-Cl-pyridinyl) | 201-202 |
| 657 | n-Pr | H | 2-Me-4-Br | CF$_3$ | 2-(3-Cl-pyridinyl) | 188-190 |
| 658 | Et | Et | 2-Cl | CF$_3$ | 2-(3-Cl-pyridinyl) | 242-243 |
| 659 | n-Pr | n-Pr | 2,4-di-Cl | Cl | 2-(3-Cl-pyridinyl) | 242-243 |
| 660 | n-Pr | H | 2,4-di-Cl | Cl | 2-(3-Cl-pyridinyl) | 218-219 |
| 661 | CH$_2$CO$_2$CH$_2$CH$_3$ | Me | 2-Me-4-Br | CF$_3$ | 2-(3-Cl-pyridinyl) | 227-228 |
| 662 | CH$_2$CO$_2$CH$_2$CH$_3$ | Me | 2,4-di-Cl | Br | 2-(3-Cl-pyridinyl) | 176-177 |
| 663 | CH$_2$CO$_2$CH$_2$CH$_3$ | Me | 2,4-di-Br | Cl | 2-(3-Cl-pyridinyl) | 198-199 |
| 664 | CH$_2$CO$_2$CH$_3$ | H | 2-Me-4-Br | CF$_3$ | 2-(3-Cl-pyridinyl) | 141-142 |
| 665 | N(CH$_3$)$_2$ | H | 2,4-di-Cl | CF$_3$ | 2-(3-Cl-pyridinyl) | 136-137 |
| 666 | Me | Me | 2,4-di-Cl | CF$_3$ | 2-(3-Cl-pyridinyl) | 225-227 |
| 667 | Et | Et | 2,4-di-Cl | CF$_3$ | 2-(3-Cl-pyridinyl) | 228-229 |
| 668 | CH$_2$CO$_2$CH$_2$CH$_3$ | Me | 2,4-di-Cl | CF$_3$ | 2-(3-Cl-pyridinyl) | 219-220 |
| 669 | Me | H | 2-Me-4-Cl | CF$_3$ | 5-(1-Me-4-Cl-pyrazolyl) | 239-241 |
| 670 | i-Pr | H | 2-Me-4-Cl | CF$_3$ | 5-(1-Me-4-Cl-pyrazolyl) | 239-241 |
| 671 | i-Pr | H | 2-Me-4-Br | OEt | 2-(3-Cl-pyridinyl) | 208-211 |
| 672 | Me | H | 2-Me-4-Br | OEt | 2-(3-Cl-pyridinyl) | 212-215 |
| 673 | i-Pr | H | 2-Me-4-Cl | OEt | 2-(3-Cl-pyridinyl) | 191-193 |
| 674 | Et | H | 2-Me-4-Cl | OEt | 2-(3-Cl-pyridinyl) | 207-209 |
| 675 | i-Pr | H | 2-Me-4-Br | OCH$_2$CF$_3$ | 2-(3-Cl-pyridinyl) | 213-215 |
| 676 | Me | H | 2-Me-4-Br | OCH$_2$CF$_3$ | 2-(3-Cl-pyridinyl) | 206-208 |
| 677 | i-Pr | H | 2-Me-4-Cl | OCH$_2$CF$_3$ | 2-(3-Cl-pyridinyl) | 211-213 |
| 678 | Et | H | 2-Me-4-Cl | OCH$_2$CF$_3$ | 2-(3-Cl-pyridinyl) | 205-207 |
| 679 (Ex. 12) | Me | H | 2-Me-4-Cl | OCH$_2$CF$_3$ | 2-(3-Cl-pyridinyl) | 195-197 |
| 680 | Et | H | 2-Me-4-Br | OCH$_2$CF$_3$ | 2-(3-Cl-pyridinyl) | 208-211 |
| 681 | t-Bu | H | 2-Me-4-Br | OCH$_2$CF$_3$ | 2-(3-Cl-pyridinyl) | 213-216 |
| 682 | i-Pr | H | 2-Me-4-Br | CF$_3$ | 5-(1-Me-4-Cl-pyrazolyl) | 256-258 |
| 683 | t-Bu | H | 2-Me-4-Br | CF$_3$ | 5-(1-Me-4-Cl-pyrazolyl) | 254-256 |
| 684 | Me | Me | 2,4-di-Br | CF$_3$ | 2-(3-Cl-pyridinyl) | 228-229 |
| 685 | i-Pr | H | 2-Me-4-Cl | OCF$_2$CHF$_2$ | 2-(3-Cl-pyridinyl) | 189-192 |
| 686 | Et | H | 2-Me-4-Cl | OCF$_2$CHF$_2$ | 2-(3-Cl-pyridinyl) | 189-192 |
| 687 | Me | H | 2-Me-4-Cl | OCF$_2$CHF$_2$ | 2-(3-Cl-pyridinyl) | 162-165 |
| 688 | i-Pr | H | 2-Me-4-Br | OCF$_2$CHF$_2$ | 2-(3-Cl-pyridinyl) | 185-188 |
| 689 | Et | H | 2-Me-4-Br | OCF$_2$CHF$_2$ | 2-(3-Cl-pyridinyl) | 195-198 |
| 690 | Me | H | 2-Me-4-Br | OCF$_2$CHF$_2$ | 2-(3-Cl-pyridinyl) | 164-167 |
| 691 | Me | Me | 2-Cl-4-Br | CF$_3$ | 2-(3-Cl-pyridinyl) | 238-239 |
| 692 | Et | Me | 2-Cl-4-Br | CF$_3$ | 2-(3-Cl-pyridinyl) | 216-217 |
| 693 | H | H | H | CF$_3$ | 2-(3-Cl-pyridinyl) | |
| 694 | Et | H | 2-Me-4-Br | CF$_3$ | 5-(1-Me-4-Cl-pyrazolyl) | 249-251 |
| 695 | i-Pr | H | 2,4-di-Cl | OCH$_2$CF3 | 2-(3-Cl-pyridinyl) | 232-235 |

INDEX TABLE A-continued

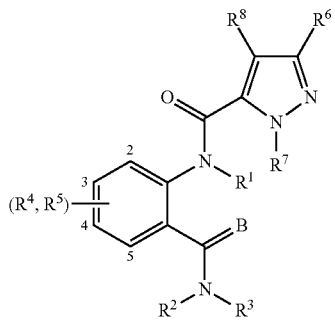

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4, R^5$ | $R^6$ | $R^7$ | m.p. (° C.) |
|---|---|---|---|---|---|---|
| 696 | Me | H | 2,4-di-Cl | $OCH_2CF_3$ | 2-(3-Cl-pyridinyl) | 192-195 |
| 697 | Me | Me | 2,4-di-Cl | $OCH_2CF_3$ | 2-(3-Cl-pyridinyl) | 132-135 |
| 698 | i-Pr | H | 2,4-di-Br | $OCH_2CF_3$ | 2-(3-Cl-pyridinyl) | 225-227 |
| 699 | Me | H | 2,4-di-Br | $OCH_2CF_3$ | 2-(3-Cl-pyridinyl) | 206-208 |
| 700 | Me | Me | 2,4-di-Br | $OCH_2CF_3$ | 2-(3-Cl-pyridinyl) | 175-177 |
| 701 | Me | H | 2-Cl-4-Br | Br | 2-(3-Cl-pyridinyl) | 226-227 |
| 702 | Me | Me | 2-Cl-4-Br | Br | 2-(3-Cl-pyridinyl) | 237-238 |
| 703 | Me | H | 2-Cl-4-Br | Cl | 2-(3-Cl-pyridinyl) | 228-229 |
| 704 | Me | Me | 2-Cl-4-Br | Cl | 2-(3-Cl-pyridinyl) | 236-237 |
| 705 | $CH_2C(Me)_2CH_2N(Me)_2$ | H | 2-Me | $CF_3$ | 2-(3-Cl-pyridinyl) | 197-200 |
| 706 | Me | H | 2-Me-4-Br | $CF_3$ | 5-(1-Me-4-Cl-pyrazolyl) | 242-244 |
| 707 | Et | H | 2-Me-4-Cl | $CF_3$ | 5-(1-Me-4-Cl-pyrazolyl) | 252-254 |
| 708 | t-Bu | H | 2-Me-4-Cl | $CF_3$ | 5-(1-Me-4-Cl-pyrazolyl) | 259-260 |
| 709 | i-Pr | H | 2,4-di-Cl | $OCBrF_2$ | 2-(3-Cl-pyridinyl) | 220-222 |
| 710 | Me | H | 2,4-di-Cl | $OCBrF_2$ | 2-(3-Cl-pyridinyl) | 188-191 |
| 711 | Me | Me | 2,4-di-Cl | $OCBrF_2$ | 2-(3-Cl-pyridinyl) | 203-205 |
| 712 | Me | H | 2-Me-4-Cl | $OCHF_2$ | 2-(3-Cl-pyridinyl) | 210-212 |
| 713 | i-Pr | H | 2-Me-4-Cl | $OCBrF_2$ | 2-(3-Cl-pyridinyl) | 194-196 |
| 714 | Me | H | 2-Me-4-Cl | $OCBrF_2$ | 2-(3-Cl-pyridinyl) | 181-183 |
| 715 | Me | H | 3,4-di-F | Cl | 2-(3-Cl-pyridinyl) | 202-203 |
| 716 | Me | Me | 3,4-di-F | Cl | 2-(3-Cl-pyridinyl) | 251-252 |
| 717 | Me | Me | 2-Me-4-F | Cl | 2-(3-Cl-pyridinyl) | 242-243 |
| 718 | Me | Me | 2-Cl-4-F | Br | 2-(3-Cl-pyridinyl) | 245-246 |
| 719 | Me | H | 2-Cl-4-F | Br | 2-(3-Cl-pyridinyl) | 217-218 |
| 720 | i-Pr | H | 2-Cl-4-F | Br | 2-(3-Cl-pyridinyl) | 168-169 |
| 721 | Me | Me | 2-Cl-4-F | Cl | 2-(3-Cl-pyridinyl) | 239-240 |
| 722 | Me | H | 2-Cl-4-F | Cl | 2-(3-Cl-pyridinyl) | 248-249 |
| 723 | i-Pr | H | 2-Cl-4-F | Cl | 2-(3-Cl-pyridinyl) | 169-170 |
| 724 | Me | Me | 2-Cl-4-F | $CF_3$ | 2-(3-Cl-pyridinyl) | 215-216 |
| 725 | Me | H | 2-Cl-4-F | $CF_3$ | 2-(3-Cl-pyridinyl) | 219-220 |
| 726 | Me | Me | 2-Br-4-F | Br | 2-(3-Cl-pyridinyl) | 235-236 |
| 727 | Me | H | 2-Br-4-F | Br | 2-(3-Cl-pyridinyl) | 238-239 |
| 728 | i-Pr | H | 2-Br-4-F | Br | 2-(3-Cl-pyridinyl) | 236-237 |
| 729 | Me | Me | 2-Br-4-F | Cl | 2-(3-Cl-pyridinyl) | 246-247 |
| 730 | Me | H | 2-Br-4-F | Cl | 2-(3-Cl-pyridinyl) | 233-234 |
| 731 | i-Pr | H | 2-Br-4-F | Cl | 2-(3-Cl-pyridinyl) | 153-154 |
| 732 | i-Pr | H | 2-Me-4-Cl | $OCHMe_2$ | 2-(3-Cl-pyridinyl) | 208-210 |
| 733 | Me | H | 2-Me-4-Cl | $OCHMe_2$ | 2-(3-Cl-pyridinyl) | 207-210 |
| 734 | i-Pr | H | 2,4-di-Cl | $OCHMe_2$ | 2-(3-Cl-pyridinyl) | 187-191 |
| 735 | Me | H | 2,4-di-Cl | $OCHMe_2$ | 2-(3-Cl-pyridinyl) | * |
| 736 | Me | Me | 2-Br-4-F | $CF_3$ | 2-(3-Cl-pyridinyl) | 191-192 |
| 737 | Me | H | 2-Br-4-F | $CF_3$ | 2-(3-Cl-pyridinyl) | 228-229 |
| 738 | i-Pr | H | 2-Br-4-F | $CF_3$ | 2-(3-Cl-pyridinyl) | 224-226 |
| 739 | Me | Me | 2-Br-4-Cl | Br | 2-(3-Cl-pyridinyl) | 188-189 |
| 740 | Me | H | 2-Br-4-Cl | Br | 2-(3-Cl-pyridinyl) | 248-249 |
| 741 | i-Pr | H | 2-Br-4-Cl | Br | 2-(3-Cl-pyridinyl) | 252-253 |
| 742 | Me | Me | 2-Br-4-Cl | Cl | 2-(3-Cl-pyridinyl) | 147-148 |
| 743 | Me | H | 2-Br-4-Cl | Cl | 2-(3-Cl-pyridinyl) | 249-250 |
| 744 | i-Pr | H | 2-Br-4-Cl | Cl | 2-(3-Cl-pyridinyl) | 239-240 |
| 745 | Me | Me | 2-Br-4-Cl | $CF_3$ | 2-(3-Cl-pyridinyl) | 200-201 |
| 746 | Me | H | 2-Br-4-Cl | $CF_3$ | 2-(3-Cl-pyridinyl) | 158-159 |
| 747 | i-Pr | H | 2-Br-4-Cl | $CF_3$ | 2-(3-Cl-pyridinyl) | 250-250 |
| 748 | Me | Me | 2-Me-4-Cl | Cl | 2-(3-Cl-pyridinyl) | 232-233 |
| 749 | Me | H | 2-$CF_3$ | $CF_3$ | 2-(3-Cl-pyridinyl) | 218-220 |
| 750 | i-Pr | H | 2-$CF_3$ | $CF_3$ | 2-(3-Cl-pyridinyl) | 242-246 |
| 751 | Me | Me | 2-$CF_3$ | $CF_3$ | 2-(3-Cl-pyridinyl) | 239-244 |
| 752 | Me | Me | 2-Me-4-Cl | Br | 2-(3-Cl-pyridinyl) | 210-211 |
| 753 | Me | Me | 2,4-di-Me | Cl | 2-(3-Cl-pyridinyl) | 223-224 |
| 754 | Me | Me | 2,4-di-Me | Br | 2-(3-Cl-pyridinyl) | 240-241 |

INDEX TABLE A-continued

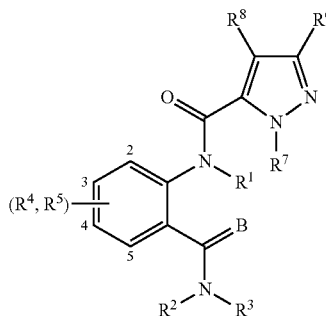

R$^1$, R$^5$, and R$^8$ are H, except where indicated; B is O, except where indicated. "CN" is bonded through carbon, not nitrogen; for example "CN—Ph" specifies cyanophenyl, not isocyanophenyl.

| Compound | R$^3$ | R$^2$ | R$^4$, R$^5$ | R$^6$ | R$^7$ | m.p. (° C.) |
|---|---|---|---|---|---|---|
| 755 | Me | H | 2-F | Br | 2-(3-Cl-pyridinyl) | 215-216 |
| 756 | i-Pr | H | 2-F | Br | 2-(3-Cl-pyridinyl) | 213-215 |
| 757 | i-Pr | H | 2-CF$_3$-4-Cl | CF$_3$ | 2-(3-Cl-pyridinyl) | 254-256 |
| 758 | Me | Me | 2-CF$_3$-4-Cl | CF$_3$ | 2-(3-Cl-pyridinyl) | 229-231 |
| 759 | Me | H | 2-CF$_3$-4-Cl | CF$_3$ | 2-(3-Cl-pyridinyl) | 235-237 |
| 760 | Me | H | 2,4-di-Cl | CF$_3$ | 2-(3-Cl-pyridinyl), R$^8$ is Cl | 225-226 |
| 761 | i-Pr | H | 2,4-di-Cl | CF$_3$ | 2-(3-Cl-pyridinyl), R$^8$ is Cl | 230-232 |
| 762 | Me | Me | 2,4-di-Cl | CF$_3$ | 2-(3-Cl-pyridinyl), R$^8$ is Cl | 194-196 |
| 763 | i-Pr | H | 2-Me-4-Cl | CF$_3$ | 3-isoxazolyl | 255-257 |
| 764 | Me | H | 2,4-di-F | Br | 2-(3-Cl-pyridinyl) | 197-198 |
| 765 | Me | Me | 2,4-di-F | Br | 2-(3-Cl-pyridinyl) | 218-222 |
| 766 | Me | H | 2-F | Cl | 2-(3-Cl-pyridinyl) | 185-187 |
| 767 | Me | H | 2-F-4-Cl | Br | 2-(3-Cl-pyridinyl) | 203-204 |
| 768 | Me | Me | 2-F-4-Cl | Br | 2-(3-Cl-pyridinyl) | 226-227 |
| 769 | i-Pr | H | 2-F-4-Cl | Br | 2-(3-Cl-pyridinyl) | 207-208 |
| 770 | Me | H | 2-F-4-Cl | Cl | 2-(3-Cl-pyridinyl) | 211-212 |
| 771 | Me | Me | 2-F-4-Cl | Cl | 2-(3-Cl-pyridinyl) | 237-238 |
| 772 | i-Pr | H | 2-Me-4-CN | CF$_3$ | 2-(3-Cl-pyridinyl) | * |
| 773 | H | H | 2-F-4-Cl | Cl | 2-(3-Cl-pyridinyl) | 116-117 |
| 774 | Me | H | 2,4-di-F | Cl | 2-(3-Cl-pyridinyl) | 159-160 |
| 775 | Me | Me | 2,4-di-F | Cl | 2-(3-Cl-pyridinyl) | 225-226 |
| 776 | i-Pr | H | 2,4-di-F | Cl | 2-(3-Cl-pyridinyl) | 201-202 |
| 777 | H | H | 2,4-di-F | Cl | 2-(3-Cl-pyridinyl) | 128-129 |
| 778 | Et | H | 2-Me-4-Cl | CF$_3$ | 5-(1-CH$_2$CF$_3$-pyrazolyl) | 172-174 |
| 779 | Me | H | 2-Me-4-Cl | CF$_3$ | 5-(1-CH$_2$CF$_3$-pyrazolyl) | 192-194 |
| 780 | Me | H | 2,4-di-Cl | F | 2-(3-Cl-pyridinyl) | * |
| 781 | Me | H | 2-F | OCH$_2$CF$_3$ | 2-(3-Cl-pyridinyl) | 202-203 |
| 782 | Me | Me | 2-F | OCH$_2$CF$_3$ | 2-(3-Cl-pyridinyl) | 178-179 |
| 783 | i-Pr | H | 2-F | OCH$_2$CF$_3$ | 2-(3-Cl-pyridinyl) | 161-162 |
| 784 | Me | H | 2-F-4-Br | Br | 2-(3-Cl-pyridinyl) | 209-210 |
| 785 | Me | Me | 2-F-4-Br | Br | 2-(3-Cl-pyridinyl) | 225-226 |
| 786 | i-Pr | H | 2-F-4-Br | Br | 2-(3-Cl-pyridinyl) | 208-209 |
| 787 | Me | H | 2-F-4-Br | Cl | 2-(3-Cl-pyridinyl) | 209-210 |
| 788 | Me | Me | 2-F-4-Br | Cl | 2-(3-Cl-pyridinyl) | 244-245 |
| 789 | Me | Me | 2-F-4-Br | Cl | 2-(3-Cl-pyridinyl) | 207-208 |
| 790 | Me | H | 2-F-4-Br | OCH$_2$CF$_3$ | 2-(3-Cl-pyridinyl) | 210-211 |
| 791 | Me | Me | 2-F-4-Br | OCH$_2$CF$_3$ | 2-(3-Cl-pyridinyl) | 206-206 |
| 792 | i-Pr | H | 2,4-di-Cl | CF$_3$ | 3-(4-Cl-5-Me-isoxazolyl) | 204-205 |
| 793 | Me | H | 2,4-di-Cl | CF$_3$ | 3-(4-Cl-5-Me-isoxazolyl) | 131-132 |
| 794 | i-Pr | H | 2-Me-4-Cl | CF$_3$ | 3-(4-Cl-5-Me-isoxazolyl) | 188-189 |
| 795 | Me | H | 2-Me-4-Cl | CF$_3$ | 3-(4-Cl-5-Me-isoxazolyl) | 210-211 |
| 796 | i-Pr | H | 2,4-di-Cl | CF$_3$ | 3-(4-Cl-isoxazolyl) | 212-213 |
| 797 | i-Pr | H | 2-Me-4-Cl | CF$_3$ | 3-(4-Cl-isoxazolyl) | 232 |
| 798 | Me | H | 2-Me-4-Cl | CF$_3$ | 3-(4-Cl-isoxazolyl) | 190-191 |
| 799 | Me | H | 2,4-di-Cl | CF$_3$ | 3-(4-Cl-isoxazolyl) | 209-210 |
| 800 | i-Pr | H | 4-Cl | CF$_3$ | 3-(4-Cl-isoxazolyl) | 241-242 |
| 801 | i-Pr | H | 2,4-di-Cl | CF$_3$ | 5-(1-CH$_2$CF$_3$-pyrazolyl) | 212-214 |
| 802 | H | H | 2,4-di-Cl | F | 2-(3-Cl-pyridinyl) | * |
| 803 | i-Pr | H | 2,4-di-Cl | F | 2-(3-Cl-pyridinyl) | * |
| 804 | Me | Me | 2,4-di-Cl | F | 2-(3-Cl-pyridinyl) | * |
| 805 | H | H | 2-Me-4-Cl | F | 2-(3-Cl-pyridinyl) | * |
| 806 | i-Pr | H | 2-Me-4-Cl | F | 2-(3-Cl-pyridinyl) | * |
| 807 | Me | H | 2-Me-4-Cl | F | 2-(3-Cl-pyridinyl) | * |
| 808 | Me | Me | 2-Me-4-Cl | F | 2-(3-Cl-pyridinyl) | * |
| 809 | Me | H | 2,4-di-Cl | CF$_3$ | 5-(1-Me-4-Cl-pyrazolyl) | 242-244 |
| 810 | Et | H | 2,4-di-Cl | CF$_3$ | 5-(1-Me-4-Cl-pyrazolyl) | 266-268 |
| 811 | i-Pr | H | 2,4-di-Cl | CF$_3$ | 5-(1-Me-4-Cl-pyrazolyl) | 241-243 |
| 812 | Me | Me | 2,4-di-Cl | CF$_3$ | 5-(1-Me-4-Cl-pyrazolyl) | 202-204 |
| 813 | t-Bu | H | 2,4-di-Cl | CF$_3$ | 5-(1-Me-4-Cl-pyrazolyl) | 128-131 |

INDEX TABLE A-continued

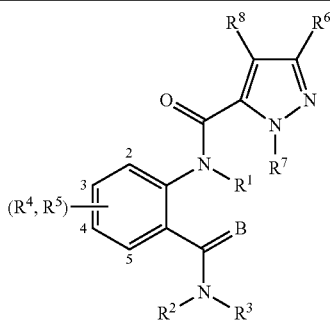

$R^1$, $R^5$, and $R^8$ are H, except where indicated; B is O, except where indicated. "CN" is bonded through carbon, not nitrogen; for example "CN—Ph" specifies cyanophenyl, not isocyanophenyl.

| Compound | $R^3$ | $R^2$ | $R^4$, $R^5$ | $R^6$ | $R^7$ | m.p. (° C.) |
|---|---|---|---|---|---|---|
| 814 | Me | H | 2,4-di-Cl | $CF_3$ | 2-(3-Cl-pyridinyl) | * |
| 815 | H | H | 2-F-4-Br | Br | 2-(3-Cl-pyridinyl) | 151-152 |
| 816 | H | H | 2-Cl-4-F | Cl | 2-(3-Cl-pyridinyl) | 133-134 |
| 817 | Me | H | 2,4-di-F | F | 2-(3-Cl-pyridinyl) | 166-167 |
| 818 | H | H | 2-F-4-Br | Cl | 2-(3-Cl-pyridinyl) | 148-149 |
| 819 | H | H | 2-Br-4-Cl | Br | 2-(3-Cl-pyridinyl) | 134-136 |
| 820 | Me | Me | 2,4-di-F | F | 2-(3-Cl-pyridinyl) | 211-212 |
| 821 | H | H | 2,4-di-F | F | 2-(3-Cl-pyridinyl) | 115-117 |
| 822 | i-Pr | H | 2,4-di-F | F | 2-(3-Cl-pyridinyl) | 157-158 |
| 823 | i-Pr | H | 2-Cl-4-I | Cl | 2-(3-Cl-pyridinyl) | 192-195 |
| 824 | i-Pr | H | 2,4-di-Cl | $OCH_3$ | 2-(3-Cl-pyridinyl) | 191-194 |
| 825 | Me | H | 2,4-di-Cl | $OCH_3$ | 2-(3-Cl-pyridinyl) | 143-145 |
| 826 | Me | H | 2-Me-4-Cl | Br | 2-(3-Cl-5-Br-pyridinyl) | 216-219 |
| 827 | Me | H | 2-F | F | 2-(3-Cl-pyridinyl) | 217-218 |
| 828 | Me | H | 2-Cl-4-F | F | 2-(3-Cl-pyridinyl) | 207-208 |
| 829 | Me | Me | 2-Cl-4-F | F | 2-(3-Cl-pyridinyl) | 221-222 |
| 830 | i-Pr | H | 2-C-4-F | F | 2-(3-Cl-pyridinyl) | 166-167 |
| 831 | H | H | 2-Cl-4-F | F | 2-(3-Cl-pyridinyl) | 133-134 |
| 832 | Me | H | 2-F-4-I | Br | 2-(3-Cl-pyridinyl) | 216-217 |
| 833 | Me | Me | 2-F-4-I | Br | 2-(3-Cl-pyridinyl) | 218-219 |
| 834 | i-Pr | H | 2-F-4-I | Br | 2-(3-Cl-pyridinyl) | 217-218 |
| 835 | H | H | 2,4-di-F | Br | 2-(3-Cl-pyridinyl) | 178-179 |
| 836 | Me | H | 2-I, 4-F | F | 2-(3-Cl-pyridinyl) | 217-218 |
| 837 | Me | Me | 2-I, 4-F | F | 2-(3-Cl-pyridinyl) | 238-239 |
| 838 | H | H | 2-Me, 4-Cl | $CF_3$ | 2-(3-F-pyridinyl) | * |
| 839 | Me | H | 2-Me, 4-Cl | $CF_3$ | 2-(3-F-pyridinyl) | * |
| 840 | Me | Me | 2-Me, 4-Cl | $CF_3$ | 2-(3-F-pyridinyl) | * |
| 841 | i-Pr | H | 2-Me, 4-Cl | $CF_3$ | 2-(3-F-pyridinyl) | * |
| 842 | H | H | 2,4-di-Cl | $CF_3$ | 2-(3-F-pyridinyl) | * |
| 843 | Me | Me | 2,4-di-Cl | $CF_3$ | 2-(3-F-pyridinyl) | * |
| 844 | i-Pr | H | 2,4-di-Cl | $CF_3$ | 2-(3-F-pyridinyl) | * |
| 845 | H | H | 2,4-di-Cl | Br | 2-(3-F-pyridinyl) | * |
| 846 | Me | H | 2,4-di-Cl | Br | 2-(3-F-pyridinyl) | * |
| 847 | Me | Me | 2,4-di-Cl | Br | 2-(3-F-pyridinyl) | * |
| 848 | i-Pr | H | 2,4-di-Cl | Br | 2-(3-F-pyridinyl) | * |
| 849 | H | H | 2-Me, 4-Cl | Br | 2-(3-F-pyridinyl) | * |
| 850 | Me | H | 2-Me, 4-Cl | Br | 2-(3-F-pyridinyl) | * |
| 851 | Me | Me | 2-Me, 4-Cl | Br | 2-(3-F-pyridinyl) | * |
| 852 | i-Pr | H | 2-Me, 4-Cl | Br | 2-(3-F-pyridinyl) | * |
| 853 | Me | H | 2,4-di-Cl | $CF_3$ | 5-(1-$CH_2CF_3$-4-Cl-pyrazolyl) | 181-183 |

* See Index Table B for $^1$H NMR data

INDEX TABLE B

| Compound | $^1$H NMR Data(CDCl$_3$ solution unless indicated otherwise)$^a$ |
|---|---|
| 185 | (DMSO-d$_6$)δ 1.03(d, 6H), 2.18(s, 3H), 3.92(m, 1H), 7.22-7.30(m, 2H), 7.35(m, 1H), 7.62(dd, 1H), 7.81(s, 1H), 8.02(d, 1H), 8.15(dd, 1H), 8.55(dd, 1H), 10.34(s, 1H). |
| 217 | (DMSO-d$_6$)δ 1.01(d, 6H), 2.16(s, 3H), 3.92(m, 1H), 7.27(m, 2H), 7.35(m, 1H), 7.89(s, 1H), 7.96(m, 1H), 8.37(s, 2H), 10.42(s, 1H). |
| 241 | (DMSO-d$_6$)δ 1.04(d, 6H), 4.0(m, 1H), 7.4(m, 2H), 7.5(m, 1H), 7.6(m, 1H), 7.78(d, 2H), 8.0(d, 2H), 8.2(d, 1H), 10.7(bs, 1H). |
| 242 | (DMSO-d$_6$)δ 1.16(d, 6H), 4.1(m, 1H), 5.9(d, 1H), 7.1(m, 1H), 7.2(m, 3H), 7.69(s, 1H), 7.73(s, 1H), 10.45(s, 1H). |
| 243 | (DMSO-d$_6$)δ 1.0(d, 6H), 3.9(m, 1H), 7.4(m, 2H), 7.6(m, 1H), 7.8(m, 2H), 8.0(d, 1H), 8.1(d, 1H), 8.3(s, 1H), 10.6(s, 1H). |
| 244 | (DMSO-d$_6$)δ 1.0(d, 6H), 4.0(m, 1H), 7.1(m, 1H), 7.43(m, 2H), 7.5(m, 4H), 7.66(m, 2H), 10.6(s, 1H). |
| 247 | (DMSO-d$_6$)δ 1.02(d, 6H), 2.18(s, 3H), 3.9-4.0(m, 1H), 7.2(m, 1H), 7.4(m, 1H), 7.8-7.9(m, 2H), 8.0(d, 2H), 8.3(s, 1H), 10.3(s, 1H). |

INDEX TABLE B-continued

| Compound | ¹H NMR Data(CDCl₃ solution unless indicated otherwise)ᵃ |
|---|---|
| 248 | (DMSO-d₆)δ 1.02(d, 6H), 2.18(s, 3H), 3.9-4.0(m, 1H), 7.2(m, 1H), 7.4(m, 1H), 7.8-7.9(m, 2H), 8.0(d, 2H), 8.3(s, 1H), 10.3(s, 1H). |
| 249 | (DMSO-d₆)δ 1.04(d, 6H), 4.0(m, 1H), 7.4(m, 2H), 7.76(s, 1H), 7.7(m, 1H), 7.74(m, 1H), 7.9(m, 1H), 7.97(d, 1H), 8.07(s, 1H), 8.2(m, 1H), 10.7 (bs, 1H). |
| 264 | (DMSO-d₆)δ 1.0(d, 6H), 2.01(s, 3H), 2.17(s, 3H), 3.9(m, 1H), 7.3(m, 2H), 7.3-7.4(m, 1H), 7.8-7.9(s, 1H), 7.9-8.0(m, 2H), 8.1-8.2(s, 1H), 10.3-10.4(s, 1H). |
| 273 | (DMSO-d₆)δ 1.21(d, 6H), 2.24(s, 3H), 4.1-4.3(m, 1H), 5.9(d, 1H), 7.02(d, 1H), 7.1-7.6(m, 7H), 7.78(s, 1H), 10.0(br s, 1H) |
| 274 | (DMSO-d₆)δ 1.03(d, 6H), 1.94(s, 3H), 2.14(s, 3H), 3.9-4.0(m, 1H), 7.1-7.4(m, 8H), 7.8(s, 1H), 7.9-8.0(d, 1H), 10.0(s, 1H). |
| 275 | (DMSO-d₆)δ 1.04(d, 6H), 2.18(s, 3H), 3.9-4.0(m, 1H), 7.2-7.4(m, 6H), 7.4-7.6(m, 2H), 7.9(s, 1H), 7.9-8.0(d, 1H), 10.1(br s, 1H). |
| 278 | δ 1.20(d, 6H), 2.19(s, 3H), 4.2(m, 1H), 5.9-6.0(d, 1H), 7.1-7.5(m, 8H), 10.4-10.5(s, 1H). |
| 314 | (DMSO-d₆)δ 1.03(d, 6H), 2.18(s, 3H), 3.31(s, 3H), 3.9-4.0(m, 1H), 7.2-7.3(m, 2H), 7.3-7.4(m, 1H), 7.81(s, 1H), 7.9(d, 1H), 8.0(br d, 1H), 8.1(dd, 1H), 8.3(d, 1H), 10.3(s, 1H). |
| 398 | δ 2.57(t, 2H), 3.57(q, 2H), 6.25(t, 1H), 7.18-7.53(m, 8H), 9.17(s, 1H) |
| 399 | δ 1.23(d, 6H), 4.13(m, 1H), 5.92(d, 1H), 7.35(m, 1H), 7.39(s, 1H) 7.42(m, 2H), 7.92(d, 1H), 8.51(d, 1H), 10.23(br s, 1H). |
| 402 | δ 1.13(d, 6H), 4.15(m, 1H), 5.99(d, 1H), 7.40(m, 1H). 7.41(m, 1H), 7.63(m, 1H), 7.80(s, 1H), 7.90(d, 1H), 8.48(d, 1H), 10.2(br s, 1H). |
| 562 | δ 1.22(d, 6H), 2.18(s, 3H), 4.15(m, 1H), 4.37(s, 1H), 5.91(d, 1H), 7.20(m, 4H), 7.30(m, 1H), 7.40(m, 1H), 7.52(m, 2H), 7.96(s, 1H), 10.23(br s, 1H). |
| 563 | (DMSO-d₆)δ 1.05(d, 6H), 2.15(s, 3H), 3.74(s, 2H), 3.93(m, 1H), 7.26–7.70(m, 8H), 8.05(s, 1H), 8.35(br s, 2H), 10.45(s, 1H). |
| 572 | δ 1.20(d, 6H), 2.01(s, 3H), 2.72(d, 3H), 4.13(m, 1H), 6.01(m, 1H), 6.45(s, 1H), 7.17(m, 5H), 7.51(m, 2H), 7.63(m, 1H), 10.41(s, 1H). |
| 586 | (DMSO-d₆)δ 1.04(d, 6H), 2.32(s, 3H), 3.91(m, 1H), 7.44-7.64(m, 4H), 7.77(s, 1H), 8.07(d, 1H), 8.27(d, 1H), 8.42(d, 1H), 10.6(s, 1H). |
| 590 | (DMSO-d₆)δ 1.03(d, 6H), 3.88(m, 1H), 7.65(dd, 1H), 7.88(s, 1H), 8.18(s, 1H), 8.22(d, 1H), 8.48-8.57(m, 3H), 10.95(s, 1H). |
| 592 | δ 1.24(d, 6H), 4.22(m, 1H), 5.98(br d, 1H), 7.30-7.55(m, 6H), 7.78(d, 1H), 7.99(d, 1H), 11.15(s, 1H). |
| 603 | δ 2.16(s, 3H), 7.1-7.3(obscured, 1H), 7.40(d, 1H), 7.47(dd, 1H), 7.93(dd, 1H), 8.03(0d, 1H), 8.5(dd, 1H). |
| 610 | (DMSO-d₆)δ 1.04(m, 6H), 4.08(s, 3H), 8.18(m, 2H), 8.22(d, 1H), 8.47(dd, 1H), 8.58(d, 1H), 9.17(d, 1H), 9.39(d, 1H), 11.48(s, 1H). |
| 611 | (DMSO-d₆)δ 1.04(m, 6H), 2.50(s, 3H), 4.09(s, 3H), 8.12(d, 1H), 8.17(s, 1H), 8.34(d, 1H), 8.37-8.52(m, 2H), 9.15(d, 1H), 9.37(d, 1H), 11.11(s, 1H). |
| 638 | δ 1.30(t, 3H), 2.32(s, 3H), 3.55(q, 2H), 6.23(br t, 1H), 7.30(s, 1H), 7.42 (dd, 1H), 7.91(d, 1H), 8.20(apparent s, 2H), 8.52(d, 1H), 10.92(s, 1H). |
| 639 | δ 2.21(s, 3H), 2.90(s, 3H), 3.12(s, 3H), 7.42(m, 2H), 7.92(d, 1H), 7.92(d, 1H), 8.00(d, 1H), 8.50(d, 1H), 9.92(br s, 1H). |
| 640 | δ 2.32(s, 3H), 4.02(t, 2H), 5.18-5.30(m, 2H), 5.82-5.98(m, 1H), 7.37(s, 1H), 7.43(dd, 1H), 7.50(br t, 1H), 7.92(d, 1H), 8.17(s, 1H), 8.37(d, 1H), 8.52(d, 1H), 11.12(br s, 1H). |
| 641 | δ 0.91(t, 3H), 1.63(m, 2H), 2.31(s, 3H), 3.40(q, 2H), 6.83(br t, 1H), 7.35(s, 1H), 7.42(dd, 1H), 7.91(d, 1H), 8.17(d, 1H), 8.24(d, 1H), 8.52(d, 1H), 11.03(s, 1H). |
| 642 | δ 1.38(d, 3H), 2.14(s, 3H), 2.35(s, 3H), 2.72(m, 2H), 4.38(m, 1H), 6.93(br d, 1H), 7.33(s, 1H), 7.43(dd, 1H), 7.91(d, 1H), 8.18(d, 1H), 8.28(d, 1H), 8.52(d, 1H), 10.93(s, 1H). |
| 643 | (DMSO-d₆)δ 2.32(s, 3H), 2.70(s, 3H), 7.63(m, 2H), 7.78(br s, 1H), 8.18(br s, 1H), 8.21(br s, 1H), 8.27(br s, 1H), 8.58(m, 2H). |
| 644 | (DMSO-d₆)δ 1.25(s, 9H), 2.31(s, 3H), 7.64(dd, 1H), 7.79(s, 1H), 8.03(br s, 2H), 8.22(d, 1H), 8.28(s, 1H), 8.54(d, 1H), 10.62(s, 1H). |
| 654 | δ 2.33(s, 3H), 2.75(br s, 6H), 6.9(br s, 1H), 7.33(s, 1H), 7.43(dd, 1H), 7.91(d, 1H), 8.19(br s, 1H), 8.23(s, 1H), 8.50(d, 1H), 10.70(br s, 1H). |
| 735 | δ 1.39(d, 6H), 2.81(d, 3H), 4.95(m, 1H), 6.59(s, 1H), 6.62(q, 1H), 7.12(s, 1H), 7.24(s, 1H), 7.26(t, 1H), 7.80(d, 1H), 8.40(d, 1H), 9.56(br s, 1H). |
| 772 | δ 1.24(d, 6H), 2.22(s, 3H), 4.20(m, 1H), 6.10(d, 1H), 7.35(s, 1H), 7.44(t, 1H), 7.55(s, 2H), 7.87(s, 1H), 8.48(d, 1H). 10.7(s, 1H). |
| 780 | δ 2.91(d, 3H), 6.3(m, 1H), 6.77(d, 1H), 7.3(obscured, 1H), 7.3-7.4(m, 2H), 7.8-7.9(d, 1H), 8.5(d, 1H), 9.6-9.7(br s, 1H). |
| 802 | (DMSO-d₆)δ 7.1(d. 1H), 7.5-7.7(m, 3H), 7.8(m, 2H), 8.1-8.2(d, 1H), 8.5(d, 1H), 10.5(br s, 1H). |
| 803 | (DMSO-d₆)δ 1.03(d, 6H), 3.9(m, 1H), 7.1(d, 1H), 7.4-7.5(m, 1H), 7.6(dd, 1H), 7.8(d, 1H), 8.2(d, 1H), 8.2(m, 1H), 8.5(d, 1H), 10.5(br s, 1H). |
| 804 | δ 2.78(s, 3H), 3.04(s, 3H), 6.9(d, 1H), 7.1(d, 1H), 7.29(d, 1H), 7.3-7.4(dd, 1H), 7.8-7.9(d, 1H), 8.5(d, 1H), 9.8(br s, 1H). |
| 805 | δ 2.18(s, 3H), 5.7(br s, 1H), 6.2(br s, 1H), 6.7(d, 1H), 7.3(m, 1H), 7.3-7.4(dd, 1H), 7.8-7.9(d, 1H), 8.4-8.5(d, 1H), 10.0(br s, 1H). |
| 806 | δ 1.23(d, 6H), 2.19(s, 3H), 4.2(m, 1H), 5.9(br s, 1H), 6.7(d, 1H), 7.21(d, 1H), 7.26(obscured, 1H), 7.3-7.4(dd, 1H), 7.8-7.9(d, 1H), 8.4-8.5(d, 1H), 10.1(br s, 1H). |
| 807 | δ 2.20(s, 3H), 2.96(m, 3H), 6.1(br s, 1H), 6.65(d, 1H), 7.2(d, 1H), 7.26(obscured, 1H), 7.3-7.4(dd, 1H), 7.8-7.9(d, 1H), 8.4-8.5(d, 1H), 10.1(br s, 1H). |
| 808 | δ 2.06(s. 3H), 2.78(s, 3H), 3.08(s, 3H), 6.9(d, 1H), 7.0(s, 1H), 7.1(s, 1H), 7.3-7.4(dd, 1H), 7.8-7.9(d. 1H), 8.4-8.5(d, 1H), 9.7-9.8(br s, 1H). |
| 814 | (DMSO-d₆)δ 2.65(d, 3H), 7.52(d, 1H), 7.6-7.8(m, 2H), 7.9(d, 1H), 8.0-8.1(t, 1H), 8.3-8.4(m, 1H), 8.4(d, 1H), 10.7(br s, 1H). |
| 838 | (DMSO-d₆)δ 2.18(s, 3H), 7.41(d, 1H), 7.5(m, 2H), 7.67(s, 1H), 7.7(m, 1H), 7.8(s, 1H), 8.0-8.1(t, 1H), 8.4(d, 1H), 10.4-10.5(br s, 1H). |
| 839 | (DMSO-d₆)δ 2.18(s, 3H), 2.66(d, 3H), 7.35(d, 1H), 7.49(d, 1H), 7.69(s, 1H), 7.7-7.8(m, 1H), 8.0-8.1(t, 1H), 8.3(m, 1H), 8.4(d, 1H), 10.4-10.5(br s, 1H). |
| 840 | δ 2.00(s. 3H), 2.75(s, 3H), 3.09(s,3H), 6.99(d, 1H), 7.03(s, 1H), 7.4-7.5(m, 1H), 7.5-7.6(t, 1H), 7.76(d, 1H), 8.4(d, 1H), 10.4-10.5(br s, 1H). |
| 841 | (DMSO-d₆)δ 1.02(d, 6H), 2.19(s, 3H), 3.9(m, 1H), 7.30(s, 1H), 7.48(d, 1H), 7.6-7.8(m, 2H), 8.0(t, 1H), 8.1(d, 1H), 8.4(d, 1H), 10.4(br s, 1H). |
| 842 | (DMSO-d₆)δ 7.56(d, 1H), 7.6(s, 1H), 7.7-7.8(m, 2H), 7.9(m, 2H), 8.0-8.1(t, 1H), 8.4(d, 1H), 10.6-10.7(br s, 1H). |
| 843 | δ 2.79(s, 3H), 3.08(s, 3H), 7.09(d, 1H), 7.25(d, 1H), 7.4- 7.5(m, 1H), 7.5-7.6(t, 1H), 7.78(d, 1H), 8.4(d, 1H), 10.5(br s, 1H). |
| 844 | (DMSO-d₆)δ 1.01(d, 6H), 3.9(m, 1H), 7.46(d, 1H), 7.7(m, 1H), 7.8(s, 1H), 7.85(d,1H), 8.0(t, 1H), 8.2-8.3(d, 1H), 8.4(d, 1H), 10.6-10.7(br s, 1H). |
| 845 | (DMSO-d₆)δ 7.39(s, 1H), 7.55(d, 1H), 7.4(s, 1H), 7.4-7.5(m, 1H), 7.8(s, 1H), 7.85(d, 1H), 8.0(t, 1H), 8.4(d, 1H), 10.5(br s, 1H). |
| 846 | (DMSO-d₆)δ 2.66(d, 3H), 7.40(s, 1H), 7.51(d, 1H), 7.6-7.7(m, 1H), 7.84(d, 1H), 8.0(t, 1H), 8.3-8.4(m, 1H), 8.4(d, 1H), 10.5-10.6(br s, 1H). |
| 847 | δ 2.80(s, 3H), 3.07(s, 3H), 7.10(s, 1H), 7.31(d, 1H), 7.35(s, 1H), 7.4(m, 1H), 7.5-7.6(t. 1H), 8.4(d, 1H), 9.5(br s, 1H). |
| 848 | (DMSO-d₆)δ 1.02(d, 6H), 3.9(m, 1H), 7.45(apparent s, 2H), 7.6-7.7 m, 1H), 7.84(d, 1H), 7.9-8.0(t, 1H), 8.2(d, 1H), 8.36(d, 1H), 10.5(br s, 1H). |
| 849 | DMSO-d₆)δ 2.17(s, 3H), 7.33(s, 1H), 7.4(d, 1H), 7.5(m, 2H), 7.6-7.7(m, 1H), 7.9(s, 1H), 8.0(t, 1H), 8.4(d, 1H), 10.3(br s, 1H). |
| 850 | (DMSO-d₆)δ 2.17(s, 3H), 2.67(d, 3H), 7.3-7.4(m, 2H), 7.5(d, 1H), 7.6-7.7(m, 1H). 8.0(t, 1H), 8.2-8.3(m, 1H), 8.4(d, 1H), 10.3(br s, 1H). |

INDEX TABLE B-continued

| Compound | $^1$H NMR Data(CDCl$_3$ solution unless indicated otherwise)$^a$ |
|---|---|
| 851 | δ 2.08(s, 3H), 2.79(s, 3H), 3.09(s. 3H), 6.99(d, 1H), 7.11(s, 1H), 7.28(d, 1H), 7.4(m, 1H), 7.5-7.6(t, 1H), 8.3-8.4(d, 1H), 9.8(br s, 1H). |
| 852 | (DMSO-d$_6$)δ 1.03(d. 6H), 2.17(s, 3H), 3.9(m, 1H), 7.3(d, 1H), 7.37(s, 1H), 7.5(d, 1H), 7.6-7.7(m, 1H), 7.9-8.0(t, 1H), 8.1(d, 1H), 8.3-8.4(d, 1H), 10.2-10.3(br s, 1H). |

$^a$$^1$H NMR data are in ppm downfield from tetramethylsilane. Couplings are designated by (s)-singlet, (d)-doublet, (t)-triplet, (q)quartet, (m)-multiplet, (dd)-double of doubles, (dt)-doublet of triplets, (br s)-broad singlet.

BIOLOGICAL EXAMPLES OF THE INVENTION

Test A

Cotton seeds coated with a composition of Compound 208 from the Nominal 1%, Nominal 2% and Nominal 3% concentration batches prepared as described in Example E and untreated seeds for comparison were planted in pots using sterile Sassafras soil and grown in a growth chamber with 16 hours of light at 28° C. and 8 hours of darkness at 24° C. and 50% relative humidity. After 31 days two plants, each having true leaves, were selected from each of the seed batches and their cotyledons were removed. Adult *Bemisia argentifolii* (silverleaf whitefly) were added for egg-laying on the plants, and plastic cylinders capped with tissue paper were fitted into the pots. Three days later, the adults were removed and the leaves were checked to verify egg deposits. Fifteen days later (about six days after egg hatching), the infested leaves were removed from the plants and the 49-day results determined by counting the dead and live nymphs on the undersides of the leaves. Adult *Bemisia argentifolii* were reintroduced for a second round of egg-laying on upper leaves of the plants, and plastic cylinders with tissue paper were fitted into the pots as before. Three days later, the adults were removed and the leaves were checked to verify egg deposits. Fourteen days later (about six days after egg hatching), the leaves were removed from the plants and the 66-day results determined by counting the dead and live nymphs on the undersides of the leaves. The results from both rating times are summarized in Table A.

TABLE A

Control of Silverleaf Whitefly by Coating Cottonseed with Compositions of Compound 208

| Treatment | 49-day % Mortality | 66-day % Mortality |
|---|---|---|
| Nominal 1% concentration | 38 | 17 |
| Nominal 2% concentration | 72 | 41 |
| Nominal 3% concentration | 95 | 81 |
| Untrated | 15 | 10 |

This test demonstrates that seed coatings according to this invention can protect cotton plants from the homopteran pest *Bemisia argentifolii* for more man 9 weeks after seeding.

Test B

Cotton seeds coated with a composition of Compound 208 from the Nominal 1%, Nominal 2% and Nominal 3% concentration hatches prepared as described in Example E and untreated seeds for comparison were planted in 10-cm pots using sterile sassafras soil and grown in a growth chamber with 16 hours of light and 8 hours of darkness at 25° C. and 50% relative humidity. Leaves were harvested from some of the plants 14 days after seeding, cut into 3 to 4 pieces, and placed one piece per well in covered 16-well translucent plastic trays in the growth chamber. Second-instar larvae of *Heliothis virescens* (tobacco budworm) were added to the leaf pieces (1 larva/well, 6-10 larvae per treatment/leaf type), and the insect mortality was determined 48 hours and 96 hours after infestation. Leaves were harvested from other of the plants 64 days after seeding, cut into 3 to 4 pieces, and placed one piece per well in covered 16-well translucent plastic frays in the growth chamber. Second-instar larvae of *Heliothis virescens* (tobacco budworm) were added to the leaf pieces (1 larva/well, 6-16 larvae per treatment/leaf location), and the insect mortality was determined 72 hours and 96 hours after infestation. The results are summarized in Tables B1 and B2.

TABLE B1

Control of Tobacco Budworm 14 Days after Seeding by Coating Cottonseed with Compositions of Compound 208

| Treatment | Leaf Type | 48-hour % Mortality | 96-hour % Mortality |
|---|---|---|---|
| Nominal 1% | True | 0 | 33 |
| concentration | Cotyledon | 10 | 70 |
| Nominal 2% | True | 17 | 33 |
| concentration | Cotyledon | 30 | 100 |
| Nominal 3% | True | 17 | 83 |
| concentration | Cotyledon | 50 | 100 |
| Untreated | True | 0 | 0 |
| Check | Cotyledon | 0 | 0 |

TABLE B2

Control of Tobacco Budworm 64 Days after Seeding by Coating Cottonseed with Compositions of Compound 208

| Treatment | Leaf Location* | 72-hour % Mortality | 96-hour % Mortality |
|---|---|---|---|
| Nominal 1% | Top | 25 | 93 |
| concentration | Bottom | 31 | 100 |
| Nominal 2% | Top | 6 | 81 |
| concentration | Bottom | 31 | 100 |
| Nominal 3% | Top | 75 | 100 |
| concentration | Bottom | 50 | 100 |
| Untreated | Top | 12 | 12 |
| Check | Bottom | 19 | 19 |

*Location on cotton plant from which leaf was removed.

This test demonstrates that seed coatings according to this invention can protect cotton plants from the lepidopteran pest *Heliothis virescens* for more than 9 weeks after seeding.

Test C

Cotton seeds treated with Compound 208 as prepared in Example E (Nominal 3% batch) and Compound 276, 486 and 502 as prepared in Example G and untreated seeds for comparison were planted in pots using either sterile Sassafras soil or Drummer soil. Plants were grown in the greenhouse and sampled when they started to produce buds (squares). The leaves from the second node and the terminal leaves greater than 15 cm$^2$ were sampled (plants had approximately 5 leaves). The clipped leaf from each plant was cut into 4 pieces and each piece was placed into a well with one second-instar larvae of *Heliothis virescens* (tobacco budworm). Larval mortality was recorded 96 hours after sampling.

TABLE C

Larval Mortality from Feeding on Leaves with
Seed Treatments Grown in Two Soil Types

|  |  | 96-hour % Larval Mortality | |
|---|---|---|---|
| Compound | Soil Type | Terminal Leaf | Base of Plant |
| 208 | Sassafras | 35.0 | 47.5 |
|  | Drummer | 58.3 | 79.2 |
| 276 | Sassafras | 81.3 | 81.3 |
|  | Drummer | 85.7 | 96.4 |
| 486 | Sassafras | 43.8 | 34.4 |
|  | Drummer | 57.1 | 67.9 |
| 502 | Sassafras | 25.0 | 46.9 |
|  | Drummer | 87.5 | 75.0 |
| Untreated | Sassafras | 9.4 | 6.3 |
|  | Drummer | 16.7 | 4.2 |

Test D

Corn seeds treated with compounds 208, 484, 486, 502, 509 and 515 as prepared in Example F were planted in pots with Sassafras soil. Plants were grown to whorl height (9th leaf) in the greenhouse and infested with 25 fall armyworm (first-instar larvae) down the whorl. Six days after infesting the plant damage associated with the feeding was recorded. Plant damage was rated on a of 0-100% (0 means no feeding).

TABLE D

Percent Plant Damage from Larval Feeding on Corn
Plants with Different Seed Treatments

| Compound | Percent Plant Damage |
|---|---|
| 208 | 8 |
| 484 | 29 |
| 486 | 23 |
| 509 | 10 |
| 502 | 10 |
| 515 | 7 |
| Untreated | 56 |

Test E

Corn seeds treated with Compound 502 as prepared in Example H at five rates (Nominal 1.75%, 1.09%, 0.58%, 0.29% and 0.15%) were planted in agricultural fields near Newark, Del. and Donna, Tex. When the plants had produced a 5th leaf at least 10 cm long it was cut. One clipped leaf from at least 16 plants for each rate was taken and placed into a well with one second-instar fall armyworm larvae. Larval mortality was recorded 72 hours after infesting.

Corn plants at the Donna site were measured to determine plant growth. Leaves were folded up into a tube, and the height from the ground to the furthest leaf tip in the tube was recorded.

TABLE E1

Larval Mortality from Feeding on the 5th Leaf of Corn with
Compound 502 Seed Treatments

|  | Percent Mortality at 72 Hr | |
|---|---|---|
| Rate | Newark | Donna |
| 1.75% | 100.0 | 58.1 |
| 1.09% | 100.0 | 71.0 |
| 0.58% | 95.8 | 54.8 |
| 0.29% | 87.5 | 35.5 |
| 0.15% | 87.5 | 29.0 |
| Untreated | 0.0 | 0.0 |

TABLE E2

Plant Height of Corn with Compound 502 Seed Treatments at Donna, TX

|  | Seed Treatment (Nominal rate) | | | | | |
|---|---|---|---|---|---|---|
|  | Untreated | 0.15% | 0.29% | 0.58% | 1.09% | 1.75% |
| Height (inches) | 41.64 | 40.76 | 42.36 | 44.28 | 45.32 | 48.32 |

As can be seen from Table E2, treatment with Compound 502 appears to have promoted plant growth in this test.

What is claimed is:

1. An invertebrate pest control composition for coating a propagule, the composition comprising (1) a biologically effective amount of a compound of Formula I, an N-oxide thereof or an agriculturally suitable salt thereof,

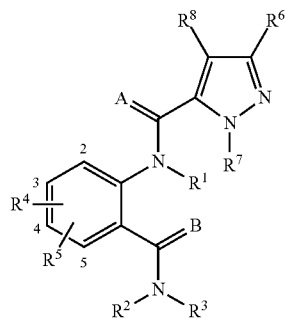

wherein
A and B are independently O or S;
$R^1$ is H, $C_1$-$C_6$ alkyl, $C_2$-$C_6$ alkoxycarbonyl or $C_2$-$C_6$ alkylcarbonyl;
$R^2$ is H or $C_1$-$C_6$ alkyl;
$R^3$ is H; $C_1$-$C_6$ alkyl, $C_2$-$C_6$ alkenyl, $C_2$-$C_6$ alkynyl, or $C_3$-$C_6$ cycloalkyl, each optionally substituted with one or more substituents selected from the group consisting of halogen, CN, $NO_2$, hydroxy, $C_1$-$C_4$ alkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_2$-$C_6$ alkoxycarbonyl, $C_2$-$C_6$ alkylcarbonyl, $C_3$-$C_6$ trialkylsilyl, phenyl, phenoxy, 5-membered heteroaromatic rings, and 6-membered heteroaromatic rings; each phenyl, phenoxy, 5-membered heteroaromatic ring, and 6-membered heteroaromatic ring optionally substituted with one to three substituents independently selected from the group consisting of $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$ $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_8$ (alkyl)(cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl and $C_3$-$C_6$ trialkylsilyl; $C_1$-$C_4$ alkoxy; $C_1$-$C_4$ alkylamino; $C_2$-$C_8$ dialkylamino; $C_3$-$C_6$ cycloalkylamino; $C_2$-$C_6$ alkoxycarbonyl or $C_2$-$C_6$ alkylcarbonyl;

$R^4$ is H, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, CN, halogen, $C_1$-$C_4$ alkoxy, $C_1$-$C_4$ haloalkoxy or $NO_2$;

$R^5$ is H, $C_1$-$C_6$ alkyl, $C_1$-$C_6$ haloalkyl, $C_1$-$C_4$ alkoxyalkyl, $C_1$-$C_4$ hydroxyalkyl, $C(O)R^{10}$, $CO_2R^{10}$, $C(O)NR^{10}R^{11}$, halogen, $C_1$-$C_4$ alkoxy, $C_1$-$C_4$ haloalkoxy, $NR^{10}R^{11}$, $N(R^{11})C(O)R^{10}$, $N(R^{11})CO_2R^{10}$ or $S(O)_nR^{12}$;

$R^6$ is H, $C_1$-$C_6$ alkyl, $C_1$-$C_6$ haloalkyl, halogen, CN, $C_1$-$C_4$ alkoxy or $C_1$-$C_4$ haloalkoxy;

$R^7$ is $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl or $C_3$-$C_6$ halocycloalkyl; or $R^7$ is a phenyl ring, a benzyl ring, a 5- or 6-membered heteroaromatic ring, a naphthyl ring system or an aromatic 8-, 9- or 10-membered fused heterobicyclic ring system, each ring or ring system optionally substituted with one to three substituents independently selected from $R^9$;

$R^8$ is H, $C_1$-$C_6$ alkyl, $C_1$-$C_6$ haloalkyl, halogen, $C_1$-$C_4$ alkoxy or $C_1$-$C_4$ haloalkoxy;

each $R^9$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, $C_4$-$C_8$ (alkyl)(cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^{10}$ is H, $C_1$-$C_4$ alkyl or $C_1$-$C_4$ haloalkyl;

$R^{11}$ is H or $C_1$-$C_4$ alkyl;

$R^{12}$ is $C_1$-$C_4$ alkyl or $C_1$-$C_4$ haloalkyl; and n is 0, 1 or 2; and (2) a film former or adhesive agent selected from the group consisting of polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxymethylcelluloses, hydroxypropylcellulose, hydroxymethylpropylcelluloses, polyvinylpyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, acrylic copolymers, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof.

2. The composition according to claim 1 wherein the film former or adhesive agent is selected from polymers and copolymers of vinyl acetate, poly-vinylpyrrolidone-vinyl acetate copolymer and water-soluble waxes.

3. The composition according to claim 1 further comprising an effective amount of at least one additional biologically active compound or agent.

4. The composition according to claim 3 wherein at least one additional biologically active compound or agent is selected from arthropodicides of the group consisting of pyrethroids, carbamates, neonicotinoids, neuronal sodium channel blockers, insecticidal macrocyclic lactones, γ-aminobutyric acid (GABA) antagonists, insecticidal ureas and juvenile hormone mimics.

5. The composition according to claim 3 wherein at least one additional biologically active compound or agent is selected from the group consisting of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben, tebufenpyrad; and biological agents such as *Bacillus thuringiensis* including ssp. *aizawai* and *kurstaki*, *Bacillus thuringiensis* delta endotoxin, baculovirus, and entomopathogenic bacteria, virus and fungi.

6. The composition according to claim 3 wherein at least one additional biologically active compound or agent is selected from fungicides of the group consisting of acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), metrafenone (AC 375839), myclobutanil, neo-asozin (ferric methanearsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin.

7. The composition according to claim 3 wherein at least one additional biologically active compound or agent is selected from fungicides in the group consisting of thiram, maneb, mancozeb and captan.

8. The composition according to claim 1 wherein the compound of Formula I is 3-bromo-N-[4-chloro-2-emthyl-6-[(methylamino)carbonyl]phenyl]-2-(3-chloro-2-pyridinyl)-H-pyrazole-5-carboxamide.

9. The composition according to claim 1 further comprising a formulation aid selected from the group consisting of a dispersant, a surfactant, a carrier, an antifoam and a dye.

10. The composition according to claim 5 wherein the at least one additional biologically active compound or agent is a neonicotinoid selected from the group consisting of clothianidin, imidacloprid and thiacloprid.

11. The composition according to claim 5 wherein the at least one additional biologically active compound or agent is a pyrethroid selected from the group consisting of cypermethirin, cyhalothrin, cyfluthrin, beta-cyfluthrin, esfenvalerate, fenvalerate and tralomethrin.

12. The composition according to claim 5 wherein the at least one additional biologically active compound or agent is an insecticidal macrocylic lactone selected from the group consisting of spinosad, abamectin, avermectin an demamectin.

13. The composition according to claim 1 wherein the composition is in the form of a liquid drench.

14. The composition according to claim 1 wherein the composition is in the form of a dry dust or powder.

* * * * *

UNITED STATES PATENT AND TRADEMARK OFFICE
CERTIFICATE OF CORRECTION

PATENT NO. : 8,637,552 B2
APPLICATION NO. : 13/571677
DATED : January 28, 2014
INVENTOR(S) : Richard A Berger et al.

It is certified that error appears in the above-identified patent and that said Letters Patent is hereby corrected as shown below:

In the Claims

In claim 8, at column 129, lines 11-13, that portion of the formula reading "2-emthyl" should read -- 2-methyl --; that portion of the formula reading "2-(3-chloro-2-pyridinyl)" should read -- 1-(3-chloro-2-pyridinyl) --; and that portion of the formula reading "H-pyrazole" should read -- 1H-pyrazole --.

Signed and Sealed this
Fourteenth Day of October, 2014

Michelle K. Lee
*Deputy Director of the United States Patent and Trademark Office*